US010351624B2

(12) United States Patent
Komai et al.

(10) Patent No.: US 10,351,624 B2
(45) Date of Patent: Jul. 16, 2019

(54) ANTI-ORAI1 ANTIBODY

(71) Applicant: Daiichi Sankyo Company, Limited, Chuo-ku, Tokyo (JP)

(72) Inventors: Tomoaki Komai, Tokyo (JP); Takako Kimura, Tokyo (JP); Daichi Baba, Tokyo (JP); Yoshikuni Onodera, Tokyo (JP); Kento Tanaka, Kanagawa (JP); Takashi Kagari, Kanagawa (JP); Anri Aki, Saitama (JP); Nobumi Nagaoka, Saitama (JP)

(73) Assignee: Daiichi Sankyo Company, Limited, Tokyo (JP)

( * ) Notice: Subject to any disclaimer, the term of this patent is extended or adjusted under 35 U.S.C. 154(b) by 0 days.

(21) Appl. No.: 15/502,088

(22) PCT Filed: Aug. 6, 2015

(86) PCT No.: PCT/JP2015/072305
§ 371 (c)(1),
(2) Date: Feb. 6, 2017

(87) PCT Pub. No.: WO2016/021674
PCT Pub. Date: Feb. 11, 2016

(65) Prior Publication Data
US 2017/0226203 A1 Aug. 10, 2017

(30) Foreign Application Priority Data
Aug. 7, 2014 (JP) ................................. 2014-161449

(51) Int. Cl.
| C07K 16/18 | (2006.01) |
| C07K 16/28 | (2006.01) |
| A61K 39/395 | (2006.01) |
| A61K 39/00 | (2006.01) |
| C12N 5/10 | (2006.01) |
| C12N 15/09 | (2006.01) |
| C07K 16/46 | (2006.01) |

(52) U.S. Cl.
CPC ............ *C07K 16/28* (2013.01); *A61K 39/395* (2013.01); *C07K 16/18* (2013.01); *C07K 16/46* (2013.01); *C12N 5/10* (2013.01); *C12N 15/09* (2013.01); *A61K 2039/505* (2013.01); *C07K 2317/24* (2013.01); *C07K 2317/51* (2013.01); *C07K 2317/515* (2013.01); *C07K 2317/56* (2013.01); *C07K 2317/565* (2013.01); *C07K 2317/622* (2013.01); *C07K 2317/71* (2013.01); *C07K 2317/76* (2013.01); *C07K 2317/92* (2013.01)

(58) Field of Classification Search
CPC .. C07K 16/28; C07K 16/18; C07K 2317/515; C07K 2317/56; C07K 2317/565; C07K 2317/622; A61K 39/395; A61K 2039/505
See application file for complete search history.

(56) References Cited

U.S. PATENT DOCUMENTS
2012/0231006 A1    9/2012 Nguyen et al.

FOREIGN PATENT DOCUMENTS
| JP | 2013511279 A | 4/2013 |
| WO | 2007/081804 A2 | 7/2007 |
| WO | 2011/063277 A1 | 5/2011 |
| WO | 2013/091903 A1 | 6/2013 |

OTHER PUBLICATIONS

Beech, D.J., "Orai1 Calcium Channels in the Vasculature," Pflügers Archiv—European Journal of Physiology 463(5):635-647, May 2012.
Extended European Search Report dated Dec. 21, 2017, issued in corresponding European Application No. 15830516.9, filed Aug. 6, 2015, 10 pages.
Cox, J.H., et al., "Antibody-Mediated Targeting of the Orai1 Calcium Channel Inhibits T Cell Function," Plos One 8(12):e82944, Dec. 2013.
Gwack, Y., et al., "Biochemical and Functional Characterization of Orai Proteins," The Journal of Biological Chemistry 282(22):16232-16243, Jun. 2007.
Hou, X., et al., "Crystal Structure of the Calcium Release-Activated Calcium Channel Orai," Science 338(6112)1308-1313, Dec. 2012.
Lin, F.-F., et al., "Generation and Characterization of Fully Human Monoclonal Antibodies Against Human Orai1 for Autoimmune Disease," The Journal of Pharmacology and Experimental Therapeutics 345:225-238, May 2013.
McCarl, C.-A., et al., "ORAI1 Deficiency and Lack of Store-Operated Ca2+ Entry Cause Immunodeficiency, Myopathy, and Ectodermal Dysplasia," The Journal of Clinical Immunology 124(6):1311-13817, Dec. 2009.
McCarl, C.-A, et al., "Store-Operated Ca2+ Entry through ORAI1 is Critical for T Cell-Mediated Autoimmunity and Allograft Rejection," The Journal of Immunology 185(10):5845-5858, Nov. 2010.
Mercer, J.C., et al., "Large Store-Operated Calcium Selective Currents Due to Co-Expression of Orai1 or Orai2 with the Intracellular Calcium Sensor, Stim1," The Journal of Biological Chemistry 281(34):24979-24990, Aug. 2006.
Vig., M., et al., "CRACM1 Multimers Form the Ion-Selective Pore of the CRAC Channel," Current Biology 16:2073-2079, Oct. 2006.
Vig, M., "CRACM1 is a Plasma Membrane Protein Essential for Store-Operated Ca2+ Entry," Science 312 (5777)1220-1223, May 2006.
Written Opinion and International Search Report dated Oct. 6, 2015, issued in corresponding International Application No. PCT/JP2015/072305, filed Aug. 6, 2015, 8 pages.

(Continued)

*Primary Examiner* — Ruixiang Li
(74) *Attorney, Agent, or Firm* — Christensen O'Connor Johnson Kindness PLLC

(57) ABSTRACT

It is intended to provide a therapeutic and/or prophylactic agent for transplant rejections, immunological diseases, allergic diseases, inflammatory diseases, thrombosis, cancers, etc., targeting human Orai1. The present invention provides, for example, a pharmaceutical composition comprising an antibody that specifically recognizes human Orai1 and has the activity of inhibiting human T cell activation.

8 Claims, 60 Drawing Sheets

Specification includes a Sequence Listing.

(56) References Cited

OTHER PUBLICATIONS

International Preliminary Report on Patentability dated Feb. 7, 2017, issued in corresponding International Application No. PCT/JP2015/072305, filed Aug. 6, 2015, 12 pages.
Derler, I., et al., "CRAC Inhibitors: Identification and Potential," Expert Opinion on Drug Discovery 3(7):787-800, Jul. 2008.
Feske, S., "Calcium Signalling in Lymphocyte Activation and Disease," Nature Reviews: Immunology 7(9):690-702, Sep. 2007.
Feske, S., et al., "A Mutation in Orail Causes Immune Deficiency by Abrogating CRAC Channel Function," Nature 441(7090):179-185, May 2006.
Park, C.Y., et al., "STIM1 Clusters and Activates CRAC Channels via Direct Binding of a Cytosolic Domain to Orai1," Cell 136(5):876-890, Mar. 2009.
Prakriya, M., et al., "Orai1 is an Essential Pore Subunit of the CRAC Channel," Nature 443(7108):230-233, Sep. 2006.

FIG. 13

| | IC$_{50}$ [ng/mL] | IC$_{80}$ [ng/mL] |
|---|---|---|
| 10F8 | >300000 | >300000 |
| 14F74 | >300000 | >300000 |
| 17F6 | >300000 | >300000 |
| 2C1.1 | 279 | >300000 |
| 5H3.1 | 83 | 60621 |
| hR198_HG1/LG1 | 4 | 137 |
| hR198_HG1-LALA/LG1 | 4 | 195 |

FIG. 14

SEQ ID NO: 10: Nucleotide sequence encoding R118 light chain
ATGAAAATGACGACACCTGCTCAGTTCCTTGGGCTTCTGTTGCTCTGGTTTCCAGGTGCCAGGTGTGACATCCA
GTTGACCCAGTCTCCATCCACATTGCCTGCATCCCTGGGAGAGAGAGTCACCATCAGTTGCAGAGCAAGTCAGA
GTATTAGCAATAGTTTAAGCTGGTTTCAACAGAAACCAGATGGAACTGTTAAACGCCTGATCTATTCTACATCC
ACTTTAGAATCTGGTGTCCCATCAAGGTTCAGTGGCAGTGGGTCTGGGACAGATTATTCTCTCTCCATCACCAG
TCTTGAGTCTGAAGATTTTGCAATGTATTACTGTCTACAGTTTGCTACTTTTCCGGACACGTTTGGAACTGGGA
CCAAACTGGAANTGAGACGGGCTGATGCTGCANCA Signal sequence (1-66), Variable region (67-384)

SEQ ID NO: 11: Amino acid sequence of R118 light chain
MKMTTPAQFLGLLLLWFPGARCDIQLTQSPSTLPASLGERVTISCRASQSISNSLSWFQQKPDGTVKRLIYSTS
TLESGVPSRFSGSGSGTDYSLSITSLESEDFAMYYCLQFATFPDTFGTGTKLEXRRADAAX Signal sequence (1-22), Variable region (23-128)

FIG. 15

SEQ ID NO: 12: Nucleotide sequence encoding R118 heavy chain
ATGGAATGGAACTGGGTCTTTCTCCTCCTCCTGTCAGTAACTGCAGAAGTCCAGTCCCAGGTCCAGCTGCAGCA
GTCTGGAGCGGAGCTGGCAAAGCCTGGCTCCTCAGTGAAGATTTCCTGCAAGGCTTCCGGCTACACCGTCACCG
CCTATTATATAAGTTGGATAAGGCAGACGATTGGACAGGGCCTTGAGTATGTTGGATATATTGACATGGGAAAT
GGAAGGACTAACTACAATGCGAGGTTCAAGGGCAAGGCCACATTGACTGTGGACAAATCCTCCAGCACAGCCTT
CATGCAACTCAGCAGCCTGACACCTGACGACTCTGCGGTCTATTACTGTGCAAGGGACTCCAACTGGGGGGTTG
ATTACTGGGGCCAAGGAGTCATGGTCACAGTCTCCTCAGCTGAAACAACAGCCCCATCTGTCTATCCACTGGCT
CCTGGAACTGCTTCTCAAAAGTNA Signal sequence (1-57), Variable region (58-408)

SEQ ID NO: 13: Amino acid sequence of R118 heavy chain
MEWNWVFLLLLSVTAEVQSQVQLQQSGAELAKPGSSVKISCKASGYTVTAYYISWIRQTIGQGLEYVGYIDMGN
GRTNYNARFKGKATLTVDKSSSTAFMQLSSLTPDDSAVYYCARDSNWGVDYWGQGVMVTVSSAETTAPSVYPLA
PGTASQKX Signal sequence (1-19), Variable region (20-136)

FIG. 16

SEQ ID NO: 14: Nucleotide sequence encoding R198 light chain
ATGAAAATGACGACACCTGCTCAGTTCCTTGGGCTTCTGTTGCTCTGGTTTCCAGGTGCCAGGTGTGACATCCA
GTTGACCCAGTCTCCATCCACATTGCCTGCATCTCTGGGAGAGAGAGTCACCATCAGTTGCAGAGCAAGTCAGA
GTATTGGCAATAGTTTAAGCTGGTTTCAGCAGAAACCAGATGGATCTGTTAAACGCCTGATCTACTCTACATCC
ACTTTAGAATCTGGTGTCCCATCAAGGTTCAGTGGCAGTGGGTCTGGGACAGATTATTCTCTCTCCATCACCAG
TCTTGAGTCTGAAGATTTTGCAATGTATTACTGTCTACAGTTTGCTACTTATCCGGACACGTTTGGAACTGGGA
CCAAACTGGAACTGAGACGGGCTGATGCTGCANCAACT Signal sequence (1-66), Variable region (67-384)

SEQ ID NO: 15: Amino acid sequence of R198 light chain
MKMTTPAQFLGLLLLWFPGARCDIQLTQSPSTLPASLGERVTISCRASQSIGNSLSWFQQKPDGSVKRLIYSTS
TLESGVPSRFSGSGSGTDYSLSITSLESEDFAMYYCLQFATYPDTFGTGTKLELRRADAAXT Signal sequence (1-22), Variable region (23-128)

FIG. 17

SEQ ID NO: 16: Nucleotide sequence encoding R198 heavy chain
ATGGAATGGAACTGGGTCTTTCTCTTCCTCCTGTCAGTAACTGCAGAAGTCCAGTCCCAGGTCCAGCTGCAGCA
GTCTGGAGCGGAGCTGGCAAAGCCTGGCTCCTCAATGAAGATTTCCTGCAAGGCTTCCGGCTACCCCGTCACCA
GCTATTATATAAGTTGGATAAAGCAGACGACTGGACAGGGCCTTGAGTATATTGGATATGTTGACATGGGAAAT
GGACGGACTAACTACAATGAGAAGTTCAAGGGCAAGGCCACATTGACTGTAGACAAATCCTCCAGCACAGCCTT
CATGCAACTCAGCAGCCTGACACCTGACGACTCTGCGGTCTATTACTGTGCAAGGGACTCCAACTGGGGGGTTG
ATTACTGGGGCCAAGGAGTCATGGTCACAGTCTCCTCAGCTGAAACAACAGCCCCATCTGTCTATCCACTGGCT
CCTGGAACTGCTCTCAAAAGTAACNCC Signal sequence (1-57), Variable region (58-408)

SEQ ID NO: 17: Amino acid sequence of R198 heavy chain
MEWNWVFLFLLSVTAEVQSQVQLQQSGAELAKPGSSMKISCKASGYPVTSYYISWIKQTTGQGLEYIGYVDMGN
GRTNYNEKFKGKATLTVDKSSSTAFMQLSSLTPDDSAVYYCARDSNWGVDYWGQGVMVTVSSAETTAPSVYPLA
PGTALKSNX Signal sequence (1-19), Variable region (20-136)

FIG. 18

SEQ ID NO: 22: Nucleotide sequence encoding human chimerized cR118 light chain
ATGGTGCTGCAGACCCAGGTGTTCATCTCCCTGCTGCTGTGGATCTCCGGCGCGTACGGCGACATCCAGTTGAC
CCAGTCTCCATCCACATTGCCTGCATCCCTGGGAGAGAGAGTCACCATCAGTTGCAGAGCAAGTCAGAGTATTA
GCAATAGTTTAAGCTGGTTTCAACAGAAACCAGATGGAACTGTTAAACGCCTGATCTATTCTACATCCACTTTA
GAATCTGGTGTCCCATCAAGGTTCAGTGGCAGTGGGTCTGGGACAGATTATTCTCTCTCCATCACCAGTCTTGA
GTCTGAAGATTTTGCAATGTATTACTGTCTACAGTTTGCTACTTTTCCGGACACGTTTGGAACTGGGACCAAAC
TGGAACTGAGACGGGCTGTGGCCGCCCCCTCCGTGTTCATCTTCCCCCCCTCCGACGAGCAGCTGAAGTCCGGC
ACCGCCTCCGTGGTGTGCCTGCTGAATAACTTCTACCCCAGAGAGGCCAAGGTGCAGTGGAAGGTGGACAACGC
CCTGCAGTCCGGGAACTCCCAGGAGAGCGTGACCGAGCAGGACAGCAAGGACAGCACCTACAGCCTGAGCAGCA
CCCTGACCCTGAGCAAAGCCGACTACGAGAAGCACAAGGTGTACGCCTGCGAGGTGACCCACCAGGGCCTGAGC
TCCCCCGTCACCAAGAGCTTCAACAGGGGGGAGTGTTAG Signal sequence (1-60), Variable region (61-378), Constant region (379-702)

SEQ ID NO: 23: Amino acid sequence of human chimerized cR118 light chain
MVLQTQVFISLLLWISGAYGDIQLTQSPSTLPASLGERVTISCRASQSISNSLSWFQQKPDGTVKRLIYSTSTL
ESGVPSRFSGSGSGTDYSLSITSLESEDFAMYYCLQFATFPDTFGTGTKLELRRAVAAPSVFIFPPSDEQLKSG
TASVVCLLNNFYPREAKVQWKVDNALQSGNSQESVTEQDSKDSTYSLSSTLTLSKADYEKHKVYACEVTHQGLS
SPVTKSFNRGEC Signal sequence (1-20), Variable region (21-126), Constant region (127-234)

FIG. 19

SEQ ID NO: 24: Nucleotide sequence encoding human chimerized cR198 light chain
ATGGTGCTGCAGACCCAGGTGTTCATCTCCCTGCTGCTGTGGATCTCCGGCGCGTACGGCGACATCCAGTTGAC
CCAGTCTCCATCCACATTGCCTGCATCTCTGGGAGAGAGAGTCACCATCAGTTGCAGAGCAAGTCAGAGTATTG
GCAATAGTTTAAGCTGGTTTCAGCAGAAACCAGATGGATCTGTTAAACGCCTGATCTACTCTACATCCACTTTA
GAATCTGGTGTCCCATCAAGGTTCAGTGGCAGTGGGTCTGGGACAGATTATTCTCTCTCCATCACCAGTCTTGA
GTCTGAAGATTTTGCAATGTATTACTGTCTACAGTTTGCTACTTATCCGGACACGTTTGGAACTGGGACCAAAC
TGGAACTGAGACGGGCTGTGGCCGCCCCCTCCGTGTTCATCTTCCCCCCCTCCGACGAGCAGCTGAAGTCCGGC
ACCGCCTCCGTGGTGTGCCTGCTGAATAACTTCTACCCCAGAGAGGCCAAGGTGCAGTGGAAGGTGGACAACGC
CCTGCAGTCCGGGAACTCCCAGGAGAGCGTGACCGAGCAGGACAGCAAGGACAGCACCTACAGCCTGAGCAGCA
CCCTGACCCTGAGCAAAGCCGACTACGAGAAGCACAAGGTGTACGCCTGCGAGGTGACCCACCAGGGCCTGAGC
TCCCCCGTCACCAAGAGCTTCAACAGGGGGGAGTGTTAG Signal sequence (1-60), Variable region (61-378), Constant region (379-702)

SEQ ID NO: 25: Amino acid sequence of human chimerized cR198 light chain
MVLQTQVFISLLLWISGAYGDIQLTQSPSTLPASLGERVTISCRASQSIGNSLSWFQQKPDGSVKRLIYSTSTL
ESGVPSRFSGSGSGTDYSLSITSLESEDFAMYYCLQFATYPDTFGTGTKLELRRAVAAPSVFIFPPSDEQLKSG
TASVVCLLNNFYPREAKVQWKVDNALQSGNSQESVTEQDSKDSTYSLSSTLTLSKADYEKHKVYACEVTHQGLS
SPVTKSFNRGEC Signal sequence (1-20), Variable region (21-126), Constant region (127-234)

FIG. 20

SEQ ID NO: 26: Nucleotide sequence encoding human chimerized cR118 heavy chain
ATGAAACACCTGTGGTTCTTCCTCCTGCTGGTGGCAGCTCCCAGATGGGTGCTGAGCCAGGTCCAGCTGCAGCA
GTCTGGAGCGGAGCTGGCAAAGCCTGGCTCCTCAGTGAAGATTTCCTGCAAGGCTTCCGGCTACACCGTCACCG
CCTATTATATAAGTTGGATAAGGCAGACGATTGGACAGGGCCTTGAGTATGTTGGATATATTGACATGGGAAAT
GGAAGGACTAACTACAATGCGAGGTTCAAGGGCAAGGCCACATTGACTGTGGACAAATCCTCCAGCACAGCCTT
CATGCAACTCAGCAGCCTGACACCTGACGACTCTGCGGTCTATTACTGTGCAAGGGACTCCAACTGGGGGGTTG
ATTACTGGGGCCAAGGAGTCATGGTCACAGTCAGCTCAGCCTCCACCAAGGGCCCAAGCGTCTTCCCCCTGGCA
CCCTCCTCCAAGAGCACCTCTGGCGGCACAGCCGCCCTGGGCTGCCTGGTCAAGGACTACTTCCCCGAACCCGT
GACCGTGAGCTGGAACTCAGGCGCCCTGACCAGCGGCGTGCACACCTTCCCCGCTGTCCTGCAGTCCTCAGGAC
TCTACTCCCTCAGCAGCGTGGTGACCGTGCCCTCCAGCAGCTTGGGCACCCAGACCTACATCTGCAACGTGAAT
CACAAGCCCAGCAACACCAAGGTGGACAAGAGAGTTGAGCCCAAATCTTGTGACAAAACTCACACATGCCCACC
CTGCCCAGCACCTGAACTCCTGGGGGGACCCTCAGTCTTCCTCTTCCCCCCAAAACCCAAGGACACCCTCATGA
TCTCCCGGACCCCTGAGGTCACATGCGTGGTGGTGGACGTGAGCCACGAAGACCCTGAGGTCAAGTTCAACTGG
TACGTGGACGGCGTGGAGGTGCATAATGCCAAGACAAAGCCCCGGGAGGAGCAGTACAACAGCACGTACCGGGT
GGTCAGCGTCCTCACCGTCCTGCACCAGGACTGGCTGAATGGCAAGGAGTACAAGTGCAAGGTCTCCAACAAAG
CCCTCCCAGCCCCCATCGAGAAAACCATCTCCAAAGCCAAAGGCCAGCCCCGGGAACCACAGGTGTACACCCTG
CCCCCATCCCGGGAGGAGATGACCAAGAACCAGGTCAGCCTGACCTGCCTGGTCAAAGGCTTCTATCCCAGCGA
CATCGCCGTGGAGTGGGAGAGCAATGGCCAGCCGGAGAACAACTACAAGACCACCCCTCCCGTGCTGGACTCCG
ACGGCTCCTTCTTCCTCTACAGCAAGCTCACCGTGGACAAGAGCAGGTGGCAGCAGGGCAACGTCTTCTCATGC
TCCGTGATGCATGAGGCTCTGCACAACCACTACACCCAGAAGAGCCTCTCCCTGTCTCCGGGCAAATGA Signal sequence (1-57), Variable region (58-408), Constant region (409-1398)

SEQ ID NO: 27: Amino acid sequence of human chimerized cR118 heavy chain
MKHLWFFLLLVAAPRWVLSQVQLQQSGAELAKPGSSVKISCKASGYTVTAYYISWIRQTIGQGLEYVGYIDMGN
GRTNYNARFKGKATLTVDKSSSTAFMQLSSLTPDDSAVYYCARDSNWGVDYWGQGVMVTVSSASTKGPSVFPLA
PSSKSTSGGTAALGCLVKDYFPEPVTVSWNSGALTSGVHTFPAVLQSSGLYSLSSVVTVPSSSLGTQTYICNVN
HKPSNTKVDKRVEPKSCDKTHTCPPCPAPELLGGPSVFLFPPKPKDTLMISRTPEVTCVVVDVSHEDPEVKFNW
YVDGVEVHNAKTKPREEQYNSTYRVVSVLTVLHQDWLNGKEYKCKVSNKALPAPIEKTISKAKGQPREPQVYTL
PPSREEMTKNQVSLTCLVKGFYPSDIAVEWESNGQPENNYKTTPPVLDSDGSFFLYSKLTVDKSRWQQGNVFSC
SVMHEALHNHYTQKSLSLSPGK Signal sequence (1-19), Variable region (20-136), Constant region (137-466)

FIG. 21

SEQ ID NO: 28: Nucleotide sequence encoding human chimerized cR198 heavy chain
ATGAAACACCTGTGGTTCTTCCTCCTGCTGGTGGCAGCTCCCAGATGGGTGCTGAGCCAGGTCCAGCTGCAGCA
GTCTGGAGCGGAGCTGGCAAAGCCTGGCTCCTCAATGAAGATTTCCTGCAAGGCTTCCGGCTACCCCGTCACCA
GCTATTATATAAGTTGGATAAAGCAGACGACTGGACAGGGCCTTGAGTATATTGGATATGTTGACATGGGAAAT
GGACGGACTAACTACAATGAGAAGTTCAAGGGCAAGGCCACATTGACTGTAGACAAATCCTCCAGCACAGCCTT
CATGCAACTCAGCAGCCTGACACCTGACGACTCTGCGGTCTATTACTGTGCAAGGGACTCCAACTGGGGGGTTG
ATTACTGGGGCCAAGGAGTCATGGTCACAGTCAGCTCAGCCTCCACCAAGGGCCCAAGCGTCTTCCCCCTGGCA
CCCTCCTCCAAGAGCACCTCTGGCGGCACAGCCGCCCTGGGCTGCCTGGTCAAGGACTACTTCCCCGAACCCGT
GACCGTGAGCTGGAACTCAGGCGCCCTGACCAGCGGCGTGCACACCTTCCCCGCTGTCCTGCAGTCCTCAGGAC
TCTACTCCCTCAGCAGCGTGGTGACCGTGCCCTCCAGCAGCTTGGGCACCCAGACCTACATCTGCAACGTGAAT
CACAAGCCCAGCAACACCAAGGTGGACAAGAGAGTTGAGCCCAAATCTTGTGACAAAACTCACACATGCCCACC
CTGCCCAGCACCTGAACTCCTGGGGGGACCCTCAGTCTTCCTCTTCCCCCCAAAACCCAAGGACACCCTCATGA
TCTCCCGGACCCCTGAGGTCACATGCGTGGTGGTGGACGTGAGCCACGAAGACCCTGAGGTCAAGTTCAACTGG
TACGTGGACGGCGTGGAGGTGCATAATGCCAAGACAAAGCCCCGGGAGGAGCAGTACAACAGCACGTACCGGGT
GGTCAGCGTCCTCACCGTCCTGCACCAGGACTGGCTGAATGGCAAGGAGTACAAGTGCAAGGTCTCCAACAAAG
CCCTCCCAGCCCCCATCGAGAAAACCATCTCCAAAGCCAAAGGCCAGCCCCGGGAACCACAGGTGTACACCCTG
CCCCCATCCCGGGAGGAGATGACCAAGAACCAGGTCAGCCTGACCTGCCTGGTCAAAGGCTTCTATCCCAGCGA
CATCGCCGTGGAGTGGGAGAGCAATGGCCAGCCCGAGAACAACTACAAGACCACCCCTCCCGTGCTGGACTCCG
ACGGCTCCTTCTTCCTCTACAGCAAGCTCACCGTGGACAAGAGCAGGTGGCAGCAGGGCAACGTCTTCTCATGC
TCCGTGATGCATGAGGCTCTGCACAACCACTACACCCAGAAGAGCCTCTCCCTGTCTCCGGCAAATGA Signal sequence (1-57), Variable region (58-408), Constant region (409-1398)

SEQ ID NO: 29: Amino acid sequence of human chimerized cR198 heavy chain
MKHLWFFLLLVAAPRWVLSQVQLQQSGAELAKPGSSMKISCKASGYPVTSYYISWIKQTTGQGLEYIGYVDMGN
GRTNYNEKFKGKATLTVDKSSSTAFMQLSSLTPDDSAVYYCARDSNWGVDYWGQGVMVTVSSASTKGPSVFPLA
PSSKSTSGGTAALGCLVKDYFPEPVTVSWNSGALTSGVHTFPAVLQSSGLYSLSSVVTVPSSSLGTQTYICNVN
HKPSNTKVDKRVEPKSCDKTHTCPPCPAPELLGGPSVFLFPPKPKDTLMISRTPEVTCVVVDVSHEDPEVKFNW
YVDGVEVHNAKTKPREEQYNSTYRVVSVLTVLHQDWLNGKEYKCKVSNKALPAPIEKTISKAKGQPREPQVYTL
PPSREEMTKNQVSLTCLVKGFYPSDIAVEWESNGQPENNYKTTPPVLDSDGSFFLYSKLTVDKSRWQQGNVFSC
SVMHEALHNHYTQKSLSLSPGK Signal sequence (1-19), Variable region (20-136), Constant region (137-466)

FIG. 22

SEQ ID NO: 30: Nucleotide sequence encoding hR198_L1 type light chain

ATGGTGCTGCAGACCCAGGTGTTCATCTCCCTGCTGCTGTGGATCTCCGGCGCGTACGGCGATATCCAGCTGAC
CCAGAGCCCTAGCAGCCTGTCTGCCAGCGTGGGCGACAGAGTGACCATCACCTGTAGAGCCAGCCAGAGCATCG
GCAACAGCCTGAGCTGGTTCCAGCAGAAACCCGGCAAGGCCCCCAAGCGGCTGATCTACAGCACCAGCACCCTG
GAAAGCGGCGTGCCCAGCAGATTTTCTGGCAGCGGCTCCGGCACCGACTACACCCTGACAATCAGCAGCCTGCA
GCCCGAGGACTTCGCCATGTACTACTGCCTGCAGTTCGCCACCTACCCCGACACCTTTGGCCAGGGCACCAAGG
TGGAAATCAAGCGTACGGTGGCCGCCCCCTCCGTGTTCATCTTCCCCCCCTCCGACGAGCAGCTGAAGTCCGGC
ACCGCCTCCGTGGTGTGCCTGCTGAATAACTTCTACCCCAGAGAGGCCAAGGTGCAGTGGAAGGTGGACAACGC
CCTGCAGTCCGGGAACTCCCAGGAGAGCGTGACCGAGCAGGACAGCAAGGACAGCACCTACAGCCTGAGCAGCA
CCCTGACCCTGAGCAAAGCCGACTACGAGAAGCACAAGGTGTACGCCTGCGAGGTGACCCACCAGGGCCTGAGC
TCCCCCGTCACCAAGAGCTTCAACAGGGGGGAGTGTTAG

Signal sequence (1-60), Variable region (61-378), Constant region (379-702)

SEQ ID NO: 31: Amino acid sequence of hR198_L1 type light chain

MVLQTQVFISLLLWISGAYGDIQLTQSPSSLSASVGDRVTITCRASQSIGNSLSWFQQKPGKAPKRLIYSTSTL
ESGVPSRFSGSGSGTDYTLTISSLQPEDFAMYYCLQFATYPDTFGQGTKVEIKRTVAAPSVFIFPPSDEQLKSG
TASVVCLLNNFYPREAKVQWKVDNALQSGNSQESVTEQDSKDSTYSLSSTLTLSKADYEKHKVYACEVTHQGLS
SPVTKSFNRGEC

Signal sequence (1-20), Variable region (21-126), Constant region (127-234)

FIG. 23

SEQ ID NO: 32: Nucleotide sequence encoding hR198_L2 type light chain
ATGGTGCTGCAGACCCAGGTGTTCATCTCCCTGCTGCTGTGGATCTCCGGCGCGTACGGCGATATCCAGCTGAC
CCAGAGCCCTAGCAGCCTGTCTGCCAGCGTGGGCGACAGAGTGACCATCACCTGTAGAGCCAGCCAGAGCATCG
GCAACAGCCTGAGCTGGTTCCAGCAGAAACCCGGCAAGGCCGTGAAGCGGCTGATCTACAGCACCAGCACCCTG
GAAAGCGGCGTGCCCAGCAGATTTTCTGGCAGCGGCTCCGGCACCGACTACACCCTGACAATCAGCAGCCTGCA
GCCCGAGGACTTCGCCATGTACTACTGCCTGCAGTTCGCCACCTACCCCGACACCTTTGGCCAGGGCACCAAGG
TGGAAATCAAGCGTACGGTGGCCGCCCCCTCCGTGTTCATCTTCCCCCCCTCCGACGAGCAGCTGAAGTCCGGC
ACCGCCTCCGTGGTGTGCCTGCTGAATAACTTCTACCCCAGAGAGGCCAAGGTGCAGTGGAAGGTGGACAACGC
CCTGCAGTCCGGGAACTCCCAGGAGAGCGTGACCGAGCAGGACAGCAAGGACAGCACCTACAGCCTGAGCAGCA
CCCTGACCCTGAGCAAAGCCGACTACGAGAAGCACAAGGTGTACGCCTGCGAGGTGACCCACCAGGGCCTGAGC
TCCCCCGTCACCAAGAGCTTCAACAGGGGGGAGTGTTAG Signal sequence (1-60), Variable region (61-378), Constant region (379-702)

SEQ ID NO: 33: Amino acid sequence of hR198_L2 type light chain
MVLQTQVFISLLLWISGAYGDIQLTQSPSSLSASVGDRVTITCRASQSIGNSLSWFQQKPGKAVKRLIYSTSTL
ESGVPSRFSGSGSGTDYTLTISSLQPEDFAMYYCLQFATYPDTFGQGTKVEIKRTVAAPSVFIFPPSDEQLKSG
TASVVCLLNNFYPREAKVQWKVDNALQSGNSQESVTEQDSKDSTYSLSSTLTLSKADYEKHKVYACEVTHQGLS
SPVTKSFNRGEC Signal sequence (1-20), Variable region (21-126), Constant region (127-234)

FIG. 24

SEQ ID NO: 34: Nucleotide sequence encoding hR198_L3 type light chain
ATGGTGCTGCAGACCCAGGTGTTCATCTCCCTGCTGCTGTGGATCTCCGGCGCGTACGGCGATATCCAGCTGAC
CCAGAGCCCTAGCAGCCTGTCTGCCAGCGTGGGCGACAGAGTGACCATCACCTGTAGAGCCAGCCAGAGCATCG
GCAACAGCCTGAGCTGGTTCCAGCAGAAACCCGGCAAGGCCCCCAAGCGGCTGATCTACAGCACCAGCACCCTG
GAAAGCGGCGTGCCCAGCAGATTTTCTGGCAGCGGCTCCGGCACCGACTACACCCTGACAATCAGCAGCCTGCA
GCCCGAGGACTTCGCCATGTACTACTGCCTGCAGTTCGCCACCTTCCCCGACACCTTTGGCCAGGGCACCAAGG
TGGAAATCAAGCGTACGGTGGCCGCCCCCTCCGTGTTCATCTTCCCCCCCTCCGACGAGCAGCTGAAGTCCGGC
ACCGCCTCCGTGGTGTGCCTGCTGAATAACTTCTACCCCAGAGAGGCCAAGGTGCAGTGGAAGGTGGACAACGC
CCTGCAGTCCGGGAACTCCCAGGAGAGCGTGACCGAGCAGGACAGCAAGGACAGCACCTACAGCCTGAGCAGCA
CCCTGACCCTGAGCAAAGCCGACTACGAGAAGCACAAGGTGTACGCCTGCGAGGTGACCCACCAGGGCCTGAGC
TCCCCCGTCACCAAGAGCTTCAACAGGGGGGAGTGTTAG Signal sequence (1-60), Variable region (61-378), Constant region (379-702)

SEQ ID NO: 35: Amino acid sequence of hR198_L3 type light chain
MVLQTQVFISLLLWISGAYGDIQLTQSPSSLSASVGDRVTITCRASQSIGNSLSWFQQKPGKAPKRLIYSTSTL
ESGVPSRFSGSGSGTDYTLTISSLQPEDFAMYYCLQFATFPDTFGQGTKVEIKRTVAAPSVFIFPPSDEQLKSG
TASVVCLLNNFYPREAKVQWKVDNALQSGNSQESVTEQDSKDSTYSLSSTLTLSKADYEKHKVYACEVTHQGLS
SPVTKSFNRGEC Signal sequence (1-20), Variable region (21-126), Constant region (127-234)

FIG. 25

SEQ ID NO: 36: Nucleotide sequence encoding hR198_L4 type light chain
ATGGTGCTGCAGACCCAGGTGTTCATCTCCCTGCTGCTGTGGATCTCCGGCGCGTACGGCGATATCCAGCTGAC
CCAGAGCCCTAGCAGCCTGTCTGCCAGCGTGGGCGACAGAGTGACCATCACCTGTAGAGCCAGCCAGAGCATCG
GCAACAGCCTGAGCTGGTTCCAGCAGAAACCCGGCAAGGCCGTGAAGCGGCTGATCTACAGCACCAGCACCCTG
GAAAGCGGCGTGCCCAGCAGATTTTCTGGCAGCGGCTCCGGCACCGACTACACCCTGACAATCAGCAGCCTGCA
GCCCGAGGACTTCGCCATGTACTACTGCCTGCAGTTCGCCACCTTCCCCGACACCTTTGGCCAGGGCACCAAGG
TGGAAATCAAGCGTACGGTGGCCGCCCCCTCCGTGTTCATCTTCCCCCCCTCCGACGAGCAGCTGAAGTCCGGC
ACCGCCTCCGTGGTGTGCCTGCTGAATAACTTCTACCCCAGAGAGGCCAAGGTGCAGTGGAAGGTGGACAACGC
CCTGCAGTCCGGGAACTCCCAGGAGAGCGTGACCGAGCAGGACAGCAAGGACAGCACCTACAGCCTGAGCAGCA
CCCTGACCCTGAGCAAAGCCGACTACGAGAAGCACAAGGTGTACGCCTGCGAGGTGACCCACCAGGGCCTGAGC
TCCCCCGTCACCAAGAGCTTCAACAGGGGGGAGTGTTAG Signal sequence (1-60), Variable region (61-378), Constant region (379-702)

SEQ ID NO: 37: Amino acid sequence of hR198_L4 type light chain
MVLQTQVFISLLLWISGAYGDIQLTQSPSSLSASVGDRVTITCRASQSIGNSLSWFQQKPGKAVKRLIYSTSTL
ESGVPSRFSGSGSGTDYTLTISSLQPEDFAMYYCLQFATFPDTFGQGTKVEIKRTVAAPSVFIFPPSDEQLKSG
TASVVCLLNNFYPREAKVQWKVDNALQSGNSQESVTEQDSKDSTYSLSSTLTLSKADYEKHKVYACEVTHQGLS
SPVTKSFNRGEC Signal sequence (1-20), Variable region (21-126), Constant region (127-234)

FIG. 26

SEQ ID NO: 38: Nucleotide sequence encoding hR198_H1 type heavy chain
ATGAAACACCTGTGGTTCTTCCTCCTGCTGGTGGCAGCTCCCAGATGGGTGCTGAGCCAGGTGCAGCTGGTGCA
GTCTGGCGCCGAAGTGAAGAAACCAGGCGCCAGCGTGAAGGTGTCCTGCAAGGCCTCTGGCTACCCCGTGACCA
GCTACTACATCAGCTGGGTCAGACAGGCCCCAGGCCAGGGCCTGGAATACATCGGCTATGTGGACATGGGCAAC
GGCCGGACCAACTACAACGAGAAGTTCAAGGGCAGAGCCACCCTGACCGTGGACAAGAGCACCAGCACCGCCTA
CATGGAACTGAGCAGCCTGCGGAGCGAGGACACCGCCGTGTACTACTGCGCCAGAGACAGCAACTGGGGCGTGG
ACTATTGGGGCCAGGGCACACTCGTGACCGTCAGCTCAGCCTCCACCAAGGGCCCAAGCGTCTTCCCCCTGGCA
CCCTCCTCCAAGAGCACCTCTGGCGGCACAGCCGCCCTGGGCTGCCTGGTCAAGGACTACTTCCCCGAACCCGT
GACCGTGAGCTGGAACTCAGGCGCCCTGACCAGCGGCGTGCACACCTTCCCCGCTGTCCTGCAGTCCTCAGGAC
TCTACTCCCTCAGCAGCGTGGTGACCGTGCCCTCCAGCAGCTTGGGCACCCAGACCTACATCTGCAACGTGAAT
CACAAGCCCAGCAACACCAAGGTGGACAAGAGAGTTGAGCCCAAATCTTGTGACAAAACTCACACATGCCCACC
CTGCCCAGCACCTGAACTCCTGGGGGGACCCTCAGTCTTCCTCTTCCCCCCAAAACCCAAGGACACCCTCATGA
TCTCCCGGACCCCTGAGGTCACATGCGTGGTGGTGGACGTGAGCCACGAAGACCCTGAGGTCAAGTTCAACTGG
TACGTGGACGGCGTGGAGGTGCATAATGCCAAGACAAAGCCCCGGGAGGAGCAGTACAACAGCACGTACCGGGT
GGTCAGCGTCCTCACCGTCCTGCACCAGGACTGGCTGAATGGCAAGGAGTACAAGTGCAAGGTCTCCAACAAAG
CCCTCCCAGCCCCCATCGAGAAAACCATCTCCAAAGCCAAAGGCCAGCCCCGGGAACCACAGGTGTACACCCTG
CCCCCATCCCGGGAGGAGATGACCAAGAACCAGGTCAGCCTGACCTGCCTGGTCAAAGGCTTCTATCCCAGCGA
CATCGCCGTGGAGTGGGAGAGCAATGGCCAGCCCGAGAACAACTACAAGACCACCCCTCCCGTGCTGGACTCCG
ACGGCTCCTTCTTCCTCTACAGCAAGCTCACCGTGGACAAGAGCAGGTGGCAGCAGGGCAACGTCTTCTCATGC
TCCGTGATGCATGAGGCTCTGCACAACCACTACACCCAGAAGAGCCTCTCCCTGTCTCCGGCAAATGA Signal sequence (1-57), Variable region (58-408), Constant region (409-1398)

SEQ ID NO: 39: Amino acid sequence of hR198_H1 type heavy chain
MKHLWFFLLLVAAPRWVLSQVQLVQSGAEVKKPGASVKVSCKASGYPVTSYYISWVRQAPGQGLEYIGYVDMGN
GRTNYNEKFKGRATLTVDKSTSTAYMELSSLRSEDTAVYYCARDSNWGVDYWGQGTLVTVSSASTKGPSVFPLA
PSSKSTSGGTAALGCLVKDYFPEPVTVSWNSGALTSGVHTFPAVLQSSGLYSLSSVVTVPSSSLGTQTYICNVN
HKPSNTKVDKRVEPKSCDKTHTCPPCPAPELLGGPSVFLFPPKPKDTLMISRTPEVTCVVVDVSHEDPEVKFNW
YVDGVEVHNAKTKPREEQYNSTYRVVSVLTVLHQDWLNGKEYKCKVSNKALPAPIEKTISKAKGQPREPQVYTL
PPSREEMTKNQVSLTCLVKGFYPSDIAVEWESNGQPENNYKTTPPVLDSDGSFFLYSKLTVDKSRWQQGNVFSC
SVMHEALHNHYTQKSLSLSPGK Signal sequence (1-19), Variable region (20-136), Constant region (137-466)

FIG. 27

SEQ ID NO: 40: Nucleotide sequence encoding hR198_H2 type heavy chain
ATGAAACACCTGTGGTTCTTCCTCCTGCTGGTGGCAGCTCCCAGATGGGTGCTGAGCCAGGTGCAGCTGGTGCA
GTCTGGCGCCGAAGTGAAGAAACCAGGCGCCAGCGTGAAGGTGTCCTGCAAGGCCTCTGGCTACCCCGTGACCA
GCTACTACATCAGCTGGATCAGACAGGCCCCAGGCCAGGGCCTGGAATACATCGGCTATGTGGACATGGGCAAC
GGCCGGACCAACTACAACGAGAAGTTCAAGGGCAGAGCCACCCTGACCGTGGACAAGAGCACCAGCACCGCCTA
CATGGAACTGAGCAGCCTGCGGAGCGAGGACACCGCCGTGTACTACTGCGCCAGAGACAGCAACTGGGGCGTGG
ACTATTGGGGCCAGGGCACACTCGTGACCGTCAGCTCAGCCTCCACCAAGGGCCCAAGCGTCTTCCCCCTGGCA
CCCTCCTCCAAGAGCACCTCTGGCGGCACAGCCGCCCTGGGCTGCCTGGTCAAGGACTACTTCCCCGAACCCGT
GACCGTGAGCTGGAACTCAGGCGCCCTGACCAGCGGCGTGCACACCTTCCCCGCTGTCCTGCAGTCCTCAGGAC
TCTACTCCCTCAGCAGCGTGGTGACCGTGCCCTCCAGCAGCTTGGGCACCCAGACCTACATCTGCAACGTGAAT
CACAAGCCCAGCAACACCAAGGTGGACAAGAGAGTTGAGCCCAAATCTTGTGACAAAACTCACACATGCCCACC
CTGCCCAGCACCTGAACTCCTGGGGGGACCCTCAGTCTTCCTCTTCCCCCCAAAACCCAAGGACACCCTCATGA
TCTCCCGGACCCCTGAGGTCACATGCGTGGTGGTGGACGTGAGCCACGAAGACCCTGAGGTCAAGTTCAACTGG
TACGTGGACGGCGTGGAGGTGCATAATGCCAAGACAAAGCCCCGGGAGGAGCAGTACAACAGCACGTACCGGGT
GGTCAGCGTCCTCACCGTCCTGCACCAGGACTGGCTGAATGGCAAGGAGTACAAGTGCAAGGTCTCCAACAAAG
CCCTCCCAGCCCCCATCGAGAAAACCATCTCCAAAGCCAAAGGCCAGCCCCGGGAACCACAGGTGTACACCCTG
CCCCCATCCCGGGAGGAGATGACCAAGAACCAGGTCAGCCTGACCTGCCTGGTCAAAGGCTTCTATCCCAGCGA
CATCGCCGTGGAGTGGGAGAGCAATGGCCAGCCCGAGAACAACTACAAGACCACCCCTCCCGTGCTGGACTCCG
ACGGCTCCTTCTTCCTCTACAGCAAGCTCACCGTGGACAAGAGCAGGTGGCAGCAGGGCAACGTCTTCTCATGC
TCCGTGATGCATGAGGCTCTGCACAACCACTACACCCAGAAGAGCCTCTCCCTGTCTCCGGCAAATGA Signal sequence (1-57), Variable region (58-408), Constant region (409-1398)

SEQ ID NO: 41: Amino acid sequence of hR198_H2 type heavy chain
MKHLWFFLLLVAAPRWVLSQVQLVQSGAEVKKPGASVKVSCKASGYPVTSYYISWIRQAPGQGLEYIGYVDMGN
GRTNYNEKFKGRATLTVDKSTSTAYMELSSLRSEDTAVYYCARDSNWGVDYWGQGTLVTVSSASTKGPSVFPLA
PSSKSTSGGTAALGCLVKDYFPEPVTVSWNSGALTSGVHTFPAVLQSSGLYSLSSVVTVPSSSLGTQTYICNVN
HKPSNTKVDKRVEPKSCDKTHTCPPCPAPELLGGPSVFLFPPKPKDTLMISRTPEVTCVVVDVSHEDPEVKFNW
YVDGVEVHNAKTKPREEQYNSTYRVVSVLTVLHQDWLNGKEYKCKVSNKALPAPIEKTISKAKGQPREPQVYTL
PPSREEMTKNQVSLTCLVKGFYPSDIAVEWESNGQPENNYKTTPPVLDSDGSFFLYSKLTVDKSRWQQGNVFSC
SVMHEALHNHYTQKSLSLSPGK Signal sequence (1-19), Variable region (20-136), Constant region (137-466)

FIG. 28

SEQ ID NO: 42: Nucleotide sequence encoding hR198_H3 type heavy chain

ATGAAACACCTGTGGTTCTTCCTCCTGCTGGTGGCAGCTCCCAGATGGGTGCTGAGCCAGGTGCAGCTGGTGCA
GTCTGGCGCCGAAGTGAAGAAACCAGGCGCCAGCGTGAAGGTGTCCTGCAAGGCCTCTGGCTACCCCGTGACCG
CCTACTACATCAGCTGGGTCAGACAGGCCCCAGGCCAGGGCCTGGAATACGTGGGCTACATCGACATGGGCAAC
GGCCGGACCAACTACAACGCCCGGTTTAAGGGCAGAGCCACCCTGACCGTGGACAAGAGCACCAGCACCGCCTA
CATGGAACTGAGCAGCCTGCGGAGCGAGGACACCGCCGTGTACTACTGCGCCAGAGACAGCAACTGGGGCGTGG
ACTATTGGGGCCAGGGCACACTCGTGACCGTCAGCTCAGCCTCCACCAAGGGCCCAAGCGTCTTCCCCCTGGCA
CCCTCCTCCAAGAGCACCTCTGGCGGCACAGCCGCCCTGGGCTGCCTGGTCAAGGACTACTTCCCCGAACCCGT
GACCGTGAGCTGGAACTCAGGCGCCCTGACCAGCGGCGTGCACACCTTCCCCGCTGTCCTGCAGTCCTCAGGAC
TCTACTCCCTCAGCAGCGTGGTGACCGTGCCCTCCAGCAGCTTGGGCACCCAGACCTACATCTGCAACGTGAAT
CACAAGCCCAGCAACACCAAGGTGGACAAGAGAGTTGAGCCCAAATCTTGTGACAAAACTCACACATGCCCACC
CTGCCCAGCACCTGAACTCCTGGGGGGACCCTCAGTCTTCCTCTTCCCCCCAAAACCCAAGGACACCCTCATGA
TCTCCCGGACCCCTGAGGTCACATGCGTGGTGGTGGACGTGAGCCACGAAGACCCTGAGGTCAAGTTCAACTGG
TACGTGGACGGCGTGGAGGTGCATAATGCCAAGACAAAGCCCCGGGAGGAGCAGTACAACAGCACGTACCGGGT
GGTCAGCGTCCTCACCGTCCTGCACCAGGACTGGCTGAATGGCAAGGAGTACAAGTGCAAGGTCTCCAACAAAG
CCCTCCCAGCCCCCATCGAGAAAACCATCTCCAAAGCCAAAGGCCAGCCCCGGGAACCACAGGTGTACACCCTG
CCCCCATCCCGGGAGGAGATGACCAAGAACCAGGTCAGCCTGACCTGCCTGGTCAAAGGCTTCTATCCCAGCGA
CATCGCCGTGGAGTGGGAGAGCAATGGCCAGCCCGAGAACAACTACAAGACCACCCCTCCCGTGCTGGACTCCG
ACGGCTCCTTCTTCCTCTACAGCAAGCTCACCGTGGACAAGAGCAGGTGGCAGCAGGGCAACGTCTTCTCATGC
TCCGTGATGCATGAGGCTCTGCACAACCACTACACCCAGAAGAGCCTCTCCCTGTCTCCGGCAAATGA

Signal sequence (1-57), Variable region (58-408), Constant region (409-1398)

SEQ ID NO: 43: Amino acid sequence of hR198_H3 type heavy chain

MKHLWFFLLLVAAPRWVLSQVQLVQSGAEVKKPGASVKVSCKASGYPVTAYYISWVRQAPGQGLEYVGYIDMGN
GRTNYNARFKGRATLTVDKSTSTAYMELSSLRSEDTAVYYCARDSNWGVDYWGQGTLVTVSSASTKGPSVFPLA
PSSKSTSGGTAALGCLVKDYFPEPVTVSWNSGALTSGVHTFPAVLQSSGLYSLSSVVTVPSSSLGTQTYICNVN
HKPSNTKVDKRVEPKSCDKTHTCPPCPAPELLGGPSVFLFPPKPKDTLMISRTPEVTCVVVDVSHEDPEVKFNW
YVDGVEVHNAKTKPREEQYNSTYRVVSVLTVLHQDWLNGKEYKCKVSNKALPAPIEKTISKAKGQPREPQVYTL
PPSREEMTKNQVSLTCLVKGFYPSDIAVEWESNGQPENNYKTTPPVLDSDGSFFLYSKLTVDKSRWQQGNVFSC
SVMHEALHNHYTQKSLSLSPGK

Signal sequence (1-19), Variable region (20-136), Constant region (137-466)

FIG. 29

SEQ ID NO: 44: Nucleotide sequence encoding hR198_H4 type heavy chain
ATGAAACACCTGTGGTTCTTCCTCCTGCTGGTGGCAGCTCCCAGATGGGTGCTGAGCCAGGTGCAGCTGGTGCA
GTCTGGCGCCGAAGTGAAGAAACCAGGCGCCAGCGTGAAGGTGTCCTGCAAGGCCTCTGGCTACCCCGTGACCG
CCTACTACATCAGCTGGATCAGACAGGCCCCAGGCCAGGGCCTGGAATACGTGGGCTACATCGACATGGGCAAC
GGCCGGACCAACTACAACGCCCGGTTTAAGGGCAGAGCCACCCTGACCGTGGACAAGAGCACCAGCACCGCCTA
CATGGAACTGAGCAGCCTGCGGAGCGAGGACACCGCCGTGTACTACTGCGCCAGAGACAGCAACTGGGGCGTGG
ACTATTGGGGCCAGGGCACACTCGTGACCGTCAGCTCAGCCTCCACCAAGGGCCCAAGCGTCTTCCCCCTGGCA
CCCTCCTCCAAGAGCACCTCTGGCGGCACAGCCGCCCTGGGCTGCCTGGTCAAGGACTACTTCCCCGAACCCGT
GACCGTGAGCTGGAACTCAGGCGCCCTGACCAGCGGCGTGCACACCTTCCCGCTGTCCTGCAGTCCTCAGGAC
TCTACTCCCTCAGCAGCGTGGTGACCGTGCCCTCCAGCAGCTTGGGCACCCAGACCTACATCTGCAACGTGAAT
CACAAGCCCAGCAACACCAAGGTGGACAAGAGAGTTGAGCCCAAATCTTGTGACAAAACTCACACATGCCCACC
CTGCCCAGCACCTGAACTCCTGGGGGGACCCTCAGTCTTCCTCTTCCCCCCAAAACCCAAGGACACCCTCATGA
TCTCCCGGACCCCTGAGGTCACATGCGTGGTGGTGGACGTGAGCCACGAAGACCCTGAGGTCAAGTTCAACTGG
TACGTGGACGGCGTGGAGGTGCATAATGCCAAGACAAAGCCCCGGGAGGAGCAGTACAACAGCACGTACCGGGT
GGTCAGCGTCCTCACCGTCCTGCACCAGGACTGGCTGAATGGCAAGGAGTACAAGTGCAAGGTCTCCAACAAAG
CCCTCCCAGCCCCCATCGAGAAAACCATCTCCAAAGCCAAAGGCCAGCCCCGGGAACCACAGGTGTACACCCTG
CCCCCATCCCGGGAGGAGATGACCAAGAACCAGGTCAGCCTGACCTGCCTGGTCAAAGGCTTCTATCCCAGCGA
CATCGCCGTGGAGTGGGAGAGCAATGGCCAGCCCGAGAACAACTACAAGACCACCCCTCCCGTGCTGGACTCCG
ACGGCTCCTTCTTCCTCTACAGCAAGCTCACCGTGGACAAGAGCAGGTGGCAGCAGGGCAACGTCTTCTCATGC
TCCGTGATGCATGAGGCTCTGCACAACCACTACACCCAGAAGAGCCTCTCCCTGTCTCCCGGCAAATGA Signal sequence (1-57), Variable region (58-408), Constant region (409-1398)

SEQ ID NO: 45: Amino acid sequence of hR198_H4 type heavy chain
MKHLWFFLLLVAAPRWVLSQVQLVQSGAEVKKPGASVKVSCKASGYPVTAYYISWIRQAPGQGLEYVGYIDMGN
GRTNYNARFKGRATLTVDKSTSTAYMELSSLRSEDTAVYYCARDSNWGVDYWGQGTLVTVSSASTKGPSVFPLA
PSSKSTSGGTAALGCLVKDYFPEPVTVSWNSGALTSGVHTFPAVLQSSGLYSLSSVVTVPSSSLGTQTYICNVN
HKPSNTKVDKRVEPKSCDKTHTCPPCPAPELLGGPSVFLFPPKPKDTLMISRTPEVTCVVVDVSHEDPEVKFNW
YVDGVEVHNAKTKPREEQYNSTYRVVSVLTVLHQDWLNGKEYKCKVSNKALPAPIEKTISKAKGQPREPQVYTL
PPSREEMTKNQVSLTCLVKGFYPSDIAVEWESNGQPENNYKTTPPVLDSDGSFFLYSKLTVDKSRWQQGNVFSC
SVMHEALHNHYTQKSLSLSPGK Signal sequence (1-19), Variable region (20-136), Constant region (137-466)

FIG. 30

SEQ ID NO: 55: Nucleotide sequence encoding hR198_LG1 type light chain
ATGGTGCTGCAGACCCAGGTGTTCATCTCCCTGCTGCTGTGGATCTCCGGCGCGTACGGCGATATCCAGCTGAC
CCAGAGCCCTAGCAGCCTGTCTGCCAGCGTGGGCGACAGAGTGACCATCACCTGTAGAGCCAGCCAGAGCATCG
GCGGCAGCCTGAGCTGGTTCCAGCAGAAACCCGGCAAGGCCCCCAAGCGGCTGATCTACAGCACCAGCACCCTG
GAAAGCGGCGTGCCCAGCAGATTTTCTGGCAGCGGCTCCGGCACCGACTACACCCTGACAATCAGCAGCCTGCA
GCCCGAGGACTTCGCCATGTACTACTGCCTGCAGTTCGCCATCTTCCCCGACAGCTTTGGCCAGGGCACCAAGG
TGGAAATCAAGCGTACGGTGGCCGCCCCCTCCGTGTTCATCTTCCCCCCCTCCGACGAGCAGCTGAAGTCCGGC
ACCGCCTCCGTGGTGTGCCTGCTGAATAACTTCTACCCCAGAGAGGCCAAGGTGCAGTGGAAGGTGGACAACGC
CCTGCAGTCCGGGAACTCCCAGGAGAGCGTGACCGAGCAGGACAGCAAGGACAGCACCTACAGCCTGAGCAGCA
CCCTGACCCTGAGCAAAGCCGACTACGAGAAGCACAAGGTGTACGCCTGCGAGGTGACCCACCAGGGCCTGAGC
TCCCCCGTCACCAAGAGCTTCAACAGGGGGGAGTGTTAG Signal sequence (1-60), Variable region (61-378), Constant region (379-702)

SEQ ID NO: 56: Amino acid sequence of hR198_LG1 type light chain
MVLQTQVFISLLLWISGAYGDIQLTQSPSSLSASVGDRVTITCRASQSIGGSLSWFQQKPGKAPKRLIYSTSTL
ESGVPSRFSGSGSGTDYTLTISSLQPEDFAMYYCLQFAIFPDSFGQGTKVEIKRTVAAPSVFIFPPSDEQLKSG
TASVVCLLNNFYPREAKVQWKVDNALQSGNSQESVTEQDSKDSTYSLSSTLTLSKADYEKHKVYACEVTHQGLS
SPVTKSFNRGEC Signal sequence (1-20), Variable region (21-126), Constant region (127-234)

FIG. 31

SEQ ID NO: 57: Nucleotide sequence encoding hR198_LG2 type light chain
ATGGTGCTGCAGACCCAGGTGTTCATCTCCCTGCTGCTGTGGATCTCCGGCGCGTACGGCGATATCCAGCTGAC
CCAGAGCCCTAGCAGCCTGTCTGCCAGCGTGGGCGACAGAGTGACCATCACCTGTCACGCCAGCCAGAACATCG
GCGGCAGCCTGAGCTGGTTCCAGCAGAAACCCGGCAAGGCCCCCAAGCGGCTGATCTACCTGACCAGCACCCTG
GACTGGGGCGTGCCCAGCAGATTTTCTGGCAGCGGCTCCGGCACCGACTACACCCTGACAATCAGCAGCCTGCA
GCCCGAGGACTTCGCCATGTACTACTGCCTGCAGTTCGCCATCTTCCCCGACAGCTTTGGCCAGGGCACCAAGG
TGGAAATCAAGCGTACGGTGGCCGCCCCCTCCGTGTTCATCTTCCCCCCCTCCGACGAGCAGCTGAAGTCCGGC
ACCGCCTCCGTGGTGTGCCTGCTGAATAACTTCTACCCCAGAGAGGCCAAGGTGCAGTGGAAGGTGGACAACGC
CCTGCAGTCCGGGAACTCCCAGGAGAGCGTGACCGAGCAGGACAGCAAGGACAGCACCTACAGCCTGAGCAGCA
CCCTGACCCTGAGCAAAGCCGACTACGAGAAGCACAAGGTGTACGCCTGCGAGGTGACCCACCAGGGCCTGAGC
TCCCCCGTCACCAAGAGCTTCAACAGGGGGGAGTGTTAG Signal sequence (1-60), Variable region (61-378), Constant region (379-702)

SEQ ID NO: 58: Amino acid sequence of hR198_LG2 type light chain
MVLQTQVFISLLLWISGAYGDIQLTQSPSSLSASVGDRVTITCHASQNIGGSLSWFQQKPGKAPKRLIYLTSTL
DWGVPSRFSGSGSGTDYTLTISSLQPEDFAMYYCLQFAIFPDSFGQGTKVEIKRTVAAPSVFIFPPSDEQLKSG
TASVVCLLNNFYPREAKVQWKVDNALQSGNSQESVTEQDSKDSTYSLSSTLTLSKADYEKHKVYACEVTHQGLS
SPVTKSFNRGEC Signal sequence (1-20), Variable region (21-126), Constant region (127-234)

FIG. 32

SEQ ID NO: 59: Nucleotide sequence encoding hR198_LG3 type light chain
ATGGTGCTGCAGACCCAGGTGTTCATCTCCCTGCTGCTGTGGATCTCCGGCGCGTACGGCGATATCCAGCTGAC
CCAGAGCCCTAGCAGCCTGTCTGCCAGCGTGGGCGACAGAGTGACCATCACCTGTCACGCCAGCCGGAACATCG
GCGGCAGCCTGAGCTGGTTCCAGCAGAAACCCGGCAAGGCCCCAAGCGGCTGATCTACCTGACCAGCAGCCTG
GACTGGGGCGTGCCCAGCAGATTTTCTGGCAGCGGCTCCGGCACCGACTACACCCTGACAATCAGCAGCCTGCA
GCCCGAGGACTTCGCCATGTACTACTGCCTGCAGTTCGCCATCTTCCCCGACAGCTTTGGCCAGGGCACCAAGG
TGGAAATCAAGCGTACGGTGGCCGCCCCCTCCGTGTTCATCTTCCCCCCTCCGACGAGCAGCTGAAGTCCGGC
ACCGCCTCCGTGGTGTGCCTGCTGAATAACTTCTACCCCAGAGAGGCCAAGGTGCAGTGGAAGGTGGACAACGC
CCTGCAGTCCGGGAACTCCCAGGAGAGCGTGACCGAGCAGGACAGCAAGGACAGCACCTACAGCCTGAGCAGCA
CCCTGACCCTGAGCAAAGCCGACTACGAGAAGCACAAGGTGTACGCCTGCGAGGTGACCCACCAGGGCCTGAGC
TCCCCCGTCACCAAGAGCTTCAACAGGGGGGAGTGTTAG Signal sequence (1-60), Variable region (61-378), Constant region (379-702)

SEQ ID NO: 60: Amino acid sequence of hR198_LG3 type light chain
MVLQTQVFISLLLWISGAYGDIQLTQSPSSLSASVGDRVTITCHASRNIGGSLSWFQQKPGKAPKRLIYLTSSL
DWGVPSRFSGSGSGTDYTLTISSLQPEDFAMYYCLQFAIFPDSFGQGTKVEIKRTVAAPSVFIFPPSDEQLKSG
TASVVCLLNNFYPREAKVQWKVDNALQSGNSQESVTEQDSKDSTYSLSSTLTLSKADYEKHKVYACEVTHQGLS
SPVTKSFNRGEC Signal sequence (1-20), Variable region (21-126), Constant region (127-234)

FIG. 33

SEQ ID NO: 61: Nucleotide sequence encoding hR198_HG1 type heavy chain
ATGAAACACCTGTGGTTCTTCCTCCTGCTGGTGGCAGCTCCCAGATGGGTGCTGAGCCAGGTGCAGCTGGTGCA
GTCTGGCGCCGAAGTGAAGAAACCAGGCGCCAGCGTGAAGGTGTCCTGCAAGGCCTCTGGCTACCCCGTGACCG
CCTACTACATCAGCTGGGTCAGACAGGCCCCAGGCCAGGGCCTGGAATACGTGGGCTACATCGACATGGGCAAC
GGCCGGACCGACTACAACGCCCGGTTTAAGGGCAGAGCCACCCTGACCGTGGACAAGAGCACCAGCACCGCCTA
CATGGAACTGAGCAGCCTGCGGAGCGAGGACACCGCCGTGTACTACTGCGCCAGAGACAGCAACTGGGGCGCCG
ACTATTGGGGCCAGGGCACACTCGTGACCGTCAGCTCAGCCTCCACCAAGGGCCCAAGCGTCTTCCCCCTGGCA
CCCTCCTCCAAGAGCACCTCTGGCGGCACAGCCGCCCTGGGCTGCCTGGTCAAGGACTACTTCCCCGAACCCGT
GACCGTGAGCTGGAACTCAGGCGCCCTGACCAGCGGCGTGCACACCTTCCCCGCTGTCCTGCAGTCCTCAGGAC
TCTACTCCCTCAGCAGCGTGGTGACCGTGCCCTCCAGCAGCTTGGGCACCCAGACCTACATCTGCAACGTGAAT
CACAAGCCCAGCAACACCAAGGTGGACAAGAGAGTTGAGCCCAAATCTTGTGACAAAACTCACACATGCCCACC
CTGCCCAGCACCTGAACTCCTGGGGGGACCCTCAGTCTTCCTCTTCCCCCCAAAACCCAAGGACACCCTCATGA
TCTCCCGGACCCCTGAGGTCACATGCGTGGTGGTGGACGTGAGCCACGAAGACCCTGAGGTCAAGTTCAACTGG
TACGTGGACGGCGTGGAGGTGCATAATGCCAAGACAAAGCCCCGGGAGGAGCAGTACAACAGCACGTACCGGGT
GGTCAGCGTCCTCACCGTCCTGCACCAGGACTGGCTGAATGGCAAGGAGTACAAGTGCAAGGTCTCCAACAAAG
CCCTCCCAGCCCCCATCGAGAAACCATCTCCAAAGCCAAAGGCCAGCCCCGGGAACCACAGGTGTACACCCTG
CCCCCATCCCGGGAGGAGATGACCAAGAACCAGGTCAGCCTGACCTGCCTGGTCAAAGGCTTCTATCCCAGCGA
CATCGCCGTGGAGTGGGAGAGCAATGGCCAGCCCGAGAACAACTACAAGACCACCCCTCCCGTGCTGGACTCCG
ACGGCTCCTTCTTCCTCTACAGCAAGCTCACCGTGGACAAGAGCAGGTGGCAGCAGGGCAACGTCTTCTCATGC
TCCGTGATGCATGAGGCTCTGCACAACCACTACACCCAGAAGAGCCTCTCCCTGTCTCCGGGCAAATGA
Signal sequence (1-57), Variable region (58-408), Constant region (409-1398)

SEQ ID NO: 62: Amino acid sequence of hR198_HG1 type heavy chain
MKHLWFFLLLVAAPRWVLSQVQLVQSGAEVKKPGASVKVSCKASGYPVTAYYISWVRQAPGQGLEYVGYIDMGN
GRTDYNARFKGRATLTVDKSTSTAYMELSSLRSEDTAVYYCARDSNWGADYWGQGTLVTVSSASTKGPSVFPLA
PSSKSTSGGTAALGCLVKDYFPEPVTVSWNSGALTSGVHTFPAVLQSSGLYSLSSVVTVPSSSLGTQTYICNVN
HKPSNTKVDKRVEPKSCDKTHTCPPCPAPELLGGPSVFLFPPKPKDTLMISRTPEVTCVVVDVSHEDPEVKFNW
YVDGVEVHNAKTKPREEQYNSTYRVVSVLTVLHQDWLNGKEYKCKVSNKALPAPIEKTISKAKGQPREPQVYTL
PPSREEMTKNQVSLTCLVKGFYPSDIAVEWESNGQPENNYKTTPPVLDSDGSFFLYSKLTVDKSRWQQGNVFSC
SVMHEALHNHYTQKSLSLSPGK
Signal sequence (1-19), Variable region (20-136), Constant region (137-466)

FIG. 34

SEQ ID NO: 63: Nucleotide sequence encoding hR198_HG2 type heavy chain
ATGAAACACCTGTGGTTCTTCCTCCTGCTGGTGGCAGCTCCCAGATGGGTGCTGAGCCAGGTGCAGCTGGTGCA
GTCTGGCGCCGAAGTGAAGAAACCAGGCGCCAGCGTGAAGGTGTCCTGCAAGGCCTCTGGCTACCCCATCACCG
CCTACTACATCAGCTGGGTCAGACAGGCCCCAGGCCAGGGCCTGGAATACGTGGGCTACATCGACATGGGCAAC
GGCCGGACCGACTACAACGGCCGGTTTAAGGGCAGAGCCACCCTGACCGTGGACAAGAGCACCAGCACCGCCTA
CATGGAACTGAGCAGCCTGCGGAGCGAGGACACCGCCGTGTACTACTGCGCCAGAGACAGCAACTGGGGCGCCG
ACTATTGGGGCCAGGGCACACTCGTGACCGTCAGCTCAGCCTCCACCAAGGGCCCAAGCGTCTTCCCCCTGGCA
CCCTCCTCCAAGAGCACCTCTGGCGGCACAGCCGCCCTGGGCTGCCTGGTCAAGGACTACTTCCCCGAACCCGT
GACCGTGAGCTGGAACTCAGGCGCCCTGACCAGCGGCGTGCACACCTTCCCCGCTGTCCTGCAGTCCTCAGGAC
TCTACTCCCTCAGCAGCGTGGTGACCGTGCCCTCCAGCAGCTTGGGCACCCAGACCTACATCTGCAACGTGAAT
CACAAGCCCAGCAACACCAAGGTGGACAAGAGAGTTGAGCCCAAATCTTGTGACAAAACTCACACATGCCCACC
CTGCCCAGCACCTGAACTCCTGGGGGACCCTCAGTCTTCCTCTTCCCCCCAAAACCCAAGGACACCCTCATGA
TCTCCCGGACCCCTGAGGTCACATGCGTGGTGGTGGACGTGAGCCACGAAGACCCTGAGGTCAAGTTCAACTGG
TACGTGGACGGCGTGGAGGTGCATAATGCCAAGACAAAGCCCCGGGAGGAGCAGTACAACAGCACGTACCGGGT
GGTCAGCGTCCTCACCGTCCTGCACCAGGACTGGCTGAATGGCAAGGAGTACAAGTGCAAGGTCTCCAACAAAG
CCCTCCCAGCCCCCATCGAGAAAACCATCTCCAAAGCCAAAGGCCAGCCCCGGGAACCACAGGTGTACACCCTG
CCCCCATCCCGGGAGGAGATGACCAAGAACCAGGTCAGCCTGACCTGCCTGGTCAAAGGCTTCTATCCCAGCGA
CATCGCCGTGGAGTGGGAGAGCAATGGCCAGCCGGAGAACAACTACAAGACCACCCCTCCCGTGCTGGACTCCG
ACGGCTCCTTCTTCCTCTACAGCAAGCTCACCGTGGACAAGAGCAGGTGGCAGCAGGGCAACGTCTTCTCATGC
TCCGTGATGCATGAGGCTCTGCACAACCACTACACCCAGAAGAGCCTCTCCCTGTCTCCGGGCAAATGA Signal sequence (1-57), Variable region (58-408), Constant region (409-1398)

SEQ ID NO: 64: Amino acid sequence of hR198_HG2 type heavy chain
MKHLWFFLLLVAAPRWVLSQVQLVQSGAEVKKPGASVKVSCKASGYPITAYYISWVRQAPGQGLEYVGYIDMGN
GRTDYNGRFKGRATLTVDKSTSTAYMELSSLRSEDTAVYYCARDSNWGADYWGQGTLVTVSSASTKGPSVFPLA
PSSKSTSGGTAALGCLVKDYFPEPVTVSWNSGALTSGVHTFPAVLQSSGLYSLSSVVTVPSSSLGTQTYICNVN
HKPSNTKVDKRVEPKSCDKTHTCPPCPAPELLGGPSVFLFPPKPKDTLMISRTPEVTCVVVDVSHEDPEVKFNW
YVDGVEVHNAKTKPREEQYNSTYRVVSVLTVLHQDWLNGKEYKCKVSNKALPAPIEKTISKAKGQPREPQVYTL
PPSREEMTKNQVSLTCLVKGFYPSDIAVEWESNGQPENNYKTTPPVLDSDGSFFLYSKLTVDKSRWQQGNVFSC
SVMHEALHNHYTQKSLSLSPGK Signal sequence (1-19), Variable region (20-136), Constant region (137-466)

FIG. 35

SEQ ID NO: 65: Nucleotide sequence encoding hR198_HG3 type heavy chain
ATGAAACACCTGTGGTTCTTCCTCCTGCTGGTGGCAGCTCCCAGATGGGTGCTGAGCCAGGTGCAGCTGGTGCA
GTCTGGCGCCGAAGTGAAGAAACCAGGCGCCAGCGTGAAGGTGTCCTGCAAGGCCTCTGGCTACCCCATCACCG
CCTACTACATCAGCTGGGTCAGACAGGCCCCAGGCCAGGGCCTGGAATACGTGGGCTACATCGACATGGGCAAC
GGCCGGACCGACTACAACATGCGGTTTAAGGGCAGAGCCACCCTGACCGTGGACAAGAGCACCAGCACCGCCTA
CATGGAACTGAGCAGCCTGCGGAGCGAGGACACCGCCGTGTACTACTGCGCCAGAGACAGCAACTGGGGCGCCG
ACTATTGGGGCCAGGGCACACTCGTGACCGTCAGCTCAGCCTCCACCAAGGGCCCAAGCGTCTTCCCCCTGGCA
CCCTCCTCCAAGAGCACCTCTGGCGGCACAGCCGCCCTGGGCTGCCTGGTCAAGGACTACTTCCCCGAACCCGT
GACCGTGAGCTGGAACTCAGGCGCCCTGACCAGCGGCGTGCACACCTTCCCCGCTGTCCTGCAGTCCTCAGGAC
TCTACTCCCTCAGCAGCGTGGTGACCGTGCCCTCCAGCAGCTTGGGCACCCAGACCTACATCTGCAACGTGAAT
CACAAGCCCAGCAACACCAAGGTGGACAAGAGAGTTGAGCCCAAATCTTGTGACAAAACTCACACATGCCCACC
CTGCCCAGCACCTGAACTCCTGGGGGGACCCTCAGTCTTCCTCTTCCCCCCAAAACCCAAGGACACCCTCATGA
TCTCCCGGACCCCTGAGGTCACATGCGTGGTGGTGGACGTGAGCCACGAAGACCCTGAGGTCAAGTTCAACTGG
TACGTGGACGGCGTGGAGGTGCATAATGCCAAGACAAAGCCCCGGGAGGAGCAGTACAACAGCACGTACCGGGT
GGTCAGCGTCCTCACCGTCCTGCACCAGGACTGGCTGAATGGCAAGGAGTACAAGTGCAAGGTCTCCAACAAAG
CCCTCCCAGCCCCCATCGAGAAAACCATCTCCAAAGCCAAAGGCCAGCCCCGGGAACCACAGGTGTACACCCTG
CCCCCATCCCGGGAGGAGATGACCAAGAACCAGGTCAGCCTGACCTGCCTGGTCAAAGGCTTCTATCCCAGCGA
CATCGCCGTGGAGTGGGAGAGCAATGGCCAGCCCGAGAACAACTACAAGACCACCCCTCCCGTGCTGGACTCCG
ACGGCTCCTTCTTCCTCTACAGCAAGCTCACCGTGGACAAGAGCAGGTGGCAGCAGGGCAACGTCTTCTCATGC
TCCGTGATGCATGAGGCTCTGCACAACCACTACACCCAGAAGAGCCTCTCCCTGTCTCCCGGCAAATGA Signal sequence (1-57), Variable region (58-408), Constant region (409-1398)

SEQ ID NO: 66: Amino acid sequence of hR198_HG3 type heavy chain
MKHLWFFLLLVAAPRWVLSQVQLVQSGAEVKKPGASVKVSCKASGYPITAYYISWVRQAPGQGLEYVGYIDMGN
GRTDYNMRFKGRATLTVDKSTSTAYMELSSLRSEDTAVYYCARDSNWGADYWGQGTLVTVSSASTKGPSVFPLA
PSSKSTSGGTAALGCLVKDYFPEPVTVSWNSGALTSGVHTFPAVLQSSGLYSLSSVVTVPSSSLGTQTYICNVN
HKPSNTKVDKRVEPKSCDKTHTCPPCPAPELLGGPSVFLFPPKPKDTLMISRTPEVTCVVVDVSHEDPEVKFNW
YVDGVEVHNAKTKPREEQYNSTYRVVSVLTVLHQDWLNGKEYKCKVSNKALPAPIEKTISKAKGQPREPQVYTL
PPSREEMTKNQVSLTCLVKGFYPSDIAVEWESNGQPENNYKTTPPVLDSDGSFFLYSKLTVDKSRWQQGNVFSC
SVMHEALHNHYTQKSLSLSPGK Signal sequence (1-19), Variable region (20-136), Constant region (137-466)

FIG. 36

SEQ ID NO: 67: Nucleotide sequence encoding hR198_H4-LALA type heavy chain
ATGAAACACCTGTGGTTCTTCCTCCTGCTGGTGGCAGCTCCCAGATGGGTGCTGAGCCAGGTGCAGCTGGTGCA
GTCTGGCGCCGAAGTGAAGAAACCAGGCGCCAGCGTGAAGGTGTCCTGCAAGGCCTCTGGCTACCCCGTGACCG
CCTACTACATCAGCTGGATCAGACAGGCCCCAGGCCAGGGCCTGGAATACGTGGGCTACATCGACATGGGCAAC
GGCCGGACCAACTACAACGCCCGGTTTAAGGGCAGAGCCACCCTGACCGTGGACAAGAGCACCAGCACCGCCTA
CATGGAACTGAGCAGCCTGCGGAGCGAGGACACCGCCGTGTACTACTGCGCCAGAGACAGCAACTGGGGCGTGG
ACTATTGGGGCCAGGGCACACTCGTGACCGTCAGCTCAGCCTCCACCAAGGGCCCAAGCGTCTTCCCCCTGGCA
CCCTCCTCCAAGAGCACCTCTGGCGGCACAGCCGCCCTGGGCTGCCTGGTCAAGGACTACTTCCCCGAACCCGT
GACCGTGAGCTGGAACTCAGGCGCCCTGACCAGCGGCGTGCACACCTTCCCCGCTGTCCTGCAGTCCTCAGGAC
TCTACTCCCTCAGCAGCGTGGTGACCGTGCCCTCCAGCAGCTTGGGCACCCAGACCTACATCTGCAACGTGAAT
CACAAGCCCAGCAACACCAAGGTGGACAAGAGAGTTGAGCCCAAATCTTGTGACAAAACTCACACATGCCCACC
CTGCCCAGCACCTGAAGCCGCGGGGGGACCCTCAGTCTTCCTCTTCCCCCCAAAACCCAAGGACACCCTCATGA
TCTCCCGGACCCCTGAGGTCACATGCGTGGTGGTGGACGTGAGCCACGAAGACCCTGAGGTCAAGTTCAACTGG
TACGTGGACGGCGTGGAGGTGCATAATGCCAAGACAAAGCCCGGGAGGAGCAGTACAACAGCACGTACCGGGT
GGTCAGCGTCCTCACCGTCCTGCACCAGGACTGGCTGAATGGCAAGGAGTACAAGTGCAAGGTCTCCAACAAAG
CCCTCCCAGCCCCCATCGAGAAAACCATCTCCAAAGCCAAAGGCCAGCCCCGGGAACCACAGGTGTACACCCTG
CCCCCATCCCGGGAGGAGATGACCAAGAACCAGGTCAGCCTGACCTGCCTGGTCAAAGGCTTCTATCCCAGCGA
CATCGCCGTGGAGTGGGAGAGCAATGGCCAGCCCGAGAACAACTACAAGACCACCCCTCCCGTGCTGGACTCCG
ACGGCTCCTTCTTCCTCTACAGCAAGCTCACCGTGGACAAGAGCAGGTGGCAGCAGGGCAACGTCTTCTCATGC
TCCGTGATGCATGAGGCTCTGCACAACCACTACACCCAGAAGAGCCTCTCCCTGTCTCCGGGCAAATGA Signal sequence (1-57), Variable region (58-408), Constant region (409-1398)

SEQ ID NO: 68: Amino acid sequence of hR198_H4-LALA type heavy chain
MKHLWFFLLLVAAPRWVLSQVQLVQSGAEVKKPGASVKVSCKASGYPVTAYYISWIRQAPGQGLEYVGYIDMGN
GRTNYNARFKGRATLTVDKSTSTAYMELSSLRSEDTAVYYCARDSNWGVDYWGQGTLVTVSSASTKGPSVFPLA
PSSKSTSGGTAALGCLVKDYFPEPVTVSWNSGALTSGVHTFPAVLQSSGLYSLSSVVTVPSSSLGTQTYICNVN
HKPSNTKVDKRVEPKSCDKTHTCPPCPAPEAAGGPSVFLFPPKPKDTLMISRTPEVTCVVVDVSHEDPEVKFNW
YVDGVEVHNAKTKPREEQYNSTYRVVSVLTVLHQDWLNGKEYKCKVSNKALPAPIEKTISKAKGQPREPQVYTL
PPSREEMTKNQVSLTCLVKGFYPSDIAVEWESNGQPENNYKTTPPVLDSDGSFFLYSKLTVDKSRWQQGNVFSC
SVMHEALHNHYTQKSLSLSPGK Signal sequence (1-19), Variable region (20-136), Constant region (137-466)

FIG. 37

SEQ ID NO: 69: Nucleotide sequence encoding hR198_HG1-LALA type heavy chain
ATGAAACACCTGTGGTTCTTCCTCCTGCTGGTGGCAGCTCCCAGATGGGTGCTGAGCCAGGTGCAGCTGGTGCA
GTCTGGCGCCGAAGTGAAGAAACCAGGCGCCAGCGTGAAGGTGTCCTGCAAGGCCTCTGGCTACCCCGTGACCG
CCTACTACATCAGCTGGGTCAGACAGGCCCCAGGCCAGGGCCTGGAATACGTGGGCTACATCGACATGGGCAAC
GGCCGGACCGACTACAACGCCCGGTTTAAGGGCAGAGCCACCCTGACCGTGGACAAGAGCACCAGCACCGCCTA
CATGGAACTGAGCAGCCTGCGGAGCGAGGACACCGCCGTGTACTACTGCGCCAGAGACAGCAACTGGGGCGCCG
ACTATTGGGGCCAGGGCACACTCGTGACCGTCAGCTCAGCCTCCACCAAGGGCCCAAGCGTCTTCCCCCTGGCA
CCCTCCTCCAAGAGCACCTCTGGCGGCACAGCCGCCCTGGGCTGCCTGGTCAAGGACTACTTCCCCGAACCCGT
GACCGTGAGCTGGAACTCAGGCGCCCTGACCAGCGGCGTGCACACCTTCCCCGCTGTCCTGCAGTCCTCAGGAC
TCTACTCCCTCAGCAGCGTGGTGACCGTGCCCTCCAGCAGCTTGGGCACCCAGACCTACATCTGCAACGTGAAT
CACAAGCCCAGCAACACCAAGGTGGACAAGAGAGTTGAGCCCAAATCTTGTGACAAAACTCACACATGCCCACC
CTGCCCAGCACCTGAAGCCGCGGGGGGACCCTCAGTCTTCCTCTTCCCCCCAAAACCCAAGGACACCCTCATGA
TCTCCCGGACCCCTGAGGTCACATGCGTGGTGGTGGACGTGAGCCACGAAGACCCTGAGGTCAAGTTCAACTGG
TACGTGGACGGCGTGGAGGTGCATAATGCCAAGACAAAGCCCCGGGAGGAGCAGTACAACAGCACGTACCGGGT
GGTCAGCGTCCTCACCGTCCTGCACCAGGACTGGCTGAATGGCAAGGAGTACAAGTGCAAGGTCTCCAACAAAG
CCCTCCCAGCCCCCATCGAGAAAACCATCTCCAAAGCCAAAGGCCAGCCCCGGGAACCACAGGTGTACACCCTG
CCCCCATCCCGGGAGGAGATGACCAAGAACCAGGTCAGCCTGACCTGCCTGGTCAAAGGCTTCTATCCCAGCGA
CATCGCCGTGGAGTGGGAGAGCAATGGCCAGCCCGAGAACAACTACAAGACCACCCCTCCCGTGCTGGACTCCG
ACGGCTCCTTCTTCCTCTACAGCAAGCTCACCGTGGACAAGAGCAGGTGGCAGCAGGGCAACGTCTTCTCATGC
TCCGTGATGCATGAGGCTCTGCACAACCACTACACCCAGAAGAGCCTCTCCCTGTCTCCGGGCAAATGA Signal sequence (1-57), Variable region (58-408), Constant region (409-1398)

SEQ ID NO: 70: Amino acid sequence of hR198_HG1-LALA type heavy chain
MKHLWFFLLLVAAPRWVLSQVQLVQSGAEVKKPGASVKVSCKASGYPVTAYYISWVRQAPGQGLEYVGYIDMGN
GRTDYNARFKGRATLTVDKSTSTAYMELSSLRSEDTAVYYCARDSNWGADYWGQGTLVTVSSASTKGPSVFPLA
PSSKSTSGGTAALGCLVKDYFPEPVTVSWNSGALTSGVHTFPAVLQSSGLYSLSSVVTVPSSSLGTQTYICNVN
HKPSNTKVDKRVEPKSCDKTHTCPPCPAPEAAGGPSVFLFPPKPKDTLMISRTPEVTCVVVDVSHEDPEVKFNW
YVDGVEVHNAKTKPREEQYNSTYRVVSVLTVLHQDWLNGKEYKCKVSNKALPAPIEKTISKAKGQPREPQVYTL
PPSREEMTKNQVSLTCLVKGFYPSDIAVEWESNGQPENNYKTTPPVLDSDGSFFLYSKLTVDKSRWQQGNVFSC
SVMHEALHNHYTQKSLSLSPGK Signal sequence (1-19), Variable region (20-136), Constant region (137-466)

FIG. 38

| L chain | SEQ ID | CDRL1 | SEQ ID | CDRL2 | SEQ ID | CDRL3 | SEQ ID |
|---|---|---|---|---|---|---|---|
| cR118 L | NO: 23 | RASQSISNSLS | NO: 116 | STSTLES | NO: 96 | LQFATFPDT | NO: 99 |
| cR198 L | NO: 25 | RASQSIGNSLS | NO: 92 | STSTLES | NO: 96 | LQFATYPDT | NO: 100 |
| hR198 L1 | NO: 31 | RASQSIGNSLS | NO: 92 | STSTLES | NO: 96 | LQFATYPDT | NO: 100 |
| hR198 L2 | NO: 33 | RASQSIGNSLS | NO: 92 | STSTLES | NO: 96 | LQFATYPDT | NO: 100 |
| hR198 L3 | NO: 35 | RASQSIGNSLS | NO: 92 | STSTLES | NO: 96 | LQFATFPDT | NO: 99 |
| hR198 L4 | NO: 37 | RASQSIGNSLS | NO: 92 | STSTLES | NO: 96 | LQFATFPDT | NO: 99 |
| hR198 LG1 | NO: 56 | RASQSIGGSLS | NO: 93 | STSTLES | NO: 96 | LQFAIFPDS | NO: 101 |
| hR198 LG2 | NO: 58 | HASQNIGGSLS | NO: 94 | LTSTLDW | NO: 97 | LQFAIFPDS | NO: 101 |
| hR198 LG3 | NO: 60 | HASRNIGGSLS | NO: 95 | LTSSLDW | NO: 98 | LQFAIFPDS | NO: 101 |

| H chain | SEQ ID | CDRH1 | SEQ ID | CDRH2 | SEQ ID | CDRH3 | SEQ ID |
|---|---|---|---|---|---|---|---|
| cR118 H | NO: 27 | AYYIS | NO: 102 | YIDMGNGRTNYNARFKG | NO: 104 | DSNWGVDY | NO: 109 |
| cR198 H | NO: 29 | SYYIS | NO: 103 | YVDMGNGRTNYNEKFKG | NO: 105 | DSNWGVDY | NO: 109 |
| hR198 H1 | NO: 39 | SYYIS | NO: 103 | YVDMGNGRTNYNEKFKG | NO: 105 | DSNWGVDY | NO: 109 |
| hR198 H2 | NO: 41 | SYYIS | NO: 103 | YVDMGNGRTNYNEKFKG | NO: 105 | DSNWGVDY | NO: 109 |
| hR198 H3 | NO: 43 | AYYIS | NO: 102 | YVDMGNGRTNYNARFKG | NO: 104 | DSNWGVDY | NO: 109 |
| hR198 H4 | NO: 45 | AYYIS | NO: 102 | YIDMGNGRTNYNARFKG | NO: 104 | DSNWGVDY | NO: 109 |
| hR198 HG1 | NO: 62 | AYYIS | NO: 102 | YIDMGNGRTDYNGRFKG | NO: 106 | DSNWGADY | NO: 110 |
| hR198 HG2 | NO: 64 | AYYIS | NO: 102 | YIDMGNGRTDYNMRFKG | NO: 107 | DSNWGVDY | NO: 109 |
| hR198 HG3 | NO: 66 | AYYIS | NO: 102 | YIDMGNGRTDYNARFKG | NO: 108 | DSNWGADY | NO: 110 |
| hR198 H4-LALA | NO: 68 | AYYIS | NO: 102 | YIDMGNGRTNYNARFKG | NO: 104 | DSNWGVDY | NO: 109 |
| hR198 HG1-LALA | NO: 70 | AYYIS | NO: 102 | YIDMGNGRTDYNARFKG | NO: 106 | DSNWGADY | NO: 110 |

FIG. 39

SEQ ID NO: 72: Nucleotide sequence encoding 2C1.1 antibody heavy chain
ATGAAACACCTGTGGTTCTTCCTCCTGCTGGTGGCAGCTCCCAGATGGGTGCTGAGCCAGGTGCAGCTGCAGCA
GTGGGGAGCCGGCCTGCTGAAGCCCAGCGAGACACTGAGCCTGACCTGCGCTGTGTACGGAGGCAGCTTCAGCG
GCTACTACTGGTCCTGGATCCGGCAGCCCCCTGGCAAGGGCCTGGAATGGATCGGCGAGATCGACCACAGCGGC
AGCACCAACTACAACCCCGCCCTGAAGTCCCGGCTGACCATCAGCGTGGACACCAGCAAGAACCAGTTCAGCCT
GAAGCTGAGCAGCGTGACAGCCGCCGACACCGCCGTGTACTACTGTGCCAGAGCCGGCAGCGGCGGCTACGAGG
ATTGGTTCGATCCTTGGGGCCAGGGCACCCTGGTGACCGTCAGCTCAGCCAGCACCAAGGGCCCTTCCGTGTTC
CCTCTGGCCCCTTGTAGCCGTTCCACCAGCGAGTCCACCGCCGCCCTTGGCTGTCTGGTGAAGGACTACTTCCC
TGAGCCTGTGACCGTGAGCTGGAACTCCGGAGCCCTTACCAGCGGCGTGCACACCTTCCCTGCCGTGCTGCAGT
CCAGCGGCCTTTACTCCCTGAGCTCCGTGGTGACCGTGCCTAGCTCCAACTTCGGCACCCAAACCTACACCTGT
AACGTGGACCACAAGCCTAGCAACACCAAGGTGGACAAGACCGTGGAGCGTAAGTGTTGTGTGGAGTGTCCTCC
TTGTCCTGCCCCTCCTGTGGCCGGACCTTCCGTGTTCCTTTTCCCTCCTAAGCCTAAGGACACCCTGATGATCA
GCCGTACCCCTGAGGTGACCTGTGTGGTGGTGGACGTGTCCCACGAGGACCCTGAGGTGCAGTTCAACTGGTAC
GTGGACGGCGTGGAGGTGCACAACGCCAAGACCAAGCCTCGTGAGGAGCAATTCAACAGCACCTTCCGTGTGGT
GTCCGTGCTTACCGTGGTGCACCAAGACTGGCTGAACGGCAAGGAGTACAAGTGTAAGGTGAGCAACAAGGGAC
TTCCTGCCCCTATCGAGAAGACCATCTCCAAGACCAAGGGCCAACCTCGTGAGCCTCAAGTGTACACCCTTCCT
CCTAGCCGTGAGGAGATGACCAAGAACCAAGTGTCCCTTACCTGTCTGGTGAAGGGCTTCTACCCTAGCGACAT
CGCCGTGGAGTGGGAGTCCAACGGACAACCTGAGAACAACTACAAGACCACCCCTCCTATGCTTGACAGCGACG
GCTCCTTCTTCCTGTACAGCAAGCTGACCGTGGACAAGTCCCGTTGGCAACAAGGCAACGTGTTCAGCTGTTCC
GTGATGCACGAGGCCCTGCACAACCACTACACCCAAAAGAGCCTTTCCCTGAGCCCTGGAAAG Signal sequence (1-57), Variable region (58-417), Constant region (418-1395)

SEQ ID NO: 73: Amino acid sequence of 2C1.1 antibody heavy chain
MKHLWFFLLLVAAPRWVLSQVQLQQWGAGLLKPSETLSLTCAVYGGSFSGYYWSWIRQPPGKGLEWIGEIDHSG
STNYNPALKSRLTISVDTSKNQFSLKLSSVTAADTAVYYCARAGSGGYEDWFDPWGQGTLVTVSSASTKGPSVF
PLAPCSRSTSESTAALGCLVKDYFPEPVTVSWNSGALTSGVHTFPAVLQSSGLYSLSSVVTVPSSNFGTQTYTC
NVDHKPSNTKVDKTVERKCCVECPPCPAPPVAGPSVFLFPPKPKDTLMISRTPEVTCVVVDVSHEDPEVQFNWY
VDGVEVHNAKTKPREEQFNSTFRVVSVLTVVHQDWLNGKEYKCKVSNKGLPAPIEKTISKTKGQPREPQVYTLP
PSREEMTKNQVSLTCLVKGFYPSDIAVEWESNGQPENNYKTTPPMLDSDGSFFLYSKLTVDKSRWQQGNVFSCS
VMHEALHNHYTQKSLSLSPGK Signal sequence (1-19), Variable region (20-139), Constant region (140-465)

FIG. 40

SEQ ID NO: 74: Nucleotide sequence encoding 2C1.1 antibody light chain
ATGGTGCTGCAGACCCAGGTGTTCATCTCCCTGCTGCTGTGGATCTCCGGCGCGTACGGCCAGTCCGTGCTGAC
CCAGCCTCCTTCCGTGTCTGGCGCCCCTGGCCAGAGAGTGACCATCAGCTGTACCGGCAGCAGCAGCAACATCG
GAGCCGGCTACAACGTGCACTGGTATCAGCAGTTCCCCCGGACCGACCCCAAGCTGCTGATCTACGTGTACAAC
ATCCGGCCCAGCGGCGTGCCCGACCGGTTTTCTGGCAGCAGAAGCGGCACAAGCGCCAGCCTGGCCATCACCGG
CCTGCAGACCGAGGACGAGGCCGACTACTACTGCCAGAGCTACGACAGCAGCCTGAGCGGCGTGGTGTTCGGCG
GAGGCACCAAGCTGACAGTGCTGGGCCAGCCCAAGGCCAACCCCACCGTGACCCTGTTCCCCCCAAGCAGCGAG
GAACTGCAGGCCAACAAGGCCACCCTGGTGTGCCTGATCAGCGACTTCTACCCTGGCGCCGTGACAGTGGCCTG
GAAGGCCGATGGATCTCCCGTGAAGGCCGGCGTGGAAACCACCAAGCCCAGCAAGCAGAGCAACAACAAATACG
CCGCCAGCAGCTACCTGAGCCTGACCCCCGAGCAGTGGAAGTCCCACCGGTCCTACAGCTGCCAGGTGACACAC
GAGGGCAGCACCGTGGAAAAGACCGTGGCCCCCACCGAGTGCAGCtaggggcccgtttaaacgggggaggcta Signal sequence (1-60), Variable region (61-393), Constant region (394-711)

SEQ ID NO: 75: Amino acid sequence of 2C1.1 antibody light chain
MVLQTQVFISLLLWISGAYGQSVLTQPPSVSGAPGQRVTISCTGSSSNIGAGYNVHWYQQFPRTDPKLLIYVYN
IRPSGVPDRFSGSRSGTSASLAITGLQTEDEADYYCQSYDSSLSGVVFGGGTKLTVLGQPKANPTVTLFPPSSE
ELQANKATLVCLISDFYPGAVTVAWKADGSPVKAGVETTKPSKQSNNKYAASSYLSLTPEQWKSHRSYSCQVTH
EGSTVEKTVAPTECS Signal sequence (1-20), Variable region (21-131), Constant region (132-237)

FIG. 41

SEQ ID NO: 76: Nucleotide sequence encoding 5H3.1 antibody heavy chain
ATGAAACACCTGTGGTTCTTCCTCCTGCTGGTGGCAGCTCCCAGATGGGTGCTGAGCCAGGTGCAGCTGGTGCA
GTCTGGCGCCGAAGTGAAGAAACCTGGCGCTAGCGTGAAGGTGTCCTGCAAGGCCAGCGGCTACACCTTCACCG
ACTACTACATGAACTGGGTGCGCCAGGCTCCAGGACAGGGCCTGGAATGGATGGGCTGGATCAACCCCAACAGC
GGCGGCACCAAATACGCCCAGAAATTCCAGGGCAGAGTGACCATGACCCGGGACACCAGCATCCGGACCGCCTA
CATGGAACTGAGCCGGCTGAGAAGCGACGACACCGCCGTGTACTACTGCGCCAGAGAGTACGGCGGCAACAGCG
ATTGGTTCGACCCCTGGGGCCAGGGCACCCTGGTGACCGTCAGCTCAGCCAGCACCAAGGGCCCTTCCGTGTTC
CCTCTGGCCCCTTGTAGCCGTTCCACCAGCGAGTCCACCGCCGCCCTTGGCTGTCTGGTGAAGGACTACTTCCC
TGAGCCTGTGACCGTGAGCTGGAACTCCGGAGCCCTTACCAGCGGCGTGCACACCTTCCCTGCCGTGCTGCAGT
CCAGCGGCCTTTACTCCCTGAGCTCCGTGGTGACCGTGCCTAGCTCCAACTTCGGCACCCAAACCTACACCTGT
AACGTGGACCACAAGCCTAGCAACACCAAGGTGGACAAGACCGTGGAGCGTAAGTGTTGTGTGGAGTGTCCTCC
TTGTCCTGCCCCTCCTGTGGCCGGACCTTCCGTGTTCCTTTTCCCTCCTAAGCCTAAGGACACCCTGATGATCA
GCCGTACCCCTGAGGTGACCTGTGTGGTGGTGGACGTGTCCCACGAGGACCCTGAGGTGCAGTTCAACTGGTAC
GTGGACGGCGTGGAGGTGCACAACGCCAAGACCAAGCCTCGTGAGGAGCAATTCAACAGCACCTTCCGTGTGGT
GTCCGTGCTTACCGTGGTGCACCAAGACTGGCTGAACGGCAAGGAGTACAAGTGTAAGGTGAGCAACAAGGGAC
TTCCTGCCCCTATCGAGAAGACCATCTCCAAGACCAAGGGCCAACCTCGTGAGCCTCAAGTGTACACCCTTCCT
CCTAGCCGTGAGGAGATGACCAAGAACCAAGTGTCCCTTACCTGTCTGGTGAAGGGCTTCTACCCTAGCGACAT
CGCCGTGGAGTGGGAGTCCAACGGACAACCTGAGAACAACTACAAGACCACCCCTCCTATGCTTGACAGCGACG
GCTCCTTCTTCCTGTACAGCAAGCTGACCGTGGACAAGTCCCGTTGGCAACAAGGCAACGTGTTCAGCTGTTCC
GTGATGCACGAGGCCCTGCACAACCACTACACCCAAAAGAGCCTTTCCCTGAGCCCTGGAAAG Signal sequence (1-57), Variable region (58-417), Constant region (418-1395)

SEQ ID NO: 77: Amino acid sequence of 5H3.1 antibody heavy chain
MKHLWFFLLLVAAPRWVLSQVQLVQSGAEVKKPGASVKVSCKASGYTFTDYYMNWVRQAPGQGLEWMGWINPNS
GGTKYAQKFQGRVTMTRDTSIRTAYMELSRLRSDDTAVYYCAREYGGNSDWFDPWGQGTLVTVSSASTKGPSVF
PLAPCSRSTSESTAALGCLVKDYFPEPVTVSWNSGALTSGVHTFPAVLQSSGLYSLSSVVTVPSSNFGTQTYTC
NVDHKPSNTKVDKTVERKCCVECPPCPAPPVAGPSVFLFPPKPKDTLMISRTPEVTCVVVDVSHEDPEVQFNWY
VDGVEVHNAKTKPREEQFNSTFRVVSVLTVVHQDWLNGKEYKCKVSNKGLPAPIEKTISKTKGQPREPQVYTLP
PSREEMTKNQVSLTCLVKGFYPSDIAVEWESNGQPENNYKTTPPMLDSDGSFFLYSKLTVDKSRWQQGNVFSCS
VMHEALHNHYTQKSLSLSPGK Signal sequence (1-19), Variable region (20-139), Constant region (140-465)

FIG. 42

SEQ ID NO: 78: Nucleotide sequence encoding 5H3.1 antibody light chain
ATGGTGCTGCAGACCCAGGTGTTCATCTCCCTGCTGCTGTGGATCTCCGGCGCGTACGGCCAGTCCGTGCTGAC
CCAGCCTCCTTCCGTGTCTGGCGCCCTGGCCAGAGAGTGACCATCAGCTGTACCGGCAGCAGCAGCAACATCG
GAGCTGGATACGACGTGCACTGGTATCAGCAGCTGCCCGGCACCGCCCCAAGCTGCTGATCTACGGCAACAGC
AACCGGCCCAGCGGCGTGCCCGATAGATTCAGCGGCAGCAAGAGCGGCACCAGCGCCAGCCTGGCCATTACCGG
ACTGCAGGCCGAGGACGAGGCCGACTACTACTGCCAGAGCTACGACAACCGGCTGAGCGACAGCGTGGTGATCG
GCGGAGGCACCAAGCTGGCCGTGCAGGGACAGCCCAAGGCCAACCCCACCGTGACCCTGTTCCCCCCAAGCAGC
GAGGAACTGCAGGCCAACAAGGCCACCCTGGTGTGCCTGATCAGCGACTTCTACCCTGGCGCCGTGACAGTGGC
CTGGAAGGCCGATGGATCTCCCGTGAAGGCCGGCGTGGAAACCACCAAGCCCAGCAAGCAGAGCAACAACAAAT
ACGCCGCCAGCAGCTACCTGAGCCTGACCCCCGAGCAGTGGAAGTCCCACCGGTCCTACAGCTGCCAGGTGACA
CACGAGGGCAGCACCGTGGAAAAGACCGTGGCCCCCACCGAGTGCAGCtaggggcccgtttaaacgggggaggc
ta Signal sequence (1-60), Variable region (61-396), Constant region (397-714)

SEQ ID NO: 79: Amino acid sequence of 5H3.1 antibody light chain
MVLQTQVFISLLLWISGAYGQSVLTQPPSVSGAPGQRVTISCTGSSSNIGAGYDVHWYQQLPGTAPKLLIYGNS
NRPSGVPDRFSGSKSGTSASLAITGLQAEDEADYYCQSYDNRLSDSVVIGGGTKLAVQGQPKANPTVTLFPPSS
EELQANKATLVCLISDFYPGAVTVAWKADGSPVKAGVETTKPSKQSNNKYAASSYLSLTPEQWKSHRSYSCQVT
HEGSTVEKTVAPTECS Signal sequence (1-20), Variable region (21-132), Constant region (133-238)

FIG. 43

SEQ ID NO: 80: Nucleotide sequence encoding 10F8 antibody heavy chain
ccagcctccggactctagagccaccATGAAGCACCTGTGGTTCTTTCTGCTGCTGGTGGCCGCTCCCAGATGGG
TGCTGTCTCAGGTGCAGCTGCAGCAGTCTGGCGCCGAACTCGTGCGGCCTGGAAGCAGCGTGAAGATCAGCTGC
AAGGCCAGCGGCTACGCCTTCCGGTCCTACTGGATGAACTGGGTCAAGCAGAGGCCAGGCCAGGGCCTGGAATG
GATCGGCCACATCTATCCCGGCGACGGCGACACCAACTACAACGGCAAGTTCAAGGGCAAGGCCACCCTGACCG
CCGACAAGAGCAGCAGCACAGCCTACATGCAGCTGTCCAGCCTGACCAGCGAGGACAGCGCCGTGTACCTGTGT
GGCAGAGGCGGCACAACCGTGGTGGTGGATTATTGGGGCCAGGGCACCACACTGACCGTGTCCAGCGCCAAGAC
CACCCCCCCATCTGTGTATCCTCTGGCCCCTGGATCTGCCGCCCAGACCAACAGCATGGTCACCCTGGGCTGCC
TCGTGAAGGGCTACTTCCCTGAGCCTGTGACCGTGACCTGGAACAGCGGCTCTCTGTCTAGCGGCGTGCACACC
TTTCCAGCCGTGCTGCAGAGCGACCTGTACACCCTGAGCAGCTCCGTGACCGTGCCTAGCAGCACCTGGCCTAG
CGAGACAGTGACCTGCAACGTGGCCCACCCTGCCAGCTCTACCAAGGTGGACAAGAAAATCGTGCCCCGGGACT
GCGGCTGCAAGCCCTGTATCTGTACCGTGCCCGAGGTGTCCTCCGTGTTCATCTTCCCACCCAAGCCCAAGGAC
GTGCTGACCATCACCCTGACACCCAAAGTGACATGTGTGGTGGTGGACATCAGCAAGGACGACCCCGAGGTGCA
GTTCAGTTGGTTCGTGGACGACGTGGAAGTGCACACAGCCCAGACCCAGCCCAGAGAGGAACAGTTCAACAGCA
CCTTCAGAAGCGTGTCCGAGCTGCCCATCATGCACCAGGACTGGCTGAACGGCAAAGAATTCAAGTGCAGAGTG
AACAGCGCCGCCTTCCCTGCCCCATCGAGAAACCATCTCCAAGACCAAGGGCAGACCCAAGGCCCCCAGGT
GTACACAATCCCCCCACCCAAAGAACAGATGGCCAAGGACAAGGTGTCCCTGACCTGCATGATCACCGATTTCT
TCCCAGAGGACATCACCGTGGAATGGCAGTGGAACGGCCAGCCCGCCGAGAACTACAAGAACACCCAGCCTATC
ATGGACACCGACGGCAGCTACTTCGTGTACAGCAAGCTGAACGTGCAGAAGTCCAACTGGGAGGCCGGCAACAC
CTTCACCTGTAGCGTGCTGCACGAGGGCCTGCACAATCACCACACCGAGAAGTCCCTGTCCCACAGCCCCGGCA
AAtgagtttaaacgggggaggctaact Signal sequence (26-82), Variable region (83-436), Constant region (437-1408)

SEQ ID NO: 81: Amino acid sequence of 10F8 antibody heavy chain
MKHLWFFLLLVAAPRWVLSQVQLQQSGAELVRPGSSVKISCKASGYAFRSYWMNWVKQRPGQGLEWIGHIYPGD
GDTNYNGKFKGKATLTADKSSSTAYMQLSSLTSEDSAVYLCGRGGTTVVVDYWGQGTTLTVSSAKTTPPSVYPL
APGSAAQTNSMVTLGCLVKGYFPEPVTVTWNSGSLSSGVHTFPAVLQSDLYTLSSSVTVPSSTWPSETVTCNVA
HPASSTKVDKKIVPRDCGCKPCICTVPEVSSVFIFPPKPKDVLTITLTPKVTCVVVDISKDDPEVQFSWFVDDV
EVHTAQTQPREEQFNSTFRSVSELPIMHQDWLNGKEFKCRVNSAAFPAPIEKTISKTKGRPKAPQVYTIPPPKE
QMAKDKVSLTCMITDFFPEDITVEWQWNGQPAENYKNTQPIMDTDGSYFVYSKLNVQKSNWEAGNTFTCSVLHE
GLHNHHTEKSLSHSPGK Signal sequence (1-19), Variable region (20-137), Constant region (138-461)

FIG. 44

SEQ ID NO: 82: Nucleotide sequence encoding 10F8 antibody light chain
ccagcctccggactctagagccaccATGGTGCTGCAGACCCAGGTGTTCATCAGCCTGCTGCTGTGGATCAGCG
GCGCCTACGGCGACATCGTGATGAGCCAGAGCCCTAGCAGCCTGGCCGTGTCTGCCGGCGAGAAAGTGACCATG
AGCTGCAAGAGCAGCCAGTCCCTGCTGAACAGCCGGACCCGGAAGAACTACCTGGCCTGGTATCAGCAGAAGCC
CGGCCAGTCCCCCAAGCTGCTGATCTACTGGGCCAGCACCAGAGAAAGCGGCGTGCCCGATAGATTCACCGGCA
GCGGCTCTGGCACCGACTTCACCCTGACAATCAGCAGCGTGCAGGCCGAGGACCTGGCTGTGTACTACTGCAAG
CAGAGCTACAACCTGCCCTGGACCTTCGGCGGAGGCACCAAGCTGGAAATCAAGAGAGCCGACGCCGCTCCCAC
CGTGTCCATCTTTCCACCTAGCAGCGAGCAGCTGACCAGCGGCGGAGCTAGCGTCGTGTGCTTCCTGAACAACT
TCTACCCCAAGGACATCAACGTGAAGTGGAAGATCGACGGCAGCGAGCGGCAGAACGGCGTGCTGAATAGCTGG
ACCGACCAGGACAGCAAGGACTCCACCTACAGCATGTCCAGCACCCTGACCCTGACCAAGGACGAGTACGAGCG
GCACAACAGCTACACATGCGAGGCCACCCACAAGACCAGCACCTCCCCCATCGTGAAGTCCTTCAACCGGAACG
AGTGCtgagtttaaacgggggaggctaact Signal sequence (26-85), Variable region (86-430), Constant region (431-745)

SEQ ID NO: 83: Amino acid sequence of 10F8 antibody light chain
MVLQTQVFISLLLWISGAYGDIVMSQSPSSLAVSAGEKVTMSCKSSQSLLNSRTRKNYLAWYQQKPGQSPKLLI
YWASTRESGVPDRFTGSGSGTDFTLTISSVQAEDLAVYYCKQSYNLPWTFGGGTKLEIKRADAAPTVSIFPPSS
EQLTSGGASVVCFLNNFYPKDINVKWKIDGSERQNGVLNSWTDQDSKDSTYSMSSTLTLTKDEYERHNSYTCEA
THKTSTSPIVKSFNRNEC Signal sequence (1-20), Variable region (21-135), Constant region (136-240)

FIG. 45

SEQ ID NO: 84: Nucleotide sequence encoding 14F74 antibody heavy chain ccagcctccggactctagagccaccATGAAGCACCTGTGGTTCTTTCTGCTGCTGGTGGCCGCTCCCAGATGGG
TGCTGTCTCAGGTGCAGCTGCAGCAGTCTGGCGCCGAACTCGTGCGGCCTGGAAGCAGCGTGAAGATCAGCTGC
AAGGCCAGCGGCTACGCCTTCAGCAGCTACTGGATGAACTGGGTCAAGCAGCGGCCAGGCCAGGGCCTGGAATG
GATCGGCCATATCTATCCCGGCGACGGCGACACCAACTACAACGGCAAGTTCAAGGGCAAGGCCACCCTGACCG
CCGACAAGAGCAGCAGCACAGCCTACATGCAGCTGAGCGGCCTGACCAGCGAGGACAGCGCCGTGTACTTCTGC
GCCAGAAGCGGCAGACTGAGATTCGCCATGGACTACTGGGGCCAGGGCACCAGCGTGACAGTGTCTAGCGCCAA
GACCACCCCCCCCAGCGTGTACCCTCTGGCTCCTGGATCTGCCGCCCAGACCAACAGCATGGTCACCCTGGGCT
GCCTCGTGAAGGGCTACTTCCCTGAGCCTGTGACCGTGACCTGGAACAGCGGCTCTCTGTCTAGCGGCGTGCAC
ACCTTTCCAGCCGTGCTGCAGAGCGACCTGTACACCCTGAGCAGCTCCGTGACCGTGCCTAGCAGCACCTGGCC
TAGCGAGACAGTGACCTGCAACGTGGCCCACCCTGCCAGCTCTACCAAGGTGGACAAGAAAATCGTGCCCCGGG
ACTGCGGCTGCAAGCCCTGTATCTGTACCGTGCCCGAGGTGTCCAGCGTGTTCATCTTCCCACCCAAGCCCAAG
GACGTGCTGACCATCACCCTGACACCCAAAGTGACCTGTGTGGTGGTGGACATCAGCAAGGACGACCCCGAGGT
GCAGTTCAGTTGGTTCGTGGACGACGTGGAAGTGCACACAGCCCAGACCCAGCCCAGAGAGGAACAGTTCAACA
GCACCTTCAGAAGCGTGTCCGAGCTGCCCATCATGCACCAGGACTGGCTGAACGGCAAAGAATTCAAGTGCAGA
GTGAACAGCGCCGCCTTCCCTGCCCCCATCGAGAAAACCATCTCCAAGACCAAGGGCAGACCCAAGGCCCCTCA
GGTGTACACAATCCCCCCACCCAAAGAACAGATGGCCAAGGACAAGGTGTCCCTGACCTGCATGATCACCGATT
TCTTCCCAGAGGACATCACCGTGGAATGGCAGTGGAACGGCCAGCCCGCCGAGAACTACAAGAACACCCAGCCT
ATCATGGACACCGACGGCAGCTACTTCGTGTACAGCAAGCTGAACGTGCAGAAGTCCAACTGGGAGGCCGGCAA
CACCTTCACCTGTAGCGTGCTGCACGAGGGCCTGCACAATCACCACACCGAGAAGTCCCTGTCCCACAGCCCCG
GCAAAtgagtttaaacgggggaggctaact Signal sequence (26-82), Variable region (83-439), Constant region (440-1411)

SEQ ID NO: 85: Amino acid sequence of 14F74 antibody heavy chain

MKHLWFFLLLVAAPRWVLSQVQLQQSGAELVRPGSSVKISCKASGYAFSSYWMNWVKQRPGQGLEWIGHIYPGD
GDTNYNGKFKGKATLTADKSSSTAYMQLSGLTSEDSAVYFCARSGRLRFAMDYWGQGTSVTVSSAKTTPPSVYP
LAPGSAAQTNSMVTLGCLVKGYFPEPVTVTWNSGSLSSGVHTFPAVLQSDLYTLSSSVTVPSSTWPSETVTCNV
AHPASSTKVDKKIVPRDCGCKPCICTVPEVSSVFIFPPKPKDVLTITLTPKVTCVVVDISKDDPEVQFSWFVDD
VEVHTAQTQPREEQFNSTFRSVSELPIMHQDWLNGKEFKCRVNSAAFPAPIEKTISKTKGRPKAPQVYTIPPPK
EQMAKDKVSLTCMITDFFPEDITVEWQWNGQPAENYKNTQPIMDTDGSYFVYSKLNVQKSNWEAGNTFTCSVLH
EGLHNHHTEKSLSHSPGK

Signal sequence (1-19), Variable region (20-138), Constant region (139-462)

FIG. 46

SEQ ID NO: 86: Nucleotide sequence encoding 14F74 antibody light chain
ccagcctccggactctagagccaccATGGTGCTGCAGACCCAGGTGTTCATCAGCCTGCTGCTGTGGATCAGCG
GCGCCTACGGCGACATCGTGATGAGCCAGAGCCCTAGCAGCCTGGCCGTGTCTGCCGGCGAGAAAGTGACCATG
AGCTGCAAGAGCAGCCAGTCCCTGCTGAACAGCCGGACCCGGAAGAACTACCTGGCCTGGTATCAGCAGAAGCC
CGGCCAGTCCCCCAAGCTGCTGATCTACTGGGCCAGCACCAGAGAAAGCGGCGTGCCCGATAGATTCACCGGCA
GCGGCTCTGGCACCGACTTCACCCTGACAATCAGCAGCGTGCAGGCCGAGGACCTGGCTGTGTACTACTGCAAG
CAGAGCTACAACCTGCGGACCTTCGGCGGAGGCACCAAGCTGGAAATCCAGAGAGCCGACGCCGCTCCCACCGT
GTCCATCTTTCCACCTAGCAGCGAGCAGCTGACCAGCGGCGGAGCTAGCGTCGTGTGCTTCCTGAACAACTTCT
ACCCCAAGGACATCAACGTGAAGTGGAAGATCGACGGCAGCGAGCGGCAGAACGGCGTGCTGAATAGCTGGACC
GACCAGGACAGCAAGGACTCCACCTACAGCATGTCCAGCACCCTGACCCTGACCAAGGACGAGTACGAGCGGCA
CAACAGCTACACATGCGAGGCCACCCACAAGACCAGCACCTCCCCCATCGTGAAGTCCTTCAACCGGAACGAGT
GCtgagtttaaacggggaggctaact Signal sequence (26-85), Variable region (86-427), Constant region (428-742)

SEQ ID NO: 87: Amino acid sequence of 14F74 antibody light chain
MVLQTQVFISLLLWISGAYGDIVMSQSPSSLAVSAGEKVTMSCKSSQSLLNSRTRKNYLAWYQQKPGQSPKLLI
YWASTRESGVPDRFTGSGSGTDFTLTISSVQAEDLAVYYCKQSYNLRTFGGGTKLEIQRADAAPTVSIFPPSSE
QLTSGGASVVCFLNNFYPKDINVKWKIDGSERQNGVLNSWTDQDSKDSTYSMSSTLTLTKDEYERHNSYTCEAT
HKTSTSPIVKSFNRNEC Signal sequence (1-20), Variable region (21-134), Constant region (135-239)

FIG. 47

SEQ ID NO: 88: Nucleotide sequence encoding 17F6 antibody heavy chain
ccagcctccggactctagagccaccATGAAGCACCTGTGGTTCTTTCTGCTGCTGGTGGCCGCTCCCAGATGGG
TGCTGTCTCAGGTGCAGCTGCAGCAGTCTGGCGCCGAACTCGTGCGGCCTGGAAGCAGCGTGAAGATCAGCTGC
AAGGCCAGCGGCTACGCCTTCAGCAGCTACTGGATGAACTGGGTCAAGCAGCGGCCAGGCCAGGGCCTGGAATG
GATCGGCCATATCTATCCCGGCGACGCCGACACCAACTACAACGGCAAGTTCAAGGGCAAGGCCACCCTGACCG
CCGACAAGAGCAGCAGCACAGCCTACATGCACCTGTCCAGCCTGACCAGCGAGGACAGCGCCGTGTACTTCTGC
AGCCGGCAGCTGGGCTTCAGATACGCCATGGACTATTGGGGCCAGGGCACCAGCGTGACCGTGTCTAGCGCCAA
GACCACCCCCCCTAGCGTGTACCCTCTGGCCCCTGGATCTGCCGCCCAGACCAACAGCATGGTCACCCTGGGCT
GCCTCGTGAAGGGCTACTTCCCTGAGCCTGTGACCGTGACCTGGAACAGCGGCTCTCTGTCTAGCGGCGTGCAC
ACCTTTCCAGCCGTGCTGCAGAGCGACCTGTACACCCTGAGCAGCTCCGTGACAGTGCCCAGCTCTACCTGGCC
CAGCGAGACAGTGACCTGCAACGTGGCCCACCCTGCCAGCAGCACCAAGGTGGACAAGAAAATCGTGCCCCGGG
ACTGCGGCTGCAAGCCCTGTATCTGTACCGTGCCCGAGGTGTCCAGCGTGTTCATCTTCCCACCCAAGCCCAAG
GACGTGCTGACCATCACCCTGACACCCAAAGTGACCTGTGTGGTGGTGGACATCAGCAAGGACGACCCCGAGGT
GCAGTTCAGTTGGTTCGTGGACGACGTGGAAGTGCACACAGCCCAGACCCAGCCCAGAGAGGAACAGTTCAACA
GCACCTTCAGAAGCGTGTCCGAGCTGCCCATCATGCACCAGGACTGGCTGAACGGCAAAGAATTCAAGTGCAGA
GTGAACAGCGCCGCCTTCCCTGCCCCCATCGAGAAAACCATCTCCAAGACCAAGGGCAGACCCAAGGCCCCCCA
GGTGTACACAATCCCCCCACCCAAAGAACAGATGGCCAAGGACAAGGTGTCCCTGACCTGCATGATCACCGATT
TCTTCCCAGAGGACATCACCGTGGAATGGCAGTGGAACGGCCAGCCCGCCGAGAACTACAAGAACACCCAGCCT
ATCATGGACACCGACGGCAGCTACTTCGTGTACAGCAAGCTGAACGTGCAGAAGTCCAACTGGGAGGCCGGCAA
CACCTTCACCTGTAGCGTGCTGCACGAGGGCCTGCACAATCACCACACCGAGAAGTCCCTGTCCCACAGCCCCG
GCAAAtgagtttaaacgggggaggctaact Signal sequence (26-82), Variable region (83-439), Constant region (440-1411)

SEQ ID NO: 89: Amino acid sequence of 17F6 antibody heavy chain
MKHLWFFLLLVAAPRWVLSQVQLQQSGAELVRPGSSVKISCKASGYAFSSYWMNWVKQRPGQGLEWIGHIYPGD
ADTNYNGKFKGKATLTADKSSSTAYMHLSSLTSEDSAVYFCSRQLGFRYAMDYWGQGTSVTVSSAKTTPPSVYP
LAPGSAAQTNSMVTLGCLVKGYFPEPVTVTWNSGSLSSGVHTFPAVLQSDLYTLSSSVTVPSSTWPSETVTCNV
AHPASSTKVDKKIVPRDCGCKPCICTVPEVSSVFIFPPKPKDVLTITLTPKVTCVVVDISKDDPEVQFSWFVDD
VEVHTAQTQPREEQFNSTFRSVSELPIMHQDWLNGKEFKCRVNSAAFPAPIEKTISKTKGRPKAPQVYTIPPPK
EQMAKDKVSLTCMITDFFPEDITVEWQWNGQPAENYKNTQPIMDTDGSYFVYSKLNVQKSNWEAGNTFTCSVLH
EGLHNHHTEKSLSHSPGK Signal sequence (1-19), Variable region (20-138), Constant region (139-462)

FIG. 48

SEQ ID NO: 90: Nucleotide sequence encoding 17F6 antibody light chain
ccagcctccggactctagagccaccATGGTGCTGCAGACCCAGGTGTTCATCAGCCTGCTGCTGTGGATCAGCG
GCGCCTACGGCGACATCGTGATGAGCCAGAGCCCTAGCAGCCTGGCCGTGTCTGCCGGCGAGAAAGTGACCATG
AGCTGCAAGAGCAGCCAGTCCCTGCTGAACAGCCGGACCCGGAAGAACTACCTGGCCTGGTATCAGCAGAAGCC
CGGCCAGTCCCCCAAGCTGCTGATCTACTGGGCCAGCACCAGAGAAAGCGGCGTGCCCGATAGATTCACCGGCA
GCGGCTCTGGCACCGACTTCACCCTGACAATCAGCAGCGTGCAGGCCGAGGACCTGGCTGTGTACTACTGCAAG
CAGAGCTACAACCTGCGGACCTTCGGCGGAGGCACCAAGCTGGAAATCAAGAGAGCCGACGCCGCTCCCACCGT
GTCCATCTTTCCACCTAGCAGCGAGCAGCTGACCAGCGGCGGAGCTAGCGTCGTGTGCTTCCTGAACAACTTCT
ACCCCAAGGACATCAACGTGAAGTGGAAGATCGACGGCAGCGAGCGGCAGAACGGCGTGCTGAATAGCTGGACC
GACCAGGACAGCAAGGACTCCACCTACAGCATGTCCAGCACCCTGACCCTGACCAAGGACGAGTACGAGCGGCA
CAACAGCTACACATGCGAGGCCACCCACAAGACCAGCACCTCCCCCATCGTGAAGTCCTTCAACCGGAACGAGT
GCtgagtttaaacgggggaggctaact
Signal sequence (26-85), Variable region (86-427), Constant region (428-742)

SEQ ID NO: 91: Amino acid sequence of 17F6 antibody light chain
MVLQTQVFISLLLWISGAYGDIVMSQSPSSLAVSAGEKVTMSCKSSQSLLNSRTRKNYLAWYQQKPGQSPKLLI
YWASTRESGVPDRFTGSGSGTDFTLTISSVQAEDLAVYYCKQSYNLRTFGGGTKLEIKRADAAPTVSIFPPSSE
QLTSGGASVVCFLNNFYPKDINVKWKIDGSERQNGVLNSWTDQDSKDSTYSMSSTLTLTKDEYERHNSYTCEAT
HKTSTSPIVKSFNRNEC
Signal sequence (1-20), Variable region (21-134), Constant region (135-239)

FIG. 49

SEQ ID NO: 111: Nucleotide sequence encoding hR198_H0

ATGAAACACCTGTGGTTCTTCCTCCTGCTGGTGGCAGCTCCCAGATGGGTGCTGAGCCAGGTGCAGCTGGTGCA
GTCTGGCGCCGAAGTGAAGAAACCAGGCGCCAGCGTGAAGGTGTCCTGCAAGGCCTCTGGCTACCCCGTGACCA
GCTACTACATCAGCTGGATCAGACAGGCCCCAGGCCAGGGCCTGGAATGGATCGGCTATGTGGACATGGGCAAC
GGCCGGACCAACTACAACGAGAAGTTCAAGGGCAGAGCCACCCTGACCGTGGACAAGAGCACCAGCACCGCCTA
CATGGAACTGAGCAGCCTGCGGAGCGAGGACACCGCCGTGTACTACTGCGCCAGAGACAGCAACTGGGGCGTGG
ACTATTGGGGCCAGGGCACACTCGTGACCGTCAGCTCAGCCTCCACCAAGGGCCCAAGCGTCTTCCCCCTGGCA
CCCTCCTCCAAGAGCACCTCTGGCGGCACAGCCGCCCTGGGCTGCCTGGTCAAGGACTACTTCCCCGAACCCGT
GACCGTGAGCTGGAACTCAGGCGCCCTGACCAGCGGCGTGCACACCTTCCCCGCTGTCCTGCAGTCCTCAGGAC
TCTACTCCCTCAGCAGCGTGGTGACCGTGCCCTCCAGCAGCTTGGGCACCCAGACCTACATCTGCAACGTGAAT
CACAAGCCCAGCAACACCAAGGTGGACAAGAGAGTTGAGCCCAAATCTTGTGACAAAACTCACACATGCCCACC
CTGCCCAGCACCTGAACTCCTGGGGGACCCTCAGTCTTCCTCTTCCCCCCAAAACCCAAGGACACCCTCATGA
TCTCCCGGACCCCTGAGGTCACATGCGTGGTGGTGGACGTGAGCCACGAAGACCCTGAGGTCAAGTTCAACTGG
TACGTGGACGGCGTGGAGGTGCATAATGCCAAGACAAAGCCCCGGGAGGAGCAGTACAACAGCACGTACCGGGT
GGTCAGCGTCCTCACCGTCCTGCACCAGGACTGGCTGAATGGCAAGGAGTACAAGTGCAAGGTCTCCAACAAAG
CCCTCCCAGCCCCCATCGAGAAAACCATCTCCAAAGCCAAAGGCCAGCCCCGGGAACCACAGGTGTACACCCTG
CCCCCATCCCGGGAGGAGATGACCAAGAACCAGGTCAGCCTGACCTGCCTGGTCAAAGGCTTCTATCCCAGCGA
CATCGCCGTGGAGTGGGAGAGCAATGGCCAGCCCGAGAACAACTACAAGACCACCCCTCCCGTGCTGGACTCCG
ACGGCTCCTTCTTCCTCTACAGCAAGCTCACCGTGGACAAGAGCAGGTGGCAGCAGGGCAACGTCTTCTCATGC
TCCGTGATGCATGAGGCTCTGCACAACCACTACACCCAGAAGAGCCTCTCCCTGTCTCCGGCAAATGA

Signal sequence (1-57), Variable region (58-408), Constant region (409-1398)

SEQ ID NO: 112: Amino acid sequence of hR198_H0

MKHLWFFLLLVAAPRWVLSQVQLVQSGAEVKKPGASVKVSCKASGYPVTSYYISWIRQAPGQGLEWIGYVDMGN
GRTNYNEKFKGRATLTVDKSTSTAYMELSSLRSEDTAVYYCARDSNWGVDYWGQGTLVTVSSASTKGPSVFPLA
PSSKSTSGGTAALGCLVKDYFPEPVTVSWNSGALTSGVHTFPAVLQSSGLYSLSSVVTVPSSSLGTQTYICNVN
HKPSNTKVDKRVEPKSCDKTHTCPPCPAPELLGGPSVFLFPPKPKDTLMISRTPEVTCVVVDVSHEDPEVKFNW
YVDGVEVHNAKTKPREEQYNSTYRVVSVLTVLHQDWLNGKEYKCKVSNKALPAPIEKTISKAKGQPREPQVYTL
PPSREEMTKNQVSLTCLVKGFYPSDIAVEWESNGQPENNYKTTPPVLDSDGSFFLYSKLTVDKSRWQQGNVFSC
SVMHEALHNHYTQKSLSLSPGK

Signal sequence (1-19), Variable region (20-136), Constant region (137-466)

FIG. 50

SEQ ID NO: 113: Nucleotide sequence encoding hR198_H5
ATGAAACACCTGTGGTTCTTCCTCCTGCTGGTGGCAGCTCCCAGATGGGTGCTGAGCCAGGTGCAGCTGGTGCA
GTCTGGCGCCGAAGTGAAGAAACCAGGCGCCAGCGTGAAGGTGTCCTGCAAGGCCTCTGGCTACCCCGTGACCG
CCTACTACATCAGCTGGATCAGACAGGCCCCAGGCCAGGGCCTGGAATGGATCGGCTACATCGACATGGGCAAC
GGCCGGACCAACTACAACGCCCGGTTTAAGGGCAGAGCCACCCTGACCGTGGACAAGAGCACCAGCACCGCCTA
CATGGAACTGAGCAGCCTGCGGAGCGAGGACACCGCCGTGTACTACTGCGCCAGAGACAGCAACTGGGGCGTGG
ACTATTGGGGCCAGGGCACACTCGTGACCGTCAGCTCAGCCTCCACCAAGGGCCCAAGCGTCTTCCCCCTGGCA
CCCTCCTCCAAGAGCACCTCTGGCGGCACAGCCGCCCTGGGCTGCCTGGTCAAGGACTACTTCCCCGAACCCGT
GACCGTGAGCTGGAACTCAGGCGCCCTGACCAGCGGCGTGCACACCTTCCCCGCTGTCCTGCAGTCCTCAGGAC
TCTACTCCCTCAGCAGCGTGGTGACCGTGCCCTCCAGCAGCTTGGGCACCCAGACCTACATCTGCAACGTGAAT
CACAAGCCCAGCAACACCAAGGTGGACAAGAGAGTTGAGCCCAAATCTTGTGACAAAACTCACACATGCCCACC
CTGCCCAGCACCTGAACTCCTGGGGGACCCTCAGTCTTCCTCTTCCCCCCAAAACCCAAGGACACCCTCATGA
TCTCCCGGACCCCTGAGGTCACATGCGTGGTGGTGGACGTGAGCCACGAAGACCCTGAGGTCAAGTTCAACTGG
TACGTGGACGGCGTGGAGGTGCATAATGCCAAGACAAAGCCCCGGGAGGAGCAGTACAACAGCACGTACCGGGT
GGTCAGCGTCCTCACCGTCCTGCACCAGGACTGGCTGAATGGCAAGGAGTACAAGTGCAAGGTCTCCAACAAAG
CCCTCCCAGCCCCCATCGAGAAAACCATCTCCAAAGCCAAAGGCCAGCCCCGGGAACCACAGGTGTACACCCTG
CCCCCATCCCGGGAGGAGATGACCAAGAACCAGGTCAGCCTGACCTGCCTGGTCAAAGGCTTCTATCCCAGCGA
CATCGCCGTGGAGTGGGAGAGCAATGGCCAGCCCGAGAACAACTACAAGACCACCCCTCCCGTGCTGGACTCCG
ACGGCTCCTTCTTCCTCTACAGCAAGCTCACCGTGGACAAGAGCAGGTGGCAGCAGGGCAACGTCTTCTCATGC
TCCGTGATGCATGAGGCTCTGCACAACCACTACACCCAGAAGAGCCTCTCCCTGTCTCCCGGCAAATGA Signal sequence (1-57), Variable region (58-408), Constant region (409-1398)

SEQ ID NO: 114: Amino acid sequence of hR198_H5
MKHLWFFLLLVAAPRWVLSQVQLVQSGAEVKKPGASVKVSCKASGYPVTAYYISWIRQAPGQGLEWIGYIDMGN
GRTNYNARFKGRATLTVDKSTSTAYMELSSLRSEDTAVYYCARDSNWGVDYWGQGTLVTVSSASTKGPSVFPLA
PSSKSTSGGTAALGCLVKDYFPEPVTVSWNSGALTSGVHTFPAVLQSSGLYSLSSVVTVPSSSLGTQTYICNVN
HKPSNTKVDKRVEPKSCDKTHTCPPCPAPELLGGPSVFLFPPKPKDTLMISRTPEVTCVVVDVSHEDPEVKFNW
YVDGVEVHNAKTKPREEQYNSTYRVVSVLTVLHQDWLNGKEYKCKVSNKALPAPIEKTISKAKGQPREPQVYTL
PPSREEMTKNQVSLTCLVKGFYPSDIAVEWESNGQPENNYKTTPPVLDSDGSFFLYSKLTVDKSRWQQGNVFSC
SVMHEALHNHYTQKSLSLSPGK Signal sequence (1-19), Variable region (20-136), Constant region (137-466)

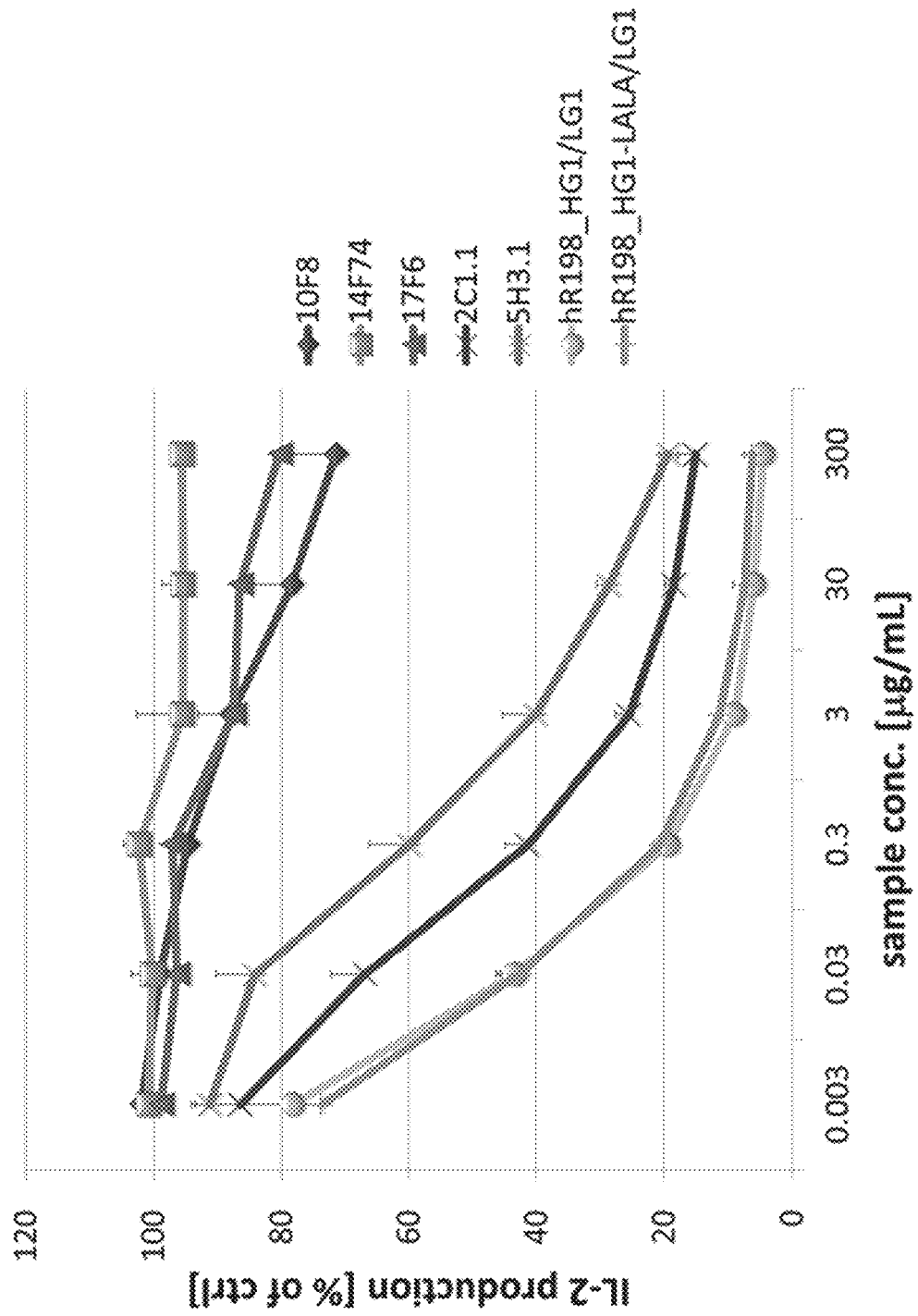

FIG. 52

| | IC$_{50}$ [ng/mL] | IC$_{80}$ [ng/mL] |
|---|---|---|
| 10F8 | >300000 | >300000 |
| 14F74 | >300000 | >300000 |
| 17F6 | >300000 | >300000 |
| 2C1.1 | 137 | 17572 |
| 5H3.1 | 950 | 250617 |
| hR198_HG1/LG1 | 19 | 282 |
| hR198_HG1-LALA/LG1 | 17 | 347 |

FIG. 54

| | $IC_{50}$ [ng/mL] | $IC_{80}$ [ng/mL] |
|---|---|---|
| 10F8 | >300000 | >300000 |
| 14F74 | >300000 | >300000 |
| 17F6 | >300000 | >300000 |
| 2C1.1 | 852 | >300000 |
| 5H3.1 | 3917 | >300000 |
| hR198_HG1/LG1 | 39 | 915 |
| hR198_HG1-LALA/LG1 | 33 | 1840 |

ANTI-ORAI1 ANTIBODY

CROSS-REFERENCE TO RELATED APPLICATIONS

This application is the National Stage of International Application No. PCT/JP2015/072305, filed Aug. 6, 2015, which claims priority to Japanese Patent Application No. 2014-161449, filed Aug. 7, 2014, each of which is incorporated herein by reference in its entirety.

TECHNICAL FIELD

The present invention relates to the provision of a more highly active anti-Orai1 antibody for the treatment of disorders and diseases.

STATEMENT REGARDING SEQUENCE LISTING

The sequence listing associated with this application is provided in text format in lieu of a paper copy and is hereby incorporated by reference into the specification.

BACKGROUND ART

Calcium release activated calcium (CRAC) channels are a subset of store-operated channels (SOC) which are opened in response to the depletion of calcium stored in the intracellular endoplasmic reticulum, and are responsible for the entry of extracellular calcium to particular non-excitable cells, particularly, cells of the immune system including T cells and mast cells, and the resulting activation of the cells. Inhibitors of CRAC channel activity are known in the art, and their identification and therapeutic potentials are described by Feske et al. (Non Patent Literature 1 and 2).

Orai1 (CRACM1: calcium release activated calcium modulator 1, transmembrane protein 142A: TMEM142A), a 4-pass transmembrane protein composed of 301 amino acid residues, has been identified as a component constituting the pore forming subunit of CRAC channels by forming a homotetramer (Patent Literature 1 and Non Patent Literature 3 to 5). The Orai gene family comprises the human Orai1 gene together with the human Orai2 and human Orai3 genes which each have 90% or higher homology to the human Orai1 gene (Non Patent Literature 6). In some cases, the possibility of forming a heterotetramer or a heterohexamer containing the Orai2 and/or Orai3 protein and Orai1 has also been reported (Non Patent Literature 7 and 8). Orai1 is constituted by N terminal and C terminal cytoplasmic regions which couple to STIM-1 (stromal interaction molecule 1) or STIM-2, which is a protein sensing the depletion of calcium stored in the intracellular endoplasmic reticulum, and 4 transmembrane domains, the first extracellular loop domain being composed of approximately 20 amino acid residues, and the second extracellular loop domain being composed of approximately 40 amino acid residues (Non Patent Literature 9). The DNA sequence and the amino acid sequence of Orai1 are available on a public database and can be referred to under, for example, Accession Nos. NM_032790 and NP_116179 (NCBI).

It has been found that a congenital defect in the function of the human Orai1 gene eliminates CRAC channel activity and cancels responses of the body to immunogens, resulting in severe immunodeficient conditions. Therefore, the molecular function of Orai1 has been proved essential for the activation of CRAC channels (Non Patent Literature 10 and 11). Thus, function blocking antibodies targeting the Orai1 molecule can serve as inhibitors of CRAC channel activity.

In the light of information suggesting that inhibitors of CRAC channel activity may be used for treating patients with immunological diseases, allergic diseases, inflammatory diseases, transplantation rejection of cells or organs, thrombosis, cancers, etc. (Non Patent Literature 12), attempts have been made to obtain anti-Orai1 antibodies with the aim of inhibiting the molecular function of Orai1, and their effects have been studied (Patent Literature 2 and 3 and Non Patent Literature 13 and 14). Although this literature indicates that each antibody alone inhibits the activation of T cells, the inhibitory activity is not yet sufficiently strong. The clinical application of these antibodies as biologics targeting Orai1 may not satisfy medical needs in terms of the need for high doses or frequent administration, limited administration methods, or the like.

CITATION LIST

Patent Literature

Patent Literature 1: International Publication No. WO07/081804
Patent Literature 2: International Publication No. WO11/063277
Patent Literature 3: International Publication No. WO13/091903

Non Patent Literature

Non Patent Literature 1: Feske S, Nature Rev. Immunol. 7, p. 690-702 (2007)
Non Patent Literature 2: Derler I, et al., Expert Opin. Drug Discovery 3 (7), p. 787-800 (2008)
Non Patent Literature 3: Prakriya M, et al., Nature 443, p. 230-233 (2006)
Non Patent Literature 4: Vig M, et al., Science 312, p. 1220-1223 (2006)
Non Patent Literature 5: Park C Y, et al., Cell 136, p. 876-890 (2008)
Non Patent Literature 6: Mercer J C, et al., J. Biol. Chem. 281, p. 24979-24990 (2006)
Non Patent Literature 7: Gwack Y, et al., J. Biol. Chem. 282, p. 16232-16243 (2007)
Non Patent Literature 8: Hou X, et al., Science 338, p. 1308-1313 (2012)
Non Patent Literature 9: Vig M, et al., Curr. Biol. 16, p. 2073-2079 (2006)
Non Patent Literature 10: Feske S, Nature 441, p. 179-185 (2006)
Non Patent Literature 11: McCarl C A, et al., J. Allergy Clin. Immunol. 124, p. 1311-1318 (2009)
Non Patent Literature 12: McCarl C A, et al., J. Immunol. 185, p. 5845-5858 (2010)
Non Patent Literature 13: Lin F, et al., J. Pharmacol. Exp. Ther. 345, p. 225-238 (2013)
Non Patent Literature 14: Cox J H, et al., PLOS ONE 8 (12), e82944 (2013)

SUMMARY OF INVENTION

Technical Problem

An object of the present invention is to provide a therapeutic and/or prophylactic agent for transplant rejections, immunological diseases, allergic diseases, inflammatory diseases, thrombosis, cancers, etc.

Solution to Problem

The present inventors have obtained rat anti-Orai1 antibodies for the purpose of searching for substances having a therapeutic and/or prophylactic effect on transplant rejections, immunological diseases, allergic diseases, inflammatory diseases, thrombosis, or cancers. The obtained rat anti-Orai1 antibodies have been humanized, and the CDRs, frameworks, and variable regions of the humanized antibodies have been engineered. In this way, the present invention has been completed.

Specifically, the present invention encompasses the following aspects:

(1) An antibody or an antigen binding fragment of the antibody which specifically binds to the amino acid sequence represented by SEQ ID NO: 2, wherein the heavy chain sequence comprises a variable region having CDRH1, CDRH2, and CDRH3, wherein the CDRH1 consists of the amino acid sequence represented by SEQ ID NO: 102, the CDRH2 consists of an amino acid sequence represented by any one of SEQ ID NOs: 104, 106, 107, and 108, and the CDRH3 consists of an amino acid sequence represented by SEQ ID NO: 109 or 110; and
the light chain sequence comprises a variable region having CDRL1, CDRL2, and CDRL3, wherein the CDRL1 consists of an amino acid sequence represented by any one of SEQ ID NOs: 93, 94, and 95, the CDRL2 consists of an amino acid sequence represented by any one of SEQ ID NOs: 96, 97, and 98, and the CDRL3 consists of the amino acid sequence represented by SEQ ID NO: 101.

(2) The antibody or the antigen binding fragment of the antibody according to (1), wherein the heavy chain sequence comprises a variable region having CDRH1, CDRH2, and CDRH3, wherein the CDRH1 consists of the amino acid sequence represented by SEQ ID NO: 102, the CDRH2 consists of the amino acid sequence represented by SEQ ID NO: 106, and the CDRH3 consists of the amino acid sequence represented by SEQ ID NO: 110; and
the light chain sequence comprises a variable region having CDRL1, CDRL2, and CDRL3, wherein the CDRL1 consists of the amino acid sequence represented by SEQ ID NO: 93, the CDRL2 consists of the amino acid sequence represented by SEQ ID NO: 96, and the CDRL3 consists of the amino acid sequence represented by SEQ ID NO: 101.

(3) The antibody or the antigen binding fragment of the antibody according to (1), wherein the heavy chain sequence comprises a variable region having CDRH1, CDRH2, and CDRH3, wherein the CDRH1 consists of the amino acid sequence represented by SEQ ID NO: 102, the CDRH2 consists of the amino acid sequence represented by SEQ ID NO: 106, and the CDRH3 consists of the amino acid sequence represented by SEQ ID NO: 110; and the light chain sequence comprises a variable region having CDRL1, CDRL2, and CDRL3, wherein the CDRL1 consists of the amino acid sequence represented by SEQ ID NO: 94, the CDRL2 consists of the amino acid sequence represented by SEQ ID NO: 97, and the CDRL3 consists of the amino acid sequence represented by SEQ ID NO: 101.

(4) The antibody or the antigen binding fragment of the antibody according to (1), wherein the heavy chain sequence comprises a variable region having CDRH1, CDRH2, and CDRH3, wherein the CDRH1 consists of the amino acid sequence represented by SEQ ID NO: 102, the CDRH2 consists of the amino acid sequence represented by SEQ ID NO: 106, and the CDRH3 consists of the amino acid sequence represented by SEQ ID NO: 110; and
the light chain sequence comprises a variable region having CDRL1, CDRL2, and CDRL3, wherein the CDRL1 consists of the amino acid sequence represented by SEQ ID NO: 95, the CDRL2 consists of the amino acid sequence represented by SEQ ID NO: 98, and the CDRL3 consists of the amino acid sequence represented by SEQ ID NO: 101.

(5) The antibody or the antigen binding fragment of the antibody according to (1), wherein the heavy chain sequence comprises a variable region having CDRH1, CDRH2, and CDRH3, wherein the CDRH1 consists of the amino acid sequence represented by SEQ ID NO: 102, the CDRH2 consists of the amino acid sequence represented by SEQ ID NO: 107, and the CDRH3 consists of the amino acid sequence represented by SEQ ID NO: 110; and
the light chain sequence comprises a variable region having CDRL1, CDRL2, and CDRL3, wherein the CDRL1 consists of the amino acid sequence represented by SEQ ID NO: 93, the CDRL2 consists of the amino acid sequence represented by SEQ ID NO: 96, and the CDRL3 consists of the amino acid sequence represented by SEQ ID NO: 101.

(6) The antibody or the antigen binding fragment of the antibody according to (1), wherein the heavy chain sequence comprises a variable region having CDRH1, CDRH2, and CDRH3, wherein the CDRH1 consists of the amino acid sequence represented by SEQ ID NO: 102, the CDRH2 consists of the amino acid sequence represented by SEQ ID NO: 108, and the CDRH3 consists of the amino acid sequence represented by SEQ ID NO: 110; and
the light chain sequence comprises a variable region having CDRL1, CDRL2, and CDRL3, wherein the CDRL1 consists of the amino acid sequence represented by SEQ ID NO: 93, the CDRL2 consists of the amino acid sequence represented by SEQ ID NO: 96, and the CDRL3 consists of the amino acid sequence represented by SEQ ID NO: 101.

(7) The antibody or the antigen binding fragment of the antibody according to (1), wherein the heavy chain sequence comprises a variable region having CDRH1, CDRH2, and CDRH3, wherein the CDRH1 consists of the amino acid sequence represented by SEQ ID NO: 102, the CDRH2 consists of the amino acid sequence represented by SEQ ID NO: 104, and the CDRH3 consists of the amino acid sequence represented by SEQ ID NO: 109; and
the light chain sequence comprises a variable region having CDRL1, CDRL2, and CDRL3, wherein the CDRL1 consists of the amino acid sequence represented by SEQ ID NO: 93, the CDRL2 consists of the amino acid sequence represented by SEQ ID NO: 96, and the CDRL3 consists of the amino acid sequence represented by SEQ ID NO: 101.

(8) The antibody or the antigen binding fragment of the antibody according to (1) or (2), wherein the antibody comprises a heavy chain variable region sequence consisting of amino acid residues from positions 20 to 136 in the amino acid sequence represented by SEQ ID NO: 62 and a light chain variable region sequence consisting of amino acid residues from positions 21 to 126 in the amino acid sequence represented by SEQ ID NO: 56.

(9) The antibody or the antigen binding fragment of the antibody according to (8), wherein the antibody consists of a heavy chain sequence consisting of amino acid residues from positions 20 to 465 or 20 to 466 in the amino acid sequence represented by SEQ ID NO: 62 and a light chain sequence consisting of amino acid residues from positions 21 to 234 in the amino acid sequence represented by SEQ ID NO: 56.

(10) The antibody or the antigen binding fragment of the antibody according to (8), wherein the antibody consists of a heavy chain sequence consisting of amino acid residues from positions 20 to 465 or 20 to 466 in the amino acid sequence represented by SEQ ID NO: 70 and a light chain sequence consisting of amino acid residues from positions 21 to 234 in the amino acid sequence represented by SEQ ID NO: 56.
(11) The antibody or the antigen binding fragment of the antibody according to (1) or (3), wherein the antibody comprises a heavy chain variable region sequence consisting of amino acid residues from positions 20 to 136 in the amino acid sequence represented by SEQ ID NO: 62 and a light chain variable region sequence consisting of amino acid residues from positions 21 to 126 in the amino acid sequence represented by SEQ ID NO: 58.
(12) The antibody or the antigen binding fragment of the antibody according to (11), wherein the antibody consists of a heavy chain sequence consisting of amino acid residues from positions 20 to 465 or 20 to 466 in the amino acid sequence represented by SEQ ID NO: 62 and a light chain sequence consisting of amino acid residues from positions 21 to 234 in the amino acid sequence represented by SEQ ID NO: 58.
(13) The antibody or the antigen binding fragment of the antibody according to (1) or (4), wherein the antibody comprises a heavy chain variable region sequence consisting of amino acid residues from positions 20 to 136 in the amino acid sequence represented by SEQ ID NO: 62 and a light chain variable region sequence consisting of amino acid residues from positions 21 to 126 in the amino acid sequence represented by SEQ ID NO: 60.
(14) The antibody or the antigen binding fragment of the antibody according to (13), wherein the antibody consists of a heavy chain sequence consisting of amino acid residues from positions 20 to 465 or 20 to 466 in the amino acid sequence represented by SEQ ID NO: 62 and a light chain sequence consisting of amino acid residues from positions 21 to 234 in the amino acid sequence represented by SEQ ID NO: 60.
(15) The antibody or the antigen binding fragment of the antibody according to (1) or (5), wherein the antibody comprises a heavy chain variable region sequence consisting of amino acid residues from positions 20 to 136 in the amino acid sequence represented by SEQ ID NO: 64 and a light chain variable region sequence consisting of amino acid residues from positions 21 to 126 in the amino acid sequence represented by SEQ ID NO: 56.
(16) The antibody or the antigen binding fragment of the antibody according to (15), wherein the antibody consists of a heavy chain sequence consisting of amino acid residues from positions 20 to 465 or 20 to 466 in the amino acid sequence represented by SEQ ID NO: 64 and a light chain sequence consisting of amino acid residues from positions 21 to 234 in the amino acid sequence represented by SEQ ID NO: 56.
(17) The antibody or the antigen binding fragment of the antibody according to (1) or (6), wherein the antibody comprises a heavy chain variable region sequence consisting of amino acid residues from positions 20 to 136 in the amino acid sequence represented by SEQ ID NO: 66 and a light chain variable region sequence consisting of amino acid residues from positions 21 to 126 in the amino acid sequence represented by SEQ ID NO: 56.
(18) The antibody or the antigen binding fragment of the antibody according to (17), wherein the antibody consists of a heavy chain sequence consisting of amino acid residues from positions 20 to 465 or 20 to 466 in the amino acid sequence represented by SEQ ID NO: 66 and a light chain sequence consisting of amino acid residues from positions 21 to 234 in the amino acid sequence represented by SEQ ID NO: 56.
(19) The antibody or the antigen binding fragment of the antibody according to (1) or (7), wherein the antibody comprises a heavy chain variable region sequence consisting of amino acid residues from positions 20 to 136 in the amino acid sequence represented by SEQ ID NO: 43 and a light chain variable region sequence consisting of amino acid residues from positions 21 to 126 in the amino acid sequence represented by SEQ ID NO: 56.
(20) The antibody or the antigen binding fragment of the antibody according to (19), wherein the antibody consists of a heavy chain sequence consisting of amino acid residues from positions 20 to 465 or 20 to 466 in the amino acid sequence represented by SEQ ID NO: 43 and a light chain sequence consisting of amino acid residues from positions 21 to 235 in the amino acid sequence represented by SEQ ID NO: 56.
(21) The antigen binding fragment of the antibody according to any one of (1) to (20), wherein the antigen binding fragment is selected from the group consisting of Fab, F(ab')2, Fab', and Fv.
(22) The antibody according to any one of (1) to (8), (11), (13), (15), (17), and (19), wherein the antibody is an scFv.
(23) A pharmaceutical composition comprising at least any one antibody or antigen binding fragment of the antibody according to (1) to (22).
(24) The pharmaceutical composition according to (23), wherein the pharmaceutical composition is a therapeutic and/or prophylactic agent for transplant rejections, immune-related diseases, allergic diseases, inflammatory diseases, or cancers, an antiplatelet or antithrombotic activator, or an inhibitor of Orai1-expressing-cell activation.
(25) The pharmaceutical composition according to (24), wherein the transplant rejections are rejection responses and host versus graft reactions to the transplantation of an organ or a tissue such as the heart, the kidney, the liver, the bone marrow, or the skin, and graft versus host disease caused by the transplantation of hematopoietic cells (bone marrow, peripheral blood, umbilical cord blood, etc.).
(26) The pharmaceutical composition according to (24), wherein the immune-related diseases are connective tissue or musculoskeletal diseases (rheumatoid arthritis, ankylosing spondylitis, systemic lupus erythematosus, scleroderma, polymyositis, dermatomyositis, etc.), hematological diseases (aplastic anemia, idiopathic thrombocytopenic purpura, etc.), gastrointestinal diseases (Crohn disease, ulcerative colitis, etc.), neurological diseases (multiple sclerosis, myasthenia gravis, etc.), ophthalmic diseases (uveitis, etc.), vascular diseases (Behcet's disease, Wegener's granulomatosis, etc.), epidermal diseases (psoriasis, pemphigus, leukoderma, etc.), endocrine diseases (type 1 diabetes mellitus, autoimmune thyroiditis, Graves' disease, Hashimoto's disease, etc.), and the like, the allergic diseases are atopic dermatitis, asthma, anaphylaxis, anaphylactoid reaction, food allergy, rhinitis, otitis media, drug reaction, insect bite reaction, reaction to plants, latex allergy, conjunctivitis, urticaria, and the like, and the inflammatory diseases are inflammatory renal diseases (glomerulonephritis, nephrosis, etc.), inflammatory pulmonary diseases (chronic obstructive pulmonary disease, cystic fibrosis, interstitial pneumonia, etc.), inflammatory bowel diseases (ulcerative colitis, ileitis, etc.), inflammatory hepatic diseases (autoimmune hepatitis, viral hepatitis, etc.), inflammatory cardiac diseases (myocarditis, ischemic heart disease, atherosclerosis, etc.), inflammatory skin diseases (contact dermatitis, eczema, etc.), inflammatory eye diseases (trachoma, endophthalmitis, etc.), inflammatory central nervous diseases (meningitis, encephalomyelitis, autoimmune encephalitis, etc.), inflammatory joint diseases (arthritis, osteoarthritis, etc.), systemic inflammations (sepsis, bleeding, hypersensitivity, shock symptoms attributed to cancer chemotherapy or the like, etc.), and the like.

(27) The pharmaceutical composition according to (24), wherein the cancers are breast cancer, lung cancer, skin cancer, leukemia, and the like, and cases in which the antiplatelet or antithrombotic activity is useful for treatment and/or prevention are myocardial infarction, stroke, ischemic heart diseases, thrombosis, and the like, and cases in which the inhibition of Orai1 expressing cell activation is useful for treatment and/or prevention are mast cell leukemia, mastocytosis, basophilic leukemia, endometriosis, tubular aggregate myopathy, Stormorken syndrome, rheumatoid arthritis, ankylosing spondylitis, atopic dermatitis, and the like.

(28) A polynucleotide encoding an antibody or an antigen binding fragment of the antibody according to any one of (1) to (22).

(29) A vector comprising a polynucleotide according to (28).

(30) A transformed host cell comprising a polynucleotide according to (28).

(31) A transformed host cell comprising a vector according to (29).

(32) A method for producing an antibody or an antigen binding fragment of the antibody according to any one of (1) to (22), comprising the step of culturing a host cell according to (30) or (31) and purifying an antibody from the culture product.

(33) An antibody or an antigen binding fragment of the antibody which specifically binds to the amino acid sequence represented by SEQ ID NO: 2, wherein the concentration at which the amount of IL-2 released from Jurkat cells treated with PMA and A23187 is inhibited by 50% is 80 ng/mL or lower.

(34) The antibody or the antigen binding fragment of the antibody according to (33), wherein the concentration at which the amount of IL-2 released from Jurkat cells treated with PMA and A23187 is inhibited by 50% is 10 ng/mL or lower.

(35) An antibody or an antigen binding fragment of the antibody which specifically binds to the amino acid sequence represented by SEQ ID NO: 2, wherein the concentration at which the amount of IL-2 released from human peripheral blood mononuclear cells (PBMC) treated with PMA and A23187 is inhibited by 50% is 100 ng/mL or lower.

(36) The antibody or the antigen binding fragment of the antibody according to (35), wherein the concentration at which the amount of IL-2 released from human PBMC treated with PMA and A23187 is inhibited by 50% is 20 ng/mL or lower.

(37) An antibody or an antigen binding fragment of the antibody which specifically binds to the amino acid sequence represented by SEQ ID NO: 2, wherein the concentration at which the amount of IFN-7 released from human PBMC treated with PMA and A23187 is inhibited by 50% is 800 ng/mL or lower.

(38) The antibody or the antigen binding fragment of the antibody according to (37), wherein the concentration at which the amount of IFN-7 released from human PBMC treated with PMA and A23187 is inhibited by 50% is 40 ng/mL or lower.

Advantageous Effects of Invention

According to the present invention, a therapeutic and/or prophylactic agent for transplant rejections, immunological diseases, allergic diseases, inflammatory diseases, thrombosis, or cancers based on the inhibition of CRAC channel activity as the mechanism of action can be obtained.

BRIEF DESCRIPTION OF DRAWINGS

FIG. 13 is a diagram showing the half maximal inhibitory concentrations ($IC_{50}$) and the 80% inhibitory concentrations ($IC_{80}$) of hR198_HG1/LG1, hR198_HG1-LALA/LG1, 2C1.1, 5H3.1, 10F8, 14F74, and 17F6 against IL-2 release from Jurkat cells.

FIG. 14 is a diagram showing a nucleotide sequence encoding a R118 light chain variable region and an amino acid sequence of the variable region.

FIG. 15 is a diagram showing a nucleotide sequence encoding a R118 heavy chain variable region and an amino acid sequence of the variable region.

FIG. 16 is a diagram showing a nucleotide sequence encoding a R198 light chain variable region and an amino acid sequence of the variable region.

FIG. 17 is a diagram showing a nucleotide sequence encoding a R198 heavy chain variable region and an amino acid sequence of the variable region.

FIG. 18 is a diagram showing a nucleotide sequence encoding a human chimerized cR118 light chain and an amino acid sequence of the light chain.

FIG. 19 is a diagram showing a nucleotide sequence encoding a human chimerized cR198 light chain and an amino acid sequence of the light chain.

FIG. 20 is a diagram showing a nucleotide sequence encoding a human chimerized cR118 heavy chain and an amino acid sequence of the heavy chain.

FIG. 21 is a diagram showing a nucleotide sequence encoding a human chimerized cR198 heavy chain and an amino acid sequence of the heavy chain.

FIG. 22 is a diagram showing a nucleotide sequence encoding a hR198_L1 type light chain and an amino acid sequence of the light chain.

FIG. 23 is a diagram showing a nucleotide sequence encoding a hR198_L2 type light chain and an amino acid sequence of the light chain.

FIG. 24 is a diagram showing a nucleotide sequence encoding a hR198_L3 type light chain and an amino acid sequence of the light chain.

FIG. 25 is a diagram showing a nucleotide sequence encoding a hR198_L4 type light chain and an amino acid sequence of the light chain.

FIG. 26 is a diagram showing a nucleotide sequence encoding a hR198_H1 type heavy chain and an amino acid sequence of the heavy chain.

FIG. 27 is a diagram showing a nucleotide sequence encoding a hR198_H2 type heavy chain and an amino acid sequence of the heavy chain.

FIG. 28 is a diagram showing a nucleotide sequence encoding a hR198_H3 type heavy chain and an amino acid sequence of the heavy chain.

FIG. 29 is a diagram showing a nucleotide sequence encoding a hR198_H4 type heavy chain and an amino acid sequence of the heavy chain.

FIG. 30 is a diagram showing a nucleotide sequence encoding a hR198_LG1 type light chain and an amino acid sequence of the light chain.

FIG. 31 is a diagram showing a nucleotide sequence encoding a hR198_LG2 type light chain and an amino acid sequence of the light chain.

FIG. 32 is a diagram showing a nucleotide sequence encoding a hR198_LG3 type light chain and an amino acid sequence of the light chain.

FIG. 33 is a diagram showing a nucleotide sequence encoding a hR198_HG1 type heavy chain and an amino acid sequence of the heavy chain.

FIG. 34 is a diagram showing a nucleotide sequence encoding a hR198_HG2 type heavy chain and an amino acid sequence of the heavy chain.

FIG. 35 is a diagram showing a nucleotide sequence encoding a hR198_HG3 type heavy chain and an amino acid sequence of the heavy chain.

FIG. 36 is a diagram showing a nucleotide sequence encoding a hR198_H4-LALA type heavy chain and an amino acid sequence of the heavy chain.

FIG. 37 is a diagram showing a nucleotide sequence encoding a hR198_HG1-LALA type heavy chain and an amino acid sequence of the heavy chain.

FIG. 38 is a diagram showing SEQ ID NOs corresponding to CDR sequences contained in each of cR118, cR198, hR198_L1 to hR198_L4, and hR198_LG1 to hR198_LG3 light chains and each of cR118, cR198, hR198_H1 to hR198_H4, hR198_HG1 to hR198_HG3, hR198_H4-LALA, and hR198_HG1-LALA heavy chains.

FIG. 39 is a diagram showing a nucleotide sequence encoding a 2C1.1 antibody heavy chain and an amino acid sequence of the heavy chain.

FIG. 40 is a diagram showing a nucleotide sequence encoding a 2C1.1 antibody light chain and an amino acid sequence of the light chain.

FIG. 41 is a diagram showing a nucleotide sequence encoding a 5H3.1 antibody heavy chain and an amino acid sequence of the heavy chain.

FIG. 42 is a diagram showing a nucleotide sequence encoding a 5H3.1 antibody light chain and an amino acid sequence of the light chain.

FIG. 43 is a diagram showing a nucleotide sequence encoding a 10F8 antibody heavy chain and an amino acid sequence of the heavy chain.

FIG. 44 is a diagram showing a nucleotide sequence encoding a 10F8 antibody light chain and an amino acid sequence of the light chain.

FIG. 45 is a diagram showing a nucleotide sequence encoding a 14F74 antibody heavy chain and an amino acid sequence of the heavy chain.

FIG. 46 is a diagram showing a nucleotide sequence encoding a 14F74 antibody light chain and an amino acid sequence of the light chain.

FIG. 47 is a diagram showing a nucleotide sequence encoding a 17F6 antibody heavy chain and an amino acid sequence of the heavy chain.

FIG. 48 is a diagram showing a nucleotide sequence encoding a 17F6 antibody light chain and an amino acid sequence of the light chain.

FIG. 49 is a diagram showing a nucleotide sequence encoding a hR198_H0 type heavy chain and an amino acid sequence of the heavy chain.

FIG. 50 is a diagram showing a nucleotide sequence encoding a hR198_H5 type heavy chain and an amino acid sequence of the heavy chain.

FIG. 51 is a diagram showing that the anti-Orai1 monoclonal antibodies each inhibit, in a concentration dependent manner, the release of IL-2 from human PBMC treated with PMA and A23187.

FIG. 52 is a diagram showing the half maximal inhibitory concentrations ($IC_{50}$) and the 80% inhibitory concentrations ($IC_{80}$) of hR198_HG1/LG1, hR198_HG1-LALA/LG1, 2C1.1, 5H3.1, 10F8, 14F74, and 17F6 against IL-2 release from human PBMC.

FIG. 54 is a diagram showing the half maximal inhibitory concentrations ($IC_{50}$) and the 80% inhibitory concentrations (IC$_{80}$) of hR198_HG1/LG1, hR198_HG1-LALA/LG1, 2C1.1, 5H3.1, 10F8, 14F74, and 17F6 against IFN-γ release from human PBMC.

DESCRIPTION OF EMBODIMENTS

Figure 1:
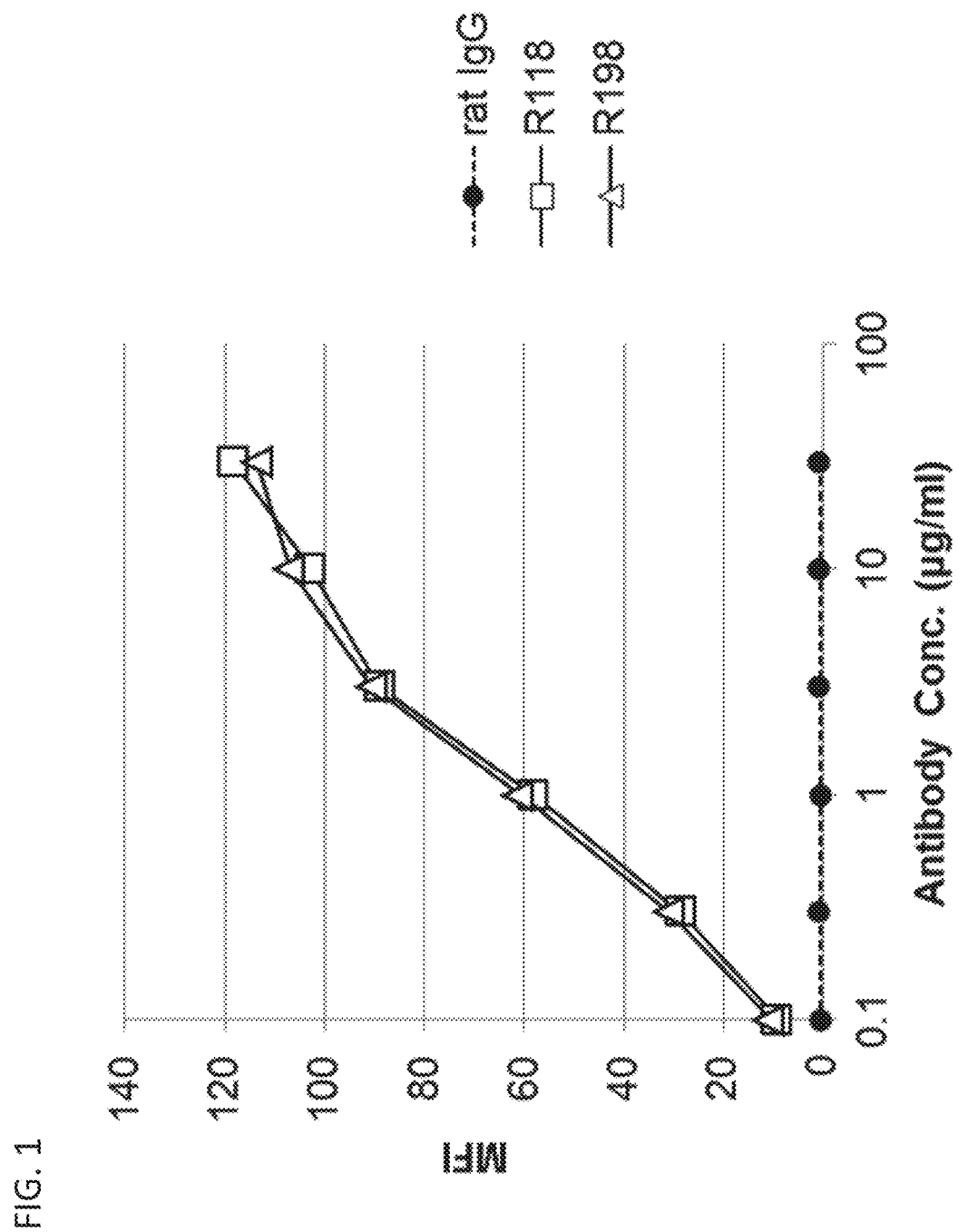
FIG. 1 is a diagram showing that R118 and R198 each bind to pcDNA3.1-hOrai1 transfected HEK293T cells in a concentration dependent manner.

In the present specification, the term "gene" includes not only DNA but mRNA, cDNA, and cRNA.

In the present specification, the term "polynucleotide" is used with the same meaning as a nucleic acid and also includes DNA, RNA, probes, oligonucleotides, and primers.

In the present specification, the term "polypeptide" and the term "protein" are used interchangeably with each other.

In the present specification, the term "RNA fraction" refers to a fraction containing RNA.

In the present specification, the term "cell" includes cells within individual animal and cultured cells.

In the present specification, the term "Orai1" is used with the same meaning as Orai1 protein.

In the present specification, the term "antigen binding fragment of the antibody" means a partial fragment of the antibody having binding activity against the antigen and includes Fab, F(ab')2, Fv, scFv, diabodies, linear antibodies, and multispecific antibodies formed from antibody fragments, etc. The antigen binding fragment of the antibody also includes Fab', which is a monovalent fragment of antibody variable regions obtained by the treatment of F(ab')2 under reducing conditions. However, the antigen binding fragment of the antibody is not limited to these molecules as long as the antigen binding fragment has the ability to bind to the antigen. Such an antigen binding fragment includes not only a fragment obtained by treating a full length molecule of the antibody protein with an appropriate enzyme but also a protein produced in appropriate host cells using a genetically engineered antibody gene.

The heavy and light chains of an antibody molecule are known to each have three complementarity determining regions (CDRs). The complementarity determining regions are also called hypervariable domains. These regions are located in the variable regions of the antibody heavy and light chains. These sites have a particularly highly variable primary structure and are separated at three positions on the respective primary structures of heavy and light chain polypeptide chains. In the present specification, the complementarity determining regions of the antibody are referred to as CDRH1, CDRH2, and CDRH3 from the amino terminus of the heavy chain amino acid sequence for the complementarity determining regions of the heavy chain and as CDRL1, CDRL2, and CDRL3 from the amino terminus of the light chain amino acid sequence for the complementarity determining regions of the light chain. These sites are proximal to each other on the three-dimensional structure and determine specificity for the antigen to be bound.

In the present invention, the phrase "hybridizing under stringent conditions" means hybridization under conditions involving hybridization at 68° C. in a commercially available hybridization solution ExpressHyb Hybridization Solution (Clontech Laboratories, Inc.), or hybridization at 68° C. in the presence of 0.7 to 1.0 M NaCl using a DNA immobilized filter, followed by washing at 68° C. using an SSC solution having a 0.1 to 2× concentration (SSC having a 1× concentration consists of 150 mM NaCl and 15 mM sodium citrate) which permits identification, or hybridization under conditions equivalent thereto.

In the present invention, the term "host versus graft reaction" refers to the hyperimmune state of a recipient observed after organ transplantation, and damage to the transplanted organ resulting therefrom.

In the present invention, the term "graft versus host disease" refers to symptoms manifested by the immunological attack of a recipient by transplanted cells after hematopoietic cell transplantation.

1. Orai1

Orai1 used in the present invention can be directly purified from T cells or mast cells of a human, a nonhuman mammal (e.g., a guinea pig, a rat, a mouse, a rabbit, a pig, a sheep, cattle, or a monkey), or a chicken, or can be used in a cell membrane fraction prepared from the cells. Alternatively, Orai1 can be synthesized in vitro or obtained by production from host cells by gene manipulation. In such gene manipulation, specifically, Orai1 cDNA is inserted into a vector that permits expression, and then Orai1 can be synthesized in a solution containing an enzyme, a substrate, and an energy substance necessary for transcription and translation, or expressed by transformation of host cells of a different prokaryote or eukaryote to obtain the protein.

The nucleotide sequence of human Orai1 cDNA is registered under Accession No: NM_032790 in GenBank. The nucleotide sequence of mouse Orai1 cDNA is registered under Accession No: NM_175423 in GenBank. The nucleotide sequence encoding human Orai1 is shown in SEQ ID NO: 1 of the Sequence Listing, and the amino acid sequence of human Orai1 is shown in SEQ ID NO: 2 of the Sequence Listing. Orai1 is also called calcium release activated calcium modulator 1 (CRACM1) or transmembrane protein 142A (TMEM142A), all of which indicate the same molecule.

The Orai1 cDNA can be obtained by a so-called PCR method which involves carrying out polymerase chain reaction (hereinafter, referred to as "PCR") (Saiki, R. K., et al., Science, (1988) 239, 487-49), for example, with a cDNA library of organs expressing Orai1 mRNA as a template using primers specifically amplifying the Orai1 cDNA.

The term "Orai1 cDNA" also includes a polynucleotide that hybridizes under stringent conditions to a polynucleotide consisting of a nucleotide sequence complementary to the nucleotide sequence encoding human or mouse Orai1 and that encodes a protein having biological activity equivalent to Orai1. The term "Orai1 cDNA" further includes a cDNA for a splicing variant that has been transcribed from the human or mouse Orai1 gene locus or a polynucleotide that hybridizes under stringent conditions to a polynucleotide consisting of a nucleotide sequence complementary to the splicing variant, and that encodes a protein having biological activity equivalent to Orai1.

The term "Orai1" also includes a protein that consists of an amino acid sequence derived from the amino acid sequence of human or mouse Orai1 or an amino acid sequence thereof free from the signal sequence by the substitution, deletion, or addition of 1, 2 or 3, or 4 or 5 amino acids, and has biological activity equivalent to Orai1. The term "Orai1" further comprises a protein that consists of an amino acid sequence encoded by a splicing variant transcribed from the human or mouse Orai1 gene locus, or an amino acid sequence derived from this amino acid sequence by the substitution, deletion, or addition of 1, 2 or 3, or 4 or 5 amino acids, and has biological activity equivalent to Orai1.

2. Production of Anti-Orai1 Antibody

The antibody against Orai1 of the present invention can be obtained according to routine methods by immunizing an animal with Orai1 or an arbitrary polypeptide selected from the amino acid sequence of Orai1 and collecting and purifying the antibody produced in vivo. The species for Orai1 used as an antigen is not limited to a human, and the animal may be immunized with Orai1 derived from a nonhuman animal such as a mouse or a rat. In this case, the obtained antibody binding to the heterologous Orai1 can be tested for its cross-reactivity with human Orai1 to select an antibody applicable to human diseases. The antigen Orai1 can be obtained by allowing host cells to produce the Orai1 gene by gene manipulation. Specifically, a vector that permits expression of the Orai1 gene is prepared and transferred to host cells to express the gene. The expressed Orai1 can be purified.

The antibody against Orai1 of the present invention can also be obtained by use of a DNA immunization method. The DNA immunization method is an approach which involves transfecting an animal (e.g., mouse or rat) with an antigen expression plasmid and expressing the antigen in the animal to induce immunity against the antigen. The transfection approach includes a method of directly injecting the plasmid into muscle, a method of injecting a complex of the plasmid and a liposome, polyethylenimine, or the like into a vein, an approach using a viral vector, an approach of injecting gold particles attached to the plasmid using a gene gun, a hydrodynamic method of rapidly injecting a plasmid solution in a large amount into a vein, and the like. A technique called in vivo electroporation, which involves applying electroporation to a site given the intramuscularly injected plasmid, is known as an approach for improving the expression level of the transfection method of injecting the expression plasmid into muscle (Aihara H, Miyazaki J., Nat Biotechnol. 1998 September; 16 (9): 867-70 or Mir L M, Bureau M F, Gehl J, Rangara R, Rouy D, Caillaud J M, Delaere P, Branellec D, Schwartz B, Scherman D., Proc Natl Acad Sci USA. 1999 Apr. 13; 96 (8): 4262-7). This approach further improves the expression level by treating the muscle with hyaluronidase before the intramuscular injection of the plasmid (McMahon JM1, Signori E, Wells K E, Fazio V M, Wells D J., Gene Ther. 2001 August; 8 (16): 1264-70).

A monoclonal antibody can also be obtained according to methods known in the art (e.g., Kohler and Milstein, Nature (1975) 256, p. 495-497; and Kennet, R. ed., Monoclonal Antibodies, p. 365-367, Plenum Press, N.Y. (1980)) by fusing antibody-producing cells that produce the antibody against Orai1 with myeloma cells to establish hybridomas. Specific examples of such a method are described in International Publication Nos. WO09/48072 (published on Apr. 16, 2009) and WO10/117011 (published on Oct. 14, 2010).

Actual examples of the rat anti-human Orai1 antibody thus established can include R118 and R198 antibodies. The amino acid sequence of the light chain variable region of the R118 antibody is shown in SEQ ID NO: 11 of the Sequence Listing, and the sequence of the heavy chain variable region of the R118 antibody is shown in SEQ ID NO: 13 of the Sequence Listing. The amino acid sequence of the light chain variable region of the R198 antibody is shown in SEQ ID NO: 15 of the Sequence Listing, and the sequence of the heavy chain variable region of the R198 antibody is shown in SEQ ID NO: 17 of the Sequence Listing.

The antibody of the present invention includes the monoclonal antibody against Orai1 described above as well as a recombinant antibody artificially engineered for the purpose of, for example, reducing heterogeneous antigenicity against humans, for example, a chimeric antibody and a humanized antibody, a human antibody, and the like. These antibodies can be produced by use of known methods.

Examples of the chimeric antibody can include a chimeric antibody comprising variable regions and constant regions of antibodies derived from different species, for example, the variable regions of a mouse- or rat-derived antibody joined to human-derived constant regions (see Proc. Natl. Acad. Sci. U.S.A., 81, 6851-6855, (1984)).

Examples of the chimeric antibody derived from the rat anti-human Orai1 antibody R118 can include an antibody consisting of a light chain comprising a light chain variable region consisting of amino acid residues at positions 21 to 126 of SEQ ID NO: 23 and a heavy chain comprising a heavy chain variable region consisting of amino acid residues at positions 20 to 136 of SEQ ID NO: 27. One example of such a R118-derived chimeric antibody can include an antibody consisting of a light chain consisting of amino acid residues at positions 21 to 234 of SEQ ID NO: 23 and a heavy chain consisting of amino acid residues at positions 20 to 466 of SEQ ID NO: 27. In the present specification, this antibody is referred to as "cR118" or a "cR118 antibody".

Examples of the chimeric antibody derived from the rat anti-human Orai1 antibody R198 can include an antibody consisting of a light chain comprising a light chain variable region consisting of amino acid residues at positions 21 to 126 of SEQ ID NO: 25 and a heavy chain comprising a heavy chain variable region consisting of amino acid residues at positions 20 to 136 of SEQ ID NO: 29. One example of such a R198-derived chimeric antibody can include an antibody consisting of a light chain consisting of amino acid residues at positions 21 to 234 of SEQ ID NO: 25 and a heavy chain consisting of amino acid residues at positions 20 to 466 of SEQ ID NO: 29. In the present specification, this antibody is referred to as "cR198" or a "cR198 antibody".

The sequence of the chimeric antibody against Orai1 described above can be artificially engineered to prepare a humanized antibody as a gene recombinant antibody, for the purpose of, for example, reducing heterogeneous antigenicity against humans. The antibody of the present invention includes an antibody whose CDRs are engineered CDRs of a humanized antibody. These antibodies can be produced by use of known methods.

Examples of the humanized antibody can include an antibody comprising complementarity determining regions (CDRs) alone grafted into a human-derived antibody (see Nature (1986) 321, p. 522-525), and an antibody comprising the CDR sequences as well as amino acid residues of a portion of the framework grafted into a human antibody (International Publication No. WO90/07861).

The humanized antibody derived from the cR118 or cR198 antibody retains all of the 6 CDR sequences derived from cR118 or cR198 and has the activity of inhibiting the activation of T cells. The light chain variable region of the humanized antibody retains any one of a CDRL1 consisting of the amino acid sequence represented by SEQ ID NO: 92 (RASQSIGNSLS) and a CDRL1 consisting of the amino acid sequence represented by SEQ ID NO: 116 (RASQSIS-NSLS), a CDRL2 consisting of the amino acid sequence represented by SEQ ID NO: 96 (STSTLES), and any one of a CDRL3 consisting of the amino acid sequence represented by SEQ ID NO: 99 (LQFATFPDT) and a CDRL3 shown in SEQ ID NO: 100 (LQFATYPDT). Also, the heavy chain variable region of the humanized antibody retains any one of a CDRH1 consisting of the amino acid sequence represented by SEQ ID NO: 102 (AYYIS) and a CDRH1 shown in SEQ ID NO: 103 (SYYIS), any one of a CDRH2 consisting of the amino acid sequence represented by SEQ ID NO: 104 (YIDMGNGRTNYNARFKG) and a CDRH2 shown in SEQ ID NO: 105 (YVDMGNGRTNYNEKFKG), and a CDRH3 consisting of the amino acid sequence represented by SEQ ID NO: 109 (DSNWGVDY). These amino acid sequences of the CDRs are also shown in FIG. 38.

Examples of the antibody having a preferred combination of the CDRs can include an antibody comprising CDRL1 consisting of the amino acid sequence represented by SEQ ID NO: 92, CDRL2 consisting of the amino acid sequence represented by SEQ ID NO: 96, CDRL3 consisting of the amino acid sequence represented by SEQ ID NO: 100, CDRH1 consisting of the amino acid sequence represented by SEQ ID NO: 103, CDRH2 consisting of the amino acid sequence represented by SEQ ID NO: 105, and CDRH3 consisting of the amino acid sequence represented by SEQ ID NO: 109, and an antibody comprising CDRL1 consisting of the amino acid sequence represented by SEQ ID NO: 92, CDRL2 consisting of the amino acid sequence represented by SEQ ID NO: 96, CDRL3 consisting of the amino acid sequence represented by SEQ ID NO: 99, CDRH1 consisting of the amino acid sequence represented by SEQ ID NO: 102, CDRH2 consisting of the amino acid sequence represented by SEQ ID NO: 104, and CDRH3 consisting of the amino acid sequence represented by SEQ ID NO: 109.

Preferred examples of the humanized antibody can include an antibody consisting of a light chain comprising a light chain variable region consisting of amino acid residues at positions 21 to 126 of SEQ ID NO: 31 and a heavy chain comprising a heavy chain variable region consisting of amino acid residues at positions 20 to 136 of SEQ ID NO: 39, an antibody consisting of a light chain comprising a light chain variable region consisting of amino acid residues at positions 21 to 126 of SEQ ID NO: 33 and a heavy chain comprising a heavy chain variable region consisting of amino acid residues at positions 20 to 136 of SEQ ID NO: 41, an antibody consisting of a light chain comprising a light chain variable region consisting of amino acid residues at positions 21 to 126 of SEQ ID NO: 35 and a heavy chain comprising a heavy chain variable region consisting of amino acid residues at positions 20 to 136 of SEQ ID NO: 43, and an antibody consisting of a light chain comprising a light chain variable region consisting of amino acid residues at positions 21 to 126 of SEQ ID NO: 37 and a heavy chain comprising a heavy chain variable region consisting of amino acid residues at positions 20 to 136 of SEQ ID NO: 45.

More preferred examples thereof can include an antibody consisting of a light chain consisting of amino acid residues at positions 21 to 234 of SEQ ID NO: 31 and a heavy chain consisting of amino acid residues at positions 20 to 466 of SEQ ID NO: 39, an antibody consisting of a light chain consisting of amino acid residues at positions 21 to 234 of SEQ ID NO: 33 and a heavy chain consisting of amino acid residues at positions 20 to 466 of SEQ ID NO: 41, an antibody consisting of a light chain consisting of amino acid residues at positions 21 to 234 of SEQ ID NO: 35 and a heavy chain consisting of amino acid residues at positions 20 to 466 of SEQ ID NO: 43, and an antibody consisting of a light chain consisting of amino acid residues at positions 21 to 234 of SEQ ID NO: 37 and a heavy chain consisting of amino acid residues at positions 20 to 466 of SEQ ID NO: 45.

The antibody of the present invention may be an antibody with enhanced ability to bind to Orai1 obtained by further mutating the humanized antibody described above. Such an approach is called affinity maturation. Specific examples of the method can include a ribosome display method. The ribosome display method is a method which involves using a tripartite complex of a protein bound to an mRNA having the genetic information thereof via a ribosome and isolating a gene sequence encoding the protein that binds to a target molecule (Stafford R L. et al., Protein Eng. Des. Sel. 2014 (4): 97-109).

The light chain variable region of the antibody genetically engineered by the method described above retains any one of a CDRL1 consisting of the amino acid sequence represented by SEQ ID NO: 93 (RASQSIGGSLS), a CDRL1 consisting of the amino acid sequence represented by SEQ ID NO: 94 (HASQNIGGSLS), and a CDRL1 consisting of the amino acid sequence represented by SEQ ID NO: 95 (HASRNIGGSLS), any one of a CDRL2 consisting of the amino acid sequence represented by SEQ ID NO: 96 (STSTLES), a CDRL2 consisting of the amino acid sequence represented by SEQ ID NO: 97 (LTSTLDW), and a CDRL2 consisting of the amino acid sequence represented by SEQ ID NO: 98 (LTSSLDW), and a CDRL3 consisting of the amino acid sequence represented by SEQ ID NO: 101 (LQFAIFPDS). Also, the heavy chain variable region of the genetically engineered antibody retains a CDRH1 consisting of the amino acid sequence represented by SEQ ID NO: 102 (AYYIS), any one of a CDRH2 consisting of the amino acid sequence represented by SEQ ID NO: 104 (YIDMGNGRT-NYNARFKG), a CDRH2 consisting of the amino acid sequence represented by SEQ ID NO: 106 (YIDMGNGRT-DYNARFKG), a CDRH2 consisting of the amino acid sequence represented by SEQ ID NO: 107 (YIDMGNGRT-DYNGRFKG), and a CDRH2 shown in SEQ ID NO: 108 (YIDMGNGRTDYNMRFKG), and a CDRH3 consisting of the amino acid sequence represented by SEQ ID NO: 109 (DSNWGVDY) or a CDRH3 consisting of the amino acid sequence represented by SEQ ID NO: 110 (DSNWGADY). These amino acid sequences of the CDRs are also shown in FIG. 38.

Examples of the antibody having a preferred combination of the CDRs can include an antibody comprising a CDRL1 consisting of the amino acid sequence represented by SEQ ID NO: 93, a CDRL2 consisting of the amino acid sequence represented by SEQ ID NO: 96, a CDRL3 consisting of the amino acid sequence represented by SEQ ID NO: 101, a CDRH1 consisting of the amino acid sequence represented by SEQ ID NO: 102, a CDRH2 consisting of the amino acid sequence represented by SEQ ID NO: 106, and a CDRH3 consisting of the amino acid sequence represented by SEQ ID NO: 110, an antibody comprising a CDRL1 consisting of the amino acid sequence represented by SEQ ID NO: 94, a CDRL2 consisting of the amino acid sequence represented by SEQ ID NO: 97, a CDRL3 consisting of the amino acid sequence represented by SEQ ID NO: 101, a CDRH1 consisting of the amino acid sequence represented by SEQ ID NO: 102, a CDRH2 consisting of the amino acid sequence represented by SEQ ID NO: 106, and a CDRH3 consisting of the amino acid sequence represented by SEQ ID NO: 110, an antibody comprising a CDRL1 consisting of the amino acid sequence represented by SEQ ID NO: 95, a CDRL2 consisting of the amino acid sequence represented by SEQ ID NO: 98, a CDRL3 consisting of the amino acid sequence represented by SEQ ID NO: 101, a CDRH1 consisting of the amino acid sequence represented by SEQ ID NO: 102, a CDRH2 consisting of the amino acid sequence represented by SEQ ID NO: 106, and a CDRH3 consisting of the amino acid sequence represented by SEQ ID NO: 110, an antibody comprising a CDRL1 consisting of the amino acid sequence represented by SEQ ID NO: 93, a CDRL2 consisting of the amino acid sequence represented by SEQ ID NO: 96, a CDRL3 consisting of the amino acid sequence represented by SEQ ID NO: 101, a CDRH1 consisting of the amino acid sequence represented by SEQ ID NO: 102, a CDRH2 consisting of the amino acid sequence represented by SEQ ID NO: 107, and a CDRH3 consisting of the amino acid sequence represented by SEQ ID NO: 110, an antibody comprising a CDRL1 consisting of the amino acid sequence represented by SEQ ID NO: 93, a CDRL2 consisting of the amino acid sequence represented by SEQ ID NO: 96, a CDRL3 consisting of the amino acid sequence represented by SEQ ID NO: 101, a CDRH1 consisting of the amino acid sequence represented by SEQ ID NO: 102, a CDRH2 consisting of the amino acid sequence represented by SEQ ID NO: 108, and a CDRH3 consisting of the amino acid sequence represented by SEQ ID NO: 110, and an antibody comprising a CDRL1 consisting of the amino acid sequence represented by SEQ ID NO: 93, a CDRL2 consisting of the amino acid sequence represented by SEQ ID NO: 96, a CDRL3 consisting of the amino acid sequence represented by SEQ ID NO: 101, a CDRH1 consisting of the amino acid sequence represented by SEQ ID NO: 102, a CDRH2 consisting of the amino acid sequence represented by SEQ ID NO: 104, and a CDRH3 consisting of the amino acid sequence represented by SEQ ID NO: 109.

Preferred examples of the genetically-engineered-CDR antibody can include an antibody consisting of a light chain comprising a light chain variable region consisting of amino acid residues at positions 21 to 126 of SEQ ID NO: 56 and a heavy chain comprising a heavy chain variable region consisting of amino acid residues at positions 20 to 136 of SEQ ID NO: 62, an antibody consisting of a light chain comprising a light chain variable region consisting of amino acid residues at positions 21 to 126 of SEQ ID NO: 58 and a heavy chain comprising a heavy chain variable region consisting of amino acid residues at positions 20 to 136 of SEQ ID NO: 62, an antibody consisting of a light chain comprising a light chain variable region consisting of amino acid residues at positions 21 to 126 of SEQ ID NO: 60 and a heavy chain comprising a heavy chain variable region consisting of amino acid residues at positions 20 to 136 of SEQ ID NO: 62, an antibody consisting of a light chain comprising a light chain variable region consisting of amino acid residues at positions 21 to 126 of SEQ ID NO: 56 and a heavy chain comprising a heavy chain variable region consisting of amino acid residues at positions 20 to 136 of SEQ ID NO: 64, an antibody consisting of a light chain comprising a light chain variable region consisting of amino acid residues at positions 21 to 126 of SEQ ID NO: 56 and a heavy chain comprising a heavy chain variable region consisting of amino acid residues at positions 20 to 136 of SEQ ID NO: 66, and an antibody consisting of a light chain comprising a light chain variable region consisting of amino acid residues at positions 21 to 126 of SEQ ID NO: 56 and a heavy chain comprising a heavy chain variable region consisting of amino acid residues at positions 20 to 136 of SEQ ID NO: 43.

Preferred examples of the antibody comprising the light chain variable region and the heavy chain variable region described above can include an antibody consisting of a light chain consisting of amino acid residues at positions 21 to 234 of SEQ ID NO: 56 and a heavy chain consisting of amino acid residues at positions 20 to 466 of SEQ ID NO: 62, an antibody consisting of a light chain consisting of amino acid residues at positions 21 to 234 of SEQ ID NO: 58 and a heavy chain consisting of amino acid residues at positions 20 to 466 of SEQ ID NO: 62, an antibody consisting of a light chain consisting of amino acid residues at positions 21 to 234 of SEQ ID NO: 60 and a heavy chain consisting of amino acid residues at positions 20 to 466 of SEQ ID NO: 62, an antibody consisting of a light chain consisting of amino acid residues at positions 21 to 234 of SEQ ID NO: 56 and a heavy chain consisting of amino acid residues at positions 20 to 466 of SEQ ID NO: 64, an antibody consisting of a light chain consisting of amino acid residues at positions 21 to 234 of SEQ ID NO: 56 and a heavy chain consisting of amino acid residues at positions 20 to 466 of SEQ ID NO: 66, and an antibody consisting of a light chain consisting of amino acid residues at positions 21 to 234 of SEQ ID NO: 56 and a heavy chain consisting of amino acid residues at positions 20 to 466 of SEQ ID NO: 43.

For circumventing cytotoxicity against normal cells expressing human Orai1, it is desirable that an antibody should have low effector activity. The effector activity is known to differ among antibody subclasses. The following characteristics are observed, for example, IgG4 has low ADCC and CDC activities, and IgG2 has CDC activity, but has low ADCC activity. On the basis of these features, it is possible to prepare an antibody with reduced ADCC and CDC activities by replacing the constant regions of IgG1 with the constant regions of IgG2 or IgG4. Also, it is possible to prepare an IgG1 antibody with reduced ADCC and CDC activities by partially substituting the constant region sequences of IgG1 with reference to IgG2 or IgG4. As one example, Marjan Hezareh et al., Journal of Virology, 75 (24): 12161-12168 (2001) shows that the ADCC and CDC activities of IgG1 are reduced by replacing each of the leucine residues at positions 234 and 235 (the positions are indicated by the EU index of Kabat et al.) of IgG1 with an alanine residue.

Examples of the heavy chain of the anti-Orai1 antibody prepared by the method described above can include a heavy chain sequence shown in SEQ ID NO: 68 or 70. The heavy chain shown in SEQ ID NO: 68 or 70 can be combined with each light chain sequence described in the present specification and used as a therapeutic antibody. Specific examples of the light chain to be combined can include the light chain described in SEQ ID NO: 31, 33, 35, 37, 56, 58, or 60. Examples of the antibody having a preferred combination of the light chain and the heavy chain can include an antibody consisting of a light chain consisting of amino acid residues at positions 21 to 234 of SEQ ID NO: 56 and a heavy chain consisting of amino acid residues at positions 20 to 466 of SEQ ID NO: 70, an antibody consisting of a light chain consisting of amino acid residues at positions 21 to 234 of SEQ ID NO: 58 and a heavy chain consisting of amino acid residues at positions 20 to 466 of SEQ ID NO: 70, an antibody consisting of a light chain consisting of amino acid residues at positions 21 to 234 of SEQ ID NO: 60 and a heavy chain consisting of amino acid residues at positions 20 to 466 of SEQ ID NO: 70.

It is known that carboxyl terminal lysine residues are deleted in the heavy chains of antibodies produced in cultured mammalian cells (Journal of Chromatography A, 705: 129-134 (1995)). It is also known that two carboxyl terminal amino acid residues (glycine and lysine) are deleted in heavy chains, and a proline residue newly positioned at the carboxyl terminus is amidated (Analytical Biochemistry, 360: 75-83 (2007)). However, such deletion and modification of heavy chain sequences has no influence on the ability of the antibody to bind to the antigen and the effector functions (complement activation and antibody dependent cellular cytotoxic effect, etc.) of the antibody. Thus, the antibody of the present invention also includes an antibody thus modified. Examples thereof can include a deletion mutant obtained by the deletion of 1 or 2 amino acids at the heavy chain carboxyl terminus, and an amidated form of this deletion mutant (e.g., a heavy chain amidated at the proline residue at the carboxyl terminal site). However, the heavy chain carboxy terminus deletion mutant of the antibody according to the present invention is not limited to the types described above as long as the deletion mutant maintains the ability to bind to the antigen and the effector functions. Two heavy chains constituting the antibody according to the present invention may be any one type of heavy chain selected from the group consisting of full length heavy chains and the heavy chains of the deletion mutants described above, or may be a combination of any two types selected therefrom. The quantitative ratio of each deletion mutant may be influenced by the type and culture conditions of cultured mammalian cells producing the antibody according to the present invention. Examples of the main component of the antibody according to the present invention can include two heavy chains, both of which lack one carboxy terminal amino acid residue. Specifically, a heavy chain consisting of amino acid residues at positions 20 to 465 in a heavy chain sequence shown in each of SEQ ID NOs: 27, 29, 39, 41, 43, 45, 62, 64, 66, 68, and 70 of the Sequence Listing, or a heavy chain consisting of amino acid residues at positions 20 to 464 therein can also be used in the antibody of the present invention.

Antibodies obtained by these methods can be evaluated for their binding activity against the antigen to select a suitable antibody. One example of another index for comparing antibody properties can include antibody stability. Differential scanning calorimetry (DSC) is a method capable of rapidly and accurately measuring a thermal denaturation midpoint (Tm), which serves as a good index for relative structural stability of proteins. Tm values can be measured using DSC and compared to determine distinctive heat stability. The storage stability of an antibody is known to correlate with the heat stability of the antibody to some extent (Lori Burton, et al., Pharmaceutical Development and Technology (2007) 12, p. 265-273). A suitable antibody can be selected with heat stability as an index. Examples of other indexes for selecting the antibody can include high yields in appropriate host cells, and low aggregation in an aqueous solution. For example, since it is not always true that an antibody having the highest yield exhibits the highest heat stability, an antibody most suitable for administration to humans has to be selected by synthetic judgment based on the indexes mentioned above.

A method for obtaining a single chain immunoglobulin by linking the full length heavy and light chain sequences of the antibody via an appropriate linker is also known (Lee, H-S, et al., Molecular Immunology (1999) 36, p. 61-71; and Schirrmann, T. et al., mAbs (2010), 2 (1), p. 73-76). Such a single chain immunoglobulin can be dimerized to thereby maintain a structure and activities similar to those of the antibody, which is originally a tetramer. Also, the antibody of the present invention may be an antibody that has a single heavy chain variable region and has no light chain sequence. Such an antibody, called a single domain antibody (sdAb) or nanobody, has actually been observed in camels and llamas and reported to maintain the ability to bind to the antigen (Muyldemans S. et al., Protein Eng. (1994) 7 (9), 1129-35; and Hamers-Casterman C. et al., Nature (1993) 363 (6428), 446-8). These antibodies may be interpreted as one kind of antigen binding fragment of the antibody according to the present invention.

The antibody dependent cellular cytotoxic activity of the antibody of the present invention may be enhanced by adjusting the modification of a sugar chain bound to the antibody. For example, methods described in WO99/54342, WO00/61739, and WO02/31140 are known as examples of such a technique of adjusting a sugar chain modification of an antibody, though this technique is not limited thereto.

In the case of preparing an antibody by temporarily isolating the antibody gene and then transferring the gene to an appropriate host, the appropriate host can be used in combination with an expression vector. Specific examples of the antibody gene can include a combination of a gene encoding a heavy chain sequence and a gene encoding a light chain sequence of the antibody described in the present specification. For the transformation of host cells, the heavy chain sequence gene and the light chain sequence gene may be inserted into the same expression vector or may be inserted into separate expression vectors. In the case of using host eukaryotic cells, animal cells, plant cells, or eukaryotic microbes can be used. Examples of the animal cells can include mammalian cells, for example, monkey COS cells (Gluzman, Y., Cell (1981) 23, p. 175-182, ATCC CRL-1650), mouse fibroblast NIH3T3 (ATCC No. CRL-1658), and dihydrofolate reductase deficient lines (Urlaub, G. and Chasin, L. A., Proc. Natl. Acad. Sci. U.S.A. (1980) 77, p. 4126-4220) of Chinese hamster ovary cells (CHO cells, ATCC CCL-61). In the case of using prokaryotic cells, examples thereof can include *E. coli* and *Bacillus subtilis*. The antibody gene of interest is transferred to these cells by transformation, and the transformed cells are cultured in vitro to obtain the antibody. Such a culture method may differ in yield depending on the sequence of the antibody. An antibody that is easy to produce as a drug can be selected, by using its yield as an index, from among antibodies having equivalent binding activity.

Examples of the isotype of the antibody of the present invention can include, but are not limited to, IgG (IgG1, IgG2, IgG3, and IgG4), IgM, IgA (IgA1 and IgA2), IgD, and IgE. The isotype can be preferably IgG or IgM, more preferably IgG1 or IgG2.

The antibody of the present invention may be an antigen binding fragment of the antibody having the antigen binding site of the antibody, or a modified form thereof. The antibody fragment can be obtained by treating the antibody with a proteolytic enzyme such as papain or pepsin or by expressing a genetically engineered antibody gene in appropriate cultured cells. Among such antibody fragments, a fragment that maintains the whole or a portion of the functions possessed by the full length molecule of the antibody can be referred to as an antigen binding fragment of the antibody.

Examples of the functions of the antibody can generally include antigen binding activity, the activity of neutralizing the activity of the antigen, the activity of enhancing the activity of the antigen, antibody dependent cellular cytotoxic activity, complement dependent cytotoxic activity, and complement dependent cellular cytotoxic activity. The function possessed by the antigen binding fragment of the antibody according to the present invention is binding activity against Orai1 and is preferably the activity of inhibiting the activation of T cells, more preferably the activity of inhibiting the production of IL-2 and/or interferon γ by T cells.

Examples of the fragment of the antibody can include Fab, F(ab')2, Fv, single chain Fv (scFv) comprising heavy and light chain Fvs linked via an appropriate linker, diabodies, linear antibodies, and multispecific antibodies formed from antibody fragments. The fragment of the antibody also includes Fab', which is a monovalent fragment of antibody variable regions obtained by the treatment of F(ab')2 under reducing conditions.

The antibody of the present invention may be a multispecific antibody having specificity for at least two different types of antigens. Such a molecule usually binds to two types of antigens (i.e., a bispecific antibody). The "multispecific antibody" according to the present invention encompasses an antibody having specificity for more types (e.g., 3 types) of antigens.

The multispecific antibody of the present invention may be an antibody consisting of a full length antibody, or may be a fragment of such an antibody (e.g., F(ab')2 bispecific antibody). The bispecific antibody may be prepared by linking the heavy and light chains (HL pairs) of two types of antibodies, or may be prepared by fusing hybridomas producing different monoclonal antibodies to prepare fusion cells producing the bispecific antibody (Millstein et al., Nature (1983) 305, p. 537-539).

The antibody of the present invention may be a single chain antibody (single chain Fv; also referred to as "scFv"). The scFv is obtained by linking the heavy and light chain variable regions of the antibody via a polypeptide linker (Pluckthun, The Pharmacology of Monoclonal Antibodies, 113 (Rosenberg and Moore ed., Springer Verlag, New York, p. 269-315 (1994); and Nature Biotechnology (2005), 23, p. 1126-1136). Also, a biscFv fragment prepared by linking two scFvs via a polypeptide linker can also be used as a bispecific antibody.

The method for preparing the scFv is well known in the art (see e.g., U.S. Pat. Nos. 4,946,778, 5,260,203, 5,091,513, and 5,455,030). In this scFv, the heavy chain variable region and the light chain variable region are linked via a linker, preferably a polypeptide linker, that prevents them from forming a conjugate (Huston, J. S. et al., Proc. Natl. Acad. Sci. U.S.A. (1988), 85, p. 5879-5883). The heavy chain variable region and the light chain variable region in the scFv may be derived from the same antibody or may be derived from different antibodies. For example, an arbitrary single chain peptide consisting of 12 to 19 residues is used as the polypeptide linker that links these variable regions.

In order to obtain DNA encoding the scFv, each DNA portion encoding the whole or desired amino acid sequence in the sequences of DNA encoding the heavy chain or heavy chain variable region of the antibody and DNA encoding the light chain or light chain variable region thereof, is used as a template and amplified by PCR using a primer pair flanking both ends of the template. Subsequently, DNA encoding the polypeptide linker moiety is further amplified in combination with a primer pair flanking both ends of the DNA so that the obtained fragment can be linked at its ends to the heavy and light chain DNAs, respectively.

Once the DNA encoding the scFv is prepared, an expression vector containing the DNA and a host transformed with the expression vector can be obtained according to routine methods. In addition, the host can be used to obtain the scFv according to routine methods. These antibody fragments can be produced by a host in the same way as above by obtaining and expressing the gene.

The antibody of the present invention may be multimerized to thereby enhance its affinity for the antigen. Antibodies of the same type may be multimerized, or a plurality of antibodies recognizing a plurality of epitopes, respectively, of the same antigen may be multimerized. Examples of a method for multimerizing these antibodies can include the binding of two scFvs to an IgG CH3 domain, the binding thereof to streptavidin, and the introduction of a helix-turn-helix motif.

The antibody of the present invention may be a polyclonal antibody which is a mixture of plural types of anti-Orai1 antibodies differing in amino acid sequence. One example of the polyclonal antibody can include a mixture of plural types of antibodies differing in CDRs. An antibody obtained by culturing a mixture of cells producing different antibodies, followed by purification from the cultures can be used as such a polyclonal antibody (see WO2004/061104).

An antibody conjugated with any of various molecules such as polyethylene glycol (PEG) can also be used as a modified form of the antibody.

The antibody of the present invention may further be any of the conjugates formed by these antibodies with other drugs (immunoconjugates). Examples of such an antibody can include the antibody conjugated with a radioactive material or a compound having a pharmacological effect (Nature Biotechnology (2005) 23, p. 1137-1146).

The obtained antibody can be purified until homogeneous. Usual protein separation and purification methods can be used for the separation and purification of the antibody. The antibody can be separated and purified by appropriately selected or combined approach(es), for example, column chromatography, filtration through a filter, ultrafiltration, salting out, dialysis, preparative polyacrylamide gel electrophoresis, and/or isoelectric focusing (Strategies for Protein Purification and Characterization: A Laboratory Course Manual, Daniel R. Marshak et al. eds., Cold Spring Harbor Laboratory Press (1996); and Antibodies: A Laboratory Manual. Ed Harlow and David Lane, Cold Spring Harbor Laboratory (1988)), though the separation and purification method is not limited thereto.

Examples of such chromatography can include affinity chromatography, ion exchange chromatography, hydrophobic chromatography, gel filtration chromatography, reverse phase chromatography, and adsorption chromatography. These chromatography approaches can be carried out using liquid chromatography such as HPLC or FPLC. Examples of the column for use in the affinity chromatography can include protein A columns and protein G columns. Examples of the protein A columns can include Hyper D, POROS, and Sepharose F. F. (Pharmacia Corp.). Also, the antibody may be purified by use of its binding activity against the antigen using an antigen immobilized carrier.

3. Drug Containing Anti-Orai1 Antibody

An antibody neutralizing the biological activity of Orai1 can be obtained from among the anti-Orai1 antibodies obtained by the methods described in the preceding paragraph "2. Production of anti-Orai1 antibody". Such an antibody, neutralizing the biological activity of Orai1, can inhibit the in vivo biological activity of Orai1, i.e., the activation of the calcium release activated calcium channels (CRAC channels) of Orai1-expressing cells typified by T cells and mast cells and as such, can be pharmaceutically used as a therapeutic and/or prophylactic agent for diseases caused by the activation of the CRAC channels of these cells.

The diseases or conditions caused by CRAC channel activation include transplant rejection, immune-related diseases, allergic diseases, inflammatory diseases, thrombosis, and cancers, etc.

Examples of the treatment and/or prevention of transplant rejection include the treatment and/or prevention of rejection response and host versus graft reaction to the transplantation of an organ or a tissue such as the heart, the kidney, the liver, bone marrow, or skin, and graft versus host disease caused by the transplantation of hematopoietic cells (bone marrow, peripheral blood, umbilical cord blood, etc.).

Examples of immune-related diseases include connective tissue or musculoskeletal diseases (rheumatoid arthritis, ankylosing spondylitis, systemic lupus erythematosus, scleroderma, polymyositis, dermatomyositis, etc.), hematological diseases (aplastic anemia, idiopathic thrombocytopenic purpura, etc.), gastrointestinal diseases (Crohn disease, ulcerative colitis, etc.), neurological diseases (multiple sclerosis, myasthenia gravis, etc.), ophthalmic diseases (uveitis, etc.), vascular diseases (Behcet's disease, Wegener's granulomatosis, etc.), epidermal diseases (psoriasis, pemphigus, leukoderma, etc.), and endocrine diseases (type 1 diabetes mellitus, autoimmune thyroiditis, Graves' disease, Hashimoto's disease, etc.).

Examples of the allergic diseases include atopic dermatitis, asthma, anaphylaxis, anaphylactoid reaction, food allergy, rhinitis, otitis media, drug reaction, insect bite reaction, reaction to plants, latex allergy, conjunctivitis, and urticaria.

Examples of the inflammatory diseases include inflammatory renal diseases (glomerulonephritis, nephrosis, etc.), inflammatory pulmonary diseases (chronic obstructive pulmonary disease, cystic fibrosis, interstitial pneumonia, etc.), inflammatory bowel diseases (ulcerative colitis, ileitis, etc.), inflammatory hepatic diseases (autoimmune hepatitis, viral hepatitis, etc.), inflammatory cardiac diseases (myocarditis, ischemic heart disease, atherosclerosis, etc.), inflammatory skin diseases (contact dermatitis, eczema, etc.), inflammatory eye diseases (trachoma, endophthalmitis, etc.), inflammatory central nervous diseases (meningitis, encephalomyelitis, autoimmune encephalitis, etc.), inflammatory joint diseases (arthritis, osteoarthritis, etc.), and systemic inflammations (sepsis, bleeding, hypersensitivity, shock symptoms attributed to cancer chemotherapy or the like, etc.).

Examples of cases in which the antiplatelet or antithrombotic activity is useful for treatment and/or prevention are myocardial infarction, stroke, ischemic heart diseases, and thrombosis.

Examples of the treatment of the cancers include breast cancer, lung cancer, skin cancer, and leukemia.

Further examples of the diseases that can be treated by the antibody of the present invention include: pathological conditions involving mast cells and basophils, such as mast cell leukemia, mastocytosis, basophilic leukemia, and endometriosis; and tubular aggregate myopathy, Stormorken syndrome, rheumatoid arthritis, ankylosing spondylitis, and atopic dermatitis, which develop or whose risk of development is increased by the genetic hyperfunction of CRAC channels.

Examples of the anti-Orai1 antibody as the drug can include humanized antibodies prepared from the R118 antibody and/or the R198 antibody, and CDR engineered forms thereof.

The in vitro neutralizing activity of the anti-Orai1 antibody against the biological activity of Orai1 can be measured on the basis of, for example, the inhibitory activity against the activation of T cells expressing Orai1. For example, the anti-Orai1 antibody is added at varying concentrations to human T cell-derived cell line Jurkat cells, and the inhibitory activity against IL-2 release from the Jurkat cells stimulated with PMA and A23187 can be measured. Also, the anti-Orai1 antibody is added at varying concentrations to human peripheral blood mononuclear cells (PBMC), and the inhibitory activity against IL-2 and interferon γ release from PBMC stimulated with PMA and A23187 can be measured.

It is an experimentally proven fact, and widely recognized, that the cells responsible for the development of graft versus host disease are T cells. When transplanted T cells recognize the recipient as foreign matter, self-propagation based on interleukin 2 (IL-2) produced by themselves, and the release of inflammatory cytokines such as interferon gamma (IFN-γ) by activation cause a systemic immunological inflammation reaction, resulting in the development of graft versus host disease. Thus, the inhibition of the production of these cytokines leads to the prevention or treatment of graft versus host disease, while the usefulness of the anti-Orai1 antibody as a therapeutic drug can be determined by using its inhibitory activity as an index.

Preferred examples of the antibody according to the present invention can include an antibody or an antigen binding fragment of the antibody which specifically binds to the amino acid sequence represented by SEQ ID NO: 2, wherein the concentration at which the amount of IL-2 released from Jurkat cells treated with PMA and A23187 is inhibited by 50% is 80 ng/mL or lower. More preferred examples of this antibody can include the antibody or the antigen binding fragment of the antibody, wherein the concentration at which the amount of IL-2 released from Jurkat cells treated with PMA and A23187 is inhibited by 50% is 10 ng/mL or lower. The antibody of the present invention also includes an antibody or an antigen binding fragment of the antibody, wherein the concentration at which the amount of IL-2 released from Jurkat cells treated with PMA and A23187 is inhibited by 80% is 60000 ng/mL or lower, and an antibody or an antigen binding fragment of the antibody, wherein the concentration at which the amount of IL-2 released from Jurkat cells treated with PMA and A23187 is inhibited by 80% is 200 ng/mL or lower.

Alternative preferred examples of the antibody according to the present invention can include an antibody or an antigen binding fragment of the antibody which specifically binds to the amino acid sequence represented by SEQ ID NO: 2, wherein the concentration at which the amount of IL-2 released from human PBMC treated with PMA and A23187 is inhibited by 50% is 100 ng/mL or lower. More preferred examples of this antibody can include the antibody or the antigen binding fragment of the antibody, wherein the concentration at which the amount of IL-2 released from human PBMC treated with PMA and A23187 is inhibited by 50% is 20 ng/mL or lower. The antibody of the present invention also includes an antibody or an antigen binding fragment of the antibody, wherein the concentration at which the amount of IL-2 released from human PBMC treated with PMA and A23187 is inhibited by 80% is 17000 ng/mL or lower, and an antibody or an antigen binding fragment of the antibody, wherein the concentration at which the amount of IL-2 released from human PBMC treated with PMA and A23187 is inhibited by 80% is 400 ng/mL or lower.

Further alternative preferred examples of the antibody according to the present invention can include an antibody or an antigen binding fragment of the antibody which specifically binds to the amino acid sequence represented by SEQ ID NO: 2, wherein the concentration at which the amount of IFN-γ released from human PBMC treated with PMA and A23187 is inhibited by 50% is 800 ng/mL or lower. More preferred examples of this antibody can include the antibody or the antigen binding fragment of the antibody, wherein the concentration at which the amount of IFN-γ released from human PBMC treated with PMA and A23187 is inhibited by 50% is 40 ng/mL or lower. The antibody of the present invention also includes an antibody or an antigen binding fragment of the antibody, wherein the concentration at which the amount of IFN-γ released from human PBMC treated with PMA and A23187 is inhibited by 80% is 300000 ng/mL or lower, and an antibody or an antigen binding fragment of the antibody, wherein the concentration at which the amount of IFN-γ released from human PBMC treated with PMA and A23187 is inhibited by 80% is 2000 ng/mL or lower.

The in vivo therapeutic or prophylactic effect of the anti-Orai1 antibody on graft versus host disease in a laboratory animal can be confirmed, for example, by measuring the inhibition of weight loss in a human PBMC transplanted mouse graft versus host disease model. Specifically, NOG or NSG mice, which are severe combined immunodeficient mice, are irradiated with X-rays of 2.0 Gy. On the next day, 200 μL of a PBS solution containing 15,000,000 to 50,000,000 cells of human PBMC per mL is transplanted to each mouse via the tail vein. An X-ray irradiated mouse group that has not received human PBMC is used as a non-graft versus host disease group, and a human PBMC transplanted group given only a vehicle solution for the antibody is used as a graft versus host disease group. Before or after the human PBMC transplantation, the anti-Orai1 antibody is administered either intravenously to the tail or intraperitoneally to measure the inhibitory effect on weight loss in the graft versus host disease group.

In addition, the therapeutic or prophylactic effect of the anti-Orai1 antibody on various diseases can also be confirmed by the following in vivo evaluation systems using a human Orai1 knock-in mouse.

For the effect on dermatitis, a protein antigen solution is intraperitoneally or intravenously administered to a mouse, and after 2 weeks, the antigen is injected thereto as a booster. Then, the same protein antigen solution as above is repetitively applied to the ear or the back 3 to 6 times at 3 day to 2 week intervals to cause dermatitis. The effect on dermatitis is evaluated by comparing the auricle thickness, the macroscopic score of dermatitis in the back, the concentrations of the antibody, cytokines, or serum biomarkers in blood or tissues, and the growth activity, cytokine producing ability, or surface antigens of cells obtained from the skin, peripheral blood, the thymus, the spleen, the lymph node, or the bone marrow between an anti-Orai1 antibody group and a non-administration group.

For the effect on pruritus, a mite antigen cream is repetitively applied to the auricle or the back 3 to 6 times at 3 day to 2 week intervals, or a hapten is applied to the auricle, the abdominal region, or the back every day to once a week, or a pruritus inducing substance is administered intracutaneously to the auricle, subcutaneously to the back, or by the intrathecal route. Pruritic action induced by such a method is quantified by measuring the number of pruritic events using magnets attached to the dorsum of both feet of the mouse and a pruritic action measurement apparatus, or by examining pathological signs in the skin, peripheral blood, or spinal cord tissues. The effect on pruritus is evaluated by comparing the obtained results between an anti-Orai1 antibody group and a non-administration group.

For the effect on psoriasis, imiquimod is applied to both sides or one side of the auricle and the shaved back, or a zymosan suspension is intraperitoneally administered, or a cytokine such as IL-23 is intracutaneously administered to one side of the mouse auricle. Psoriatic dermatitis induced by such a method is quantified by the examination of the weight and thickness of an inflammation site, the myeloperoxidase activity of neutrophils infiltrated into the site, the flow cytometry analysis of the infiltrated cells, gene analysis, cytokine concentration measurement, etc. The effect on psoriasis is evaluated by comparing the obtained results between an anti-Orai1 antibody group and a non-administration group.

For the effect on multiple sclerosis, a solution of myelin oligodendrocyte glycoprotein or a partial peptide antigen thereof is emulsified by mixing with an aqueous solution of a Freund's complete adjuvant in equal amounts. This emulsion is intracutaneously administered to the flank or abdominal region of a mouse. Then, an aqueous pertussis toxin solution is administered to the tail vein. After a few days, the pertussis toxin solution is further administered again to the tail vein to induce experimental encephalomyelitis. Paralysis symptoms that develop after 1 week to 2 weeks of the experiment and expand from the tail to the lower legs and the anterior limbs are scored by macroscopic observation. The effect on multiple sclerosis is evaluated by comparing the obtained results between an anti-Orai1 antibody group and a non-administration group.

For the effect on arthritis, an emulsion obtained by mixing bovine type II collagen and a Freund's complete adjuvant is intracutaneously administered to the tail base of a mouse. After 2 to 3 weeks, the same administration as above is carried out. Then, the effect on arthritis is evaluated by comparing the score of joint swelling, the concentrations of the antibody, cytokines, or serum biomarkers in blood or tissues, the growth activity, cytokine producing ability, or surface antigens of cells obtained from the skin, peripheral blood, the thymus, the spleen, the lymph node, or the bone marrow, etc. between an anti-Orai1 antibody group and a non-administration group.

For the effect on colitis, trinitrobenzenesulfonic acid is administered into the intestinal tract of a mouse fasted for 24 hours, or a mouse is allowed to drink freely an aqueous solution containing 1 to 10% sodium dextran sulfate from a water feed bottle for 4 days to 2 weeks, or CD4+CD25-CD45RBhi T-cells collected and purified from the lymph node and the spleen of a human Orai1 knock-in mouse are intraperitoneally transplanted into a Rag2−/− mouse. The effect on colitis induced by such a method is evaluated by comparing the body weight during the observation period, the degree of thickening of the intestinal tract, the number and size of polyps, and pathological signs examined by autopsy after the completion of the test, the concentrations of the antibody, cytokines, or serum biomarkers in blood or tissues, the growth activity, cytokine producing ability, or surface antigens of cells obtained from the intestinal tract, peripheral blood, the thymus, the spleen, the lymph node, or the bone marrow, etc. between an anti-Orai1 antibody group and a non-administration group.

For the effect on systemic lupus erythematosus, egg albumin or another non-stimulating antigen is intraperitoneally or subcutaneously administered a maximum of 15 times at 5 to 10 day intervals to induce systemic lupus erythematosus-like symptoms. The effect on systemic lupus erythematosus is evaluated by comparing the concentrations of the antibody, cytokines, or serum biomarkers in blood or tissues collected over time during the observation period, the antibody titer or biomarker concentration in urine, symptoms induced in an untreated mouse by the transplantation of cells prepared from an organ such as the spleen or the lymph node collected after the completion of the test, etc., between an anti-Orai1 antibody group and a non-administration group.

For the effect on hepatitis, D-galactosamine is intraperitoneally administered either alone or in combination with lipopolysaccharide to a mouse, or concanavalin A is intravenously administered alone to the tail. The effect on hepatitis induced by such a method is evaluated by comparing GOT and GPT concentrations in blood collected 1 hour to 1 week after the administration of the causative substance, and the histopathological conditions of liver lesions between an anti-Orai1 antibody group and a non-administration group.

For the effect on the graft survival rate in bone marrow cell transplantation or the prophylactic effect on graft versus host disease, cells within the bone marrow collected from the thigh bone or the shinbone of a human Orai1 knock-in mouse are transplanted to an X-ray irradiated recipient mouse either alone or in combination with spleen cells collected from the spleen of the human Orai1 knock-in mouse. The effect on the graft survival rate or the prophylactic effect is evaluated by comparing change in body weight or survival rates for 4 to 16 weeks, the concentrations of the antibody, cytokines, or serum biomarkers in blood or tissues at the completion of the test, and the surface antigens, growth activity, or cytokine producing ability of cells obtained from the intestinal tract, peripheral blood, the thymus, the spleen, the lymph node, or the bone marrow between an anti-Orai1 antibody group and a non-administration group.

For the effect on the graft survival rate of a transplanted organ, the skin collected from the tail base of a host mouse is fixed to the panniculus carnosus exposed by cutting the skin in the back of a human Orai1 knock-in mouse. The size of the transplant and its status of engraftment are scored for 4 to 16 weeks after transplantation. The effect on the graft survival rate is evaluated by comparing the obtained results between an anti-Orai1 antibody group and a non-administration group.

The thus-obtained antibody, which neutralizes the biological activity of Orai1, is useful as a drug, particularly, as an antibody for the prevention or treatment of transplant rejections, immune-related diseases, allergic diseases, inflammatory diseases, thrombosis, or cancers, etc.

As one example, the anti-Orai1 antibody can be administered either alone or in combination with at least one additional therapeutic agent for the treatment or prevention of transplant rejections, immune-related diseases, allergic diseases, inflammatory diseases, thrombosis, or cancers. Examples of the additional therapeutic agent that can be administered in combination with the anti-Orai1 antibody can include, but are not limited to, antifolates, calcineurin inhibitors, adrenal cortical steroids, antithymocyte globulins, nucleic acid antimetabolites, nucleic acid synthesis inhibitors, biologics targeting cell surface antigens, and biologics targeting cytokines or cytokine receptors.

Specific examples of these therapeutic agents can include: methotrexate as the antifolate; cyclosporine and tacrolimus as the calcineurin inhibitors; methylprednisolone as the adrenal cortical steroid; cyclophosphamide as the nucleic acid synthesis inhibitor; Zetbulin, lymphoglobuline, and thymoglobulin as the antithymocyte globulins; mycophenolate mofetil as the nucleic acid antimetabolite; alemtuzumab and rituximab as the biologics targeting cell surface antigens; and infliximab, etanercept, and rituximab as the biologics targeting cytokines or cytokine receptors.

Depending on the conditions of transplant rejections, immune-related diseases, allergic diseases, inflammatory diseases, thrombosis, or cancers or the goal of treatment and/or prevention thereof, 2, 3, or more types of additional therapeutic agents may be administered, and these additional therapeutic agents can be enclosed in the same preparation and administered at the same time. The additional therapeutic agent and the anti-Orai1 antibody may be enclosed in the same preparation and administered at the same time. Alternatively, the anti-Orai1 antibody and the additional therapeutic agent may be enclosed in separate preparations and administered at the same time. Furthermore, the additional therapeutic agent and the anti-Orai1 antibody may be separately administered in a staggered manner. Specifically, the therapeutic agent containing the anti-Orai1 antibody or the antigen binding fragment of the antibody as an active ingredient may be administered after administration of the additional therapeutic agent, or the additional therapeutic agent may be administered after administration of the therapeutic agent containing the anti-Orai1 antibody or the antigen binding fragment of the antibody as an active ingredient. In the case of administration for gene therapy, a gene of a proteinous therapeutic agent and the gene of the anti-Orai1 antibody can be inserted downstream of separate promoter regions or the same promoter region and introduced into separate vectors or the same vector.

The anti-Orai1 antibody or the fragment thereof can be conjugated with a therapeutic agent to produce a targeted drug conjugate described in M. C. Garnet, "Targeted drug conjugates: principles and progress", Advanced Drug Delivery Reviews, (2001) 53, 171-216. For this purpose, the antibody molecule as well as any antibody fragment is applicable as long as the antibody fragment does not completely lose the property of recognizing T cells. Examples of the fragment can include Fab, F(ab')2, and Fv fragments. As such, the antibody and the fragment can be used in the present invention. The conjugation pattern between the anti-Orai1 antibody or the fragment of the antibody and the therapeutic agent can be any of various patterns described in M. C. Garnet, "Targeted drug conjugates: principles and progress", Advanced Drug Delivery Reviews, (2001) 53, 171-216, G. T. Hermanson, "Bioconjugate Techniques", Academic Press, California (1996), Putnam and J. Kopecek, "Polymer Conjugates with Anticancer Activity", Advances in Polymer Science (1995) 122, 55-123, etc. Specific examples thereof can include a pattern in which the anti-Orai1 antibody and the therapeutic agent are conjugated directly in a chemical manner or via a spacer such as an oligopeptide, and a pattern in which the anti-Orai1 antibody and the therapeutic agent are conjugated via an appropriate drug carrier. Examples of the drug carrier can include liposomes and water soluble polymers. Examples of such a pattern mediated by these drug carriers can more specifically include a pattern in which the antibody and the therapeutic agent are enclosed in a liposome by the conjugation of the liposome and the antibody, and a pattern in which the therapeutic agent is conjugated with a water soluble polymer (a compound having a molecular weight in the order of 1000 to 100,000) directly in a chemical manner or via a spacer such as an oligopeptide while the antibody is conjugated with the water soluble polymer. The conjugation of the antibody (or the fragment) with the therapeutic agent or the drug carrier (e.g., liposome and water soluble polymer) can be carried out by a method well known to those skilled in the art, for example, a method described in G. T. Hermanson, "Bioconjugate Techniques", Academic Press, California (1996), and Putnam and J. Kopecek, "Polymer Conjugates with Anticancer Activity", Advances in Polymer Science (1995) 122, 55-123. The enclosure of the therapeutic agent in the liposome can be carried out by a method well known to those skilled in the art, for example, a method described in D. D. Lasic, "Liposomes: From Physics to Applications", Elsevier Science Publishers B. V., Amsterdam (1993), etc. The conjugation of the therapeutic agent with the water soluble polymer can be carried out by a method well known to those skilled in the art, for example, a method described in D. Putnam and J Kopecek, "Polymer Conjugates with Anticancer Activity", Advances in Polymer Science (1995) 122, 55-123. The conjugate of the antibody (or the fragment) and a proteinous therapeutic agent (or the fragment) can be prepared by any of the methods described above as well as genetic engineering methods well known to those skilled in the art.

The present invention also provides a pharmaceutical composition comprising a therapeutically and/or prophylactically effective amount of the anti-Orai1 antibody and a pharmaceutically acceptable diluent, vehicle, solubilizer, emulsifier, preservative, and/or additive.

The present invention also provides a pharmaceutical composition comprising a therapeutically and/or prophylactically effective amount of the anti-Orai1 antibody, a therapeutically and/or prophylactically effective amount of at least one therapeutic agent, and a pharmaceutically acceptable diluent, vehicle, solubilizer, emulsifier, preservative, and/or additive. Examples of the therapeutic agent can include, but are not limited to the aforementioned antifolates, calcineurin inhibitors, adrenal cortical steroids, anti-thymocyte globulins, nucleic acid antimetabolites, nucleic acid synthesis inhibitors, biologics targeting cell surface antigens, and biologics targeting cytokines or cytokine receptors.

It is preferred that the pharmaceutically acceptable substance used in the pharmaceutical composition of the present invention should be nontoxic to a recipient of the pharmaceutical composition, preferably in terms of a dose or an administered concentration.

The pharmaceutical composition of the present invention can contain pharmaceutical materials for changing or maintaining pH, osmotic pressure, viscosity, transparency, color, Isotonicity, sterility, stability, solubility, sustained release, absorbability, or permeability. Examples of the pharmaceutical materials can include, but are not limited to, the following: amino acids such as glycine, alanine, glutamine, asparagine, arginine, and lysine; antimicrobial agents; antioxidants such as ascorbic acid, sodium sulfate, and sodium bisulfite; buffers such as phosphate, citrate, or borate buffers, sodium bicarbonate, and Tris-HCl solutions; fillers such as mannitol and glycine; chelating agents such as ethylenediaminetetraacetic acid (EDTA); complexing agents such as caffeine, polyvinylpyrrolidine, β-cyclodextrin, and hydroxypropyl-β-cyclodextrin; bulking agents such as glucose, mannose, and dextrin; other carbohydrates such as monosaccharides and disaccharides; coloring agents; corrigents; diluents; emulsifiers; hydrophilic polymers such as polyvinylpyrrolidine; low molecular weight polypeptides; salt forming counterions; antiseptics such as benzalkonium chloride, benzoic acid, salicylic acid, thimerosal, phenethyl alcohol, methylparaben, propylparaben, chlorhexidine, sorbic acid, and hydrogen peroxide; solvents such as glycerin, propylene glycol, and polyethylene glycol; sugar alcohols such as mannitol and sorbitol; suspending agents; surfactants such as sorbitan ester, polysorbates such as polysorbate 20 and polysorbate 80, triton, tromethamine, lecithin, and cholesterol; stability enhancers such as sucrose and sorbitol; elasticity enhancers such as sodium chloride, potassium chloride, mannitol, and sorbitol; transport agents; excipients; and/or pharmaceutical additives. The amount of these pharmaceutical materials added is preferably 0.01 to 100 times, particularly, 0.1 to 10 times the weight of the anti-Orai1 antibody. A suitable recipe for the pharmaceutical composition in a preparation can be appropriately determined by those skilled in the art according to an applicable disease, an applicable administration route, etc.

The excipient or the vehicle in the pharmaceutical composition may be liquid or solid. Appropriate excipients or vehicles may be other materials usually used in injectable water, physiological saline, artificial cerebrospinal fluids, and parenteral administration. Neutral physiological saline or physiological saline containing serum albumin may be used as a vehicle. The pharmaceutical composition can contain a Tris buffer of pH 7.0 to 8.5, an acetate buffer of pH 4.0 to 5.5, or a citrate buffer of pH 3.0 to 6.2. These buffers can also contain sorbitol or other compounds. Examples of the pharmaceutical composition of the present invention can include a pharmaceutical composition comprising the anti-Orai1 antibody, and a pharmaceutical composition comprising the anti-Orai1 antibody and at least one therapeutic agent. The pharmaceutical composition of the present invention is prepared in the form of a freeze dried product or a liquid as a drug having a selected recipe and a required purity. The pharmaceutical composition comprising the anti-Orai1 antibody, or the pharmaceutical composition comprising the anti-Orai1 antibody and at least one therapeutic agent can also be formed as a freeze dried product using an appropriate excipient such as sucrose.

The pharmaceutical composition of the present invention may be prepared for parenteral administration or may be prepared for absorption in the digestive tract through an oral route. The recipe and concentration of the preparation can be determined according to the administration method. The higher the affinity of the anti-Orai1 antibody contained in the pharmaceutical composition of the present invention for Orai1, i.e., a lower dissociation constant (Kd value) for Orai1, the lower the dose of the anti-Orai1 antibody which can show efficacy in a human. Therefore, the dose of the pharmaceutical composition of the present invention to a human can also be determined on the basis of this result. The dose for the administration of the human type anti-Orai1 antibody to a human is approximately 0.1 to 100 mg/kg, which can be administered once per 1 to 180 days.

Examples of the form of the pharmaceutical composition of the present invention can include injections including intravenous drips, suppositories, transnasal formulations, sublingual formulations, and transdermal absorption formulations.

Although most approved antibody preparations are intravenously administered, subcutaneous administration is often more preferred in medical practice. In such a case, the volume is limited to 1.0 to 1.5 mL. Therefore, an antibody solution having a high concentration is required depending on the dose. However, since a higher concentration increases the viscosity of the drug solution, there may exist a situation in which the drug solution cannot be injected by use of an injection needle having a thickness routinely used, due to its high viscosity. In short, in the case of selecting an injection as the form of the pharmaceutical composition, the low viscosity is an important property that should be given the highest priority. Thus, a suitable antibody can be selected with the viscosity as an index.

EXAMPLES

Hereinafter, the present invention will be specifically described with reference to Examples. However, the present invention is not intended to be limited by them. Each procedure related to gene manipulation in the Examples below was performed according to the methods described in "Molecular Cloning" (Sambrook, J., Fritsch, E. F. and Maniatis, T., Cold Spring Harbor Laboratory Press, 1989), or using commercially available reagents or kits according to the instruction manuals of the commercial products, unless otherwise specified.

[Example 1] Preparation of Rat Anti-Human Orai1 Antibody

1)-1 Immunization

1)-1-1 Construction of Human Orai1 Expression Vector (pcDNA3.1-hOrai1)

Ultimate ORF clone (Clone No. IOH40869, Life Technologies Corp.) cloned in pDONR221 (Life Technologies Corp.) was purchased and used as the gene sequence of human Orai1. The gene sequence is shown in SEQ ID NO: 1 of the Sequence Listing, and the amino acid sequence is shown in SEQ ID NO: 2 of the Sequence Listing. Also, pcDNA3.1(+) was modified into a destination vector with Gateway Vector Conversion System (Life Technologies Corp.) to prepare pcDNA3.1-DEST. The gene sequence was recombined with pcDNA3.1-DEST within the att sequence using Gateway LR Clonase Enzyme mix (Life Technologies Corp.) to prepare a human Orai1 expression vector pcDNA3.1-hOrai1. EndoFree Plasmid Giga Kit (Qiagen N.V.) was used in the large scale preparation of the human Orai1 expression vector.

1)-1-2 Rat Immunization

Female WKY/Izm rats (Japan SLC, Inc.) were used in immunization. First, both lower legs of each rat were pretreated with hyaluronidase (Sigma-Aldrich Corp.), and then, pcDNA3.1-hOrai1 was intramuscularly injected to these sites. Subsequently, in vivo electroporation was carried out at the sites using ECM830 (BTX) and a two-needle electrode. After repeating of similar in vivo electroporation once every two weeks, the lymph node of the rat was collected and used in hybridoma preparation.

1)-2 Hybridoma Preparation

The lymph node cells were electrically fused with mouse myeloma SP2/0-ag14 cells using Hybrimune Hybridoma Production System (Cyto Pulse Sciences Inc.). The fused cells were diluted with ClonaCell-HY Selection Medium D (StemCell Technologies Inc.) and cultured. Hybridoma colonies that appeared were recovered to prepare monoclonal hybridomas. Each hybridoma colony recovered was cultured, and the obtained hybridoma culture supernatant was used to screen for a hybridoma producing the anti-human Orai1 antibody.

1)-3 Primary Screening by Cell-ELISA

1)-3-1 Preparation of Antigen Gene Expressing Cell for Cell-ELISA

HEK293 cells were prepared at $7.5 \times 10^5$ cells/mL in a DMEM medium containing 10% FBS. The cells were transfected with pcDNA3.1-hOrai1 or pcDNA3.1-DEST as a control according to transfection procedures using Lipofectamine 2000, dispensed at 50 μl/well to a 96-well plate (Corning Inc.), and cultured at 37° C. for two nights under 5% $CO_2$ conditions in a DMEM medium containing 10% FBS. The obtained transfected cells were used in the attached state in Cell-ELISA.

1)-3-2 Cell-ELISA

After removal of the culture supernatant from the HEK293 cells transfected with the expression-vector prepared in Example 1)-1-1, each hybridoma culture supernatant was added to the pcDNA3.1-hOrai1 or pcDNA3.1-DEST transfected HEK293 cells, and the plate was incubated at 4° C. for 1 hour. The cells in the wells were washed once with PBS containing 5% FBS. Then, Anti-Rat IgG-Peroxidase antibody produced in rabbit (Sigma-Aldrich Corp.) diluted 500-fold with PBS containing 5% FBS was added thereto, and the plate was incubated at 4° C. for 1 hour. The cells in the wells were washed 6 times with PBS containing 5% FBS. Then, an OPD chromogenic solution (OPD solution (o-phenylenediamine dihydrochloride (Wako Pure Chemicals Industries, Ltd.) and $H_2O_2$ dissolved at concentrations of 0.4 mg/mL and 0.6% (v/v), respectively, in 0.05 M trisodium citrate and 0.1 M disodium hydrogen phosphate dodecahydrate, pH 4.5)) was added thereto at 25 μL/well. Color reaction was performed with occasional stirring and stopped by the addition of 1 M HCl at 25 μL/well. Then, the absorbance was measured at 490 nm using a plate reader (ENVISION; PerkinElmer, Inc.). In order to select a hybridoma producing an antibody specifically binding to human Orai1 expressed on the cell membrane surface, hybridomas that yielded a culture supernatant exhibiting higher absorbance for the pcDNA3.1-hOrai1 expression-vector-transfected HEK293 cells compared with the control pcDNA3.1-DEST transfected HEK293 cells were selected as anti-human Orai1 antibody positive hybridomas.

1)-4 Secondary Screening by Flow Cytometry

1)-4-1 Preparation of Antigen Gene Expressing Cell for Flow Cytometry Analysis

HEK293T cells were inoculated at $5 \times 10^4$ cells/cm$^2$ onto a 225 cm$^2$ flask and cultured overnight at 37° C. under 5% $CO_2$ conditions in a DMEM medium containing 10% FBS. On the next day, the HEK293T cells were transfected with pcDNA3.1-hOrai1 or pcDNA3.1-DEST as a control using Lipofectamine 2000 and further cultured at 37° C. for two nights under 5% $CO_2$ conditions. On the next day, the expression vector transfected HEK293T cells were treated with TrypLE Express (Life Technologies Corp.), washed with DMEM containing 10% FBS, and then suspended in PBS containing 5% FBS. The obtained cell suspension was used in flow cytometry analysis.

1)-4-2 Flow Cytometry Analysis

The human Orai1 binding specificity of the antibody produced by each hybridoma confirmed to be positive by Cell-ELISA in Example 1)-3 was further confirmed by flow cytometry. Each HEK293T cell suspension prepared in Example 1)-4-1 was centrifuged to remove supernatant. Then, the pcDNA3.1-DEST transfected HEK293T cells or the pcDNA3.1-hOrai1 transfected HEK293T cells were suspended by the addition of the hybridoma culture supernatant and incubated at 4° C. for 1 hour. The cells were washed once with PBS containing 5% FBS, then suspended by the addition of Anti-Rat IgG FITC conjugate (Sigma-Aldrich Corp.) diluted 500-fold with PBS containing 5% FBS, and left standing at 4° C. for 1 hour. The cells were washed 3 times with PBS containing 5% FBS and then resuspended in PBS containing 5% FBS and 2 μg/mL 7-aminoactinomycin D (Molecular Probes, Inc.), followed by detection using a flow cytometer (FC500; Beckman Coulter Inc.). The data was analyzed using Flowjo (Tree Star Inc.). After exclusion of 7-aminoactinomycin D positive dead cells by gating, the FITC fluorescence intensity of live cells was plotted as a histogram. Hybridomas that yielded a sample exhibiting a shift to stronger fluorescence intensity in the histogram of the pcDNA3.1-hOrai1 transfected HEK293T cells compared with the fluorescence intensity histogram of the control pcDNA3.1-DEST transfected HEK293T cells were obtained as hybridomas producing the anti-human Orai1 antibody. As a result, 225 hybridomas exhibiting a significant shift were obtained.

1)-5 Isotyping of Antibody

The antibodies R118 and R198, which were suggested to bind to human Orai1 strongly, were selected from among the rat anti-human Orai1 antibodies produced by the hybridomas obtained in 1)-4, and isotyped. Their isotypes were determined using a Rat monoclonal isotyping test kit (AbD Serotec). As a result, the isotypes of the rat anti-human Orai1 monoclonal antibodies R118 and R198 were both found to be IgG2a and κ chains.

1)-6 Preparation of Rat Anti-Human Orai1 Antibody

Each rat anti-human Orai1 monoclonal antibody was purified from the hybridoma culture supernatant.

First, the hybridoma producing R118 or R198 was grown into a sufficient amount with ClonaCell-HY Selection Medium E. Then, the medium was replaced with Hybridoma SFM (Life Technologies Corp.) supplemented with 20% of Ultra Low IgG FBS (Life Technologies Corp.), followed by culture for 5 days. This culture supernatant was collected and sterilized through a 0.45 μm filter.

The antibody was purified from the hybridoma supernatant by protein G affinity chromatography (at 4 to 6° C.) in one step. The buffer replacement step after the purification by protein G affinity chromatography was carried out at 4 to 6° C. First, the hybridoma culture supernatant was applied to a column packed with protein G (GE Healthcare BioSciences Corp.) equilibrated with PBS. After entry of the whole culture supernatant in the column, the column was washed with PBS of 2 or more times the volume of the column. Next, fractions containing the antibody were collected by elution with a 0.1 M aqueous glycine hydrochloride solution (pH 2.7). The collected fractions were prepared at pH 7.0 to 7.5 by the addition of 1 M Tris-HCl (pH 9.0) and then buffer replaced with PBS using Centrifugal UF Filter Device VIVASPIN 20 (molecular weight cutoff: UF30K, Sartorius Japan K.K., 4 to 6° C.) while concentrated into an antibody concentration of 0.2 mg/mL or higher. Finally, the antibody solution was filtered through a Minisart-Plus filter (Sartorius Japan K.K.) and used as a purified sample.

[Example 2] In Vitro Evaluation of Rat Anti-Human Orai1 Antibody

2)-1 Evaluation of Ability of Rat Anti-Human Orai1 Antibody to Bind by Flow Cytometry In order to evaluate Orai1 binding specificity, the pcDNA3.1-DEST transfected HEK293T cell suspension or the pcDNA3.1-hOrai1 transfected HEK293T cell suspension prepared by the method shown in 1)-4-1 was centrifuged to remove the supernatant. Then, the HEK293T cells were suspended by the addition of the rat anti-human Orai1 monoclonal antibody R118 or R198 prepared in 1)-6 or a rat IgG control antibody (Beckman Coulter Inc.), and incubated at 4° C. for 30 minutes. The cells were washed twice with PBS containing 5% FBS, then suspended by the addition of Anti-Rat IgG FITC conjugate diluted 320-fold with PBS containing 5% FBS, and incubated at 4° C. for 30 minutes. The cells were washed twice with PBS containing 5% FBS and then resuspended in PBS containing 5% FBS and 1 μg/mL propidium iodide (Life Technologies Corp.), followed by detection using a flow cytometer (FC500). The data was analyzed using Flowjo. After exclusion of propidium iodide positive dead cells by gating, the FITC fluorescence intensity of live cells was plotted as a histogram to calculate mean fluorescence intensity (MFI). R118 and R198 did not bind to the pcDNA3.1-DEST transfected HEK293T cells and, as shown in FIG. 1, each bound only to the pcDNA3.1-hOrai1 transfected HEK293T cells in a concentration dependent manner, demonstrating that these antibodies each specifically bind to human Orai1. On the other hand, such binding was not observed in the rat IgG control antibody.

2)-2 T Cell Activation Inhibitory Effect of Rat Anti-Human Orai1 Antibody

Figure 2:
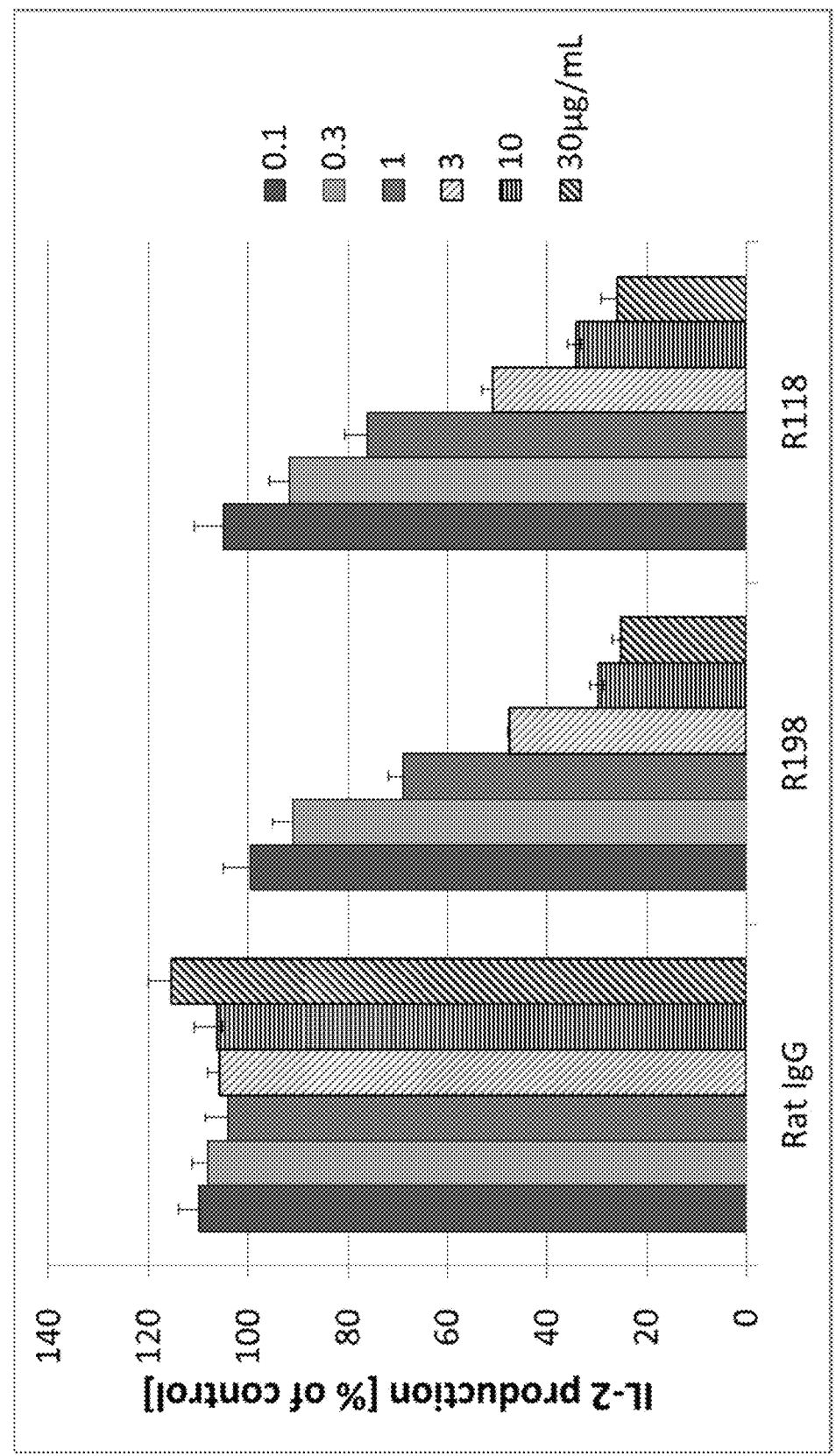
FIG. 2 is a diagram showing that R118 and R198 each inhibit, in a concentration dependent manner, the release of IL-2 from Jurkat cells treated with PMA and A23187.

Human T cell line Jurkat cells were prepared at a concentration of $1.5 \times 10^6$ cells/mL in RPMI1640 (Life Technologies Corp.) containing 10% FBS, 100 U/mL penicillin, and 100 μg/mL streptomycin (Life Technologies Corp.), inoculated at 80 μL/well to a 96-well cell culture plate, and pretreated with the rat anti-human Orai1 monoclonal antibody R118 or R198 or a rat IgG control antibody added at 10 μL/well at 37° C. for 60 minutes under 5% $CO_2$ conditions. Then, 100 ng/mL PMA (Sigma-Aldrich Corp.) and 1 μg/mL A23187 (Sigma-Aldrich Corp.) were added at 10 μL/well (final concentration: 10 ng/mL PMA and 100 ng/mL A23187) and well stirred, followed by culture at 37° C. for approximately 16 hours under 5% $CO_2$ conditions. The plate was well stirred and then centrifuged at 600 g for 3 minutes. The interleukin-2 (IL-2) concentration contained in the supernatant was measured by ELISA (R&D systems, Inc.). FIG. 2 shows that the obtained rat anti-human Orai1 monoclonal antibodies each inhibit, in a concentration dependent manner, the release of IL-2 from Jurkat cells treated with PMA and A23187. R118 and R198 each inhibited the IL-2 release from the Jurkat cells in a concentration dependent manner. On the other hand, such inhibition was not observed in the rat IgG control antibody.

[Example 3] Determination of Nucleotide Sequences of cDNAs Encoding Variable Regions of Rat Anti-Human Orai1 Antibody 3)-1 cDNA Synthesis A cell lysate (50 mM Tris-HCl (pH 7.5), 250 mM LiCl, 5 mM EDTA (pH 8), 0.5% lithium dodecyl sulfate (LiDS), 2.5 mM dithiothreitol (DTT)) of the hybridoma producing each antibody R118 or R198 was mixed with magnetic beads (Dynabeads mRNA DIRECT Kit, Invitrogen Corp.) bound with oligo dT25 so that mRNA bound to the magnetic beads. Next, the magnetic beads were washed once each with mRNA washing solution A (10 mM Tris-HCl (pH 7.5), 0.15 M LiCl, 1 mM EDTA, 0.1% LiDS, 0.1% Triton X-100) and a solution for cDNA synthesis (50 mM Tris-HCl (pH 8.3), 75 mM KCl, 3 mM $MgCl_2$, 5 mM DTT, 0.5 mM dNTP, 0.2% Triton X-100, 1.2 units of RNase inhibitor (Life Technologies Corp.)), followed by cDNA synthesis using a solution for cDNA synthesis supplemented with 12 units of SuperScript III Reverse Transcriptase (Life Technologies Corp.). Subsequently, the magnetic beads were washed with a 3' tailing reaction solution (50 mM potassium phosphate, 4 mM $MgCl_2$, 0.5 mM dGTP, 0.2% Triton X-100, 1.2 units of RNase inhibitor (Life Technologies Corp.)), followed by 3' tailing reaction using a reaction solution supplemented with 48 units of Terminal Transferase, recombinant (F. Hoffmann-La Roche, Ltd.).

3)-2 Amplification and Sequencing of Rat Immunoglobulin Heavy and Light Chain Variable Region Gene Fragments The magnetic beads were washed with a TE solution (10 mM Tris-HCl (pH 7.5), 1 mM EDTA, 0.1% Triton X-100), and then the rat immunoglobulin heavy and light chain genes were amplified by 5'-RACE PCR. Specifically, the magnetic beads were transferred to a PCR reaction solution (0.2 µM primer, 0.2 mM dNTP, 0.25 units of PrimeSTAR HS DNA Polymerase (Takara Bio Inc.)) and subjected to 35 cycles of reaction each involving 94° C. for 30 seconds-68° C. for 90 seconds. The primer sets used were as follows:
PCR Primer Set (for the Heavy Chain)

```
(Nhe-polyC-S)
                                    (SEQ ID NO: 3)
5'-GCTAGCGCTACCGGACTCAGATCCCCCCCCCCCCCDN-3'

(rIgγ-AS1)
                                    (SEQ ID NO: 4)
5'-TCACTGAGCTGGTGAGAGTGTAGAGCCC-3'

(rIgγ-AS2)
                                    (SEQ ID NO: 5)
5'-TCACCGAGCTGCTGAGGGTGTAGAGCCC-3'
```

PCR Primer Set (for the Light Chain)

```
(Nhe-polyC-S)
                                    (SEQ ID NO: 6)
5'-GCTAGCGCTACCGGACTCAGATCCCCCCCCCCCCCDN-3'
(the same as that for the heavy chain)

(rIgκ-AS)
                                    (SEQ ID NO: 7)
5'-TCAGTAACACTGTCCAGGACACCATCTC-3'
```

The fragments amplified by the PCR reaction were sequenced to analyze their nucleotide sequences. An oligonucleotide having a nucleotide sequence of 5'-CTGGCTCAGGGAAATAGCC-3' (rIgγ-seq) (SEQ ID NO: 8) was used as a sequencing primer for the heavy chain, and an oligonucleotide having a nucleotide sequence of 5'-TCCAGTTGCTAACTGTTCC-3' (rIgκ-seq) (SEQ ID NO: 9) was used as a sequencing primer for the light chain.

The sequencing analysis was carried out using a gene sequence analysis apparatus ("ABI PRISM 3700 DNA Analyzer; Applied Biosystems, Inc." or "Applied Biosystems 3730xl Analyzer; Applied Biosystems, Inc."). Dye Terminator Cycle Sequencing System with AmpliTaq DNA polymerase (Life Technologies Corp.) and GeneAmp 9700 (Applied Biosystems, Inc.) were used in the sequencing reaction.

The determined nucleotide sequences encoding the heavy and light chain variable regions of R118 and R198 are shown in SEQ ID NOs: 10 (R118 light chain) and 12 (R118 heavy chain) and SEQ ID NOs: 14 (R198 light chain) and 16 (R198 heavy chain), respectively, of the Sequence Listing. The amino acid sequences of the variable regions are shown in SEQ ID NOs: 11 (R118 light chain) and 13 (R118 heavy chain) and SEQ ID NOs: 15 (R198 light chain) and 17 (R198 heavy chain), respectively, of the Sequence Listing. SEQ ID NOs: 10 and 11 are shown in FIG. 14. SEQ ID NOs: 12 and 13 are shown in FIG. 15. SEQ ID NOs: 14 and 15 are shown in FIG. 16. SEQ ID NOs: 16 and 17 are shown in FIG. 17.

[Example 4] Preparation of Human Chimerized Anti-Human Orai1 Antibody

4)-1 Construction of Chimerized and Humanized Light Chain Expression Vector pCMA-LK A fragment of approximately 5.4 kb obtained by the digestion of a plasmid pcDNA3.3-TOPO/LacZ (Life Technologies Corp.) with restriction enzymes XbaI and PmeI was ligated with a DNA fragment (shown in SEQ ID NO: 18 of the Sequence Listing) comprising a sequence encoding a human κ chain secretion signal and a human κ chain constant region using In-Fusion Advantage PCR cloning kit (Clontech Laboratories, Inc.) to prepare pcDNA3.3/LK.

pcDNA3.3/LK was used as a template in PCR using the primer set given below. The obtained fragment of approximately 3.8 kb was phosphorylated and then self-ligated to construct a chimerized and humanized antibody light chain expression vector pCMA-LK having a signal sequence, a cloning site, and the human κ chain-constant region-encoding-sequence downstream of a CMV promoter.
Primer Set

```
        (SEQ ID NO: 19; primer 3.3-F1)
        5'-TATACCGTCGACCTCTAGCTAGAGCTTGGC-3'

(SEQ ID NO: 20; primer 3.3-R1)
        5'-GCTATGGCAGGGCCTGCCGCCCCGACGTTG-3'
```

4)-2 Construction of Chimerized and Humanized IgG1 Type Heavy Chain Expression Vector pCMA-G1

A DNA fragment obtained by the digestion of pCMA-LK with XbaI and PmeI to remove the sequence encoding a κ chain secretion signal and a human κ chain constant region was ligated with a DNA fragment (shown in SEQ ID NO: 21 of the Sequence Listing) comprising a sequence encoding a human heavy chain signal sequence and amino acids of a human IgG1 constant region using an In-Fusion Advantage PCR cloning kit to construct a chimeric and humanized antibody IgG1 type heavy chain expression vector pCMA-G1 having a signal sequence, a cloning site, and the human IgG1 heavy chain constant-region-encoding-sequence downstream of a CMV promoter.

4)-3 Construction of Human Chimerized Anti-Human Orai1 Antibody Light Chain Expression Vector 4)-3-1 Construction of Human Chimerized R118 Light Chain cR118_L Expression Vector A DNA fragment comprising the R118 light chain variable-region-encoding-sequence obtained in Example 3)-2 was synthesized (GeneArt Artificial Gene Synthesis service). A DNA fragment of approximately 0.7 kb obtained by the cleavage of the DNA fragment comprising the R118 light chain variable-region-encoding-sequence with restriction enzymes XbaI and PmeI was inserted into a DNA fragment of approximately 3.4 kb obtained by the cleavage of the general purpose vector pCMA-LK for chimerized and humanized antibody light chain expression with the same restriction enzymes as above using Ligation High ver. 2 (Toyobo Co., Ltd.) to construct a human chimerized R118 light chain (cR118_L) expression vector. The obtained expression vector was designated as "pCMA-LK/cR118_L". The nucleotide sequence encoding the human chimerized cR118 light chain and the amino acid sequence of the light chain are shown in SEQ ID NOs: 22 and 23 (FIG. 18), respectively, of the Sequence Listing.

4)-3-2 Construction of Human Chimerized R198 Light Chain cR198_L Expression Vector A DNA fragment comprising the R198 light chain variable-region-encoding-sequence obtained in Example 3)-2 was synthesized (GeneArt Artificial Gene Synthesis service). A DNA fragment of approximately 0.7 kb obtained by the cleavage of the DNA fragment comprising the R198 light chain variable-region-encoding-sequence with restriction enzymes XbaI and PmeI was inserted into a DNA fragment of approximately 3.4 kb obtained by the cleavage of the general purpose vector pCMA-LK for chimerized and humanized antibody light chain expression with the same restriction enzymes as above using Ligation High ver. 2 (Toyobo Co., Ltd.) to construct a human chimerized R198 light chain (cR198_L) expression vector. The obtained expression vector was designated as "pCMA-LK/cR198_L". The nucleotide sequence encoding the human chimerized cR198 light chain and the amino acid sequence of the light chain are shown in SEQ ID NOs: 24 and 25 (FIG. 19), respectively, of the Sequence Listing.

4)-4 Construction of Human Chimerized Anti-Human Orai1 Antibody Heavy Chain Expression Vector 4)-4-1 Construction of Human Chimerized R118 Heavy Chain cR118_H Expression Vector A DNA fragment comprising the R118 heavy chain variable-region-encoding-sequence obtained in Example 3)-2 was synthesized (GeneArt Artificial Gene Synthesis service). A DNA fragment of approximately 0.3 kb obtained by the cleavage of the DNA fragment comprising the R118 heavy chain variable-region-encoding-sequence with a restriction enzyme BlpI was inserted into a DNA fragment of approximately 4.5 kb obtained by the cleavage of the chimerized and humanized IgG1 type heavy chain expression vector pCMA-G1 with the same restriction enzyme as above using Ligation High ver. 2 to construct a human chimerized R118 heavy chain (cR118_H) expression vector. The obtained expression vector was designated as "pCMA-G1/cR118_H". The nucleotide sequence encoding the human chimerized cR118 heavy chain and the amino acid sequence of the heavy chain are shown in SEQ ID NOs: 26 and 27 (FIG. 20), respectively, of the Sequence Listing.

4)-4-2 Construction of Human Chimerized R198 Heavy Chain cR198_H Expression Vector A DNA fragment comprising the R198 heavy chain variable-region-encoding-sequence obtained in Example 3)-2 was synthesized (GeneArt Artificial Gene Synthesis service). A DNA fragment of approximately 0.3 kb obtained by the cleavage of the DNA fragment comprising the R198 heavy chain variable-region-encoding-sequence with a restriction enzyme BlpI was inserted into a DNA fragment of approximately 4.5 kb obtained by the cleavage of the chimerized and humanized IgG1 type heavy chain expression vector pCMA-G1 with the same restriction enzyme as above using Ligation High ver. 2 to construct a human chimerized R198 heavy chain (cR198_H) expression vector. The obtained expression vector was designated as "pCMA-G1/cR198_H". The nucleotide sequence encoding the human chimerized cR198 heavy chain and the amino acid sequence of the heavy chain are shown in SEQ ID NOs: 28 and 29 (FIG. 21), respectively, of the Sequence Listing.

4)-5 Preparation of Human Chimerized Anti-Human Orai1 Antibody

4)-5-1 Production of Human Chimerized Anti-Human Orai1 Antibody

FreeStyle 293F cells (Life Technologies Corp.) were subcultured and cultured according to the manual.

$10^7$ FreeStyle 293F cells (Life Technologies Corp.) in the logarithmic growth phase were inoculated into a 30 mL bottle (Thermo Fisher Scientific Inc.), prepared at 9 mL by dilution with FreeStyle 293 expression medium (Life Technologies Corp.), and then shake cultured at 135 rpm at 37° C. for 1 hour in an 8% $CO_2$ incubator. 30 µg of polyethyleneimine (Polysciences #24765) was dissolved in 500 µL of Opti-Pro SFM (Life Technologies Corp.). Next, each human chimerized anti-human Orai1 antibody heavy chain expression vector (4 µg) and each human chimerized anti-human Orai1 antibody light chain expression vector (6 µg), prepared using QIAGEN Plasmid Maxi Kit (Qiagen N.V.), were suspended in 500 µL of Opti-Pro SFM. 500 µL of the expression vector/Opti-Pro SFM mixed solution was added to 500 µL of the polyethyleneimine/Opti-Pro SFM mixed solution, and the mixture was gently stirred, further left for 5 minutes, and then added to the FreeStyle 293F cells. The cells were shake cultured at 95 rpm at 37° C. for 5 to 7 days in an 8% $CO_2$ incubator, and the obtained culture supernatant was filtered through a 0.22 µm Millex Filter (Millipore Corp.).

Human chimerized R118 obtained by the combination of pCMA-G1/cR118_H and pCMA-LK/cR118_L was designated as "cR118". Likewise, human chimerized R198 obtained by the combination of pCMA-G1/cR198_H and pCMA-LK/cR198_L was designated as "cR198".

4)-5-2 Purification of Human Chimerized Anti-Human Orai1 Antibody

Each culture supernatant obtained in 4)-5-1 was purified by rProtein A affinity chromatography in one step. First, 10 mL of the culture supernatant was applied to MabSelect-SuRe (GE Healthcare Bio-Sciences Corp.) equilibrated with PBS. After entry of the whole culture solution in the column, the column was washed with 7 mL of PBS. Next, elution was performed with 5 mL of 2 M arginine-HCl, pH 4.0, and the eluate was buffer replaced with 4 mL of a histidine buffer (25 mM histidine, 5% sorbitol, pH 6.0) using a PD-10 desalting column (GE Healthcare Bio-Sciences Corp.). Finally, the solution was concentrated into approximately 100 µL using Amicon Ultracel 30K (molecular weight cutoff: 30 K, Millipore Corp.) and used as a purified sample.

[Example 5] In Vitro Activity of Human Chimerized Anti-Human Orai1 Antibody

Figure 3:
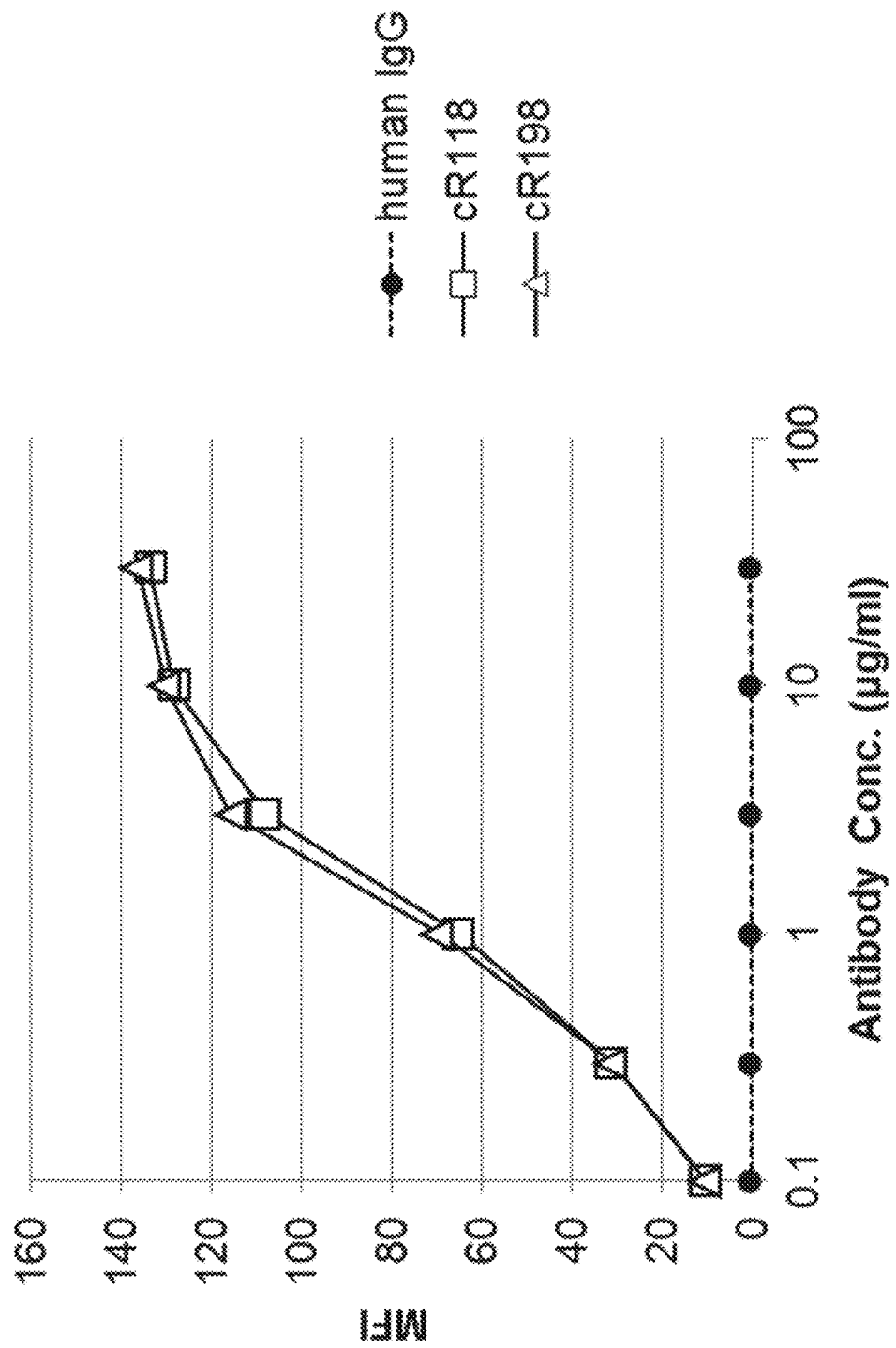
FIG. 3 is a diagram showing that cR118 and cR198 each bind to pcDNA3.1-hOrai1 transfected HEK293T cells in a concentration dependent manner.

5)-1 Antigen Binding Activity of Human Chimerized Anti-Human Orai1 Antibody by Flow Cytometry In order to evaluate human Orai1 binding specificity, the pcDNA3.1-DEST transfected HEK293T cell suspension or the pcDNA3.1-hOrai1 transfected HEK293T cell suspension prepared by the method shown in 1)-4-1 was centrifuged to remove a supernatant. Then, the HEK293T cells were suspended by the addition of the human chimerized anti-human Orai1 antibody cR118 or cR198 prepared in 4)-5 or a human IgG control antibody (Jackson ImmunoResearch Laboratories, Inc.), and incubated at 4° C. for 30 minutes. The cells were washed twice with PBS containing 5% FBS, then suspended by the addition of Anti-human IgG FITC conjugate (Jackson ImmunoResearch Laboratories, Inc.) diluted 100-fold with PBS containing 5% FBS, and incubated at 4° C. for 30 minutes. The cells were washed twice with PBS containing 5% FBS and then resuspended in PBS containing 5% FBS and 1 µg/mL propidium iodide (Invitrogen Corp.), followed by detection using a flow cytometer (FC500). The data was analyzed using Flowjo. After exclusion of propidium iodide positive dead cells by gating, the FITC fluorescence intensity of live cells was plotted as a histogram to calculate mean fluorescence intensity (MFI). cR118 and cR198 did not bind to the pcDNA3.1-DEST transfected HEK293T cells and, as shown in FIG. 3, each bound only to the pcDNA3.1-hOrai1 transfected HEK293T cells in a concentration dependent manner, demonstrating that these antibodies each specifically bind to human Orai1. On the other hand, such binding was not observed in the human IgG control antibody.

Figure 4:
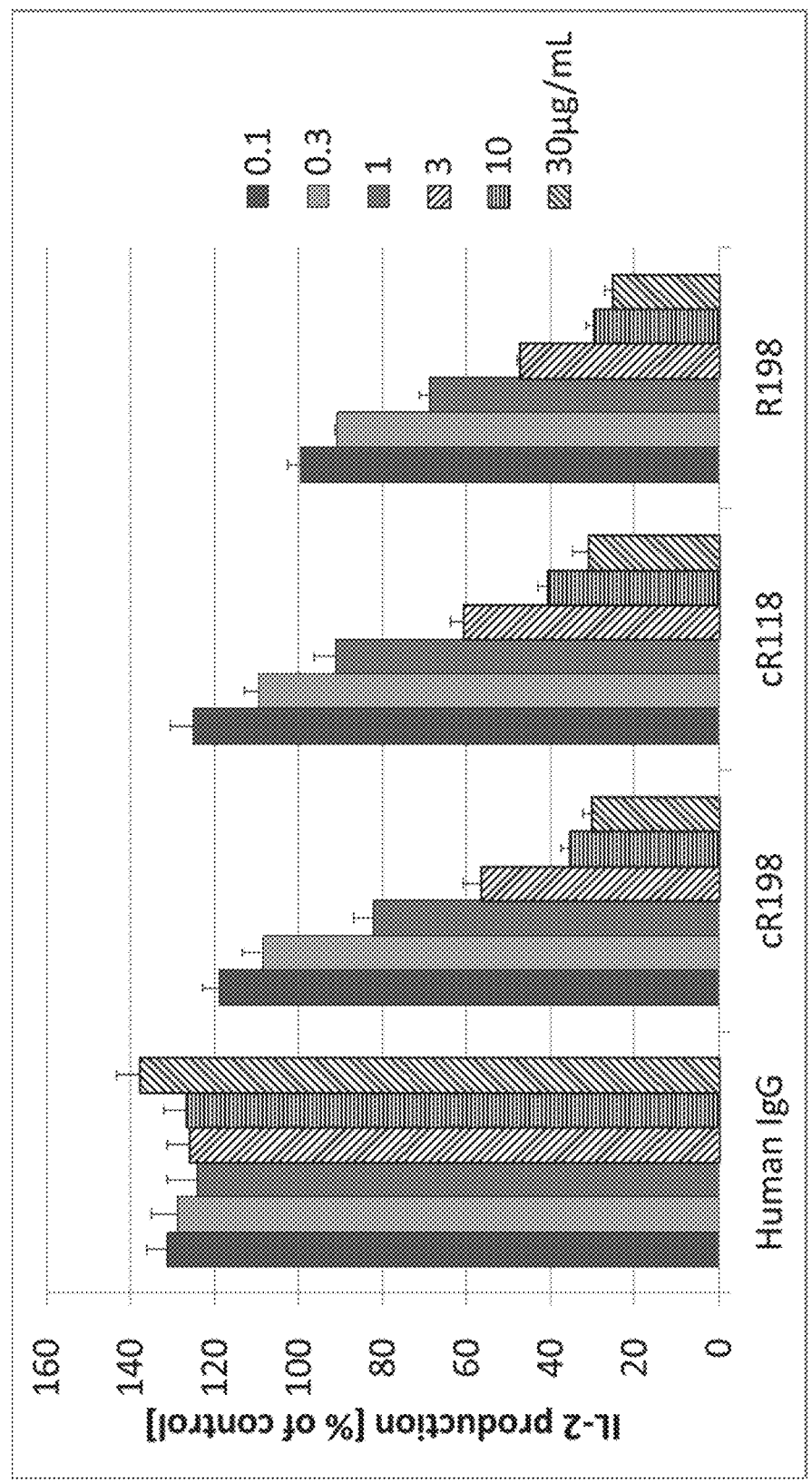
FIG. 4 is a diagram showing that cR118 and cR198 each inhibit, in a concentration dependent manner, the release of IL-2 from Jurkat cells treated with PMA and A23187.

5)-2 Human T Cell Line Activation Inhibitory Effect of Human Chimerized Anti-Human Orai1 Antibody Human T cell line Jurkat cells were prepared at a concentration of $1.5 \times 10^6$ cells/mL in RPMI1640 containing 10% FBS, 100 U/mL penicillin, and 100 μg/mL streptomycin, inoculated at 80 μL/well onto a 96-well cell culture plate, and pretreated with the human chimerized anti-human Orai1 antibody cR198 or cR118, the parent antibody R198, or a human IgG control antibody added at 10 μL/well at 37° C. for 60 minutes under 5% $CO_2$ conditions. Then, 100 ng/mL PMA and 1 μg/mL A23187 were added at 10 μL/well and well stirred, followed by culture at 37° C. for approximately 16 hours under 5% $CO_2$ conditions. The plate was well stirred and then centrifuged at 600 g for 3 minutes. The IL-2 concentration contained in the supernatant was measured by ELISA. FIG. 4 shows that the prepared human chimerized anti-human Orai1 antibodies each inhibit, in a concentration dependent manner, the release of IL-2 from Jurkat cells treated with PMA and A23187. cR118 and cR198 each inhibited the IL-2 release from the Jurkat cells in a concentration dependent manner with their inhibition strength equivalent to that of the parent antibody R198. On the other hand, such inhibition was not observed in the human IgG control antibody.

[Example 6] Design of Humanized Version hR198 of Human Chimerized Anti-Human Orai1 Antibody cR198

6)-1 Molecular Modeling of Variable Regions of R198

The molecular modeling of the variable regions of cR198 was carried out by a method generally known as homology modeling (Methods in Enzymology, 203, 121-153, (1991)). The variable regions of R198 determined above were compared with the primary sequences (three-dimensional structures derived from X-ray crystal structures are available) of human immunoglobulin variable regions registered in Protein Data Bank (Nuc. Acid Res. 28, 235-242 (2000)). As a result, 1AJ7 was selected as the one having the highest sequence homology to the light chain variable region of cR198. Also, 1XGY was selected as the one having the highest sequence homology to the heavy chain variable region of cR198. The three-dimensional structures of framework regions were prepared as a "framework model" by combining the coordinates of 1AJ7 and 1XGY corresponding to the light chain and the heavy chain of cR198. The CDRs of cR198 were assigned as clusters 11A, 7A, 9A, 10A, and 10A to CDRL1, CDRL2, CDRL3, CDRH1, and CDRH2, respectively, according to the classification of Thornton et al. (J. Mol. Biol., 263, 800-815, (1996)). Its CDRH3 was classified into k(6)—according to the H3 rule (FEBS letter, 399, 1-8 (1996)). Subsequently, the typical conformation of each CDR was incorporated into the framework model.

Finally, an energy calculation for excluding disadvantageous interatomic contact was conducted in order to obtain possible molecular models of the cR198 variable regions in terms of energy. These procedures were performed using a commercially available protein three-dimensional structure prediction program Prime and conformation search program MacroModel (Schrodinger, LLC).

6)-2 Design of Amino Acid Sequence of Humanized R198

The humanized R198 antibody was constructed by a method generally known as CDR grafting (Proc. Natl. Acad. Sci. USA 86, 10029-10033 (1989)). An acceptor antibody was selected on the basis of the homology of amino acids in framework regions.

The sequences of the cR198 framework regions were compared with the sequences of all human frameworks registered in the Kabat database (Nuc. Acid Res., 29, 205-206 (2001)) of antibody amino acid sequences. As a result, a 1C10'CL antibody was selected as an acceptor due to its 71% sequence homology as to framework regions. The amino acid residues of framework regions in 1C10'CL were aligned with the amino acid residues of the cR198 framework regions to identify the positions of amino acids that did not match therebetween. The positions of these residues were analyzed using the three-dimensional model of cR198 constructed above. Then, the donor residues to be grafted onto the acceptor were selected according to the criteria provided by Queen et al. (Proc. Natl. Acad. Sci. USA 86, 10029-10033 (1989)).

Some donor residues thus selected were transferred to the acceptor antibody to construct the humanized R198 sequence as described in the Examples below.

In addition, 1 to 5 amino acid residues in each CDR or FR of cR198 were replaced with amino acid residues of cR118 to construct a CDR engineered humanized R198 sequence as described in the Examples below.

6)-3 Design of Humanized R198 Light Chain hR198_L

6)-3-1 hR198_L1 Type Light Chain:

A humanized R198 light chain designed by replacing a threonine residue at amino acid position 30 with a serine residue, a proline residue at amino acid position 32 with a serine residue, a leucine residue at amino acid position 35 with a valine residue, a glutamic acid residue at amino acid position 37 with an aspartic acid residue, a serine residue at amino acid position 42 with a threonine residue, an aspartic acid residue at amino acid position 61 with a glycine residue, a glycine residue at amino acid position 62 with a lysine residue, a serine residue at amino acid position 63 with an alanine residue, a valine residue at amino acid position 64 with a proline residue, a serine residue at amino acid position 92 with a threonine residue, a serine residue at amino acid position 94 with a threonine residue, a threonine residue at amino acid position 96 with a serine residue, a glutamic acid residue at amino acid position 99 with a glutamine residue, a serine residue at amino acid position 100 with a proline residue, a threonine residue at amino acid position 120 with a glutamine residue, a leucine residue at amino acid position 124 with a valine residue, a leucine residue at amino acid position 126 with an isoleucine residue, an arginine residue at amino acid position 127 with a lysine residue, and an alanine residue at amino acid position 129 with a threonine residue as to the cR198 light chain shown in SEQ ID NO: 25 of the Sequence Listing was designated as a "hR198_L1 type light chain".

The nucleotide sequence encoding the hR198_L1 type light chain is shown in SEQ ID NO: 30 of the Sequence Listing. Nucleotide positions 61 to 702 encode a mature light chain formed by the cleavage of the signal sequence. Nucleotide positions 61 to 378 encode the variable region. The amino acid sequence of the hR198_L1 type light chain is shown in SEQ ID NO: 31 of the Sequence Listing. Amino acid positions 21 to 234 represent the mature light chain formed by the cleavage of the signal sequence. Amino acid positions 21 to 126 represent the variable region. Both of the sequences of SEQ ID NOs: 30 and 31 are also shown in FIG. 22. Each CDR sequence and its corresponding SEQ ID NO are shown in FIG. 38.

6)-3-2 hR198_L2 Type Light Chain:

A humanized R198 light chain designed by replacing a threonine residue at amino acid position 30 with a serine residue, a proline residue at amino acid position 32 with a serine residue, a leucine residue at amino acid position 35 with a valine residue, a glutamic acid residue at amino acid position 37 with an aspartic acid residue, a serine residue at amino acid position 42 with a threonine residue, an aspartic acid residue at amino acid position 61 with a glycine residue, a glycine residue at amino acid position 62 with a lysine residue, a serine residue at amino acid position 63 with an alanine residue, a serine residue at amino acid position 92 with a threonine residue, a serine residue at amino acid position 94 with a threonine residue, a threonine residue at amino acid position 96 with a serine residue, a glutamic acid residue at amino acid position 99 with a glutamine residue, a serine residue at amino acid position 100 with a proline residue, a threonine residue at amino acid position 120 with a glutamine residue, a leucine residue at amino acid position 124 with a valine residue, a leucine residue at amino acid position 126 with an isoleucine residue, an arginine residue at amino acid position 127 with a lysine residue, and an alanine residue at amino acid position 129 with a threonine residue as to the cR198 light chain shown in SEQ ID NO: 25 of the Sequence Listing was designated as a "hR198_L2 type light chain".

The nucleotide sequence encoding the hR198_L2 type light chain is shown in SEQ ID NO: 32 of the Sequence Listing. Nucleotide positions 61 to 702 encode a mature light chain formed by the cleavage of the signal sequence. Nucleotide positions 61 to 378 encode the variable region. The amino acid sequence of the hR198_L2 type light chain is shown in SEQ ID NO: 33 of the Sequence Listing. Amino acid positions 21 to 234 represent the mature light chain formed by the cleavage of the signal sequence. Amino acid positions 21 to 126 represent the variable region. Both of the sequences of SEQ ID NOs: 32 and 33 are also shown in FIG. 23. Each CDR sequence and its corresponding SEQ ID NO are shown in FIG. 38.

6)-3-3 hR198_L3 Type Light Chain:

A humanized R198 light chain designed by replacing a threonine residue at amino acid position 30 with a serine residue, a proline residue at amino acid position 32 with a serine residue, a leucine residue at amino acid position 35 with a valine residue, a glutamic acid residue at amino acid position 37 with an aspartic acid residue, a serine residue at amino acid position 42 with a threonine residue, an aspartic acid residue at amino acid position 61 with a glycine residue, a glycine residue at amino acid position 62 with a lysine residue, a serine residue at amino acid position 63 with an alanine residue, a valine residue at amino acid position 64 with a proline residue, a serine residue at amino acid position 92 with a threonine residue, a serine residue at amino acid position 94 with a threonine residue, a threonine residue at amino acid position 96 with a serine residue, a glutamic acid residue at amino acid position 99 with a glutamine residue, a serine residue at amino acid position 100 with a proline residue, a tyrosine residue at amino acid position 114 with a phenylalanine residue, a threonine residue at amino acid position 120 with a glutamine residue, a leucine residue at amino acid position 124 with a valine residue, a leucine residue at amino acid position 126 with an isoleucine residue, an arginine residue at amino acid position 127 with a lysine residue, and an alanine residue at amino acid position 129 with a threonine residue as to the cR198 light chain shown in SEQ ID NO: 25 of the Sequence Listing was designated as a "hR198_L3 type light chain".

The nucleotide sequence encoding the hR198_L3 type light chain is shown in SEQ ID NO: 34 of the Sequence Listing. Nucleotide positions 61 to 702 encode a mature light chain formed by the cleavage of the signal sequence. Nucleotide positions 61 to 378 encode the variable region. The amino acid sequence of the hR198_L3 type light chain is shown in SEQ ID NO: 35 of the Sequence Listing. Amino acid positions 21 to 234 represent the mature light chain formed by the cleavage of the signal sequence. Amino acid positions 21 to 126 represent the variable region. Both of the sequences of SEQ ID NOs: 34 and 35 are also shown in FIG. 24. Each CDR sequence and its corresponding SEQ ID NO are shown in FIG. 38.

6)-3-4 hR198_L4 Type Light Chain:

A humanized R198 light chain designed by replacing a threonine residue at amino acid position 30 with a serine residue, a proline residue at amino acid position 32 with a serine residue, a leucine residue at amino acid position 35 with a valine residue, a glutamic acid residue at amino acid position 37 with an aspartic acid residue, a serine residue at amino acid position 42 with a threonine residue, an aspartic acid residue at amino acid position 61 with a glycine residue, a glycine residue at amino acid position 62 with a lysine residue, a serine residue at amino acid position 63 with an alanine residue, a serine residue at amino acid position 92 with a threonine residue, a serine residue at amino acid position 94 with a threonine residue, a threonine residue at amino acid position 96 with a serine residue, a glutamic acid residue at amino acid position 99 with a glutamine residue, a serine residue at amino acid position 100 with a proline residue, a tyrosine residue at amino acid position 114 with a phenylalanine residue, a threonine residue at amino acid position 120 with a glutamine residue, a leucine residue at amino acid position 124 with a valine residue, a leucine residue at amino acid position 126 with an isoleucine residue, an arginine residue at amino acid position 127 with a lysine residue, and an alanine residue at amino acid position 129 with a threonine residue as to the cR198 light chain shown in SEQ ID NO: 25 of the Sequence Listing was designated as a "hR198_L4 type light chain".

The nucleotide sequence encoding the hR198_L4 type light chain is shown in SEQ ID NO: 36 of the Sequence Listing. Nucleotide positions 61 to 702 encode a mature light chain formed by the cleavage of the signal sequence. Nucleotide positions 61 to 378 encode the variable region. The amino acid sequence of the hR198_L4 type light chain is shown in SEQ ID NO: 37 of the Sequence Listing. Amino acid positions 21 to 234 represent the mature light chain formed by the cleavage of the signal sequence. Amino acid positions 21 to 126 represent the variable region. Both of the sequences of SEQ ID NOs: 36 and 37 are also shown in FIG. 25. Each CDR sequence and its corresponding SEQ ID NO are shown in FIG. 38.

6)-4 Design of Humanized R198 Heavy Chain hR198_H

6)-4-1 hR198_H1 Type Heavy Chain:

A humanized R198 heavy chain designed by replacing a glutamine residue at amino acid position 24 with a valine residue, a leucine residue at amino acid position 30 with a valine residue, an alanine residue at amino acid position 31 with a lysine residue, a serine residue at amino acid position 35 with an alanine residue, a methionine residue at amino acid position 37 with a valine residue, an isoleucine residue at amino acid position 39 with a valine residue, an isoleucine residue at amino acid position 56 with a valine residue, a lysine residue at amino acid position 57 with an arginine residue, a threonine residue at amino acid position 59 with an alanine residue, a threonine residue at amino acid position 60 with a proline residue, a lysine residue at amino acid position 86 with an arginine residue, a serine residue at amino acid position 95 with a threonine residue, a phenylalanine residue at amino acid position 99 with a tyrosine residue, a glutamine residue at amino acid position 101 with a glutamic acid residue, a threonine residue at amino acid position 106 with an arginine residue, a proline residue at amino acid position 107 with a serine residue, an aspartic acid residue at amino acid position 108 with a glutamic acid residue, a serine residue at amino acid position 110 with a threonine residue, a valine residue at amino acid position 130 with a threonine residue, and a methionine residue at amino acid position 131 with a leucine residue as to the cR198 heavy chain shown in SEQ ID NO: 29 of the Sequence Listing was designated as a "hR198_H1 type heavy chain".

The nucleotide sequence encoding the hR198_H1 type heavy chain is shown in SEQ ID NO: 38 of the Sequence Listing. Nucleotide positions 58 to 1398 encode a mature heavy chain formed by the cleavage of the signal sequence. Nucleotide positions 58 to 408 encode the variable region. The amino acid sequence of the hR198_H1 type heavy chain is shown in SEQ ID NO: 39 of the Sequence Listing. Amino acid positions 20 to 466 represent the mature heavy chain formed by the cleavage of the signal sequence. Amino acid positions 20 to 136 represent the variable region. Both of the sequences of SEQ ID NOs: 38 and 39 are also shown in FIG. 26. Each CDR sequence and its corresponding SEQ ID NO are shown in FIG. 38.

6)-4-2 hR198_H2 Type Heavy Chain:

A humanized R198 heavy chain designed by replacing a glutamine residue at amino acid position 24 with a valine residue, a leucine residue at amino acid position 30 with a valine residue, an alanine residue at amino acid position 31 with a lysine residue, a serine residue at amino acid position 35 with an alanine residue, a methionine residue at amino acid position 37 with a valine residue, an isoleucine residue at amino acid position 39 with a valine residue, a lysine residue at amino acid position 57 with an arginine residue, a threonine residue at amino acid position 59 with an alanine residue, a threonine residue at amino acid position 60 with a proline residue, a lysine residue at amino acid position 86 with an arginine residue, a serine residue at amino acid position 95 with a threonine residue, a phenylalanine residue at amino acid position 99 with a tyrosine residue, a glutamine residue at amino acid position 101 with a glutamic acid residue, a threonine residue at amino acid position 106 with an arginine residue, a proline residue at amino acid position 107 with a serine residue, an aspartic acid residue at amino acid position 108 with a glutamic acid residue, a serine residue at amino acid position 110 with a threonine residue, a valine residue at amino acid position 130 with a threonine residue, and a methionine residue at amino acid position 131 with a leucine residue as to the cR198 heavy chain shown in SEQ ID NO: 29 of the Sequence Listing was designated as a "hR198_H2 type heavy chain".

The nucleotide sequence encoding the hR198_H2 type heavy chain is shown in SEQ ID NO: 40 of the Sequence Listing. Nucleotide positions 58 to 1398 encode a mature heavy chain formed by the cleavage of the signal sequence. Nucleotide positions 58 to 408 encode the variable region. The amino acid sequence of the hR198_H2 type heavy chain is shown in SEQ ID NO: 41 of the Sequence Listing. Amino acid positions 20 to 466 represent the mature heavy chain formed by the cleavage of the signal sequence. Amino acid positions 20 to 136 represent the variable region. Both of the sequences of SEQ ID NOs: 40 and 41 are also shown in FIG. 27. Each CDR sequence and its corresponding SEQ ID NO are shown in FIG. 38.

6)-4-3 hR198_H3 Type Heavy Chain:

A humanized R198 heavy chain designed by replacing a glutamine residue at amino acid position 24 with a valine residue, a leucine residue at amino acid position 30 with a valine residue, an alanine residue at amino acid position 31 with a lysine residue, a serine residue at amino acid position 35 with an alanine residue, a methionine residue at amino acid position 37 with a valine residue, an isoleucine residue at amino acid position 39 with a valine residue, a serine residue at amino acid position 50 with an alanine residue, an isoleucine residue at amino acid position 56 with a valine residue, a lysine residue at amino acid position 57 with an arginine residue, a threonine residue at amino acid position 59 with an alanine residue, a threonine residue at amino acid position 60 with a proline residue, an isoleucine residue at amino acid position 67 with a valine residue, a valine residue at amino acid position 70 with an isoleucine residue, a glutamic acid residue at amino acid position 81 with an alanine residue, a lysine residue at amino acid position 82 with an arginine residue, a lysine residue at amino acid position 86 with an arginine residue, a serine residue at amino acid position 95 with a threonine residue, a phenylalanine residue at amino acid position 99 with a tyrosine residue, a glutamine residue at amino acid position 101 with a glutamic acid residue, a threonine residue at amino acid position 106 with an arginine residue, a proline residue at amino acid position 107 with a serine residue, an aspartic acid residue at amino acid position 108 with a glutamic acid residue, a serine residue at amino acid position 110 with a threonine residue, a valine residue at amino acid position 130 with a threonine residue, and a methionine residue at amino acid position 131 with a leucine residue as to the cR198 heavy chain shown in SEQ ID NO: 29 of the Sequence Listing was designated as a "hR198_H3 type heavy chain".

The nucleotide sequence encoding the hR198_H3 type heavy chain is shown in SEQ ID NO: 42 of the Sequence Listing. Nucleotide positions 58 to 1398 encode a mature heavy chain formed by the cleavage of the signal sequence. Nucleotide positions 58 to 408 encode the variable region. The amino acid sequence of the hR198_H3 type heavy chain is shown in SEQ ID NO: 43 of the Sequence Listing. Amino acid positions 20 to 466 represent the mature heavy chain formed by the cleavage of the signal sequence. Amino acid positions 20 to 136 represent the variable region. Both of the sequences of SEQ ID NOs: 42 and 43 are also shown in FIG. 28. Each CDR sequence and its corresponding SEQ ID NO are shown in FIG. 38.

6)-4-4 hR198_H4 Type Heavy Chain:

A humanized R198 heavy chain designed by replacing a glutamine residue at amino acid position 24 with a valine residue, a leucine residue at amino acid position 30 with a valine residue, an alanine residue at amino acid position 31 with a lysine residue, a serine residue at amino acid position 35 with an alanine residue, a methionine residue at amino acid position 37 with a valine residue, an isoleucine residue at amino acid position 39 with a valine residue, a serine residue at amino acid position 50 with an alanine residue, a lysine residue at amino acid position 57 with an arginine residue, a threonine residue at amino acid position 59 with an alanine residue, a threonine residue at amino acid position 60 with a proline residue, an isoleucine residue at amino acid position 67 with a valine residue, a valine residue at amino acid position 70 with an isoleucine residue, a glutamic acid residue at amino acid position 81 with an alanine residue, a lysine residue at amino acid position 82 with an arginine residue, a lysine residue at amino acid position 86 with an arginine residue, a serine residue at amino acid position 95 with a threonine residue, a phenylalanine residue at amino acid position 99 with a tyrosine residue, a glutamine residue at amino acid position 101 with a glutamic acid residue, a threonine residue at amino acid position 106 with an arginine residue, a proline residue at amino acid position 107 with a serine residue, an aspartic acid residue at amino acid position 108 with a glutamic acid residue, a serine residue at amino acid position 110 with a threonine residue, a valine residue at amino acid position 130 with a threonine residue, and a methionine residue at amino acid position 131 with a leucine residue as to the cR198 heavy chain shown in SEQ ID NO: 29 of the Sequence Listing was designated as a "hR198_H4 type heavy chain".

The nucleotide sequence encoding the hR198_H4 type heavy chain is shown in SEQ ID NO: 44 of the Sequence Listing. Nucleotide positions 58 to 1398 encode a mature heavy chain formed by the cleavage of the signal sequence. Nucleotide positions 58 to 408 encode the variable region. The amino acid sequence of the hR198_H4 type heavy chain is shown in SEQ ID NO: 45 of the Sequence Listing. Amino acid positions 20 to 466 represent the mature heavy chain formed by the cleavage of the signal sequence. Amino acid positions 20 to 136 represent the variable region. Both of the sequences of SEQ ID NOs: 44 and 45 are also shown in FIG. 29. Each CDR sequence and its corresponding SEQ ID NO are shown in FIG. 38.

[Example 7] Preparation of Humanized Anti-Human Orai1 Antibody

7)-1 Construction of Humanized Anti-Human Orai1 Antibody Light Chain hR198_L Expression Vector 7)-1-1 Construction of hR198_L1 Expression Vector A DNA fragment comprising the hR198_L1 variable-region-encoding-sequence shown in nucleotide positions 38 to 402 in the nucleotide sequence of hR198_L1 represented by SEQ ID NO: 30 of the Sequence Listing was synthesized (GeneArt Artificial Gene Synthesis service). The synthesized DNA fragment was cleaved with restriction enzymes AvaI and EcoRV and inserted into the corresponding site of the chimeric and humanized antibody light chain expression vector pCMA-LK cleaved with the same restriction enzymes as above to construct a hR198_L1 expression vector. The obtained expression vector was designated as "pCMA-LK/hR198_L1".

7)-1-2 Construction of hR198_L2 Expression Vector

A DNA fragment comprising the hR198_L2 variable-region-encoding-sequence shown in nucleotide positions 38 to 402 in the nucleotide sequence of hR198_L2 represented by SEQ ID NO: 32 of the Sequence Listing was synthesized (GeneArt Artificial Gene Synthesis service). The DNA fragment comprising the hR198_L2 variable-region-encoding-sequence was amplified with the synthesized DNA fragment as a template using KOD -Plus- (Toyobo Co., Ltd.), cleaved with restriction enzyme BsiWI, and inserted into the corresponding site of the chimeric and humanized antibody light chain expression vector pCMA-LK cleaved with the restriction enzyme BsiWI to construct a hR198_L2 expression vector. The obtained expression vector was designated as "pCMA-LK/hR198_L2".

7)-1-3 Construction of hR198_L3 and hR198_L4 Expression Vectors

A DNA fragment comprising the hR198_L4 variable-region-encoding-sequence shown in nucleotide positions 38 to 402 in the nucleotide sequence of hR198_L4 represented by SEQ ID NO: 36 of the Sequence Listing was synthesized (GeneArt Artificial Gene Synthesis service). A hR198_L4 expression vector was constructed by the same method as in Example 7)-1-2. The obtained expression vector was designated as "pCMA-LK/hR198_L4".

A mutation to replace the valine residue at amino acid position 64 with a proline residue was introduced with pCMA-LK/hR198_L4 as the template using a QuikChange Site-Directed Mutagenesis Kit (Stratagene Corp.). The obtained expression vector comprising the nucleotide sequence represented by SEQ ID NO: 34 of the Sequence Listing was designated as "pCMA-LK/hR198_L3".

7)-2 Construction of Humanized Anti-Human Orai1 Antibody Heavy Chain hR198_H Expression Vector 7)-2-1 Construction of hR198_H1 and hR198_H2 Expression Vectors A DNA fragment comprising the hR198_H0 variable region encoding the sequence shown in nucleotide positions 36 to 425 in the nucleotide sequence of hR198_H0 represented by SEQ ID NO: 111 of the Sequence Listing was synthesized as a candidate for the humanization of the anti-Orai1 antibody heavy chain hR198 (GeneArt Artificial Gene Synthesis service). The DNA fragment comprising the hR198_H0 variable-region-encoding-sequence was amplified with the synthesized DNA fragment as a template using KOD -Plus- and inserted into the corresponding site of the chimeric and humanized antibody IgG1 type heavy chain expression vector pCMA-G1 cleaved with restriction enzyme BlpI using an In-Fusion HD PCR cloning kit (Clontech Laboratories, Inc.) to construct a hR198_H0 expression vector. The obtained expression vector was designated as "pCMA-G1/hR198_H0". The amino acid sequence of hR198_H0 is shown in SEQ ID NO: 112.

Next, a mutation to replace a tryptophan residue at amino acid position 66 with a tyrosine residue was introduced with pCMA-G1/hR198_H0 as the template using a KOD -Plus- mutagenesis kit (Toyobo Co., Ltd.). The obtained expression vector comprising the nucleotide sequence represented by SEQ ID NO: 40 of the Sequence Listing was designated as "pCMA-G1/hR198_H2".

Next, a mutation to replace an isoleucine residue at amino acid position 56 with a valine residue was introduced with pCMA-G1/hR198_H2 as the template using a QuikChange Site-Directed Mutagenesis Kit (Stratagene Corp.) and the primer set given below. The obtained expression vector comprising the nucleotide sequence represented by SEQ ID NO: 38 of the Sequence Listing was designated as "pCMA-G1/hR198_H1".

7)-2-2 Construction of hR198_H3, hR198_H4 and hR198_H5 Expression Vectors

A DNA fragment comprising the hR198_H5 variable region encoding the sequence shown in nucleotide positions 36 to 425 in the nucleotide sequence of hR198_H5 represented by SEQ ID NO: 113 of the Sequence Listing was synthesized as a candidate for the humanization of the anti-Orai1 antibody heavy chain hR198 (GeneArt Artificial Gene Synthesis service). A hR198_H5 expression vector was constructed by the same method as in Example 7)-2-1.

The obtained expression vector was designated as "pCMA-G1/hR198_H5". The amino acid sequence of hR198_H5 is shown in SEQ ID NO: 114.

Next, mutations to replace a tryptophan residue at amino acid position 66 and an isoleucine residue at amino acid position 67 with a tyrosine residue and a valine residue, respectively, were introduced with pCMA-G1/H5 as the template using a KOD -Plus- mutagenesis kit. The obtained expression vector comprising the nucleotide sequence represented by SEQ ID NO: 44 was designated as "pCMA-G1/hR198_H4".

Next, a mutation to replace an isoleucine residue at amino acid position 56 with a valine residue was introduced by the same method as in Example 7)-2-1 with pCMA-G1/hR198_H4 as a template. The obtained expression vector comprising the nucleotide sequence represented by SEQ ID NO: 44 of the Sequence Listing was designated as "pCMA-G1/hR198_H3".

7)-3 Preparation of Humanized Anti-Human Orai1 Antibody hR198

FreeStyle 293F cells were transfected with each humanized anti-human Orai1 antibody heavy chain expression vector and each humanized anti-human Orai1 antibody light chain expression vector by the same method as in 4)-5-1 to obtain a culture supernatant containing the antibody.

Humanized anti-human Orai1 antibodies obtained by the combination of pCMA-G1/hR198_H1 and pCMA-LK/hR198_L1, the combination of pCMA-G1/hR198_H2 and pCMA-LK/hR198_L2, the combination of pCMA-G1/hR198_H3 and pCMA-LK/hR198_L3, and the combination of pCMA-G1/hR198_H4 and pCMA-LK/hR198_L4 were designated as "hR198_H1/L1", "hR198_H2/L2", "hR198_H3/L3", and "hR198_H4/L4", respectively.

Each obtained culture supernatant was purified by rProtein A affinity chromatography by the same method as in 4)-5-2 to obtain a purified antibody sample.

[Example 8] In Vitro Activity of Humanized Anti-Human Orai1 Antibody

Figure 5:
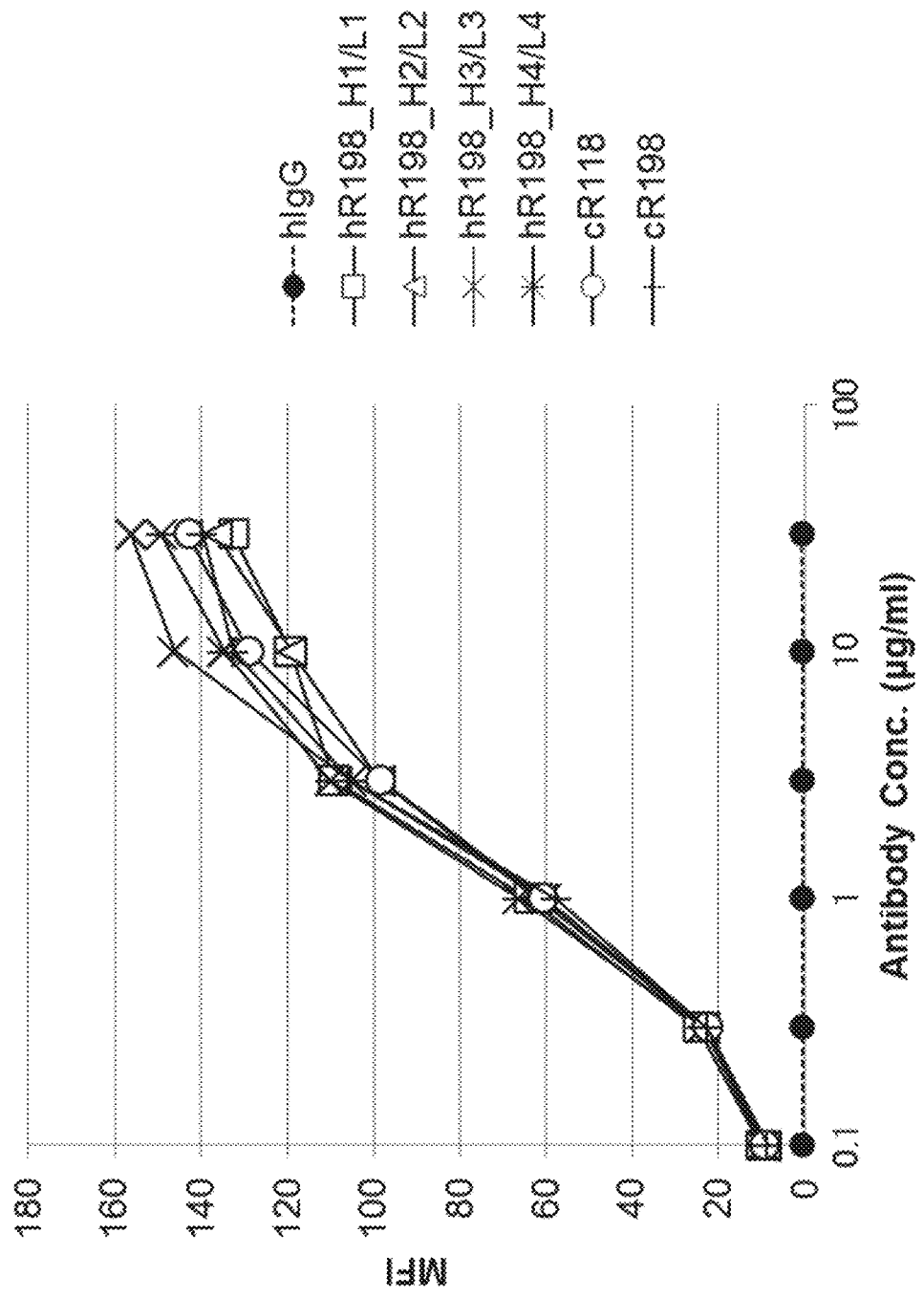
FIG. 5 is a diagram showing that humanized anti-human Orai1 antibodies hR198_H1/L1, hR198_H2/L2, hR198_H3/L3, and hR198_H4/L4 each bind to pcDNA3.1-hOrai1 transfected HEK293T cells in a concentration dependent manner, as with the parent antibody cR118 or cR198.

8)-1 Antigen Binding Activity of Humanized Anti-Human Orai1 Antibody by Flow Cytometry In order to evaluate human Orai1 binding specificity, the pcDNA3.1-DEST transfected HEK293T cell suspension or the pcDNA3.1-hOrai1 transfected HEK293T cell suspension prepared by the method shown in 1)-4-1 was centrifuged to remove supernatant. Then, the HEK293T cells were suspended by the addition of the humanized anti-Orai1 antibody hR198_H1/L1, hR198_H2/L2, hR198_H3/L3, or hR198_H4/L4 prepared in 7)-5 or the parent antibody cR118 or cR198, and incubated at 4° C. for 30 minutes. The cells were washed twice with PBS containing 5% FBS, then suspended by the addition of Anti-human IgG FITC conjugate diluted 100-fold with PBS containing 5% FBS, and incubated at 4° C. for 30 minutes. The cells were washed twice with PBS containing 5% FBS and then resuspended in PBS containing 5% FBS and 1 μg/mL propidium iodide, followed by detection using a flow cytometer (FC500). The data was analyzed using Flowjo. After exclusion of propidium iodide positive dead cells by gating, the FITC fluorescence intensity of live cells was plotted as a histogram to calculate mean fluorescence intensity (MFI). The humanized anti-human Orai1 antibodies hR198_H1/L1, hR198_H2/L2, hR198_H3/L3, and hR198_H4/L4 did not bind to the pcDNA3.1-DEST transfected HEK293T cells and, as shown in FIG. 5, each bound only to the pcDNA3.1-hOrai1 transfected HEK293T cells in a concentration dependent manner, as with the parent antibody cR118 or cR198, demonstrating that these antibodies each specifically bind to human Orai1.

Figure 6:
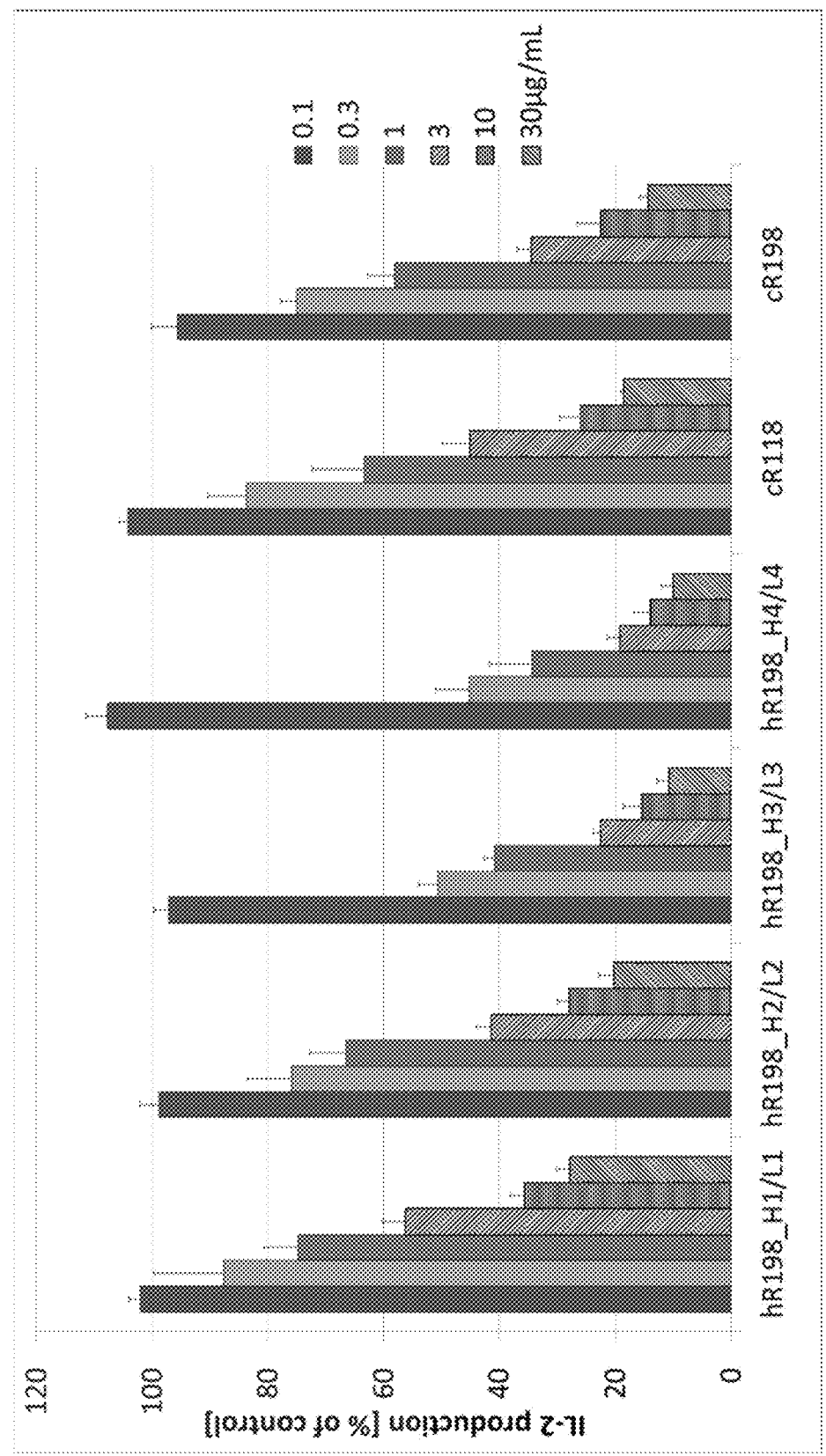
FIG. 6 is a diagram showing that the humanized anti-human Orai1 antibodies each inhibit, in a concentration dependent manner, the release of IL-2 from Jurkat cells treated with PMA and A23187.

8)-2 Human T cell line activation inhibitory effect of humanized anti-human Orai1 antibody Human T cell line Jurkat cells were prepared at a concentration of $1.5 \times 10^6$ cells/mL in RPMI1640 containing 10% FBS, 100 U/mL penicillin, and 100 μg/mL streptomycin, inoculated at 80 μL/well to a 96-well cell culture plate, and pretreated with the humanized anti-human Orai1 antibody hR198_H1/L1, hR198_H2/L2, hR198_H3/L3, or hR198_H4/L4 or the human chimerized anti-human Orai1 antibody cR118 or cR198 added at 10 μL/well at 37° C. for 60 minutes under 5% $CO_2$ conditions. Then, 100 ng/mL PMA and 1 μg/mL A23187 were added at 10 μL/well and well stirred, followed by culture at 37° C. for approximately 16 hours under 5% $CO_2$ conditions. The plate was well stirred and then centrifuged at 600 g for 3 minutes. The IL-2 concentration contained in the supernatant was measured by ELISA. FIG. 6 shows that the humanized anti-human Orai1 antibodies each inhibit, in a concentration dependent manner, the release of IL-2 from Jurkat cells treated with PMA and A23187. The humanized anti-human Orai1 antibodies each inhibited the IL-2 release from the Jurkat cells in a concentration dependent manner, and the inhibitory activity of hR198_H1/L1 and hR198_H2/L2 was equivalent to that of the human chimerized anti-human Orai1 antibodies cR118 and cR198. On the other hand, hR198_H3/L3 and hR198_H4/L4 exhibited inhibitory activity at a lower concentration than that of cR118 and cR198.

[Example 9] Identification of Activity Enhancing Mutation by Ribosome Display

9)-1 Preparation of H Chain and L Chain Libraries

A library containing mutated H chains or L chains was constructed with the humanized anti-human Orai1 antibody hR198_H4/L4 as a template and subjected to the identification of an activity enhancing mutation by ribosome display.

9)-1-1 Preparation of H Chain Library 80 cycles of PCR were carried out with the hR198_H4 gene as a template using the primer set given below and rTaq DNA polymerase (Toyobo Co., Ltd.) to mutate the gene region randomly.

Primer Set

```
(SEQ ID NO: 46; primer Orai1 HF)
5'-ATGCAAGTCCAACTGGTTCAATC-3'

(SEQ ID NO: 47; primer Orai1 CH FR)
5'-TGACGGAGCCAGCGGGAAGAC-3'
```

Next, overlap PCR was carried out with each randomly mutated H chain gene, a 5'UTR site comprising a T7 promoter, and a TolA gene fragment comprising 5' added c-Myc and a 3' added SecM sequence as templates using the primer set given below to prepare an H chain library.

Primer Set

```
(SEQ ID NO: 48; primer M13 rev long)
5'-CAGGAAACAGCTATGACCATG-3'

(SEQ ID NO: 49; primer SecM Stop R)
5'-CTCGAGTTATTCATTAGGTGAGGCGTTGAGG-3'
```

9)-1-2 Preparation of L Chain Library 80 cycles of PCR were carried out with the hR198_L4 gene as a template using the primer set given below and rTaq DNA polymerase to mutate the gene region randomly.

Primer Set

```
(SEQ ID NO: 50; primer Orai1 Lc F)
5'-ATGGACATTCAACTGACCCAAAGC-3'

(SEQ ID NO: 51; primer Orai1 CL-FR)
5'-GATAAAAACACTCGGGGCCGCCAC-3'
```

In the same way as in the description of 9)-1-1, overlap PCR was carried out using each randomly mutated L chain gene and the two gene fragments described above as templates to prepare an L chain library.

9)-1-3 Preparation of H Chain Gene Fragment

The H chain gene region was amplified by PCR with the hR198_H4 gene as a template using the primer set given below and KOD -Plus-.

Primer Set

```
(SEQ ID NO: 46; primer Orai1 HF)
5'-ATGCAAGTCCAACTGGTTCAATC-3'

(SEQ ID NO: 52; primer Orai1 HR-FLAG R)
5'-TCATTATTTGTCATCGTCATCTTTATAGTCGAATTCTTCGCCACG
ATTAAAGGATTTGGTGAC-3'
```

Next, overlap PCR was carried out with the gene fragment and a 5'UTR site comprising a T7 promoter as templates using the primer set given below to prepare an H chain gene fragment.

Primer Set

```
(SEQ ID NO: 48; primer M13 rev long)
5'-CAGGAAACAGCTATGACCATG-3'

(SEQ ID NO: 52; primer Orai1 HR-FLAG R)
5'-TCATTATTTGTCATCGTCATCTTTATAGTCGAATTCTTCGCCACGAT
TAAAGGATTTGGTGAC-3'
```

9)-1-4 Preparation of L Chain Gene Fragment

The L chain gene region was amplified by PCR with the hR198_L4 gene as a template using the primer set given below and KOD -Plus-.

Primer Set

```
(SEQ ID NO: 50; primer Orai1 Lc F)
5'-ATGGACATTCAACTGACCCAAAGC-3'

(SEQ ID NO: 53; primer Orai1 CL-FLAG R)
5'-TCATTATTTGTCATCGTCATCTTTATAGTCGAATTCTTCGCCACGA
TTAAAGGATTTGGTGAC-3'
```

Next, in the same way as in the description of 9)-1-3 overlap PCR was carried out to prepare an L chain gene fragment.

Primer Set

```
(SEQ ID NO: 48; primer M13 rev long)
5'-CAGGAAACAGCTATGACCATG-3'

(SEQ ID NO: 53; primer Orai1 CL-FLAG R)
5'-TCATTATTTGTCATCGTCATCTTTATAGTCGAATTCTTCGCCACGA
TTAAAGGATTTGGTGAC-3'
```

9)-1-5 Preparation of mRNA

Each mRNA was synthesized with the libraries and the gene fragments prepared in Examples 9)-1-1 to 9)-1-4 as templates using the T7 RiboMax Express Large Scale RNA Production System (Promega Corp.).

9)-2 Screening by Ribosome Display

H chain ribosome display Fabs were prepared by the combination of the H chain library and the L chain gene fragment, and L chain ribosome display Fabs were prepared by the combination of the L chain library and the H chain gene fragment. 20 pmol of the H chain (or L chain) library mRNAs and 100 pmol of ribosomes were added to a PUREfrex reaction solution (GeneFrontier Corp.), and the mixture was incubated at 30° C. for 45 minutes. Likewise, 40 pmol of the L chain (or H chain) mRNAs and 200 pmol of ribosomes were added to a PUREfrex reaction solution, and the mixture was incubated at 30° C. for 45 minutes. Next, the posttranslational reaction solutions of the H chain (or L chain) library and the L chain (or H chain) were mixed and further incubated at 30° C. for 90 minutes to prepare H chain (or L chain) ribosome display Fabs. Then, the reaction was terminated by cooling to 4° C. Subsequently, an antigen was added to the reaction solution, and the mixture was gently stirred at 4° C. for 1 hour so that each Fab bound to the antigen. The antigen used was a formalin fixed sample of CHO cells constitutively expressing human Orai1 which were established by use of pcDNA3.1-hOrai1 prepared in 1)-1-1, or the biotin-PEGylated human Orai1 loop region peptide (Sigma-Aldrich Corp.) shown below.

Biotin-PEGylated human Orai1 loop region peptide Biotin-PEG-

```
                                          (SEQ ID NO: 115)
SGSGFLPLKKQPGQPRPTSKPPASGAAANVSTSGITPGQAAAIASTTI
```

The ribosome display Fabs bound with the antigen were recovered using Nonolink Streptavidin magnetic beads (SoluLink, Inc.). Subsequently, the antigen was washed with 50 mM Tris-HCl (pH 7.4), 150 mM NaCl, 15 mM Mg(OAc)$_2$, 0.05% Tween 20, and 1 mg/mL yeast RNA, and with 50 mM Tris-HCl (pH 7.4), 150 mM NaCl, 15 mM Mg(OAc)$_2$, and 0.05% Tween 20. Then, 50 mM Tris-HCl (pH 7.4), 150 mM NaCl, 15 mM Mg(OAc)$_2$, and 50 mM EDTA were added to the antigen, and the mixture was left standing at room temperature for 10 minutes, followed by the recovery of a supernatant containing mRNAs by centrifugation. cDNAs were formed from the recovered mRNAs using a Transcriptor High Fidelity cDNA Synthesis Kit (F. Hoffmann-La Roche, Ltd.) and then amplified as DNAs by PCR using the primer set given below and KOD -Plus-. mRNAs were synthesized with the DNAs as templates and further screened in the same way as above. The screening cycle was carried out plural times to select a gene of an antibody strongly binding to the antigen.

Primer Set

```
(SEQ ID NO: 50; primer Orai1-LcF)
5'-ATGGACATTCAACTGACCCAAAGC-3'

(SEQ ID NO: 54; primer Myc-R)
5'-CAGATCCTCCTCAGAGATCAGCTTCTGCTC-3'
```

9)-3 Preparation of Fab Protein

The selected genes were subcloned into vectors for expression in *E. coli* and screened by Cell ELISA for clones with improved binding activity against CHO cells constitutively expressing human Orai1. First, each selected DNA was cleaved with restriction enzymes EcoRV and XhoI and inserted into a vector for Fab expression (GeneFrontier Corp.) cleaved with the same enzymes as above, which was then transferred to *E. coli* BL21 (DE3). The transformants thus obtained were cultured at 37° C. for 4 to 5 hours in 150 µL of carbenicillin/0.1% glucose/2× YT per well on a round bottom 96-well plate. Next, the plate was cooled to 4° C., and then, IPTG was added thereto at a final concentration of 0.5 mM, followed by overnight shake culture at 30° C. Next, the bacterial cells were recovered by centrifugation, and then a lysis buffer (2.5 mg/mL lysozyme, 100 U DNase I) was added thereto, followed by shaking at room temperature for 60 minutes. Subsequently, supernatant was recovered by centrifugation to prepare Fab samples.

9)-4 Screening by Cell ELISA

Cells expressing human Orai1 were cultured in a 384-well plate until becoming a confluent sheet. Then, the plate was washed with a washing buffer (PBS(−), 20 mM MgSO$_4$, 2.5% FBS). Next, the Fab samples were added to the plate, and the plate was shaken at 4° C. for 1 hour. After washing four times with a washing buffer, a peroxidase labeled anti-human F(ab')$_2$ goat antibody (Jackson ImmunoResearch Laboratories, Inc.) was added thereto, and the plate was shaken at 4° C. for 30 minutes. The plate was washed three times with a washing buffer and then washed three times with PBS(−) and 20 mM MgSO$_4$. Then, a chromogenic reagent (0.4 mg/mL tetramethyl-benzidine, 200 mM sodium acetate (pH 3.4), 0.01% aqueous hydrogen peroxide solution) was added thereto, and the plate was shaken at room temperature for 15 minutes. Then, 2 N HCl was added thereto, followed by the measurement of OD$_{450}$. A Fab sample exhibiting higher OD$_{450}$ against the CHO cells constitutively expressing human Orai1, as compared with control CHO cells, was selected.

Figure 7A:
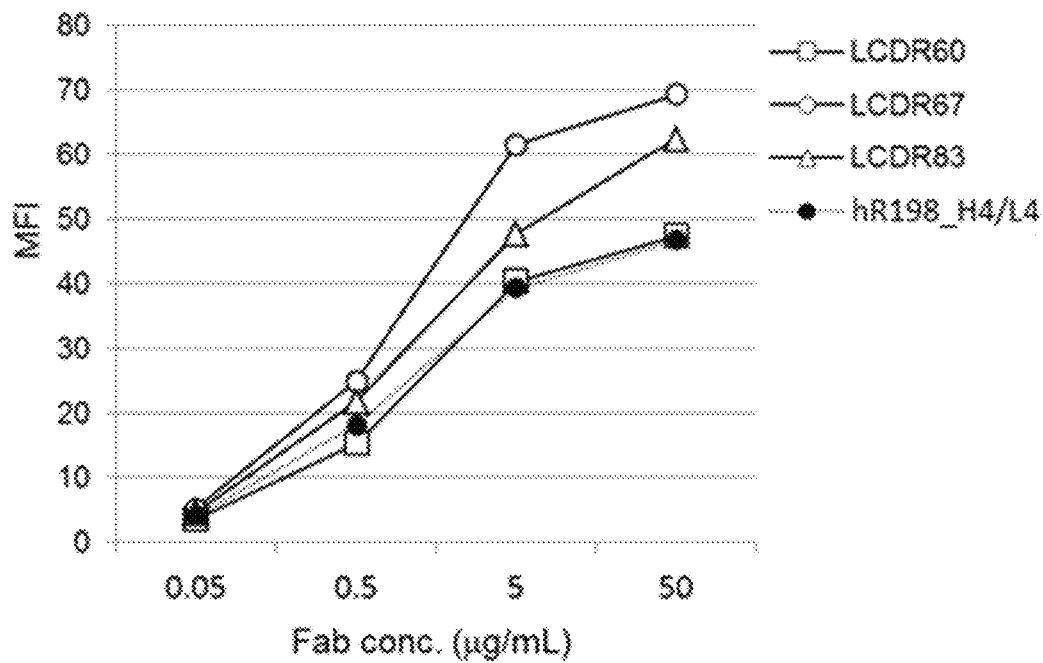
FIGS. 7A-7C are diagrams showing that mutated Fab clones LCDR60, LCDR67, and LCDR83 (FIG. 7A), CE151 and PE057 (FIG. 7B), and HCDR046, HCDR047, HEP087, HEP124, and HEP237 (FIG. 7C) obtained by ribosome display each strongly bind to pcDNA3.1-hOrai1 transfected HEK293T cells as compared with the parent antibody Fab hR198_H4/L4-Fab.
Figure 7B:
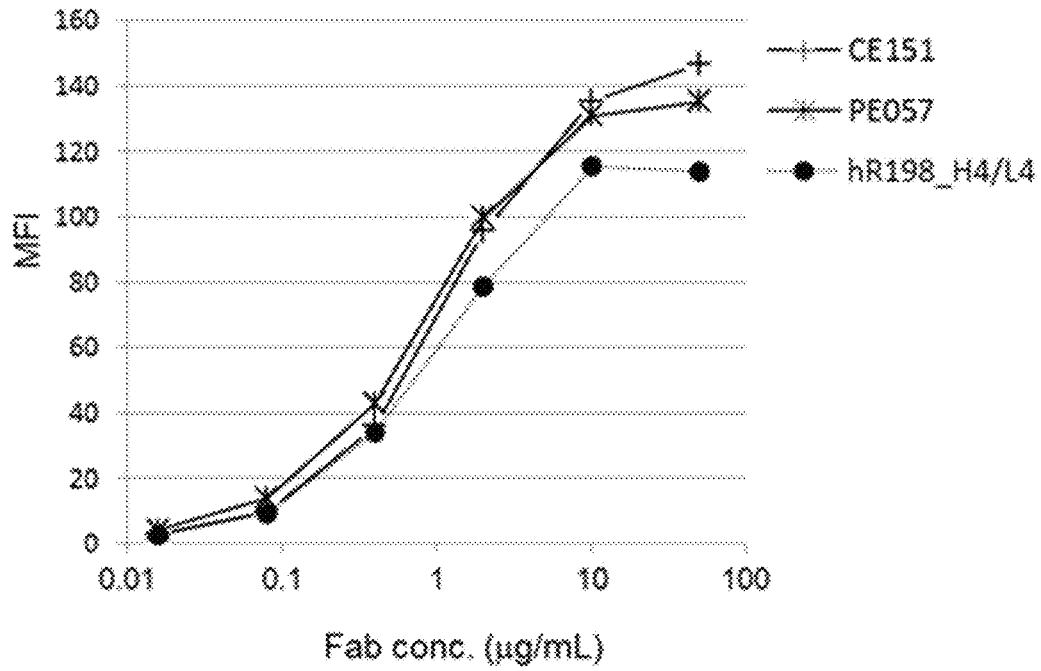
Figure 7C:
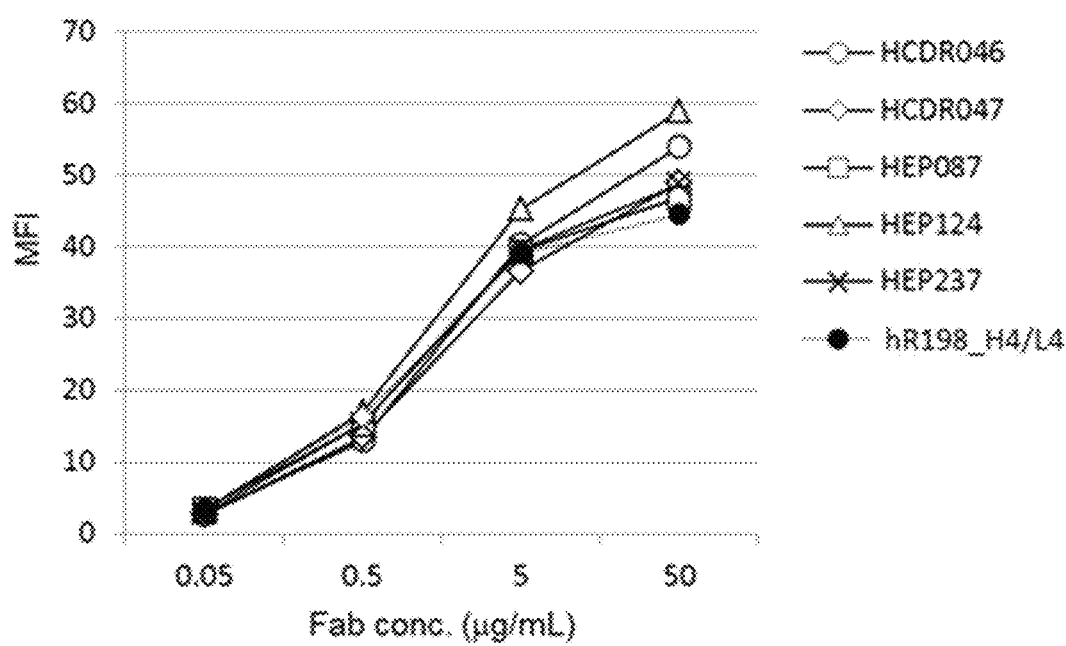

9)-5 Antigen Binding Activity of Anti-Human Orai1 Antibody Fab by Flow Cytometry In order to evaluate human Orai1 binding specificity, the pcDNA3.1-DEST transfected HEK293T cell suspension or the pcDNA3.1-hOrai1 transfected HEK293T cell suspension prepared by the method shown in 1)-4-1 was centrifuged to remove supernatant. Then, the HEK293T cells were suspended by the addition of the light chain mutated clone LCDR60, LCDR67, LCDR83, CE151, or PE057 or the heavy chain mutated clone HCDR046, HCDR047, HEP087, HEP124, or HEP237 selected in 9)-4, or the parent antibody Fab hR198_H4/L4-Fab, and left standing at 4° C. for 30 minutes. The cells were washed twice with PBS containing 5% FBS, then suspended by the addition of Anti-human IgG FITC conjugate diluted 100-fold with PBS containing 5% FBS, and left standing at 4° C. for 30 minutes. The cells were washed twice with PBS containing 5% FBS and then resuspended in PBS containing 5% FBS and 1 µg/mL propidium iodide, followed by detection using a flow cytometer (FC500). The data was analyzed using Flowjo. After removal of propidium iodide positive dead cells by gating, the FITC fluorescence intensity of live cells was plotted to a histogram to calculate mean fluorescence intensity (MFI). The light chain mutated clones LCDR60, LCDR67, LCDR83, CE151, and PE057 and the heavy chain mutated clones HCDR046, HCDR047, HEP087, HEP124, and HEP237 did not bind to the pcDNA3.1-DEST transfected HEK293T cells, as with the parent antibody Fab hR198_H4/L4-Fab, and, as shown in FIGS. 7A-7C, each tended to bind to human Orai1 in the pcDNA3.1-hOrai1 transfected HEK293T cells at a level equivalent to or stronger than that of the parent antibody Fab.

[Example 10] Preparation of Affinity Maturation Antibody of Humanized Anti-Human Orai1 Antibody 100 or more types of engineered hR198_H3/L3 antibodies were prepared by the transfer of some of the activity enhancing mutations found in the light chain mutated clones LCDR60, LCDR67, LCDR83, CE151, and PE057 and the heavy chain mutated clones HCDR046, HCDR047, HEP087, HEP124, and HEP237 selected in Example 9) to hR198_H3/L3, and evaluated from the viewpoint of binding affinity, in vitro activity, productivity, and heterogeneous antigenicity against humans. As a result, antibodies shown below were selected.

10)-1 Design of Affinity Maturation Antibody of Humanized Anti-Human Orai1 Antibody 10)-1-1 hR198_LG1 Type Light Chain:

A humanized R198 light chain designed by replacing an asparagine residue at amino acid position 51 with a glycine residue, a threonine residue at amino acid position 113 with an isoleucine residue, and a threonine residue at amino acid position 117 with a serine residue as to the hR198_L3 light chain shown in SEQ ID NO: 35 of the Sequence Listing was designated as a "hR198_LG1 type light chain".

The nucleotide sequence encoding the hR198_LG1 type light chain is shown in SEQ ID NO: 55 of the Sequence Listing. Nucleotide positions 61 to 702 encode a mature light chain formed by the cleavage of the signal sequence. Nucleotide positions 61 to 378 encode the variable region. The amino acid sequence of the hR198_LG1 type light chain is shown in SEQ ID NO: 56 of the Sequence Listing. Amino acid positions 21 to 234 represent the mature light chain formed by the cleavage of the signal sequence. Amino acid positions 21 to 126 represent the variable region. Both of the sequences of SEQ ID NOs: 55 and 56 are also shown in FIG. 30. Each CDR sequence and its corresponding SEQ ID NO are shown in FIG. 38.

10)-1-2 hR198_LG2 Type Light Chain:

A humanized R198 light chain designed by replacing an arginine residue at amino acid position 44 with a histidine residue, a serine residue at amino acid position 48 with an asparagine residue, an asparagine residue at amino acid position 51 with a glycine residue, a serine residue at amino acid position 70 with a leucine residue, a glutamic acid residue at amino acid position 75 with an aspartic acid residue, a serine residue at amino acid position 76 with a tryptophan residue, a threonine residue at amino acid position 113 with an isoleucine residue, and a threonine residue at amino acid position 117 with a serine residue as to the hR198_L3 light chain shown in SEQ ID NO: 35 of the Sequence Listing was designated as a "hR198_LG2 type light chain".

The nucleotide sequence encoding the hR198_LG2 type light chain is shown in SEQ ID NO: 57 of the Sequence Listing. Nucleotide positions 61 to 702 encode a mature light chain formed by the cleavage of the signal sequence. Nucleotide positions 61 to 378 encode the variable region. The amino acid sequence of the hR198_LG2 type light chain is shown in SEQ ID NO: 58 of the Sequence Listing. Amino acid positions 21 to 234 represent the mature light chain formed by the cleavage of the signal sequence. Amino acid positions 21 to 126 represent the variable region. Both of the sequences of SEQ ID NOs: 57 and 58 are also shown in FIG. 31. Each CDR sequence and its corresponding SEQ ID NO are shown in FIG. 38.

10)-1-3 hR198_LG3 Type Light Chain:

A humanized R198 light chain designed by replacing an arginine residue at amino acid position 44 with a histidine residue, a glutamine residue at amino acid position 47 with an arginine residue, a serine residue at amino acid position 48 with an asparagine residue, an asparagine residue at amino acid position 51 with a glycine residue, a serine residue at amino acid position 70 with a leucine residue, a threonine residue at amino acid position 73 with a serine residue, a glutamic acid residue at amino acid position 75 with an aspartic acid residue, a serine residue at amino acid position 76 with a tryptophan residue, a threonine residue at amino acid position 113 with an isoleucine residue, and a threonine residue at amino acid position 117 with a serine residue as to the hR198_L3 light chain shown in SEQ ID NO: 35 of the Sequence Listing was designated as a "hR198_LG3 type light chain".

The nucleotide sequence encoding the hR198_LG3 type light chain is shown in SEQ ID NO: 59 of the Sequence Listing. Nucleotide positions 61 to 702 encode a mature light chain formed by the cleavage of the signal sequence. Nucleotide positions 61 to 378 encode the variable region. The amino acid sequence of the hR198_LG3 type light chain is shown in SEQ ID NO: 60 of the Sequence Listing. Amino acid positions 21 to 234 represent the mature light chain formed by the cleavage of the signal sequence. Amino acid positions 21 to 126 represent the variable region. Both of the sequences of SEQ ID NOs: 59 and 60 are also shown in FIG. 32. Each CDR sequence and its corresponding SEQ ID NO are shown in FIG. 38.

10)-1-4 hR198_HG1 Type Heavy Chain:

A humanized R198 heavy chain designed by replacing an asparagine residue at amino acid position 78 with an aspartic acid residue, and a valine residue at amino acid position 123 with an alanine residue as to the hR198_H3 heavy chain shown in SEQ ID NO: 43 of the Sequence Listing was designated as a "hR198_HG1 type heavy chain".

The nucleotide sequence encoding the hR198_HG1 type heavy chain is shown in SEQ ID NO: 61 of the Sequence Listing. Nucleotide positions 58 to 1398 encode a mature heavy chain formed by the cleavage of the signal sequence. Nucleotide positions 58 to 408 encode the variable region. The amino acid sequence of the hR198_HG1 type heavy chain is shown in SEQ ID NO: 62 of the Sequence Listing. Amino acid positions 20 to 466 represent the mature heavy chain formed by the cleavage of the signal sequence. Amino acid positions 20 to 135 represent the variable region. Both of the sequences of SEQ ID NOs: 61 and 62 are also shown in FIG. 33. Each CDR sequence and its corresponding SEQ ID NO are shown in FIG. 38.

10)-1-5 hR198_HG2 Type Heavy Chain:

A humanized R198 heavy chain designed by replacing a valine residue at amino acid position 48 with an isoleucine residue, an asparagine residue at amino acid position 78 with an aspartic acid residue, an alanine residue at amino acid position 81 with a glycine residue, and a valine residue at amino acid position 123 with an alanine residue as to the hR198_H3 heavy chain shown in SEQ ID NO: 43 of the Sequence Listing was designated as a "hR198_HG2 type heavy chain".

The nucleotide sequence encoding the hR198_HG2 type heavy chain is shown in SEQ ID NO: 63 of the Sequence Listing. Nucleotide positions 58 to 1398 encode a mature heavy chain formed by the cleavage of the signal sequence. Nucleotide positions 58 to 408 encode the variable region. The amino acid sequence of the hR198_HG2 type heavy chain is shown in SEQ ID NO: 64 of the Sequence Listing. Amino acid positions 20 to 466 represent the mature heavy chain formed by the cleavage of the signal sequence. Amino acid positions 20 to 135 represent the variable region. Both of the sequences of SEQ ID NOs: 63 and 64 are also shown in FIG. 34. Each CDR sequence and its corresponding SEQ ID NO are shown in FIG. 38.

10)-1-6 hR198_HG3 Type Heavy Chain:

A humanized R198 heavy chain designed by replacing a valine residue at amino acid position 48 with an isoleucine residue, an asparagine residue at amino acid position 78 with an aspartic acid residue, an alanine residue at amino acid position 81 with a methionine residue, and a valine residue at amino acid position 123 with an alanine residue as to the hR198_H3 heavy chain shown in SEQ ID NO: 43 of the Sequence Listing was designated as a "hR198_HG3 type heavy chain".

The nucleotide sequence encoding the hR198_HG3 type heavy chain is shown in SEQ ID NO: 65 of the Sequence Listing. Nucleotide positions 58 to 1398 encode a mature heavy chain formed by the cleavage of the signal sequence. Nucleotide positions 58 to 408 encode the variable region. The amino acid sequence of the hR198_HG3 type heavy chain is shown in SEQ ID NO: 66 of the Sequence Listing. Amino acid positions 20 to 466 represent the mature heavy chain formed by the cleavage of the signal sequence. Amino acid positions 20 to 135 represent the variable region. Both of the sequences of SEQ ID NOs: 65 and 66 are also shown in FIG. 35. Each CDR sequence and its corresponding SEQ ID NO are shown in FIG. 38.

10)-2 Preparation of Affinity Maturation Antibody Expression Vector of Humanized Anti-Human Orai1 Antibody
10)-2-1 Construction of hR198_LG1 Type Light Chain Expression Vector Mutations to replace an asparagine residue at amino acid position 51 with a glycine residue, a threonine residue at amino acid position 113 with an isoleucine residue, and a threonine residue at amino acid position 117 with a serine residue were introduced with pCMA-LK/hR198_L3 as the template using KOD -Plus- mutagenesis. The obtained expression vector comprising the nucleotide sequence represented by SEQ ID NO: 55 of the Sequence Listing was designated as "pCMA-LK/hR198_LG1".

10)-2-2 Construction of hR198_LG2 and LG3 Type Light Chain Expression Vectors

A DNA fragment comprising the hR198_LG3 variable-region-encoding-sequence shown in nucleotide positions 38 to 402 in the nucleotide sequence of hR198_LG3 represented by SEQ ID NO: 59 of the Sequence Listing was synthesized (GeneArt Artificial Gene Synthesis service). The synthesized DNA fragment was cleaved with restriction enzymes EcoRV and AvaI and inserted to pCMA-LK/hR198_LG1 cleaved with the same restriction enzymes as above to construct a hR198_LG3 expression vector. The obtained expression vector was designated as "pCMA-LK/hR198_LG3".

Mutations to replace an arginine residue at amino acid position 47 with a glutamine residue and a serine residue at amino acid position 73 with a threonine residue were introduced with pCMA-LK/hR198_LG3 as the template using KOD -Plus- mutagenesis. The obtained expression vector comprising the nucleotide sequence represented by SEQ ID NO: 57 of the Sequence Listing was designated as "pCMA-LK/hR198_LG2".

10)-2-3 Construction of hR198_HG1 Type Heavy Chain Expression Vector

Mutations to replace an asparagine residue at amino acid position 78 with an aspartic acid residue and a valine residue at amino acid position 123 with an alanine residue were introduced with pCMA-G1/hR198_H3 as the template using KOD -Plus- mutagenesis. The obtained expression vector comprising the nucleotide sequence represented by SEQ ID NO: 61 of the Sequence Listing was designated as "pCMA-G1/hR198_HG1".

10)-2-4 Construction of hR198_HG2 Type Heavy Chain Expression Vector

Mutations to replace a valine residue at amino acid position 48 with an isoleucine residue and an alanine residue at amino acid position 81 with a glycine residue were introduced with pCMA-G1/hR198_HG1 as the template using KOD -Plus- mutagenesis. The obtained expression vector comprising the nucleotide sequence represented by SEQ ID NO: 63 of the Sequence Listing was designated as "pCMA-G1/hR198_HG2".

10)-2-5 Construction of hR198_HG3 Type Heavy Chain Expression Vector

A mutation to replace a glycine residue at amino acid position 81 with a methionine residue was introduced with pCMA-G1/hR198_HG2 as the template using KOD -Plus- mutagenesis. The obtained expression vector comprising the nucleotide sequence represented by SEQ ID NO: 65 of the Sequence Listing was designated as "pCMA-G1/hR198_HG3".

10)-3 Preparation of Affinity Maturation Antibody of Humanized Anti-Human Orai1 Antibody FreeStyle 293F cells were transfected with each humanized anti-human Orai1 antibody heavy chain expression vector and each humanized anti-human Orai1 antibody light chain expression vector prepared in 10)-2 by the same method as in 4)-5-1 to obtain a culture supernatant containing the antibody.

Humanized anti-human Orai1 antibodies obtained by the combination of the templated pCMA-G1/hR198_H3 or pCMA-G1/hR198_HG1, pCMA-G1/hR198_HG2, or pCMA-G1/hR198_HG3 containing the mutation(s) with pCMA-LK/hR198_LG1, pCMA-LK/hR198_LG2, or pCMA-LK/hR198_LG3 were designated as "hR198_H3/LG1", "hR198_HG1/LG1", "hR198_HG1/LG2", "hR198_HG1/LG3", "hR198_HG2/LG1", and "hR198_HG3/LG1", respectively.

Each obtained culture supernatant was purified by rProtein A affinity chromatography by the same method as in 4)-5-2 to obtain a purified antibody sample.

[Example 11] In Vitro Activity of Affinity Maturation Antibody

Figure 8:
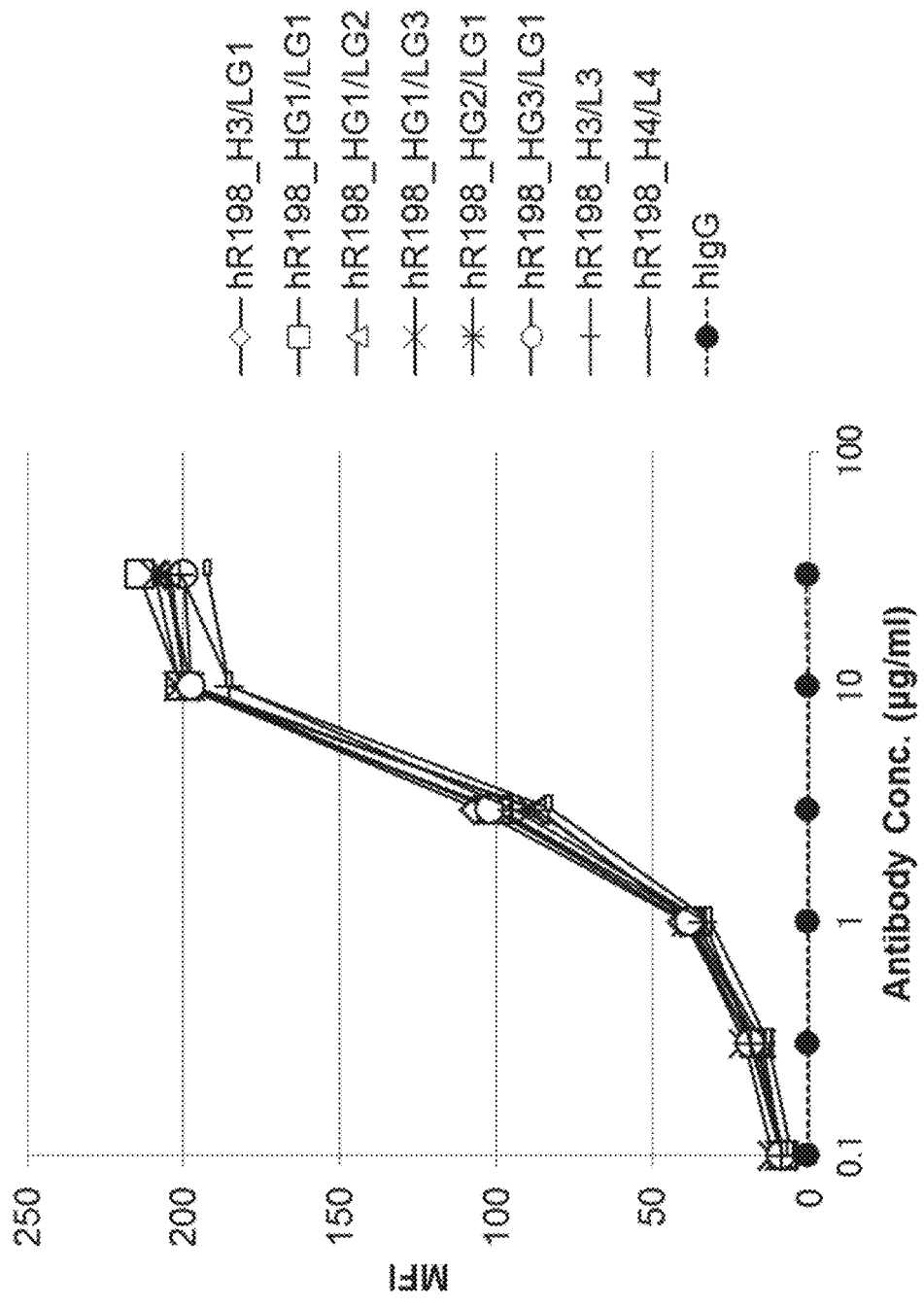
FIG. 8 is a diagram showing that affinity maturation antibodies hR198_H3/LG1, hR198_HG1/LG1, hR198_HG1/LG2, hR198_HG1/LG3, hR198_HG2/LG1, and hR198_HG3/LG1 each bind to pcDNA3.1-hOrai1 transfected HEK293T cells at a level equivalent to or stronger than that of the parent antibody hR198_H3/L3 or hR198_H4/L4.

11)-1 Evaluation of Ability of Affinity Maturation Antibody to Bind by Flow Cytometry In order to evaluate human Orai1 binding specificity, the pcDNA3.1-DEST transfected HEK293T cell suspension or the pcDNA3.1-hOrai1 transfected HEK293T cell suspension prepared by the method shown in 1)-4-1 was centrifuged to remove supernatant. Then, the HEK293T cells were suspended by the addition of the affinity maturation antibody hR198_H3/LG1, hR198_HG1/LG1, hR198_HG1/LG2, hR198_HG1/LG3, hR198_HG2/LG1, or hR198_HG3/LG1 prepared in 10)-3 or the parent antibody hR198_H3/L3 or hR198_H4/L4, and incubated at 4° C. for 30 minutes. The cells were washed twice with PBS containing 5% FBS, then suspended by the addition of Anti-human IgG FITC conjugate diluted 100-fold with PBS containing 5% FBS, and incubated at 4° C. for 30 minutes. The cells were washed twice with PBS containing 5% FBS and then resuspended in PBS containing 5% FBS and 1 μg/mL propidium iodide, followed by detection using a flow cytometer (FC500). The data was analyzed using Flowjo. After exclusion of propidium iodide positive dead cells by gating, the FITC fluorescence intensity of live cells was plotted as a histogram to calculate mean fluorescence intensity (MFI). The affinity maturation antibodies hR198_H3/LG1, hR198_HG1/LG1, hR198_HG1/LG2, hR198_HG1/LG3, hR198_HG2/LG1, and hR198_HG3/LG1 did not bind to the pcDNA3.1-DEST transfected HEK293T cells, as with the parent antibody hR198_H3/L3 or hR198_H4/L4, and, as shown in FIG. 8, each tended to bind to human Orai1 in the pcDNA3.1-hOrai1 transfected HEK293T cells at a level equivalent to or stronger than that of the parent antibody.

11)-2 T Cell Activation Inhibitory Effect of Affinity Maturation Antibody

Figure 9:
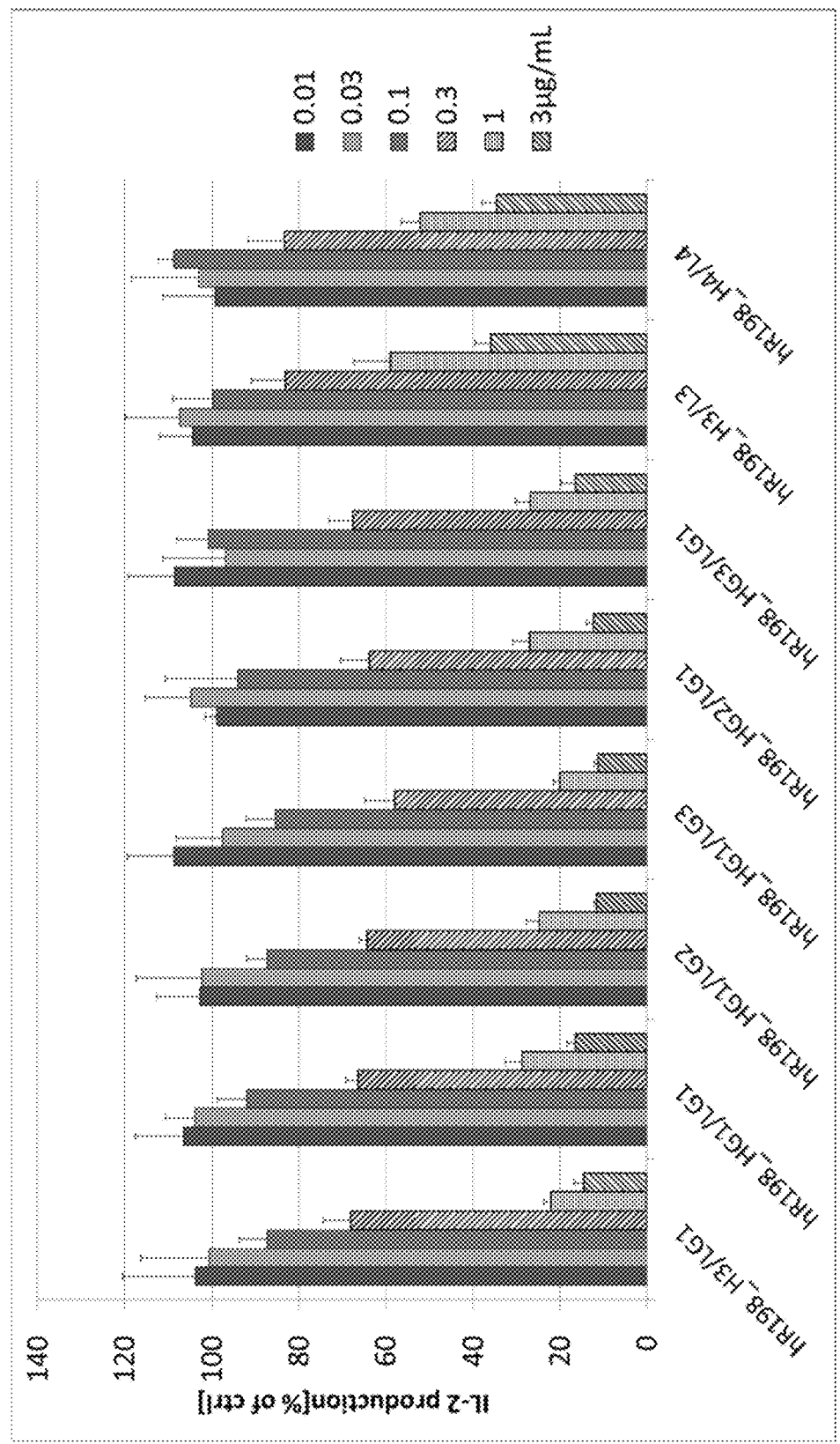
FIG. 9 is a diagram showing that the affinity maturation antibodies each inhibit, in a concentration dependent manner, the release of IL-2 from Jurkat cells treated with PMA and A23187.

Human T cell line Jurkat cells were prepared at a concentration of $1.5 \times 10^6$ cells/mL in RPMI1640 containing 10% FBS, 100 U/mL penicillin, and 100 μg/mL streptomycin, inoculated at 80 μL/well onto a 96-well cell culture plate, and pretreated with the affinity maturation antibody hR198_H3/LG1, hR198_HG1/LG1, hR198_HG1/LG2, hR198_HG1/LG3, hR198_HG2/LG1, or hR198_HG3/LG1 or the humanized anti-human Orai1 antibody hR198_H3/L3 or hR198_H4/L4 added at 10 μL/well at 37° C. for 60 minutes under 5% $CO_2$ conditions. Then, 100 ng/mL PMA and 1 μg/mL A23187 were added at 10 μL/well and well stirred, followed by culture at 37° C. for approximately 16 hours under 5% $CO_2$ conditions. The plate was well stirred and then centrifuged at 600 g for 3 minutes. The IL-2 concentration contained in the supernatant was measured by ELISA. FIG. 9 shows that the affinity maturation antibodies each inhibit, in a concentration dependent manner, the release of IL-2 from Jurkat cells treated with PMA and A23187. The affinity maturation antibodies each inhibited the IL-2 release from the Jurkat cells in a concentration dependent manner and were all superior in inhibitory activity to the humanized anti-human Orai1 antibodies hH3/L3 and hH4/L4, which were parent antibodies.

[Example 12] Preparation of Engineered Form with Reduced Effector Activity of Affinity Maturation Antibody A constant region engineered hR198_HG1-LALA sequence derived from hR198_HG1 by the substitution of two amino acid residues in the constant region was constructed as described in the Examples below.

12)-1 Design of LALA Type Heavy Chain Expression Vector

For circumventing cytotoxicity against normal cells expressing human Orai1, it is desirable that an antibody should have low effector activity. The effector activity is known to differ among antibody subclasses. The following characteristics are observed, for example, IgG4 has low ADCC and CDC activities, and IgG2 has CDC activity, but has low ADCC activity. On the basis of these features, it is possible to prepare an IgG1 antibody with reduced ADCC and CDC activities by partially substituting the constant region sequences of IgG1 with reference to IgG2 or IgG4. As one example, Marjan Hezareh et al., Journal of Virology, 75 (24): 12161-12168 (2001) shows that the ADCC and CDC activities of IgG1 are reduced by replacing each of the leucine residues at positions 234 and 235 (the positions are indicated by the EU index of Kabat et al.) of IgG1 with an alanine residue. Accordingly, a humanized anti-human Orai1 antibody heavy chain designed by replacing a leucine residue at amino acid position 253 with an alanine residue and a leucine residue at amino acid position 254 with an alanine residue as to the hR198_HG1 type heavy chain prepared in 10)-1 was designated as a "hR198_HG1-LALA type heavy chain".

12)-2 Construction of LALA Type Heavy Chain Expression Vector

12)-2-1 Construction of hR198_HG1-LALA Type Heavy Chain Expression Vector

The mutations were introduced with the hR198_H4 type heavy chain pCMA-G1/hR198_H4 prepared in 7)-2 as a template using a KOD -Plus- Mutagenesis Kit to construct a hR198_H4-LALA type heavy chain expression vector. The obtained expression vector was designated as "pCMA-G1-LALA/hR198_H4". The nucleotide sequence encoding the hR198_H4-LALA type heavy chain and the amino acid sequence of the heavy chain are shown in SEQ ID NOs: 67 and 68 (FIG. 36), respectively, of the Sequence Listing.

A DNA fragment of approximately 0.6 kb comprising the antibody variable-region-encoding-sequence was obtained by the digestion of pCMA-G1/hR198_HG1 prepared in 10)-2 with restriction enzymes PstI and XbaI, and inserted into a DNA fragment of approximately 4.2 kb obtained by the digestion of pCMA-G1-LALA/hR198_H4 with the same restriction enzymes as above using Ligation High ver. 2 to construct a hR198_HG1-LALA type heavy chain expression vector. The obtained expression vector was designated as "pCMA-G1-LALA/hR198_HG1". The nucleotide sequence encoding the hR198_HG1-LALA type heavy chain and the amino acid sequence of the heavy chain are shown in SEQ ID NOs: 69 and 70 (FIG. 37), respectively, of the Sequence Listing.

12)-3 Preparation of Engineered Form with Reduced Effector Activity of Affinity Maturation Antibody 12)-3-1 Production of Engineered Form with Reduced Effector Activity of Affinity Maturation Antibody FreeStyle 293F cells (Life Technologies Corp.) were subcultured and cultured according to the manual. $1.2 \times 10^9$ FreeStyle 293F cells (Life Technologies Corp.) in the logarithmic growth phase were inoculated to 3 L Fernbach Erlenmeyer Flask (Corning Inc.), prepared at $1.0 \times 10^6$ cells/mL by dilution with FreeStyle 293 expression medium (Invitrogen Corp.), and then shake cultured at 90 rpm at 37° C. for 1 hour in an 8% $CO_2$ incubator. 3.6 mg of polyethyleneimine (Polysciences #24765) was dissolved in 20 mL of Opti-Pro SFM (Life Technologies Corp.). Next, each light chain expression vector (0.8 mg) and each heavy chain expression vector (0.4 mg) prepared using PureLink HiPure Plasmid kit (Life Technologies Corp.) were added to 20 mL of Opti-Pro SFM (Life Technologies Corp.). 20 mL of the expression vector/Opti-Pro SFM mixed solution was added to 20 ml of the polyethyleneimine/Opti-Pro SFM mixed solution, and the mixture was gently stirred, further left for 5 minutes, and then added to the FreeStyle 293F cells. The cells were shake cultured at 90 rpm at 37° C. for 7 days in an 8% $CO_2$ incubator, and the obtained culture supernatant was filtered through Disposable Capsule Filter (ADVANTEC #CCS-045-E1H). hR198_HG1/LG1 was produced by the combination of pCMA-G1/hR198_HG1 and pCMA-LK/hR198_LG1, and hR198_HG1-LALA/LG1 was produced by the combination of pCMA-G1-LALA/hR198_HG1 and pCMA-LK/hR198_LG1.

12)-3-2 Purification in Two Steps of Engineered Form with Reduced Effector Activity of Affinity Maturation Antibody Each antibody was purified from the culture supernatant obtained in Example 12)-3-1 in two steps using rProtein A affinity chromatography (at 4 to 6° C.) and ceramic hydroxyapatite (at room temperature). The buffer replacement step after the purification by rProtein A affinity chromatography and after the purification by ceramic hydroxyapatite was carried out at 4 to 6° C. The culture supernatant was applied to MabSelectSuRe (GE Healthcare Bio-Sciences Corp., HiTrap column) equilibrated with PBS. After entry of the whole culture supernatant in the column, the column was washed with PBS in 2 or more times the volume of the column. Next, fractions containing the antibody were collected by elution with a 2 M arginine hydrochloride solution (pH 4.0). The buffers of the fractions were replaced with PBS by dialysis (Thermo Fisher Scientific Inc., Slide-A-Lyzer Dialysis Cassette) and then diluted 5-fold with a buffer of 5 mM sodium phosphate/50 mM MES (pH 7.0). The resulting antibody solution was applied to a ceramic hydroxyapatite column (Bio-Rad Laboratories, Inc., Bio-Scale CHT Type-1 Hydroxyapatite Column) equilibrated with a buffer of 5 mM NaPi/50 mM MES/30 mM NaCl (pH 7.0). Fractions containing the antibody were collected by linear concentration gradient elution with sodium chloride. The buffers of the fractions were replaced with HBSor (25 mM histidine/5% sorbitol, pH 6.0) by dialysis (Thermo Fisher Scientific Inc., Slide-A-Lyzer Dialysis Cassette). The solution was concentrated into an IgG concentration of 5 mg/mL or higher using Centrifugal UF Filter Device VIVASPIN 20 (molecular weight cutoff: UF10K, Sartorius Japan K.K., 4° C.) Finally, the antibody solution was filtered through Minisart-Plus filter (Sartorius Japan K.K.) and used as a purified sample.

[Example 13] Preparation of Human Anti-Human Orai1 Antibody 2C1.1 and 5H3.1 Expression Vectors 2C1.1 and 5H3.1 antibodies were prepared on the basis of the amino acid sequences of light and heavy chains described in WO2011063277A1.

13)-1 Construction of Chimerized and Humanized IgG2 Type Heavy Chain Expression Vector pCMA-G2

A DNA fragment obtained by the digestion of pCMA-LK with XbaI and PmeI to remove the sequence encoding a κ chain secretion signal and a human κ chain constant region was ligated with a DNA fragment (shown in SEQ ID NO: 71 of the Sequence Listing) comprising a sequence encoding a human heavy chain secretion signal and amino acids of a human IgG2 constant region using In-Fusion Advantage PCR cloning kit to construct a chimeric and humanized IgG2 type heavy chain expression vector pCMA-G2 having a signal sequence, a cloning site, and the human IgG2 heavy chain constant-region-encoding-sequence downstream of a CMV promoter.

13)-2 Construction of 2C1.1 Antibody Heavy Chain Expression Vector

A DNA fragment comprising the 2C1.1 antibody heavy chain variable-region-encoding-sequence shown in nucleotide positions 36 to 434 in the 2C1.1 antibody heavy chain encoding nucleotide sequence represented by SEQ ID NO: 72 of the Sequence Listing was synthesized (GeneArt Artificial Gene Synthesis service). The DNA fragment comprising the 2C1.1 antibody heavy chain variable region encoding sequence was amplified with the synthesized DNA fragment as a template using KOD -Plus- and inserted into the corresponding site of the chimeric and humanized antibody IgG2 type heavy chain expression vector pCMA-G2 cleaved with a restriction enzyme BlpI using an In-Fusion HD PCR cloning kit to construct a 2C1.1 antibody heavy chain expression vector. The obtained expression vector was designated as "pCMA-G2/2C1.1".

The amino acid sequence of the 2C1.1 antibody heavy chain is shown in SEQ ID NO: 73 of the Sequence Listing.

13)-3 Construction of 2C1.1 Antibody Light Chain Expression Vector

A DNA fragment comprising the 2C1.1 antibody light chain variable region and constant region (λ chain) encoding sequences shown in nucleotide positions 38 to 739 in the 2C1.1 antibody light chain-encoding-nucleotide-sequence represented by SEQ ID NO: 74 of the Sequence Listing was synthesized (GeneArt Artificial Gene Synthesis service). The DNA fragment comprising the 2C1.1 antibody light chain variable region and constant region-encoding sequences was amplified with the synthesized DNA fragment as a template using KOD -Plus- and inserted into the corresponding site of the chimeric and humanized antibody light chain expression vector pCMA-LK cleaved with restriction enzymes BsiWI and PmeI using an In-Fusion HD PCR cloning kit to construct a 2C1.1 antibody light chain expression vector. The obtained expression vector was designated as "pCMA-L/2C1.1".

The amino acid sequence of the 2C1.1 antibody light chain is shown in SEQ ID NO: 75 of the Sequence Listing.

13)-4 Construction of 5H3.1 Antibody Heavy Chain Expression Vector

A DNA fragment comprising the 5H3.1 antibody heavy chain variable-region-encoding-sequence shown in nucleotide positions 36 to 434 in the 5H3.1 antibody heavy chain encoding nucleotide sequence represented by SEQ ID NO: 76 of the Sequence Listing was synthesized (GeneArt Artificial Gene Synthesis service). A 5H3.1 antibody heavy chain expression vector was constructed by the same method as in Example 13)-2. The obtained expression vector was designated as "pCMA-G2/5H3.1".

The amino acid sequence of the 5H3.1 antibody heavy chain is shown in SEQ ID NO: 77 of the Sequence Listing.

13)-5 Construction of 5H3.1 Antibody Light Chain Expression Vector

A DNA fragment comprising the 5H3.1 antibody light chain variable region and constant region-encoding sequences shown in nucleotide positions 38 to 742 in the 5H3.1 antibody light chain encoding nucleotide sequence represented by SEQ ID NO: 78 of the Sequence Listing was synthesized (GeneArt Artificial Gene Synthesis service). A 5H3.1 antibody light chain expression vector was constructed by the same method as in Example 13)-3. The obtained expression vector was designated as "pCMA-L/5H3.1".

The amino acid sequence of the 5H3.1 antibody light chain is shown in SEQ ID NO: 79 of the Sequence Listing.

13)-6 Preparation of 2C1.1 and 5H3.1 Antibodies

13)-6-1 Production of 2C1.1 and 5H3.1 Antibodies

Each antibody was produced by the same method as in Example 12)-3-1. The 2C1.1 antibody was produced by the combination of pCMA-G2/2C1.1 and pCMA-L/2C1.1, and the 5H3.1 antibody was produced by the combination of pCMA-G2/5H3.1 and pCMA-L/5H3.1.

13)-6-2 Purification in Two Steps of 2C1.1 and 5H3.1 Antibodies

Each antibody was purified in two steps by the same method as in Example 12)-3-2 from the culture supernatant produced in Example 13)-6-1.

[Example 14] Preparation of Mouse Anti-Human Orai1 Antibodies 10F8, 14F74, and 17F6

10F8, 14F74, and 17F6 antibodies were prepared on the basis of the amino acid sequences of light and heavy chains described in WO2013091903A1.

14)-1 Construction of 10F8 Antibody Heavy Chain Expression Vector

A DNA fragment comprising the 10F8 antibody heavy chain-encoding nucleotide sequence represented by SEQ ID NO: 80 of the Sequence Listing was synthesized (GeneArt Artificial Gene Synthesis service). The DNA fragment comprising the 10F8 antibody heavy chain-encoding sequence was amplified with the synthesized DNA fragment as a template using KOD -Plus- and inserted into the site from which the sequence encoding a κ chain secretion signal and a human κ chain constant region was removed by the digestion of the chimeric and humanized antibody light chain expression vector pCMA-LK with restriction enzymes XbaI and PmeI, using an In-Fusion HD PCR cloning kit to construct a 10F8 antibody heavy chain expression vector. The obtained expression vector was designated as "pCMA/10F8H".

The amino acid sequence of the 10F8 antibody heavy chain is shown in SEQ ID NO: 81 of the Sequence Listing.

14)-2 Construction of 10F8 Antibody Light Chain Expression Vector

A DNA fragment comprising the 10F8 antibody light chain encoding nucleotide sequence represented by SEQ ID NO: 82 of the Sequence Listing was synthesized (GeneArt Strings DNA Fragments). The synthesized DNA fragment inserted into the site from which the sequence encoding a κ chain secretion signal and a human κ chain constant region was removed by the digestion of the chimeric and humanized antibody light chain expression vector pCMA-LK with restriction enzymes XbaI and PmeI, using an In-Fusion HD PCR cloning kit to construct a 10F8 antibody light chain expression vector. The obtained expression vector was designated as "pCMA/10F8L".

The amino acid sequence of the 10F8 antibody light chain is shown in SEQ ID NO: 83 of the Sequence Listing.

14)-3 Construction of 14F74 Antibody Heavy Chain Expression Vector

A DNA fragment comprising the 14F74 antibody heavy chain encoding nucleotide sequence represented by SEQ ID NO: 84 of the Sequence Listing was synthesized (GeneArt Artificial Gene Synthesis service). A 14F74 antibody heavy chain expression vector was constructed by the same method as in Example 14)-1. The obtained expression vector was designated as "pCMA/14F74H".

The amino acid sequence of the 14F74 antibody heavy chain is shown in SEQ ID NO: 85 of the Sequence Listing.

14)-4 Construction of 14F74 Antibody Light Chain Expression Vector

A DNA fragment comprising the 14F74 antibody light chain-encoding nucleotide sequence represented by SEQ ID NO: 86 of the Sequence Listing was synthesized (GeneArt Strings DNA Fragments). A 14F74 antibody light chain expression vector was constructed by the same method as in Example 14)-2. The obtained expression vector was designated as "pCMA/14F74L".

The amino acid sequence of the 14F74 antibody light chain is shown in SEQ ID NO: 87 of the Sequence Listing.

14)-5 Construction of 17F6 Antibody Heavy Chain Expression Vector

A DNA fragment comprising the 17F6 antibody heavy chain-encoding nucleotide sequence represented by SEQ ID NO: 88 of the Sequence Listing was synthesized (GeneArt Artificial Gene Synthesis service). A 17F6 antibody heavy chain expression vector was constructed by the same method as in Example 14)-1. The obtained expression vector was designated as "pCMA/17F6H".

The amino acid sequence of the 17F6 antibody heavy chain is shown in SEQ ID NO: 89 of the Sequence Listing.

14)-6 Construction of 17F6 Antibody Light Chain Expression Vector

A DNA fragment comprising the 17F6 antibody light chain-encoding nucleotide sequence represented by SEQ ID NO: 90 of the Sequence Listing was synthesized (GeneArt Strings DNA Fragments). A 17F6 antibody light chain expression vector was constructed by the same method as in Example 14)-2. The obtained expression vector was designated as "pCMA/17F6L".

The amino acid sequence of the 17F6 antibody light chain is shown in SEQ ID NO: 91 of the Sequence Listing.

14)-7 Preparation of 10F8, 14F74, and 17F6 Antibodies

14)-7-1 Production of 10F8, 14F74, and 17F6 Antibodies

Each antibody was produced by the same method as in Example 12)-3-1. The 10F8 antibody was produced by the combination of pCMA/10F8H and pCMA/10F8L. The 14F74 antibody was produced by the combination of pCMA/14F74H and pCMA/14F74L. The 17F6 antibody was produced by the combination of pCMA/17F6H and pCMA/17F6L.

14)-7-2 Purification in Two Steps of 10F8, 14F74, and 17F6 Antibodies

Each antibody was purified in two steps by the same method as in Example 12)-3-2 from the culture supernatant obtained in Example 14)-7-1.

Figure 10:
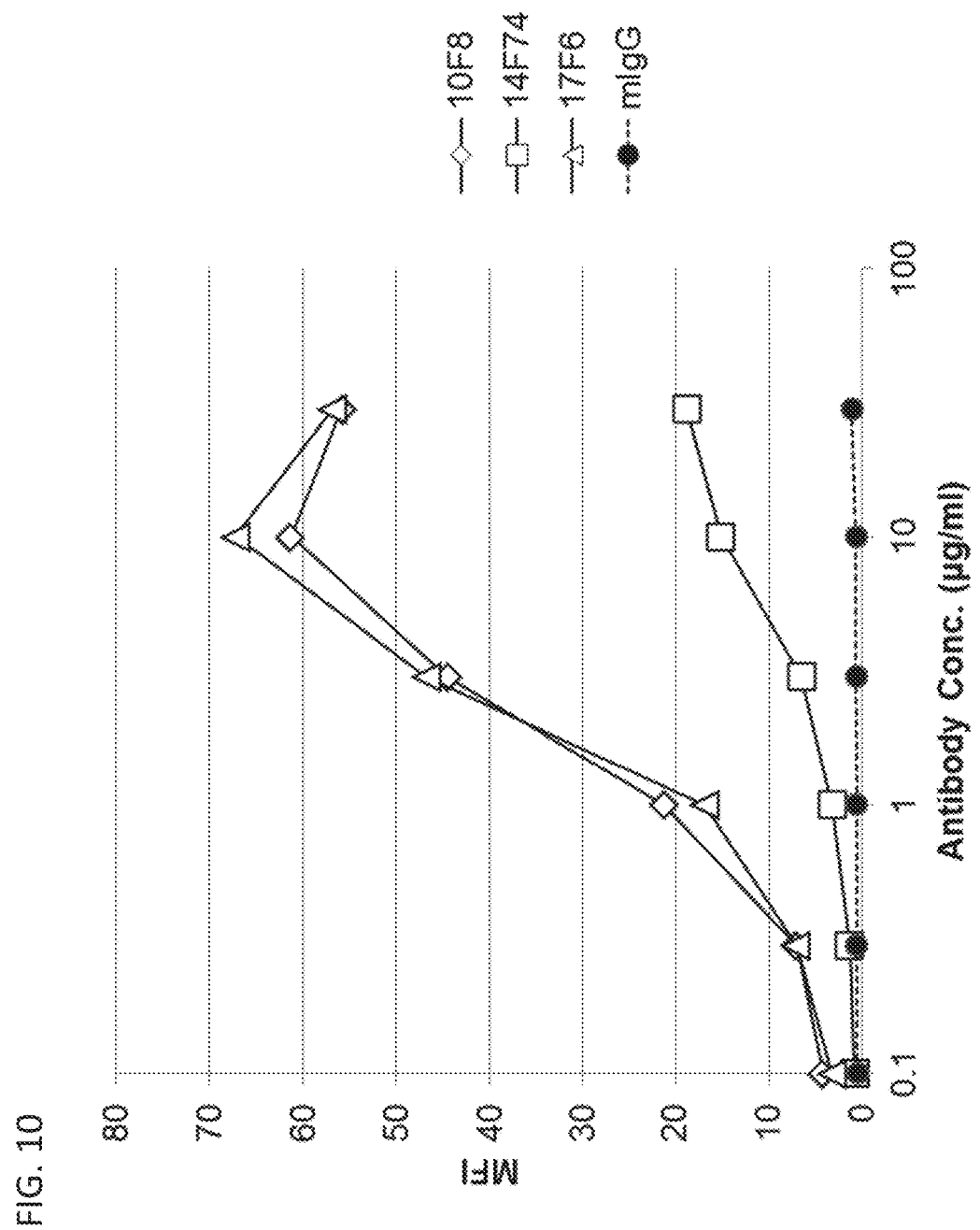
FIG. 10 is a diagram showing that 10F8, 14F74, and 17F6 antibodies each bind to pcDNA3.1-hOrai1 transfected HEK293T cells.
Figure 11:
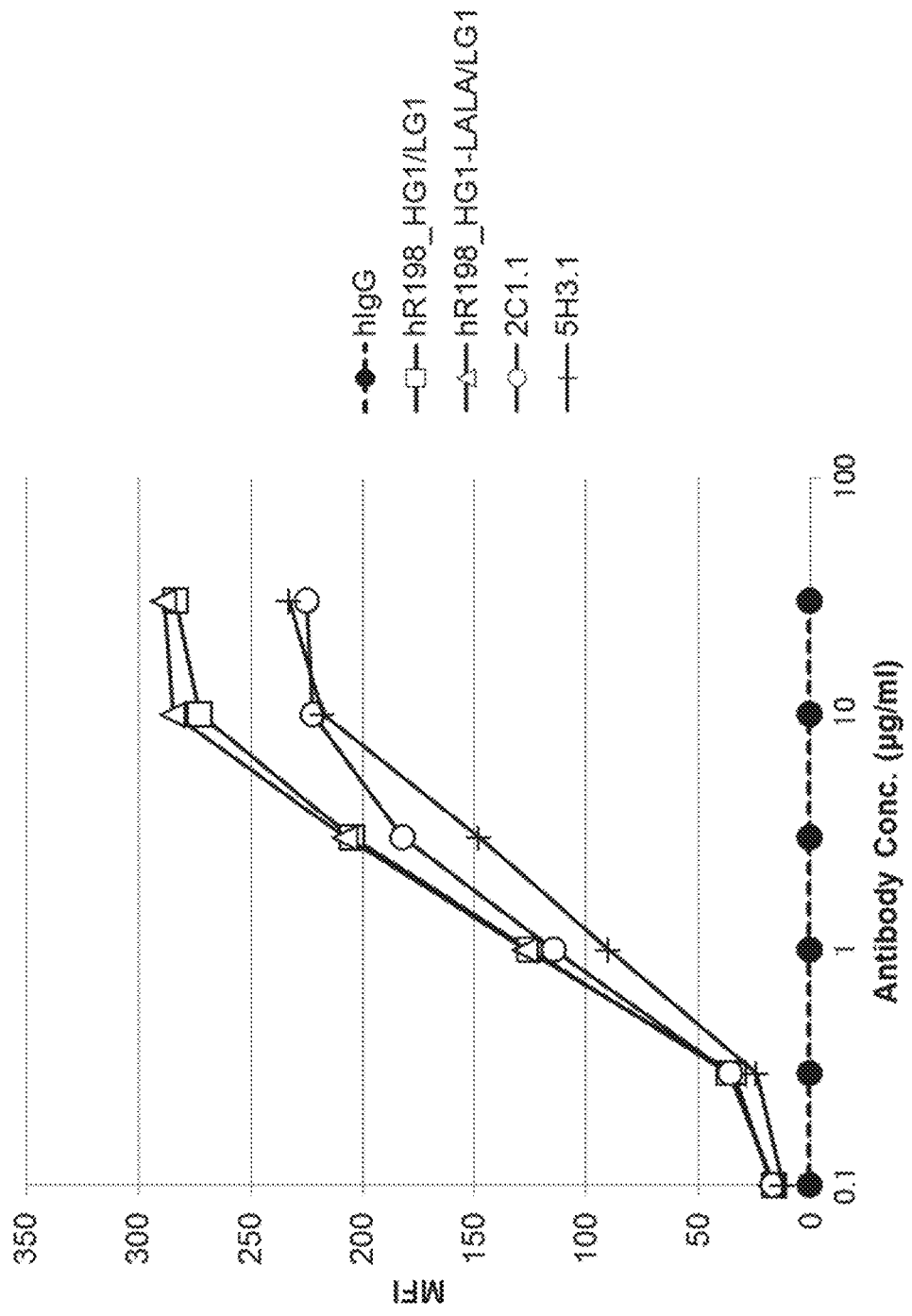
FIG. 11 is a diagram showing that hR198_HG1/LG1, hR198_HG1-LALA/LG1, 2C1.1, and 5H3.1 antibodies each bind to pcDNA3.1-hOrai1 transfected HEK293T cells.

[Example 15] In Vitro Activity Comparison of Engineered Form with Reduced Effector Activity of Affinity Maturation Antibody with Other Anti-Human Orai1 Antibodies 15)-1 Antigen Binding Activity of Anti-Human Orai1 Antibody by Flow Cytometry A cell suspension of HEK293T cells transfected by the method shown in 1)-4-2 with each human Orai1 expression vector constructed in 1)-1-1 was centrifuged to remove a supernatant. Then, the pcDNA3.1-hOrai1 transfected HEK293T cells or the pcDNA3.1-DEST transfected HEK293T cells were suspended by the addition of hR198_HG1/LG1 or hR198_HG1/LG1-LALA prepared in 12)-3, 2C1.1 or 5H3.1 prepared in 13)-6, 10F8, 14F74, or 17F6 prepared in 14)-7, or a human IgG control antibody or a mouse IgG control antibody as a control, and incubated at 4° C. for 30 minutes. The cells were washed twice with PBS containing 5% FBS, then suspended by the addition of Anti-human IgG FITC conjugate diluted 100-fold with PBS containing 5% FBS for the human antibodies or Anti-mouse IgG FITC conjugate (Cappel Laboratories, Inc.) for the mouse antibodies, and incubated at 4° C. for 30 minutes. The cells were washed twice with PBS containing 5% FBS and then resuspended in PBS containing 5% FBS and 1 µg/mL propidium iodide, followed by detection using a flow cytometer (FC500). The data was analyzed using Flowjo. After exclusion of propidium iodide positive dead cells by gating, the FITC fluorescence intensity of live cells was plotted as a histogram to calculate mean fluorescence intensity (MFI). hR198_HG1/LG1, hR198_HG1-LALA/LG1, 2C1.1, 5H3.1, 10F8, 14F74, and 17F6 did not bind to the pcDNA3.1-DEST transfected HEK293T cells, and, as shown in FIG. 10 (human antibodies) and FIG. 11 (mouse antibodies), each bound to the pcDNA3.1-hOrai1 transfected HEK293T cells, demonstrating that all of these antibodies specifically bind to human Orai1. On the other hand, no such binding was observed in the mouse IgG control antibody.

Figure 12:
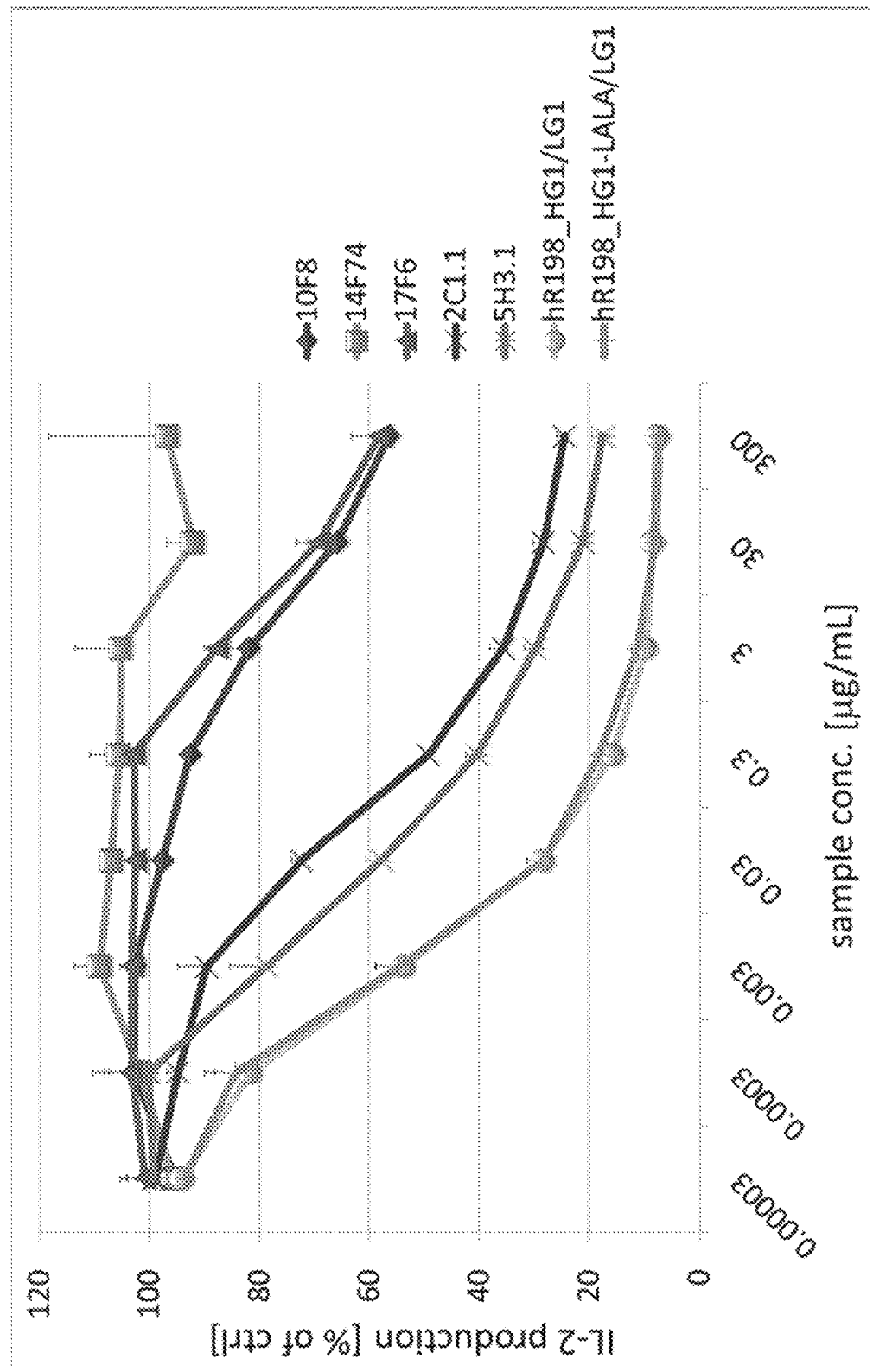
FIG. 12 is a diagram showing that the anti-Orai1 monoclonal antibodies each inhibit, in a concentration dependent manner, the release of IL-2 from Jurkat cells treated with PMA and A23187.

15)-2 Human T Cell Line Activation Inhibitory Effect of Anti-Human Orai1 Antibody Human T cell line Jurkat cells were prepared at a concentration of $1.5 \times 10^6$ cells/mL in RPMI1640 (containing 10% FBS, 100 U/mL penicillin, and 100 µg/mL streptomycin), inoculated at 80 µL/well to a 96-well cell culture plate, and pretreated with hR198_HG1/LG1, hR198_HG1-LALA/LG1, 2C1.1, 5H3.1, 10F8, 14F74, or 17F6 added at 10 µL/well at 37° C. for 60 minutes under 5% $CO_2$ conditions. Then, 100 ng/mL PMA and 1 µg/mL A23187 were added at 10 µL/well (final concentration: 10 ng/mL PMA and 100 ng/mL A23187) and well stirred, followed by culture at 37° C. for approximately 16 hours under 5% $CO_2$ conditions. The plate was well stirred and then centrifuged at 600 g for 3 minutes. The IL-2 concentration contained in the supernatant was measured by ELISA. FIG. 12 shows that the anti-human Orai1 antibodies each inhibit, in a concentration dependent manner, the release of IL-2 from Jurkat cells treated with PMA and A23187. FIG. 13 shows the half maximal inhibitory concentrations ($IC_{50}$) and the 80% inhibitory concentrations ($IC_{80}$) of hR198_HG1/LG1, hR198_HG1-LALA/LG1, 2C1.1, 5H3.1, 10F8, 14F74, and 17F6 with the IL-2 concentration in the absence of the antibody defined as 100%. $IC_{50}$ of the antibodies of the prior techniques was 80 ng/mL or higher, whereas $IC_{50}$ of the typical antibodies of the present invention was 10 ng/mL or lower. $IC_{80}$ of the antibodies of the prior techniques was 60000 ng/mL or higher, whereas $IC_H$ of the typical antibodies of the present invention was 200 ng/mL or lower.

Figure 53:
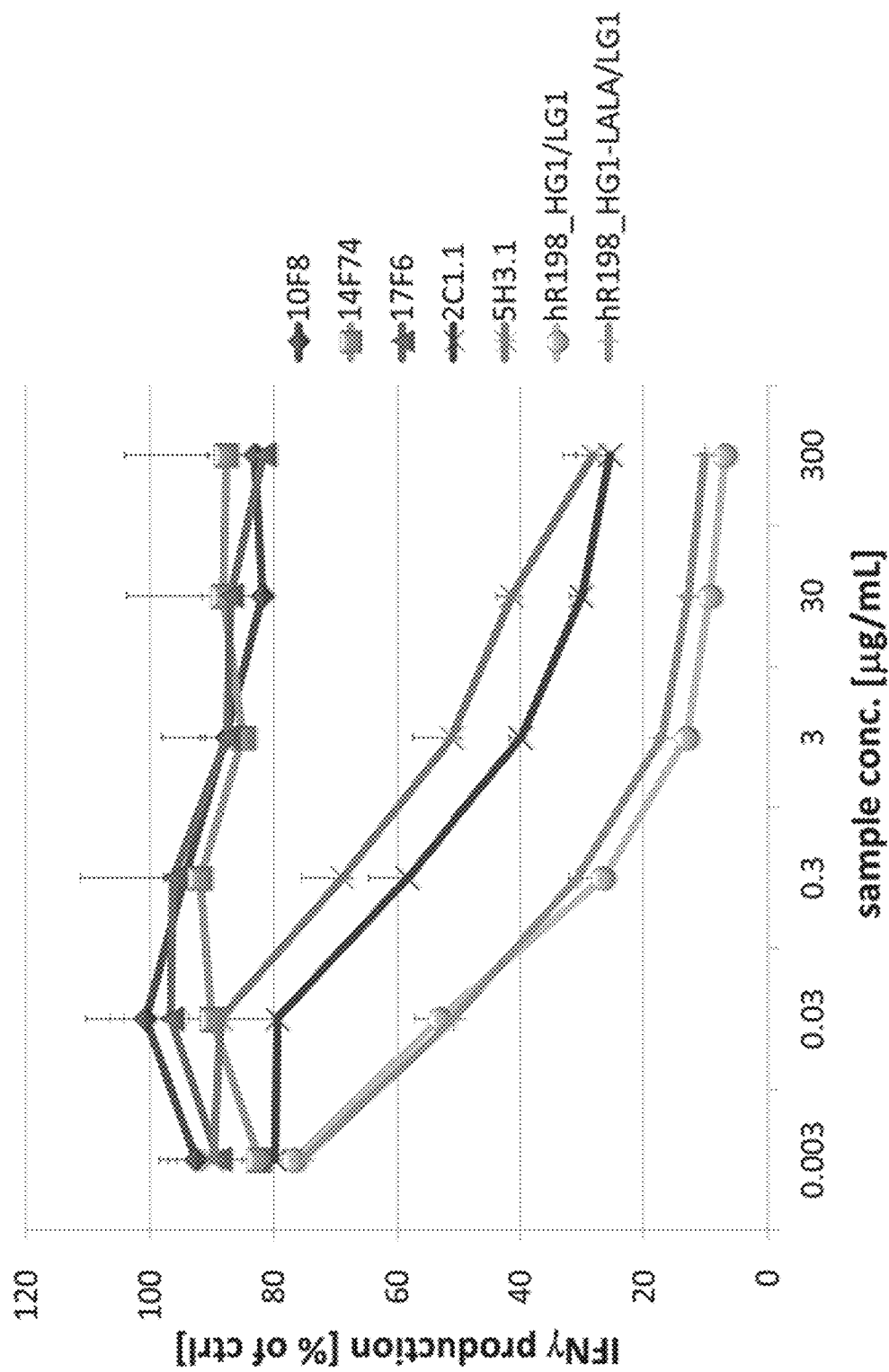
FIG. 53 is a diagram showing that the anti-Orai1 monoclonal antibodies each inhibit, in a concentration dependent manner, the release of IFN-7 from human PBMC treated with PMA and A23187.

15)-3 Human Peripheral Blood Mononuclear Cell Activation Inhibitory Effects of Engineered Form with Reduced Effector Activity of Affinity Maturation Antibody and Other Anti-Human Orai1 Antibodies Human peripheral blood mononuclear cells (PBMC) were purchased as a frozen product from Cellular Technology Ltd. and used after being thawed according to the instruction manual. PBMC prepared at a concentration of $2.0 \times 10^6$ cells/mL in RPMI1640 containing 10% FBS, 100 U/mL penicillin, and 100 µg/mL streptomycin was inoculated at 80 µL/well onto a 96-well cell culture plate, and pretreated with each anti-human Orai1 antibody added at 10 µL/well for 60 minutes in an incubator at 37° C. Then, 100 ng/mL PMA and 1 µg/mL A23187 were added at 10 µL/well and well stirred, followed by culture at 37° C. for approximately 16 hours under 5% $CO_2$ conditions. The plate was well stirred and then centrifuged at 600 g for 3 minutes. The IL-2 concentration and the interferon gamma (IFN-γ) concentration (Mabtech AB) contained in the supernatant were measured by ELISA. FIG. 51 shows that the anti-human Orai1 antibodies each inhibit, in a concentration dependent manner, the release of IL-2 from human PBMC treated with PMA and A23187. FIG. 52 shows the half maximal inhibitory concentrations ($IC_{50}$) and the 80% inhibitory concentrations ($IC_{80}$) of hR198_HG1/LG1, hR198_HG1-LALA/LG1, 2C1.1, 5H3.1, 10F8, 14F74, and 17F6 with the IL-2 concentration in the absence of the antibody defined as 100%. $IC_{50}$ of the antibodies of the prior techniques was 100 ng/mL or higher, whereas $IC_{50}$ of the typical antibodies of the present invention was 20 ng/mL or lower. $IC_{80}$ of the antibodies of the prior techniques was 17000 ng/mL or higher, whereas $IC_{80}$ of the typical antibodies of the present invention was 400 ng/mL or lower. FIG. 53 shows that the anti-human Orai1 antibodies each inhibit, in a concentration dependent manner, the release of IFN-γ from human PBMC treated with PMA and A23187. FIG. 54 shows the half maximal inhibitory concentrations ($IC_{50}$) and the 80% inhibitory concentrations ($IC_{80}$) of hR198_HG1/LG1, hR198_HG1-LALA/LG1, 2C1.1, 5H3.1, 10F8, 14F74, and 17F6 with the IFN-γ concentration in the absence of the antibody defined as 100%. $IC_{50}$ of the antibodies of the prior techniques was 800 ng/mL or higher, whereas $IC_{50}$ of the typical antibodies of the present invention was 40 ng/mL or lower. $IC_{80}$ of the antibodies of the prior techniques was 300000 ng/mL or higher, whereas $IC_H$ of the typical antibodies of the present invention was 2000 ng/mL or lower.

[Example 16] In Vivo Activity of hR198_HG1/LG1

Figure 55:
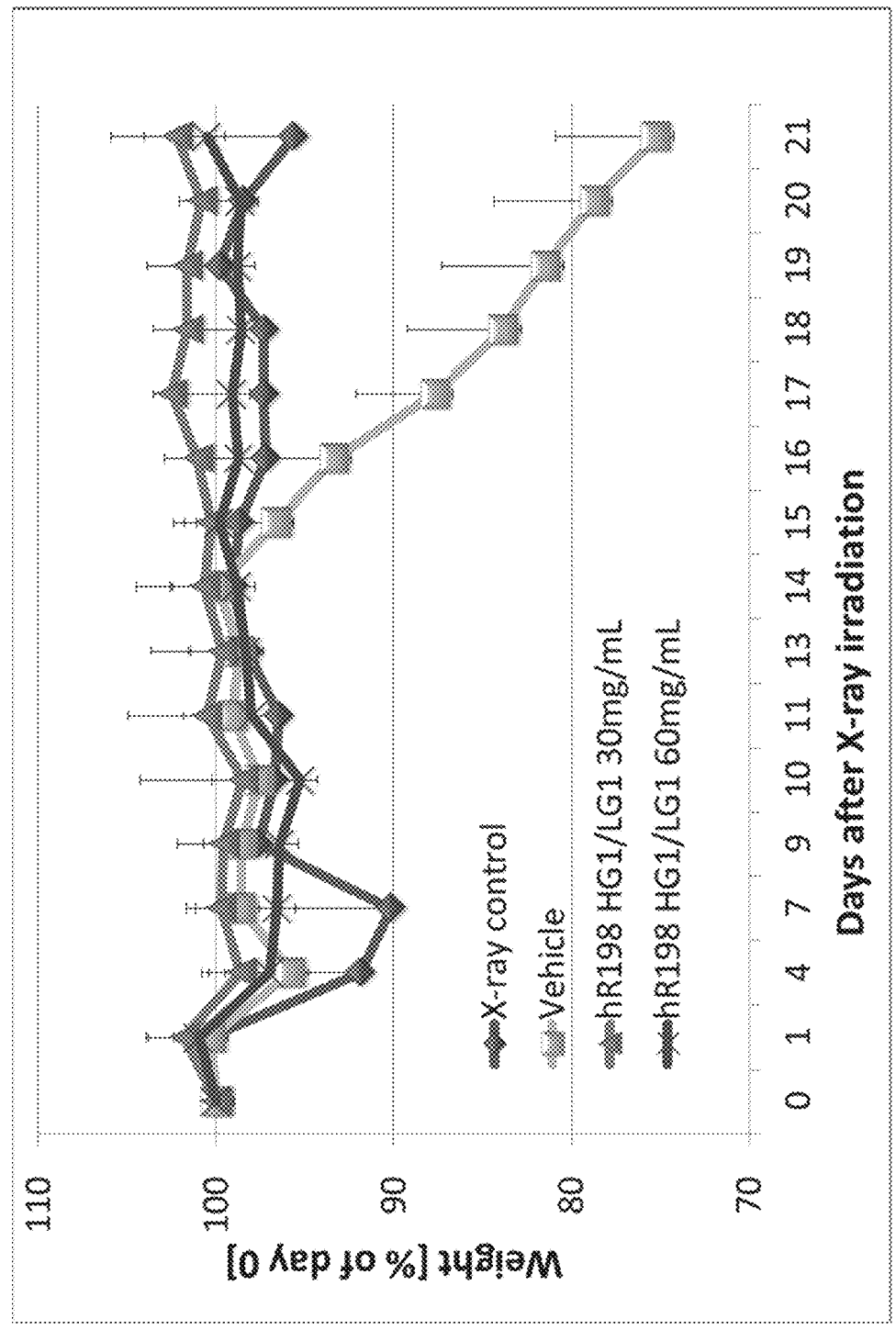
FIG. 55 is a diagram showing that hR198_HG1/LG1 inhibits weight loss associated with graft versus host disease that develops by the transplantation of human PBMC to severe combined immunodeficient mice.

16)-1 Effect of Administration of hR198_HG1/LG1 on Human PBMC Transplanted Mouse Graft Versus Host Disease Model It is known that human graft versus host disease-like reaction can be induced by the transplantation of human PBMC to NSG mice (NOD.Cg-Prkdc$^{scid}$Il2rg$^{tm1Wjl}$/SzJ), which are severe combined immunodeficient mice (Clinical and Experimental Immunology, 157: 104-118 (2009)). 17 six-week-old male NSG mice purchased from Charles River Laboratories Japan, Inc. were irradiated with X-rays of 2.0 Gy (Hitachi X-ray irradiation apparatus MBR-1520R-4). Then, the mice were divided into 1 group involving two mice and 3 groups each involving 5 mice. hR198_HG1/LG1 prepared at 3 mg/mL and 6 mg/mL with HBSor (25 mM histidine/5% sorbitol, pH 6.0) was intravenously administered at 10 mL/kg, i.e., 30 mg/kg and 60 mg/kg, to the tails of the mice of 2 groups (n=5). Only HBSor was administered to a further 1 group (n=5) as a vehicle group. On the next day, frozen human PBMC (Cellular Technology Ltd.) was thawed using CTL-antiaggregate (Cellular Technology Ltd.) according to the protocol, and 3,000,000 cells of human PBMC were suspended in 200 μL of PBS and transplanted into the mice of the 3 groups (n=5), while the human PBMC was not transplanted to the 1 group (n=2), which was observed over time as an X-ray irradiated control group. 0, 7, 14, and 21 days after the X-ray irradiation, hR198_HG1/LG1 or HBSor was administered at the same dose as above to the administration groups. The body weight of each mouse was measured at days 0, 1, 4, 7, 9, 10, 11, and 13, and subsequently every day. Change in body weight was calculated in percentage terms with the body weight at day 0 defined as 100%. The change in the average body weight of each group is shown in FIG. 55. Decrease in the average body weight of the vehicle administration group started to be observed from about day 16. The experiment was terminated at day 21 when the average body weight of the vehicle administration group fell below 80%. At this point in time, the X-ray irradiated control group that had not received human PBMC did not exhibit weight loss. The mice given hR198_HG1/LG1 at 30 mg/kg and 60 mg/kg did not lose their body weights, and the average body weight was equivalent to that of the human PBMC non-transplanted mice. hR198_HG1/LG1 (anti-Orai1 antibody) which remarkably suppressed the symptoms of graft versus host disease caused by the activation of human PBMC in this system is expected to have a therapeutic and/or prophylactic effect on human graft versus host disease.

16)-2 In Vivo Activity Evaluation of hR198_HG1/LG1 Using Human Orai1 Knock-in Mouse 16)-2-1 Preparation of Human Orai1 Knock-in Mouse Human Orai1 knock-in mice in which the amino acid sequence of the extracellular loop domain of mouse Orai1 was replaced with a human Orai1 sequence were prepared by Institute of Immunology Co., Ltd. according to a standard method of genetically engineered mouse preparation. In short, a human Orai1 gene knock-in targeting vector was constructed by replacing the DNA sequence of a BAC clone coding region comprising the mouse Orai1 gene locus with the human Orai1 gene locus while introducing thereto a neomycin resistance gene flanked by loxP sequences. Mouse ES cells were transfected with this targeting vector to establish a G418 resistant line. An ES cell line having the specifically recombined target gene locus was screened by Southern hybridization. The selection marker was removed by transfection with a Cre expression vector, and the resulting ES cell line was utilized to prepare chimeric F1 mice. Genotyping was carried out by Southern hybridization to select heterozygous mutant individuals from among the F1 mice. The selected F1 heterozygous mutant individuals were mated to prepare human Orai1 knock-in mice as F2 homozygous mutants.

16)-2-2 Passive Cutaneous Anaphylaxis (PCA) Reaction Suppressing Effect of hR198_HG1/LG1

Figure 56:
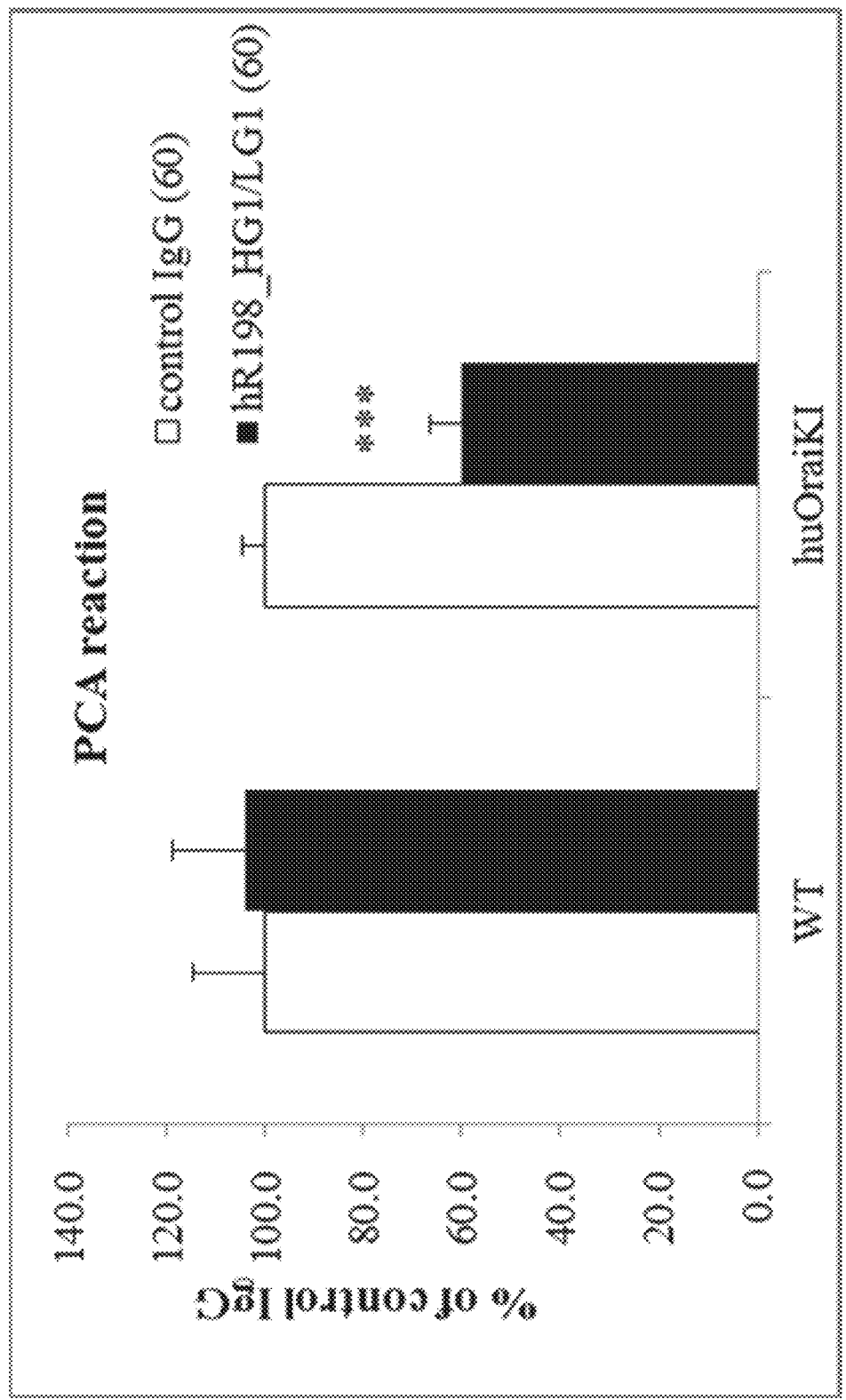
FIG. 56 is a diagram showing that hR198_HG1/LG1 suppresses passive cutaneous anaphylaxis reaction induced in human Orai1 knock-in mice.

Mouse PCA reaction was carried out according to a standard method. Eight-week-old human Orai1 knock-in mice produced by Institute of Immunology Co., Ltd., or wild type litter mice were retained in positioners. Then, hR198_HG1/LG1 prepared at 6 mg/mL with HBSor was intravenously administered at 10 mL/kg, i.e., 60 mg/kg, to the tails of the mice. Only HBSor was administered to a vehicle group. On the next day, 10 μL of Monoclonal anti-OVA IgE (Chondrex, Inc.) adjusted to 10 μg/mL with physiological saline was intracutaneously administered to the auricle of each mouse under inhalation anesthesia with isoflurane (Pfizer Japan Inc.). After 24 hours, physiological saline containing 2 mg/mL OVA (Albumin from chicken egg white, Sigma-Aldrich Corp.) and 20 mg/mL Evans blue (Merck KGaA) was intravenously administered at 5 mg/kg OVA and 100 mg/kg Evans blue to the tail. After 30 minutes, each mouse was sacrificed by bloodletting under deep anesthesia with isoflurane, and its auricle was excised and dipped in 0.5 mL of DMSO, followed by the extraction of Evans blue (37° C., 72 hours). The DMSO solution containing the extracted Evans blue was transferred at 200 μL/well to a 96-well microplate, and O.D. 650 nm was measured using a microplate reader (Molecular Devices Corp., SpectraMax M5e). The absorbance of the extravasated Evans blue was determined according to a calculation method given below and indicated with the average value of the vehicle administration group defined as 100%. The absorbance of a DMSO solution was determined as a blank. %=(OD650 sample−OD650 blank)/(OD650 vehicle−OD650 blank). FIG. 56 shows that hR198_HG1/LG1 suppresses the PCA reaction induced in human Orai1 knock-in mice. The mouse PCA reaction is a basic model system of immediate type allergy reproducing anaphylaxis, which is type I allergic reaction in humans, and this system is known to be usable in the evaluation of antiallergic drugs (Archives internationales de pharmacodynamie et de therapie, 165: 92-102 (1967); and International archives of allergy and applied immunology, 78: 113-117 (1985)). hR198_HG1/LG1 (anti-Orai1 antibody), confirmed in this system to have inhibitory activity against IgE dependent mast cell degranulation, is expected to have a therapeutic and/or prophylactic effect on bronchial asthma, allergic rhinitis, and atopic dermatitis found in existing mast cell degranulation inhibitors, and similar type I allergic diseases in humans, for example, allergic asthma.

16)-2-3 Delayed Type Hypersensitivity (DTH) Reaction Suppressing Effect of hR198_HG1/LG1

Figure 57A:
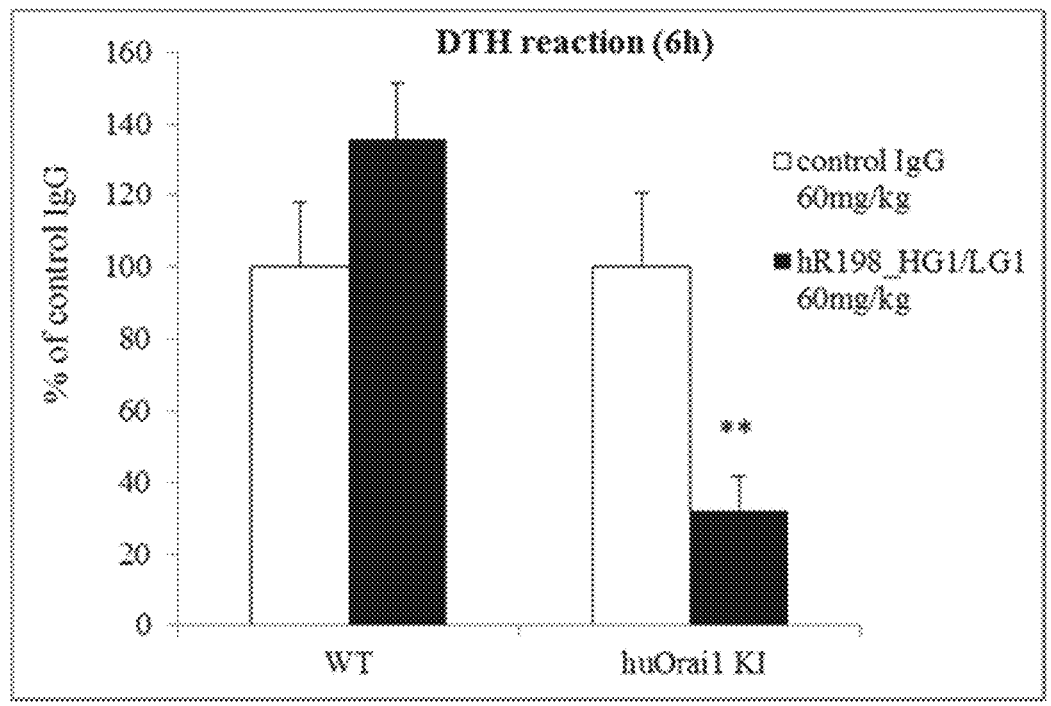
FIGS. 57A-57C are diagrams showing that hR198_HG1/LG1 suppressed delayed type hypersensitivity reaction induced in human Orai1 knock-in mice, at each point in time of 6 hours (FIG. 57A), 24 hours (FIG. 57B), and 48 hours (FIG. 57C) after antigen administration.
Figure 57B:
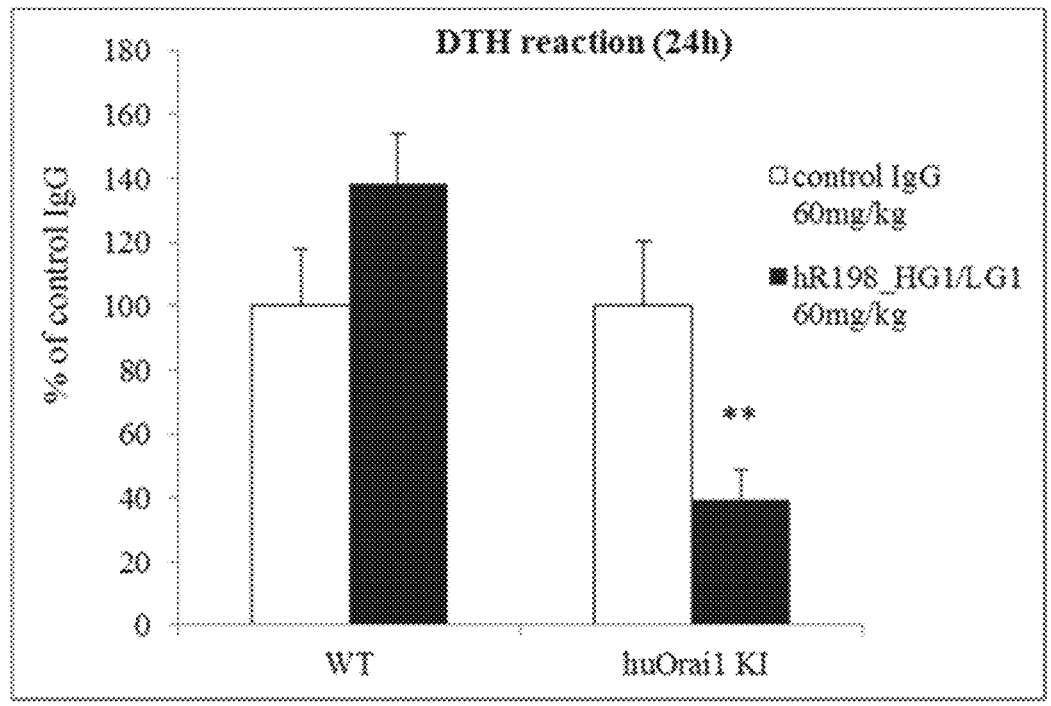
Figure 57C:
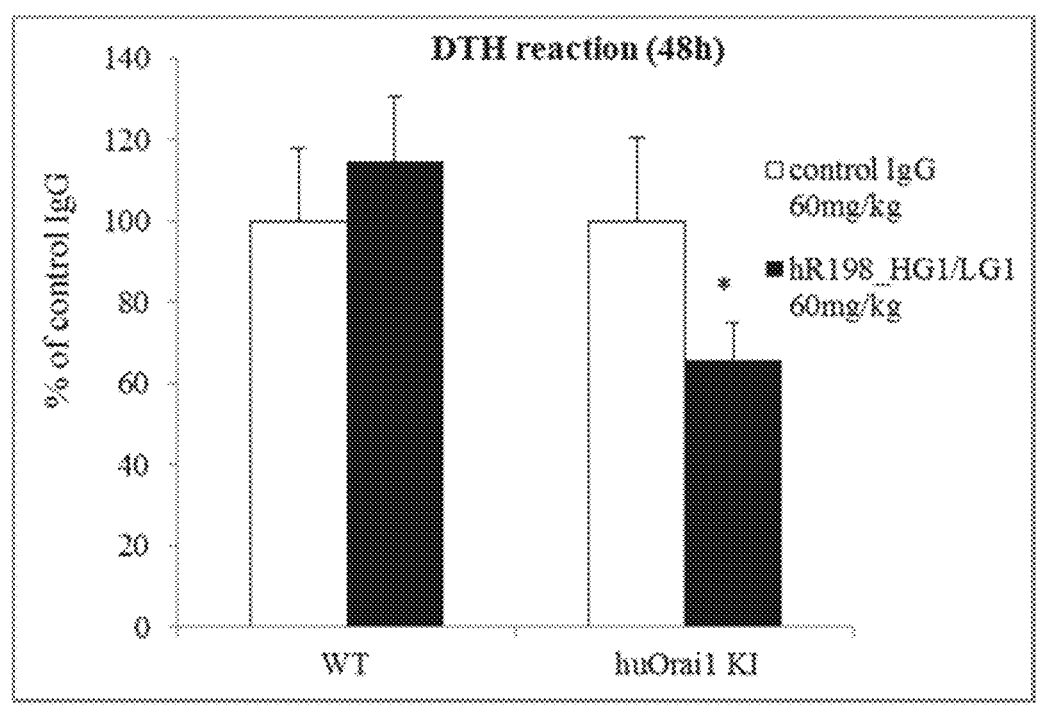

Mouse DTH reaction was carried out according to a standard method. Eight-week-old human Orai1 knock-in mice produced by Institute of Immunology Co., Ltd., or wild type litter mice were retained in positioners. Then, hR198_HG1/LG1 prepared at 6 mg/mL with HBSor was intravenously administered at 10 mL/kg, i.e., 60 mg/kg, to the tails of the mice. Only HBSor was administered to a vehicle group. On the next day, 50 μL of an emulsion prepared by mixing mBSA (Albumin Bovine Methylated, Sigma-Aldrich Corp.) diluted into 5 mg/mL with physiological saline and a Freund's complete adjuvant (Difco Laboratories) in equal amounts was subcutaneously administered to each of both axillae of each mouse for immunization. After 6 days, hR198_HG1/LG1 was intravenously administered again at 60 mg/kg to the tail. On the next day, mBSA prepared at 0.5 mg/mL with physiological saline, and physiological saline were each intracutaneously administered to the lower leg under inhalation anesthesia with isoflurane. 6, 24, and 48 hours after the administration, swelling in the leg was measured using a dial gauge. Time dependent change in the thickness of the swelling in the leg was calculated with the swelling at 0 hours as 0 ($10^{-2}$ mm) and determined with the average value of the vehicle administration group defined as 100%. FIGS. 57A-57C shows that hR198_HG1/LG1 suppressed the DTH reaction induced in the human Orai1 knock-in mice at each point in time of 6 hours (A), 24 hours (B), and 48 hours (C) after the antigen administration. The mouse DTH reaction is a system for observing the establishment and response of T cell dependent immunization, and it is well known that a drug exhibiting activity in this system was developed as a strong immunosuppressant (Clinical and Experimental Immunology, 52: 599-606 (1983)). hR198_HG1/LG1 (anti-Orai1 antibody), confirmed in this system to have suppressing activity against T cell immunization, is expected to have a therapeutic and/or prophylactic effect on responses of the body or diseases caused by T cells activity in humans, for example, transplant rejections, immunological diseases, and inflammatory diseases.

16)-2-4 Study on Suppressing Activity of Anti-Orai1 Antibody Against Dermatitis

Dermatitis is induced by any of the following methods: 0.5 mL of an albumin antigen solution is intraperitoneally administered to a mouse, and after 2 weeks, the same amount as above of the antigen is injected thereto as a booster. Then, the albumin antigen solution is repetitively applied to the ear (20 μL) or the back (100 μL) 3 to 6 times at 3 day to 2 week intervals. Alternatively, a mite antigen cream is repetitively applied to the ear (20 μL) or the back (100 μL) 3 to 6 times at 3 day to 2 week intervals. A hapten picryl chloride or dinitrofluorobenzene is prepared according to the protocol and applied to the ear (20 μL) or the back (100 μL) once or twice a week for 8 weeks at the maximum. Alternatively, a cutaneous reaction-inducing substance histamine, Compound 40/80, 5- (and 6-) carboxyfluorescein diacetate succinimidyl ester, fluorescein isothiocyanate, or bombesin-like peptide is administered to the ear (20 μL), the back (100 μL), or the spinal cord (5 μL). The anti-Orai1 antibody is intravenously or subcutaneously administered one day before the dermatitis induction or 1 hour to 4 hours before the dermatitis induction. Then, the frequency of administration is set to 7 day to 28 day intervals to continue the antibody administration. After the dermatitis induction, the measurement of the auricle thickness using a dial thickness gauge or the macroscopic scoring of dermatitis is carried out over time. After the completion of the test period, the quantification of the concentrations of the antibody, cytokines, or serum biomarkers in blood or tissues, the examination of the growth activity, cytokine producing ability, surface antigens, or the like of cells obtained from the skin, peripheral blood, the thymus, the spleen, the lymph node, or the bone marrow, histopathological analysis, etc. are carried out to determine the suppressing activity of the anti-Orai1 antibody against dermatitis.

16)-2-5 Study on Suppressing Activity of Anti-Orai1 Antibody Against Psoriasis

In the case of using imiquimod, psoriatic dermatitis is induced by application to both sides or one side of the auricle (5 to 30 mg) and the shaved back (50 to 100 mg). Alternatively, dermatitis is induced by the intraperitoneal administration of 200 μL of a 10 mg/mL zymosan suspension in a phosphate buffer solution. In the case of using a cytokine (IL-23, etc.) as a prophlogistic substance, psoriatic dermatitis is induced by the intracutaneous administration of 20 to 50 μL of a solution containing 0.1 to 2 μg of the cytokine to one side of the mouse auricle under deep anesthesia with 1 to 5% isoflurane. The anti-Orai1 antibody is intravenously or subcutaneously administered one day before the dermatitis induction or 1 hour to 4 hours before the dermatitis induction. Then, the frequency of administration is set to 7 day to 28 day intervals to continue the antibody administration. After the dermatitis induction, the measurement of the auricle thickness using a dial thickness gauge or the macroscopic scoring of dermatitis is carried out over time. After the completion of the test period, the examination of the weight of an inflammation site, the myeloperoxidase activity of neutrophils infiltrated into the site, the flow cytometry analysis of the infiltrated cells, gene analysis, cytokine concentration measurement, etc. are carried out to determine the suppressing activity of the anti-Orai1 antibody against psoriasis.

16)-2-6 Study on Suppressing Activity of Anti-Orai1 Antibody Against Multiple Sclerosis Myelin oligodendrocyte glycoprotein or a peptide antigen thereof is adjusted to 4 mg/mL with physiological saline and emulsified by mixing with a Freund's complete adjuvant adjusted to 8 mg/mL with physiological saline, in equal amounts. 200 μL of this mixed solution is intracutaneously administered to the flank or abdominal region of a mouse. Immediately thereafter, 100 μL of a 2 μg/mL aqueous pertussis toxin solution is administered to this mouse from the tail vein. After 2 days, the pertussis toxin solution mentioned above is further administered again from the tail vein to induce experimental encephalomyelitis. After 1 week to 2 weeks into the experiment, encephalomyelitis develops, and paralysis expands from the tail to the lower legs and the anterior limbs. The degree of this paralysis is scored by macroscopically observing the movement of the limbs and the tail. The anti-Orai1 antibody is intravenously or subcutaneously administered one day before the encephalomyelitis induction or 1 hour to 4 hours before the encephalomyelitis induction. Then, the frequency of administration is set to 7 day to 28 day intervals to continue the antibody administration. The effect of the administration of the anti-Orai1 antibody on multiple sclerosis is determined.

16)-2-7 Study on Suppressing Activity of Anti-Orai1 Antibody Against Arthritis

100 μL of an emulsion obtained by mixing 2 mg/mL bovine type II collagen and a Freund's complete adjuvant at a volume ratio of 1:1.3 is intracutaneously administered to the tail base of a mouse using a 1 mL syringe and a tuberculin needle. After 2 to 3 weeks, the same treatment as above is carried out. Then, joint swelling in the limbs is scored macroscopically or using a dial thickness gauge. At the completion of the test period, the concentrations of the antibody, cytokines, or serum biomarkers in blood or tissues, the growth activity, cytokine producing ability, or surface antigens of cells obtained from the skin, peripheral blood, the thymus, the spleen, the lymph node, or the bone marrow, etc. are measured. The anti-Orai1 antibody is intravenously or subcutaneously administered one day before the arthritis induction or 1 hour to 4 hours before the arthritis induction. Then, the frequency of administration is set to 7 day to 28 day intervals to continue the antibody administration. The effect of the administration of the anti-Orai1 antibody on arthritis is determined.

16)-2-8 Study on Suppressing Activity of Anti-Orai1 Antibody Against Colitis

Lymphocytes collected and purified from the lymph node and the spleen of a human Orai1 knock-in mouse are isolated with a cell sorter using an anti-CD4 antibody GK1.5, an anti-CD25 antibody PC61.5, and an anti-CD45R antibody C363.16A (all from eBioscience). The cells obtained by this method are confirmed in a flow cytometer to be CD4+CD25−CD45RBhi T-cells having a purity of 95% or higher. Then, 500,000 cells are intraperitoneally transplanted to a 12- to 16-week-old Rag2−/− mouse. Then, body weight measurement and observation of symptoms such as diarrhea are carried out for 12 weeks. After the completion of the observation period, the degree of thickening of the intestinal tract, the number and size of polyps, and the presence or absence of pathological signs are examined by autopsy. Also, the concentrations of the antibody, cytokines, or serum biomarkers in blood or tissues are quantified, and the growth activity, cytokine producing ability, surface antigens, or the like of cells obtained from the intestinal tract, peripheral blood, the thymus, the spleen, the lymph node, or the bone marrow are analyzed. The anti-Orai1 antibody is intravenously or subcutaneously administered one day before the cell transplantation or 1 hour to 4 hours before the cell transplantation. Then, the frequency of administration is set to 7 day to 28 day intervals to continue the antibody administration. The effect of the administration of the anti-Orai1 antibody on colitis is determined.

16)-2-9 Study on Effect of Anti-Orai1 Antibody on Bone Marrow Cell Transplantation System Thigh bone and shinbone are excised from a human Orai1 knock-in mouse, and the cells in the bone marrow are pushed out by the injection of 1 to 5 mL of an RPMI1640 medium containing 10% FBS from the epiphysis using a syringe with a needle. After treatment with a cell strainer, the bone marrow cells are recovered by centrifugation and adjusted such that 10,000,000 bone marrow cells are contained in 200 µL of an injection buffer containing 10 mM HEPES, 0.5 mM EDTA, and 0.5% penicillin/streptomycin. At the same time therewith, spleen cells are collected from the spleen of the human Orai1 knock-in mouse according to a standard method. A 10- to 13-week-old BALB/c mouse as a recipient is irradiated with X-rays of 2.0 to 8.0 Gy. Then, 0 to 4,000,000 donor spleen cells are added to 200 µL of the donor bone marrow cells, and this cell mixed solution is injected to the tail vein of the recipient. Then, change in body weight and survival rate are examined for 4 to 16 weeks. At the completion of the test, the concentrations of the antibody, cytokines, or serum biomarkers in the blood or the tissues of the recipient mouse, and the surface antigens, growth activity, or cytokine producing ability of cells obtained from the intestinal tract, peripheral blood, the thymus, the spleen, the lymph node, or the bone marrow are measured. The anti-Orai1 antibody is intravenously or subcutaneously administered to the recipient mouse one day before the bone marrow transplantation or 1 hour to 4 hours before the bone marrow transplantation. Then, the frequency of administration is set to 7 day to 28 day intervals to continue the antibody administration. The effect of the anti-Orai1 antibody on the engraftment of the transplanted cells or the incidence of graft versus host disease is determined.

Figure 58:
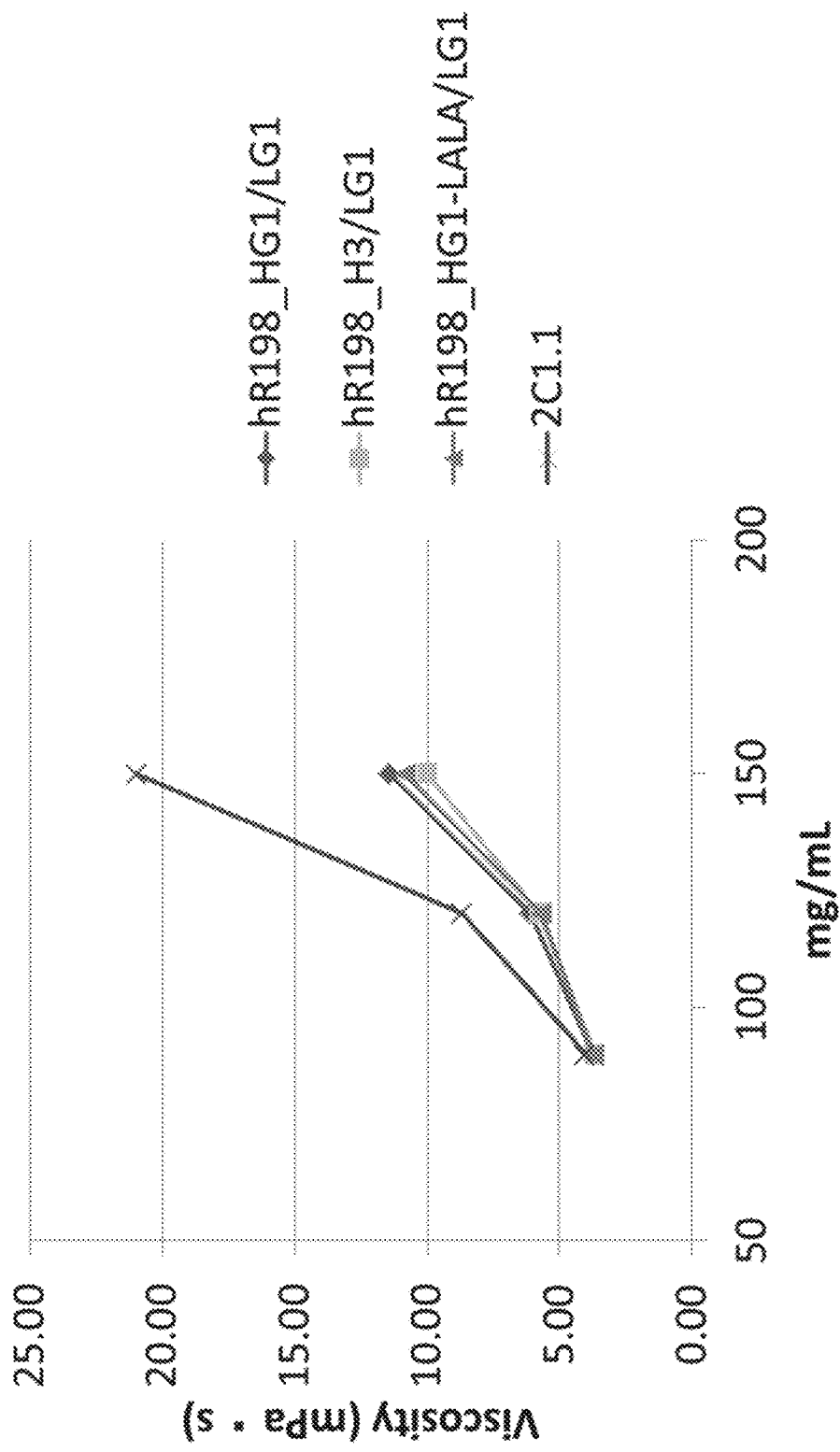
FIG. 58 is a diagram showing viscosity measured at concentrations of 90 mg/mL, 120 mg/mL, and 150 mg/mL of the hR198_HG1/LG1, hR198_H3/LG1, hR198_HG1-LALA/LG1, and 2C1.1 antibodies.

[Example 17] Comparison of Physicochemical Properties Between Affinity Matured Antibody and Other Anti-Human Orai1 Antibodies Viscosity Measurement Using m-VROC hR198_HG1/LG1 or hR198_H3/LG1 prepared in 10)-3, hR198_HG1-LALA/LG1 prepared in 12)-3, or 2C1.1 prepared in 13)-6 was concentrated to 150 mg/mL or higher with VIVAPORE 5 (Sartorius Japan K.K.) and then prepared at 90, 120, and 150 mg/mL with HBSor. The viscosity at 25° C. was measured three times for each concentration using m-VROC (RheoSense, Inc.) to calculate an average viscosity (mPa·s). The results are shown in FIG. 58 and Table 1. The viscosities of hR198_HG1/LG1, hR198_H3/LG1, and hR198_HG1-LALA/LG1 at all of the concentrations were lower than the viscosity of 2C1.1. Particularly, at 150 mg/mL, the viscosities of hR198_HG1/LG1, hR198_H3/LG1, and hR198_HG1-LALA/LG1 were 11.4, 10.0, and 10.8 mPa·s, respectively, whereas the viscosity of 2C1.1 was 21.0 mPa·s, demonstrating that the affinity matured antibodies have a low viscosity even at a high concentration, as compared with 2C1.1.

TABLE 1

| Sample | Concentration [mg/mL] | Average Viscosity [mPa · s] | SD Viscosity [mPa · s] |
|---|---|---|---|
| hR198_HG1/LG1 | 90 | 3.74 | 0.05 |
|  | 120 | 6.11 | 0.02 |
|  | 150 | 11.43 | 0.09 |
| hR198_H3/LG1 | 90 | 3.66 | 0.04 |
|  | 120 | 5.78 | 0.07 |
|  | 150 | 9.98 | 0.10 |
| hR198_HG1-LALA/LG1 | 90 | 3.74 | 0.06 |
|  | 120 | 5.68 | 0.20 |
|  | 150 | 10.82 | 0.37 |
| 2C1.1 | 90 | 4.05 | 0.02 |
|  | 120 | 8.67 | 0.12 |
|  | 150 | 20.96 | 0.08 |

INDUSTRIAL APPLICABILITY

The humanized anti-Orai1 antibody of the present invention has a stronger T cell activity inhibitory effect than that of antibodies known in the art, and can serve as a therapeutic or prophylactic agent for transplantation rejection, etc.

FREE TEXT OF SEQUENCE LISTING

SEQ ID NO: 1: Gene sequence of human Orai1
SEQ ID NO: 2: Amino acid sequence of human Orai1
SEQ ID NO: 3: PCR primer Nhe-polyC-S
SEQ ID NO: 4: PCR primer rIgγ-AS1
SEQ ID NO: 5: PCR primer rIgγ-AS2
SEQ ID NO: 6: PCR primer Nhe-polyC-S
SEQ ID NO: 7: PCR primer rIgκ-AS
SEQ ID NO: 8: Sequencing primer rIgγ-seq
SEQ ID NO: 9: Sequencing primer rIgκ-seq
SEQ ID NO: 10: Nucleotide sequence encoding the R118 light chain
SEQ ID NO: 11: Amino acid sequence of the R118 light chain SEQ ID NO: 12: Nucleotide sequence encoding the R118 heavy chain
SEQ ID NO: 13: Amino acid sequence of the R118 heavy chain
SEQ ID NO: 14: Nucleotide sequence encoding the R198 light chain
SEQ ID NO: 15: Amino acid sequence of the R198 light chain
SEQ ID NO: 16: Nucleotide sequence encoding the R198 heavy chain
SEQ ID NO: 17: Amino acid sequence of the R198 heavy chain
SEQ ID NO: 18: DNA fragment comprising a sequence encoding a human κ chain secretion signal and a human κ chain constant region
SEQ ID NO: 19: PCR primer 3.3-F1
SEQ ID NO: 20: PCR primer 3.3-R1
SEQ ID NO: 21: DNA fragment comprising a sequence encoding a human heavy chain signal sequence and amino acids of a human IgG1 constant region
SEQ ID NO: 22: Nucleotide sequence encoding the human chimerized cR118 light chain
SEQ ID NO: 23: Amino acid sequence of the human chimerized cR118 light chain
SEQ ID NO: 24: Nucleotide sequence encoding the human chimerized cR198 light chain
SEQ ID NO: 25: Amino acid sequence of the human chimerized cR198 light chain
SEQ ID NO: 26: Nucleotide sequence encoding the human chimerized cR118 heavy chain
SEQ ID NO: 27: Amino acid sequence of the human chimerized cR118 heavy chain
SEQ ID NO: 28: Nucleotide sequence encoding the human chimerized cR198 heavy chain
SEQ ID NO: 29: Amino acid sequence of the human chimerized cR198 heavy chain
SEQ ID NO: 30: Nucleotide sequence encoding the hR198_L1 type light chain
SEQ ID NO: 31: Amino acid sequence of the hR198_L1 type light chain
SEQ ID NO: 32: Nucleotide sequence encoding the hR198_L2 type light chain
SEQ ID NO: 33: Amino acid sequence of the hR198_L2 type light chain
SEQ ID NO: 34: Nucleotide sequence encoding the hR198_L3 type light chain
SEQ ID NO: 35: Amino acid sequence of the hR198_L3 type light chain
SEQ ID NO: 36: Nucleotide sequence encoding the hR198_L4 type light chain
SEQ ID NO: 37: Amino acid sequence of the hR198_L4 type light chain
SEQ ID NO: 38: Nucleotide sequence encoding the hR198_H1 type heavy chain
SEQ ID NO: 39: Amino acid sequence of the hR198_H1 type heavy chain
SEQ ID NO: 40: Nucleotide sequence encoding the hR198_H2 type heavy chain
SEQ ID NO: 41: Amino acid sequence of the hR198_H2 type heavy chain
SEQ ID NO: 42: Nucleotide sequence encoding the hR198_H3 type heavy chain
SEQ ID NO: 43: Amino acid sequence of the hR198_H3 type heavy chain
SEQ ID NO: 44: Nucleotide sequence encoding the hR198_H4 type heavy chain
SEQ ID NO: 45: Amino acid sequence of the hR198_H4 type heavy chain
SEQ ID NO: 46: PCR primer Orai1 HF
SEQ ID NO: 47: PCR primer Orai1 CH FR
SEQ ID NO: 48: PCR primer M13 rev long
SEQ ID NO: 49: PCR primer SecM Stop R
SEQ ID NO: 50: PCR primer Orai1 Lc F
SEQ ID NO: 51: PCR primer Orai1 CL-FR
SEQ ID NO: 52: PCR primer Orai1 HR-FLAG R
SEQ ID NO: 53: PCR primer Orai1 CL-FLAG R
SEQ ID NO: 54: PCR primer Myc-R
SEQ ID NO: 55: Nucleotide sequence encoding the hR198_LG1 type light chain
SEQ ID NO: 56: Amino acid sequence of the hR198_LG1 type light chain
SEQ ID NO: 57: Nucleotide sequence encoding the hR198_LG2 type light chain
SEQ ID NO: 58: Amino acid sequence of the hR198_LG2 type light chain
SEQ ID NO: 59: Nucleotide sequence encoding the hR198_LG3 type light chain
SEQ ID NO: 60: Amino acid sequence of the hR198_LG3 type light chain
SEQ ID NO: 61: Nucleotide sequence encoding the hR198_HG1 type heavy chain
SEQ ID NO: 62: Amino acid sequence of the hR198_HG1 type heavy chain
SEQ ID NO: 63: Nucleotide sequence encoding the hR198_HG2 type heavy chain
SEQ ID NO: 64: Amino acid sequence of the hR198_HG2 type heavy chain
SEQ ID NO: 65: Nucleotide sequence encoding the hR198_HG3 type heavy chain
SEQ ID NO: 66: Amino acid sequence of the hR198_HG3 type heavy chain
SEQ ID NO: 67: Nucleotide sequence encoding the hR198_H4-LALA type heavy chain
SEQ ID NO: 68: Amino acid sequence of the hR198_H4-LALA type heavy chain
SEQ ID NO: 69: Nucleotide sequence encoding the hR198_HG1-LALA type heavy chain
SEQ ID NO: 70: Amino acid sequence of the hR198_HG1-LALA type heavy chain
SEQ ID NO: 71: DNA fragment comprising a sequence encoding a human heavy chain secretion signal and amino acids of a human IgG2 constant region
SEQ ID NO: 72: Nucleotide sequence encoding the 2C1.1 antibody heavy chain
SEQ ID NO: 73: Amino acid sequence of the 2C1.1 antibody heavy chain
SEQ ID NO: 74: Nucleotide sequence encoding the 2C1.1 antibody light chain
SEQ ID NO: 75: Amino acid sequence of the 2C1.1 antibody light chain
SEQ ID NO: 76: Nucleotide sequence encoding the 5H3.1 antibody heavy chain
SEQ ID NO: 77: Amino acid sequence of the 5H3.1 antibody heavy chain
SEQ ID NO: 78: Nucleotide sequence encoding the 5H3.1 antibody light chain
SEQ ID NO: 79: Amino acid sequence of the 5H3.1 antibody light chain
SEQ ID NO: 80: Nucleotide sequence encoding the 10F8 antibody heavy chain
SEQ ID NO: 81: Amino acid sequence of the 10F8 antibody heavy chain SEQ ID NO: 82: Nucleotide sequence encoding the 10F8 antibody light chain
SEQ ID NO: 83: Amino acid sequence of the 10F8 antibody light chain
SEQ ID NO: 84: Nucleotide sequence encoding the 14F74 antibody heavy chain
SEQ ID NO: 85: Amino acid sequence of the 14F74 antibody heavy chain
SEQ ID NO: 86: Nucleotide sequence encoding the 14F74 antibody light chain
SEQ ID NO: 87: Amino acid sequence of the 14F74 antibody light chain
SEQ ID NO: 88: Nucleotide sequence encoding the 17F6 antibody heavy chain
SEQ ID NO: 89: Amino acid sequence of the 17F6 antibody heavy chain
SEQ ID NO: 90: Nucleotide sequence encoding the 17F6 antibody light chain
SEQ ID NO: 91: Amino acid sequence of the 17F6 antibody light chain
SEQ ID NO: 92: Rat CDRL1 (which was derived from R198 and used for the hR198_L1 to hR198_L4 type light chains)
SEQ ID NO: 93: Engineered CDRL1 (which was used for the hR198_LG1 type light chain)
SEQ ID NO: 94: Engineered CDRL1 (which was used for the hR198_LG2 type light chain)
SEQ ID NO: 95: Engineered CDRL1 (which was used for the hR198_LG3 type light chain)
SEQ ID NO: 96: Rat CDRL2 (which was common to R118 and R198 and used for the hR198_L1 to hR198_L4 and hR198_LG1 type light chains)
SEQ ID NO: 97: Engineered CDRL2 (which was used for the hR198_LG2 type light chain)
SEQ ID NO: 98: Engineered CDRL2 (which was used for the hR198_LG3 type light chain)
SEQ ID NO: 99: Rat CDRL3 (which was derived from R118 and used for the hR198_L3 and hR198_L4 type light chains)
SEQ ID NO: 100: Rat CDRL3 (which was derived from R198 and used for the hR198_L1 and hR198_L2 type light chains)
SEQ ID NO: 101: Engineered CDRL3 (which was used for the hR198_LG1 to hR198_LG3 type light chains)
SEQ ID NO: 102: Rat CDRH1 (which was derived from R118 and used for the hR198_H3, hR198_H4, and hR198_HG1 to hR198_HG3 type heavy chains)
SEQ ID NO: 103: Rat CDRH1 (which was derived from R198 and used for the hR198_H1 and hR198_H2 type heavy chains)
SEQ ID NO: 104: Rat CDRH2 (which was derived from R118 and used for the hR198_H3 and hR198_H4 type heavy chains)
SEQ ID NO: 105: Rat CDRH2 (which was derived from R198 and used for the hR198_H1 and hR198_H2 type heavy chains)
SEQ ID NO: 106: Engineered CDRH2 (which was used for the hR198_HG1 type heavy chain)
SEQ ID NO: 107: Engineered CDRH2 (which was used for the hR198_HG2 type heavy chain)
SEQ ID NO: 108: Engineered CDRH2 (which was used for the hR198_HG3 type heavy chain)
SEQ ID NO: 109: Rat CDRH3 (which was common to R118 and R198 and used for the hR198_H1 to hR198_H4 type heavy chain)
SEQ ID NO: 110: Engineered CDRH3 (which was used for the hR198_HG1 to hR198_HG3 type heavy chains)
SEQ ID NO: 111: Nucleotide sequence encoding the hR198_H0 type heavy chain
SEQ ID NO: 112: Amino acid sequence of the hR198_H0 type heavy chain
SEQ ID NO: 113: Nucleotide sequence encoding the hR198_H5 type heavy chain
SEQ ID NO: 114: Amino acid sequence of the hR198_H5 type heavy chain
SEQ ID NO: 115: Biotin-PEGylated human Orai1 loop region peptide sequence
SEQ ID NO: 116: Rat CDRL1 (which was derived from R118, but was not used for humanized antibodies)

The invention claimed is:

1. An antibody or an antigen binding fragment of the antibody which specifically binds to the amino acid sequence represented by SEQ ID NO: 2, wherein the heavy chain sequence comprises a variable region having CDRH1, CDRH2, and CDRH3, wherein the CDRH1 consists of the amino acid sequence represented by SEQ ID NO: 102, the CDRH2 consists of an amino acid sequence represented by any one of SEQ ID NOs: 104, 106, 107, and 108, and the CDRH3 consists of an amino acid sequence represented by SEQ ID NO: 109 or 110; and the light chain sequence comprises a variable region having CDRL1, CDRL2, and CDRL3, wherein the CDRL1 consists of an amino acid sequence represented by any one of SEQ ID NOs: 93, 94, and 95, the CDRL2 consists of an amino acid sequence represented by any one of SEQ ID NOs: 96, 97, and 98, and the CDRL3 consists of the amino acid sequence represented by SEQ ID NO: 101.

2. The antibody or the antigen binding fragment of the antibody according to claim 1, wherein the heavy chain sequence comprises a variable region having CDRH1, CDRH2, and CDRH3, wherein the CDRH1 consists of the amino acid sequence represented by SEQ ID NO: 102, the CDRH2 consists of the amino acid sequence represented by SEQ ID NO: 106, and the CDRH3 consists of the amino acid sequence represented by SEQ ID NO: 110; and the light chain sequence comprises a variable region having CDRL1, CDRL2, and CDRL3, wherein the CDRL1 consists of the amino acid sequence represented by SEQ ID NO: 93, the CDRL2 consists of the amino acid sequence represented by SEQ ID NO: 96, and the CDRL3 consists of the amino acid sequence represented by SEQ ID NO: 101.

3. The antibody or the antigen binding fragment of the antibody according to claim 1, wherein the antibody comprises a heavy chain variable region sequence consisting of amino acid residues from positions 20 to 136 in the amino acid sequence represented by SEQ ID NO: 62 and a light chain variable region sequence consisting of amino acid residues from positions 21 to 126 in the amino acid sequence represented by SEQ ID NO: 56.

4. The antibody or the antigen binding fragment of the antibody according to claim 3, wherein the antibody consists of a heavy chain sequence consisting of amino acid residues from positions 20 to 465 or 20 to 466 in the amino acid sequence represented by SEQ ID NO: 62 and a light chain sequence consisting of amino acid residues from positions 21 to 234 in the amino acid sequence represented by SEQ ID NO: 56.

5. The antibody or the antigen binding fragment of the antibody according to claim 3, wherein the antibody consists of a heavy chain sequence consisting of amino acid residues from positions 20 to 465 or 20 to 466 in the amino acid sequence represented by SEQ ID NO: 70 and a light chain sequence consisting of amino acid residues from positions 21 to 234 in the amino acid sequence represented by SEQ ID NO: 56.

6. The antigen binding fragment of the antibody according to claim 1, wherein the antigen binding fragment is selected from the group consisting of Fab, F(ab') 2, Fab', and Fv.

7. The antibody according to claim 1, wherein the antibody is an scFv.

8. A pharmaceutical composition comprising at least any one antibody or antigen binding fragment of the antibody according to claim 1.

* * * * *

```
                         SEQUENCE LISTING

<160> NUMBER OF SEQ ID NOS: 116

<210> SEQ ID NO 1
<211> LENGTH: 906
<212> TYPE: DNA
<213> ORGANISM: Homo sapiens

<400> SEQUENCE: 1
atgcatccgg agcccgcccc gccccgagc cgtagcagtc ccgagcttcc cccaagcggc      60
ggcagcacca ccagcggcag ccgccggagc cgccgccgca gcggggacgg ggagcccccg     120
ggggccccgc caccgccgcc gtccgccgtc acctacccgg actggatcgg ccagagttac     180
tccgaggtga tgagcctcaa cgagcactcc atgcaggcgc tgtcctggcg caagctctac     240
ttgagccgcg ccaagcttaa agcctccagc cggacctcgg ctctgctctc cggcttcgcc     300
atggtggcaa tggtggaggt gcagctggac gctgaccacg actacccacc ggggctgctc     360
atcgccttca gtgcctgcac cacagtgctg gtggctgtgc acctgtttgc gctcatgatc     420
agcacctgca tcctgcccaa catcgaggcg gtgagcaacg tgcacaatct caactcggtc     480
aaggagtccc cccatgagcg catgcaccgc acatcgagc tggcctgggc cttctccacc     540
gtcattggca cgctgctctt cctagctgag gtggtgctgc tctgctgggt caagttcttg     600
```

```
cccctcaaga agcagccagg ccagccaagg cccaccagca agccccccgc cagtggcgca      660
gcagccaacg tcagcaccag cggcatcacc ccgggccagg cagctgccat cgcctcgacc      720
accatcatgg tgcccttcgg cctgatcttt atcgtcttcg ccgtccactt ctaccgctca      780
ctggttagcc ataagaccga ccacagttc caggagctca acgagctggc ggagtttgcc       840
cgcttacagg accagctgga ccacagaggg gaccacccc tgacgcccgg cagccactat       900
gcctag                                                                906
```

```
<210> SEQ ID NO 2
<211> LENGTH: 301
<212> TYPE: PRT
<213> ORGANISM: Homo sapiens

<400> SEQUENCE: 2
```

Met His Pro Glu Pro Ala Pro Pro Pro Ser Arg Ser Ser Pro Glu Leu
1               5                   10                  15

Pro Pro Ser Gly Gly Ser Thr Thr Ser Gly Ser Arg Arg Ser Arg Arg
            20                  25                  30

Arg Ser Gly Asp Gly Glu Pro Pro Gly Ala Pro Pro Pro Pro Pro Ser
        35                  40                  45

Ala Val Thr Tyr Pro Asp Trp Ile Gly Gln Ser Tyr Ser Glu Val Met
    50                  55                  60

Ser Leu Asn Glu His Ser Met Gln Ala Leu Ser Trp Arg Lys Leu Tyr
65                  70                  75                  80

Leu Ser Arg Ala Lys Leu Lys Ala Ser Ser Arg Thr Ser Ala Leu Leu
                85                  90                  95

Ser Gly Phe Ala Met Val Ala Met Val Glu Val Gln Leu Asp Ala Asp
            100                 105                 110

His Asp Tyr Pro Pro Gly Leu Leu Ile Ala Phe Ser Ala Cys Thr Thr
        115                 120                 125

Val Leu Val Ala Val His Leu Phe Ala Leu Met Ile Ser Thr Cys Ile
    130                 135                 140

Leu Pro Asn Ile Glu Ala Val Ser Asn Val His Asn Leu Asn Ser Val
145                 150                 155                 160

Lys Glu Ser Pro His Glu Arg Met His Arg His Ile Glu Leu Ala Trp
                165                 170                 175

Ala Phe Ser Thr Val Ile Gly Thr Leu Leu Phe Leu Ala Glu Val Val
            180                 185                 190

Leu Leu Cys Trp Val Lys Phe Leu Pro Leu Lys Lys Gln Pro Gly Gln
        195                 200                 205

Pro Arg Pro Thr Ser Lys Pro Pro Ala Ser Gly Ala Ala Ala Asn Val
    210                 215                 220

Ser Thr Ser Gly Ile Thr Pro Gly Gln Ala Ala Ile Ala Ser Thr
225                 230                 235                 240

Thr Ile Met Val Pro Phe Gly Leu Ile Phe Ile Val Phe Ala Val His
                245                 250                 255

Phe Tyr Arg Ser Leu Val Ser His Lys Thr Asp Arg Gln Phe Gln Glu
            260                 265                 270

Leu Asn Glu Leu Ala Glu Phe Ala Arg Leu Gln Asp Gln Leu Asp His
        275                 280                 285

Arg Gly Asp His Pro Leu Thr Pro Gly Ser His Tyr Ala
    290                 295                 300

```
<210> SEQ ID NO 3
```

```
<211> LENGTH: 37
<212> TYPE: DNA
<213> ORGANISM: artificial
<220> FEATURE:
<223> OTHER INFORMATION: PCR Primer Nhe-polyC-S
<220> FEATURE:
<221> NAME/KEY: misc_feature
<222> LOCATION: (37)..(37)
<223> OTHER INFORMATION: n is a, c, g, or t

<400> SEQUENCE: 3
gctagcgcta ccggactcag atccccccccc ccccdn                              37

<210> SEQ ID NO 4
<211> LENGTH: 28
<212> TYPE: DNA
<213> ORGANISM: artificial
<220> FEATURE:
<223> OTHER INFORMATION: PCR Primer rIg gamma-AS1

<400> SEQUENCE: 4
tcactgagct ggtgagagtg tagagccc                                        28

<210> SEQ ID NO 5
<211> LENGTH: 28
<212> TYPE: DNA
<213> ORGANISM: artificial
<220> FEATURE:
<223> OTHER INFORMATION: PCR Primer rIG gamma-AS2

<400> SEQUENCE: 5
tcaccgagct gctgagggtg tagagccc                                        28

<210> SEQ ID NO 6
<211> LENGTH: 37
<212> TYPE: DNA
<213> ORGANISM: artificial
<220> FEATURE:
<223> OTHER INFORMATION: PCR Primer Nhe-polyC-S
<220> FEATURE:
<221> NAME/KEY: misc_feature
<222> LOCATION: (37)..(37)
<223> OTHER INFORMATION: n is a, c, g, or t

<400> SEQUENCE: 6
gctagcgcta ccggactcag atccccccccc ccccdn                              37

<210> SEQ ID NO 7
<211> LENGTH: 28
<212> TYPE: DNA
<213> ORGANISM: artificial
<220> FEATURE:
<223> OTHER INFORMATION: rIg kappa-AS

<400> SEQUENCE: 7
tcagtaacac tgtccaggac accatctc                                        28

<210> SEQ ID NO 8
<211> LENGTH: 19
<212> TYPE: DNA
<213> ORGANISM: artificial
<220> FEATURE:
<223> OTHER INFORMATION: rIG gamma-seq

<400> SEQUENCE: 8
ctggctcagg gaaatagcc                                                  19
```

-continued

```
<210> SEQ ID NO 9
<211> LENGTH: 19
<212> TYPE: DNA
<213> ORGANISM: artificial
<220> FEATURE:
<223> OTHER INFORMATION: rIG kappa-seq

<400> SEQUENCE: 9
tccagttgct aactgttcc                                                  19

<210> SEQ ID NO 10
<211> LENGTH: 405
<212> TYPE: DNA
<213> ORGANISM: Rattus rattus
<220> FEATURE:
<221> NAME/KEY: misc_feature
<222> LOCATION: (382)..(382)
<223> OTHER INFORMATION: n is a, c, g, or t
<220> FEATURE:
<221> NAME/KEY: misc_feature
<222> LOCATION: (403)..(403)
<223> OTHER INFORMATION: n is a, c, g, or t

<400> SEQUENCE: 10
atgaaaatga cgacacctgc tcagttcctt gggcttctgt tgctctggtt tccaggtgcc     60
aggtgtgaca tccagttgac ccagtctcca tccacattgc ctgcatccct gggagagaga   120
gtcaccatca gttgcagagc aagtcagagt attagcaata gtttaagctg gtttcaacag   180
aaaccagatg gaactgttaa acgcctgatc tattctacat ccactttaga atctggtgtc   240
ccatcaaggt tcagtggcag tgggtctggg acagattatt ctctctccat caccagtctt   300
gagtctgaag attttgcaat gtattactgt ctacagtttg ctacttttcc ggacacgttt   360
ggaactggga ccaaactgga antgagacgg gctgatgctg canca                    405

<210> SEQ ID NO 11
<211> LENGTH: 135
<212> TYPE: PRT
<213> ORGANISM: Rattus rattus
<220> FEATURE:
<221> NAME/KEY: misc_feature
<222> LOCATION: (128)..(128)
<223> OTHER INFORMATION: Xaa can be any naturally occurring amino acid
<220> FEATURE:
<221> NAME/KEY: misc_feature
<222> LOCATION: (135)..(135)
<223> OTHER INFORMATION: Xaa can be any naturally occurring amino acid

<400> SEQUENCE: 11

Met Lys Met Thr Thr Pro Ala Gln Phe Leu Gly Leu Leu Leu Leu Trp
1               5                   10                  15

Phe Pro Gly Ala Arg Cys Asp Ile Gln Leu Thr Gln Ser Pro Ser Thr
            20                  25                  30

Leu Pro Ala Ser Leu Gly Glu Arg Val Thr Ile Ser Cys Arg Ala Ser
        35                  40                  45

Gln Ser Ile Ser Asn Ser Leu Ser Trp Phe Gln Gln Lys Pro Asp Gly
    50                  55                  60

Thr Val Lys Arg Leu Ile Tyr Ser Thr Ser Thr Leu Glu Ser Gly Val
65                  70                  75                  80

Pro Ser Arg Phe Ser Gly Ser Gly Ser Gly Thr Asp Tyr Ser Leu Ser
                85                  90                  95

Ile Thr Ser Leu Glu Ser Glu Asp Phe Ala Met Tyr Tyr Cys Leu Gln
            100                 105                 110

Phe Ala Thr Phe Pro Asp Thr Phe Gly Thr Gly Thr Lys Leu Glu Xaa
```

Arg Arg Ala Asp Ala Ala Xaa
    130                 135

<210> SEQ ID NO 12
<211> LENGTH: 468
<212> TYPE: DNA
<213> ORGANISM: Rattus rattus
<220> FEATURE:
<221> NAME/KEY: misc_feature
<222> LOCATION: (467)..(467)
<223> OTHER INFORMATION: n is a, c, g, or t

<400> SEQUENCE: 12

```
atggaatgga actgggtctt tctcctcctc ctgtcagtaa ctgcagaagt ccagtcccag      60
gtccagctgc agcagtctgg agcggagctg gcaaagcctg gctcctcagt gaagatttcc     120
tgcaaggctt ccggctacac cgtcaccgcc tattatataa gttggataag gcagacgatt     180
ggacagggcc ttgagtatgt tggatatatt gacatgggaa atggaaggac taactacaat     240
gcgaggttca aggcaaggc cacattgact gtggacaaat cctccagcac agccttcatg     300
caactcagca gcctgacacc tgacgactct gcggtctatt actgtgcaag ggactccaac     360
tgggggggttg attactgggg ccaaggagtc atggtcacag tctcctcagc tgaaacaaca     420
gccccatctg tctatccact ggctcctgga actgcttctc aaaagtna                 468
```

<210> SEQ ID NO 13
<211> LENGTH: 156
<212> TYPE: PRT
<213> ORGANISM: Rattus rattus
<220> FEATURE:
<221> NAME/KEY: misc_feature
<222> LOCATION: (156)..(156)
<223> OTHER INFORMATION: Xaa can be any naturally occurring amino acid

<400> SEQUENCE: 13

Met Glu Trp Asn Trp Val Phe Leu Leu Leu Leu Ser Val Thr Ala Glu
1               5                   10                  15

Val Gln Ser Gln Val Gln Leu Gln Gln Ser Gly Ala Glu Leu Ala Lys
            20                  25                  30

Pro Gly Ser Ser Val Lys Ile Ser Cys Lys Ala Ser Gly Tyr Thr Val
        35                  40                  45

Thr Ala Tyr Tyr Ile Ser Trp Ile Arg Gln Thr Ile Gly Gln Gly Leu
    50                  55                  60

Glu Tyr Val Gly Tyr Ile Asp Met Gly Asn Gly Arg Thr Asn Tyr Asn
65                  70                  75                  80

Ala Arg Phe Lys Gly Lys Ala Thr Leu Thr Val Asp Lys Ser Ser Ser
                85                  90                  95

Thr Ala Phe Met Gln Leu Ser Ser Leu Thr Pro Asp Asp Ser Ala Val
            100                 105                 110

Tyr Tyr Cys Ala Arg Asp Ser Asn Trp Gly Val Asp Tyr Trp Gly Gln
        115                 120                 125

Gly Val Met Val Thr Val Ser Ser Ala Glu Thr Thr Ala Pro Ser Val
    130                 135                 140

Tyr Pro Leu Ala Pro Gly Thr Ala Ser Gln Lys Xaa
145                 150                 155

<210> SEQ ID NO 14
<211> LENGTH: 408
<212> TYPE: DNA

```
<213> ORGANISM: Rattus rattus
<220> FEATURE:
<221> NAME/KEY: misc_feature
<222> LOCATION: (403)..(403)
<223> OTHER INFORMATION: n is a, c, g, or t

<400> SEQUENCE: 14
atgaaaatga cgacacctgc tcagttcctt gggcttctgt tgctctggtt tccaggtgcc      60
aggtgtgaca tccagttgac ccagtctcca tccacattgc ctgcatctct gggagagaga     120
gtcaccatca gttgcagagc aagtcagagt attggcaata gtttaagctg gtttcagcag     180
aaaccagatg gatctgttaa acgcctgatc tactctacat ccactttaga atctggtgtc     240
ccatcaaggt tcagtggcag tgggtctggg acagattatt ctctctccat caccagtctt     300
gagtctgaag attttgcaat gtattactgt ctacagtttg ctacttatcc ggacacgttt     360
ggaactggga ccaaactgga actgagacgg gctgatgctg cancaact                  408

<210> SEQ ID NO 15
<211> LENGTH: 136
<212> TYPE: PRT
<213> ORGANISM: Rattus rattus
<220> FEATURE:
<221> NAME/KEY: misc_feature
<222> LOCATION: (135)..(135)
<223> OTHER INFORMATION: Xaa can be any naturally occurring amino acid

<400> SEQUENCE: 15

Met Lys Met Thr Thr Pro Ala Gln Phe Leu Gly Leu Leu Leu Leu Trp
1               5                   10                  15

Phe Pro Gly Ala Arg Cys Asp Ile Gln Leu Thr Gln Ser Pro Ser Thr
            20                  25                  30

Leu Pro Ala Ser Leu Gly Glu Arg Val Thr Ile Ser Cys Arg Ala Ser
        35                  40                  45

Gln Ser Ile Gly Asn Ser Leu Ser Trp Phe Gln Gln Lys Pro Asp Gly
    50                  55                  60

Ser Val Lys Arg Leu Ile Tyr Ser Thr Ser Thr Leu Glu Ser Gly Val
65                  70                  75                  80

Pro Ser Arg Phe Ser Gly Ser Gly Ser Gly Thr Asp Tyr Ser Leu Ser
                85                  90                  95

Ile Thr Ser Leu Glu Ser Glu Asp Phe Ala Met Tyr Tyr Cys Leu Gln
            100                 105                 110

Phe Ala Thr Tyr Pro Asp Thr Phe Gly Thr Gly Thr Lys Leu Glu Leu
        115                 120                 125

Arg Arg Ala Asp Ala Ala Xaa Thr
    130                 135

<210> SEQ ID NO 16
<211> LENGTH: 471
<212> TYPE: DNA
<213> ORGANISM: Rattus rattus
<220> FEATURE:
<221> NAME/KEY: misc_feature
<222> LOCATION: (469)..(469)
<223> OTHER INFORMATION: n is a, c, g, or t

<400> SEQUENCE: 16
atggaatgga actgggtctt tctcttcctc ctgtcagtaa ctgcagaagt ccagtcccag      60
gtccagctgc agcagtctgg agcggagctg gcaaagcctg gctcctcaat gaagatttcc     120
tgcaaggctt ccggctaccc cgtcaccagc tattatataa gttggataaa gcagacgact     180
```

```
ggacagggcc ttgagtatat tggatatgtt gacatgggaa atggacggac taactacaat      240
gagaagttca agggcaaggc cacattgact gtagacaaat cctccagcac agccttcatg      300
caactcagca gcctgacacc tgacgactct gcggtctatt actgtgcaag ggactccaac      360 tgggggttg attactgggg ccaaggagtc atggtcacag tctcctcagc tgaaacaaca       420
gccccatctg tctatccact ggctcctgga actgctctca aaagtaacnc c               471
```

<210> SEQ ID NO 17
<211> LENGTH: 157
<212> TYPE: PRT
<213> ORGANISM: Rattus rattus
<220> FEATURE:
<221> NAME/KEY: misc_feature
<222> LOCATION: (157)..(157)
<223> OTHER INFORMATION: Xaa can be any naturally occurring amino acid

<400> SEQUENCE: 17

```
Met Glu Trp Asn Trp Val Phe Leu Phe Leu Leu Ser Val Thr Ala Glu
1               5                   10                  15

Val Gln Ser Gln Val Gln Leu Gln Gln Ser Gly Ala Glu Leu Ala Lys
            20                  25                  30

Pro Gly Ser Ser Met Lys Ile Ser Cys Lys Ala Ser Gly Tyr Pro Val
        35                  40                  45

Thr Ser Tyr Tyr Ile Ser Trp Ile Lys Gln Thr Thr Gly Gln Gly Leu
    50                  55                  60

Glu Tyr Ile Gly Tyr Val Asp Met Gly Asn Gly Arg Thr Asn Tyr Asn
65                  70                  75                  80

Glu Lys Phe Lys Gly Lys Ala Thr Leu Thr Val Asp Lys Ser Ser Ser
                85                  90                  95

Thr Ala Phe Met Gln Leu Ser Ser Leu Thr Pro Asp Asp Ser Ala Val
            100                 105                 110

Tyr Tyr Cys Ala Arg Asp Ser Asn Trp Gly Val Asp Tyr Trp Gly Gln
        115                 120                 125

Gly Val Met Val Thr Val Ser Ser Ala Glu Thr Thr Ala Pro Ser Val
    130                 135                 140

Tyr Pro Leu Ala Pro Gly Thr Ala Leu Lys Ser Asn Xaa
145                 150                 155
```

<210> SEQ ID NO 18
<211> LENGTH: 449
<212> TYPE: DNA
<213> ORGANISM: artificial
<220> FEATURE:
<223> OTHER INFORMATION: Nucleotide Sequence coding Human Light Chain
      Secretory Signal and Human Kappa Constant Region

<400> SEQUENCE: 18

```
gcctccggac tctagagcca ccatggtgct gcagacccag gtgttcatct ccctgctgct     60
gtggatctcc ggcgcgtacg gcgatatcgt gatgattaaa cgtacggtgg ccgccccctc    120
cgtgttcatc ttcccccccct ccgacgagca gctgaagtcc ggcaccgcct ccgtggtgtg   180
cctgctgaat aacttctacc ccagagaggc caaggtgcag tggaaggtgg acaacgccct    240
gcagtccggg aactcccagg agagcgtgac cgagcaggac agcaaggaca gcacctacag    300
cctgagcagc accctgaccc tgagcaaagc cgactacgag aagcacaagg tgtacgcctg    360
cgaggtgacc caccagggcc tgagctcccc cgtcaccaag agcttcaaca gggggagtg    420 ttaggggccc gtttaaacgg gggaggcta                                      449
```

<210> SEQ ID NO 19
<211> LENGTH: 30
<212> TYPE: DNA
<213> ORGANISM: artificial
<220> FEATURE:
<223> OTHER INFORMATION: PCR Primer 3.3-F1

<400> SEQUENCE: 19
tataccgtcg acctctagct agagcttggc                    30

<210> SEQ ID NO 20
<211> LENGTH: 30
<212> TYPE: DNA
<213> ORGANISM: artificial
<220> FEATURE:
<223> OTHER INFORMATION: PCR Primer 3.3-R1

<400> SEQUENCE: 20
gctatggcag ggcctgccgc cccgacgttg                    30

<210> SEQ ID NO 21
<211> LENGTH: 1132
<212> TYPE: DNA
<213> ORGANISM: artificial
<220> FEATURE:
<223> OTHER INFORMATION: Nucleotide Sequence coding Human Heavy Chain
      Secretory Signal and Human IgG1 Constant Region

<400> SEQUENCE: 21
gcctccggac tctagagcca ccatgaaaca cctgtggttc ttcctcctgc tggtggcagc     60
tcccagatgg gtgctgagcc aggtgcaatt gtgcaggcgg ttagctcagc ctccaccaag    120
ggcccaagcg tcttcccct ggcaccctcc tccaagagca cctctggcgg cacagccgcc    180
ctgggctgcc tggtcaagga ctacttcccc gaacccgtga ccgtgagctg gaactcaggc    240
gccctgacca gcggcgtgca caccttcccg gctgtcctgc agtcctcagg actctactcc    300
ctcagcagcg tggtgaccgt gccctccagc agcttgggca cccagaccta catctgcaac    360
gtgaatcaca agcccagcaa caccaaggtg gacaagagag ttgagcccaa atcttgtgac    420
aaaactcaca catgcccacc ctgcccagca cctgaactcc tggggggacc ctcagtcttc    480
ctcttccccc caaaacccaa ggacaccctc atgatctccc ggacccctga ggtcacatgc    540
gtggtggtgg acgtgagcca cgaagaccct gaggtcaagt tcaactggta cgtggacggc    600
gtggaggtgc ataatgccaa gacaaagccc cgggaggagc agtacaacag cacgtaccgg    660
gtggtcagcg tcctcaccgt cctgcaccag gactggctga atggcaagga gtacaagtgc    720
aaggtctcca acaaagccct cccagccccc atcgagaaaa ccatctccaa agccaaaggc    780
cagccccggg aaccacaggt gtacaccctg cccccatccc gggaggagat gaccaagaac    840
caggtcagcc tgacctgcct ggtcaaaggc ttctatccca gcgacatcgc cgtggagtgg    900
gagagcaatg gccagcccga gaacaactac aagaccaccc ctcccgtgct ggactccgac    960
ggctccttct tcctctacag caagctcacc gtggacaaga gcaggtggca gcagggcaac   1020
gtcttctcat gctccgtgat gcatgaggct ctgcacaacc actacaccca gaagagcctc   1080
tccctgtctc ccggcaaatg agatatcggg cccgtttaaa cgggggaggc ta           1132

<210> SEQ ID NO 22
<211> LENGTH: 705
<212> TYPE: DNA
<213> ORGANISM: artificial
<220> FEATURE:

<223> OTHER INFORMATION: Nucleotide Sequence coding cR118_L

<400> SEQUENCE: 22

```
atggtgctgc agacccaggt gttcatctcc ctgctgctgt ggatctccgg cgcgtacggc      60
gacatccagt tgacccagtc tccatccaca ttgcctgcat ccctgggaga gagagtcacc     120
atcagttgca gagcaagtca gagtattagc aatagtttaa gctggtttca acagaaacca     180
gatggaactg ttaaacgcct gatctattct acatccactt tagaatctgg tgtcccatca     240
aggttcagtg gcagtgggtc tgggacagat tattctctct ccatcaccag tcttgagtct     300
gaagattttg caatgtatta ctgtctacag tttgctactt ttccggacac gtttggaact     360
gggaccaaac tggaactgag acgggctgtg gccgccccct ccgtgttcat cttcccccc     420
tccgacgagc agctgaagtc cggcaccgcc tccgtggtgt gcctgctgaa taacttctac     480
cccagagagg ccaaggtgca gtggaaggtg gacaacgccc tgcagtccgg aactcccag     540
gagagcgtga ccgagcagga cagcaaggac agcacctaca gcctgagcag caccctgacc     600
ctgagcaaag ccgactacga aagcacaag gtgtacgcct gcgaggtgac ccaccagggc     660
ctgagctccc ccgtcaccaa gagcttcaac aggggggagt gttag                    705
```

<210> SEQ ID NO 23
<211> LENGTH: 234
<212> TYPE: PRT
<213> ORGANISM: artificial
<220> FEATURE:
<223> OTHER INFORMATION: Amino Acid Sequence of cR118_L

<400> SEQUENCE: 23

```
Met Val Leu Gln Thr Gln Val Phe Ile Ser Leu Leu Leu Trp Ile Ser
1               5                   10                  15

Gly Ala Tyr Gly Asp Ile Gln Leu Thr Gln Ser Pro Ser Thr Leu Pro
            20                  25                  30

Ala Ser Leu Gly Glu Arg Val Thr Ile Ser Cys Arg Ala Ser Gln Ser
        35                  40                  45

Ile Ser Asn Ser Leu Ser Trp Phe Gln Gln Lys Pro Asp Gly Thr Val
    50                  55                  60

Lys Arg Leu Ile Tyr Ser Thr Ser Thr Leu Glu Ser Gly Val Pro Ser
65                  70                  75                  80

Arg Phe Ser Gly Ser Gly Ser Gly Thr Asp Tyr Ser Leu Ser Ile Thr
                85                  90                  95

Ser Leu Glu Ser Glu Asp Phe Ala Met Tyr Tyr Cys Leu Gln Phe Ala
            100                 105                 110

Thr Phe Pro Asp Thr Phe Gly Thr Gly Thr Lys Leu Glu Leu Arg Arg
        115                 120                 125

Ala Val Ala Ala Pro Ser Val Phe Ile Phe Pro Pro Ser Asp Glu Gln
    130                 135                 140

Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
                165                 170                 175

Gly Asn Ser Gln Glu Ser Val Thr Glu Gln Asp Ser Lys Asp Ser Thr
            180                 185                 190

Tyr Ser Leu Ser Ser Thr Leu Thr Leu Ser Lys Ala Asp Tyr Glu Lys
        195                 200                 205

His Lys Val Tyr Ala Cys Glu Val Thr His Gln Gly Leu Ser Ser Pro
    210                 215                 220
```

Val Thr Lys Ser Phe Asn Arg Gly Glu Cys
225                 230

<210> SEQ ID NO 24
<211> LENGTH: 705
<212> TYPE: DNA
<213> ORGANISM: artificial
<220> FEATURE:
<223> OTHER INFORMATION: Nucleotide Sequence coding cR198_L

<400> SEQUENCE: 24

```
atggtgctgc agacccaggt gttcatctcc ctgctgctgt ggatctccgg cgcgtacggc        60
gacatccagt tgacccagtc tccatccaca ttgcctgcat ctctgggaga gagagtcacc      120
atcagttgca gagcaagtca gagtattggc aatagtttaa gctggtttca gcagaaacca      180
gatggatctg ttaaacgcct gatctactct acatccactt tagaatctgg tgtcccatca      240
aggttcagtg gcagtgggtc tgggacagat tattctctct ccatcaccag tcttgagtct      300
gaagattttg caatgtatta ctgtctacag tttgctactt atccggacac gtttggaact      360
gggaccaaac tggaactgag acgggctgtg gccgcccct ccgtgttcat cttcccccc       420
tccgacgagc agctgaagtc cggcaccgcc tccgtggtgt gcctgctgaa taacttctac      480
cccagagagg ccaaggtgca gtggaaggtg gacaacgccc tgcagtccgg aactcccag       540
gagagcgtga ccgagcagga cagcaaggac agcacctaca gcctgagcag caccctgacc      600
ctgagcaaag ccgactacga gaagcacaag gtgtacgcct gcgaggtgac ccaccagggc      660
ctgagctccc ccgtcaccaa gagcttcaac agggggagt gttag                        705
```

<210> SEQ ID NO 25
<211> LENGTH: 234
<212> TYPE: PRT
<213> ORGANISM: artificial
<220> FEATURE:
<223> OTHER INFORMATION: Amino Acid Sequence of cR198_L

<400> SEQUENCE: 25

Met Val Leu Gln Thr Gln Val Phe Ile Ser Leu Leu Leu Trp Ile Ser
1               5                   10                  15

Gly Ala Tyr Gly Asp Ile Gln Leu Thr Gln Ser Pro Ser Thr Leu Pro
            20                  25                  30

Ala Ser Leu Gly Glu Arg Val Thr Ile Ser Cys Arg Ala Ser Gln Ser
        35                  40                  45

Ile Gly Asn Ser Leu Ser Trp Phe Gln Gln Lys Pro Asp Gly Ser Val
    50                  55                  60

Lys Arg Leu Ile Tyr Ser Thr Ser Thr Leu Glu Ser Gly Val Pro Ser
65                  70                  75                  80

Arg Phe Ser Gly Ser Gly Ser Gly Thr Asp Tyr Ser Leu Ser Ile Thr
                85                  90                  95

Ser Leu Glu Ser Glu Asp Phe Ala Met Tyr Tyr Cys Leu Gln Phe Ala
            100                 105                 110

Thr Tyr Pro Asp Thr Phe Gly Thr Gly Thr Lys Leu Glu Leu Arg Arg
        115                 120                 125

Ala Val Ala Ala Pro Ser Val Phe Ile Phe Pro Pro Ser Asp Glu Gln
    130                 135                 140

Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser

```
                    165                 170                 175
Gly Asn Ser Gln Glu Ser Val Thr Glu Gln Asp Ser Lys Asp Ser Thr
                180                 185                 190

Tyr Ser Leu Ser Ser Thr Leu Thr Leu Ser Lys Ala Asp Tyr Glu Lys
        195                 200                 205

His Lys Val Tyr Ala Cys Glu Val Thr His Gln Gly Leu Ser Ser Pro
    210                 215                 220

Val Thr Lys Ser Phe Asn Arg Gly Glu Cys
225                 230
```

<210> SEQ ID NO 26
<211> LENGTH: 1401
<212> TYPE: DNA
<213> ORGANISM: artificial
<220> FEATURE:
<223> OTHER INFORMATION: Nucleotide Sequence coding cR118_H

<400> SEQUENCE: 26

| | | |
|---|---|---|
| atgaaacacc tgtggttctt cctcctgctg gtggcagctc ccagatgggt gctgagccag | 60 |
| gtccagctgc agcagtctgg agcggagctg gcaaagcctg gctcctcagt gaagatttcc | 120 |
| tgcaaggctt ccggctacac cgtcaccgcc tattatataa gttggataag gcagacgatt | 180 |
| ggacagggcc ttgagtatgt tggatatatt gacatgggaa atggaaggac taactacaat | 240 |
| gcgaggttca aggcaaggc cacattgact gtggacaaat cctccagcac agccttcatg | 300 |
| caactcagca gcctgacacc tgacgactct gcggtctatt actgtgcaag ggactccaac | 360 |
| tggggggttg attactgggg ccaaggagtc atggtcacag tcagctcagc ctccaccaag | 420 |
| ggcccaagcg tcttccccct ggcaccctcc tccaagagca cctctggcgg cacagccgcc | 480 |
| ctgggctgcc tggtcaagga ctacttcccc gaacccgtga ccgtgagctg gaactcaggc | 540 |
| gccctgacca gcggcgtgca caccttcccc gctgtcctgc agtcctcagg actctactcc | 600 |
| ctcagcagcg tggtgaccgt gccctccagc agcttgggca cccagaccta catctgcaac | 660 |
| gtgaatcaca agcccagcaa caccaaggtg gacaagagag ttgagcccaa atcttgtgac | 720 |
| aaaactcaca catgcccacc ctgcccagca cctgaactcc tggggggacc ctcagtcttc | 780 |
| ctcttccccc caaaacccaa ggacaccctc atgatctccc ggacccctga ggtcacatgc | 840 |
| gtggtggtgg acgtgagcca cgaagaccct gaggtcaagt tcaactggta cgtggacggc | 900 |
| gtggaggtgc ataatgccaa gacaaagccc cgggaggagc agtacaacag cacgtaccgg | 960 |
| gtggtcagcg tcctcaccgt cctgcaccag gactggctga atggcaagga gtacaagtgc | 1020 |
| aaggtctcca acaaagccct cccagccccc atcgagaaaa ccatctccaa agccaaaggc | 1080 |
| cagccccggg aaccacaggt gtacaccctg cccccatccc gggaggagat gaccaagaac | 1140 |
| caggtcagcc tgacctgcct ggtcaaaggc ttctatccca gcgacatcgc cgtggagtgg | 1200 |
| gagagcaatg gccagcccga gaacaactac aagaccaccc ctcccgtgct ggactccgac | 1260 |
| ggctccttct tcctctacag caagctcacc gtggacaaga gcaggtggca gcagggcaac | 1320 |
| gtcttctcat gctccgtgat gcatgaggct ctgcacaacc actacaccca gaagagcctc | 1380 |
| tccctgtctc cggcaaatg a | 1401 |

<210> SEQ ID NO 27
<211> LENGTH: 466
<212> TYPE: PRT
<213> ORGANISM: artificial
<220> FEATURE:
<223> OTHER INFORMATION: Amino Acid Sequence of cR118_H

<400> SEQUENCE: 27

```
Met Lys His Leu Trp Phe Phe Leu Leu Leu Val Ala Ala Pro Arg Trp
1               5                   10                  15

Val Leu Ser Gln Val Gln Leu Gln Gln Ser Gly Ala Glu Leu Ala Lys
            20                  25                  30

Pro Gly Ser Ser Val Lys Ile Ser Cys Lys Ala Ser Gly Tyr Thr Val
        35                  40                  45

Thr Ala Tyr Tyr Ile Ser Trp Ile Arg Gln Thr Gly Gln Gly Leu
    50                  55                  60

Glu Tyr Val Gly Tyr Ile Asp Met Gly Asn Gly Arg Thr Asn Tyr Asn
65                  70                  75                  80

Ala Arg Phe Lys Gly Lys Ala Thr Leu Thr Val Asp Lys Ser Ser Ser
                85                  90                  95

Thr Ala Phe Met Gln Leu Ser Ser Leu Thr Pro Asp Asp Ser Ala Val
            100                 105                 110

Tyr Tyr Cys Ala Arg Asp Ser Asn Trp Gly Val Asp Tyr Trp Gly Gln
        115                 120                 125

Gly Val Met Val Thr Val Ser Ser Ala Ser Thr Lys Gly Pro Ser Val
130                 135                 140

Phe Pro Leu Ala Pro Ser Ser Lys Ser Thr Ser Gly Gly Thr Ala Ala
145                 150                 155                 160

Leu Gly Cys Leu Val Lys Asp Tyr Phe Pro Glu Pro Val Thr Val Ser
                165                 170                 175

Trp Asn Ser Gly Ala Leu Thr Ser Gly Val His Thr Phe Pro Ala Val
            180                 185                 190

Leu Gln Ser Ser Gly Leu Tyr Ser Leu Ser Ser Val Val Thr Val Pro
        195                 200                 205

Ser Ser Ser Leu Gly Thr Gln Thr Tyr Ile Cys Asn Val Asn His Lys
210                 215                 220

Pro Ser Asn Thr Lys Val Asp Lys Arg Val Glu Pro Lys Ser Cys Asp
225                 230                 235                 240

Lys Thr His Thr Cys Pro Pro Cys Pro Ala Pro Glu Leu Leu Gly Gly
                245                 250                 255

Pro Ser Val Phe Leu Phe Pro Pro Lys Pro Lys Asp Thr Leu Met Ile
            260                 265                 270

Ser Arg Thr Pro Glu Val Thr Cys Val Val Val Asp Val Ser His Glu
        275                 280                 285

Asp Pro Glu Val Lys Phe Asn Trp Tyr Val Asp Gly Val Glu Val His
290                 295                 300

Asn Ala Lys Thr Lys Pro Arg Glu Glu Gln Tyr Asn Ser Thr Tyr Arg
305                 310                 315                 320

Val Val Ser Val Leu Thr Val Leu His Gln Asp Trp Leu Asn Gly Lys
                325                 330                 335

Glu Tyr Lys Cys Lys Val Ser Asn Lys Ala Leu Pro Ala Pro Ile Glu
            340                 345                 350

Lys Thr Ile Ser Lys Ala Lys Gly Gln Pro Arg Glu Pro Gln Val Tyr
        355                 360                 365

Thr Leu Pro Pro Ser Arg Glu Glu Met Thr Lys Asn Gln Val Ser Leu
370                 375                 380

Thr Cys Leu Val Lys Gly Phe Tyr Pro Ser Asp Ile Ala Val Glu Trp
385                 390                 395                 400

Glu Ser Asn Gly Gln Pro Glu Asn Asn Tyr Lys Thr Thr Pro Pro Val
```

```
                        405                  410                  415
Leu Asp Ser Asp Gly Ser Phe Phe Leu Tyr Ser Lys Leu Thr Val Asp
            420                  425                  430

Lys Ser Arg Trp Gln Gln Gly Asn Val Phe Ser Cys Ser Val Met His
        435                  440                  445

Glu Ala Leu His Asn His Tyr Thr Gln Lys Ser Leu Ser Leu Ser Pro
    450                  455                  460

Gly Lys
465

<210> SEQ ID NO 28
<211> LENGTH: 1401
<212> TYPE: DNA
<213> ORGANISM: artificial
<220> FEATURE:
<223> OTHER INFORMATION: Nucleotide Sequence coding cR198_H

<400> SEQUENCE: 28
atgaaacacc tgtggttctt cctcctgctg gtggcagctc ccagatgggt gctgagccag      60
gtccagctgc agcagtctgg agcggagctg gcaaagcctg gctcctcaat gaagatttcc     120
tgcaaggctt ccggctaccc cgtcaccagc tattatataa gttggataaa gcagacgact     180
ggacagggcc ttgagtatat tggatatgtt gacatgggaa atggacggac taactacaat     240
gagaagttca gggcaaggc cacattgact gtagacaaat cctccagcac agccttcatg      300
caactcagca gcctgacacc tgacgactct gcggtctatt actgtgcaag ggactccaac     360
tggggggttg attactgggg ccaaggagtc atggtcacag tcagctcagc ctccaccaag     420
ggcccaagcg tcttccccct ggcaccctcc tccaagagca cctctggcgg cacagccgcc     480
ctgggctgcc tggtcaagga ctacttcccc gaacccgtga ccgtgagctg gaactcaggc     540
gccctgacca gcggcgtgca caccttcccc gctgtcctgc agtcctcagg actctactcc     600
ctcagcagcg tggtgaccgt gccctccagc agcttgggca cccagaccta catctgcaac     660
gtgaatcaca agcccagcaa caccaaggtg gacaagagag ttgagcccaa atcttgtgac     720
aaaactcaca catgcccacc ctgcccagca cctgaactcc tggggggacc ctcagtcttc     780
ctcttccccc caaaacccaa ggacaccctc atgatctccc ggacccctga ggtcacatgc     840
gtggtggtgg acgtgagcca cgaagaccct gaggtcaagt tcaactggta cgtggacggc     900
gtggaggtgc ataatgccaa gacaaagccc cgggaggagc agtacaacag cacgtaccgg     960
gtggtcagcg tcctcaccgt cctgcaccag gactggctga atggcaagga gtacaagtgc    1020
aaggtctcca acaaagccct cccagccccc atcgagaaaa ccatctccaa agccaaaggc    1080
cagccccggg aaccacaggt gtacaccctg cccccatccc gggaggagat gaccaagaac    1140
caggtcagcc tgacctgcct ggtcaaaggc ttctatccca gcgacatcgc cgtggagtgg    1200
gagagcaatg gccagcccga gaacaactac aagaccaccc ctcccgtgct ggactccgac    1260
ggctccttct tcctctacag caagctcacc gtggacaaga gcaggtggca gcagggcaac    1320
gtcttctcat gctccgtgat gcatgaggct ctgcacaacc actacaccca gaagagcctc    1380
tccctgtctc cggcaaatg a                                               1401

<210> SEQ ID NO 29
<211> LENGTH: 466
<212> TYPE: PRT
<213> ORGANISM: artificial
<220> FEATURE:
<223> OTHER INFORMATION: Amino Acid Sequence of cR198_H
```

<400> SEQUENCE: 29

Met Lys His Leu Trp Phe Phe Leu Leu Val Ala Ala Pro Arg Trp
1               5                   10                  15

Val Leu Ser Gln Val Gln Leu Gln Gln Ser Gly Ala Glu Leu Ala Lys
            20                  25                  30

Pro Gly Ser Ser Met Lys Ile Ser Cys Lys Ala Ser Gly Tyr Pro Val
            35                  40                  45

Thr Ser Tyr Tyr Ile Ser Trp Ile Lys Gln Thr Thr Gly Gln Gly Leu
    50                  55                  60

Glu Tyr Ile Gly Tyr Val Asp Met Gly Asn Gly Arg Thr Asn Tyr Asn
65              70                  75                  80

Glu Lys Phe Lys Gly Lys Ala Thr Leu Thr Val Asp Lys Ser Ser Ser
                85                  90                  95

Thr Ala Phe Met Gln Leu Ser Ser Leu Thr Pro Asp Asp Ser Ala Val
            100                 105                 110

Tyr Tyr Cys Ala Arg Asp Ser Asn Trp Gly Val Asp Tyr Trp Gly Gln
            115                 120                 125

Gly Val Met Val Thr Val Ser Ser Ala Ser Thr Lys Gly Pro Ser Val
130                 135                 140

Phe Pro Leu Ala Pro Ser Ser Lys Ser Thr Ser Gly Gly Thr Ala Ala
145                 150                 155                 160

Leu Gly Cys Leu Val Lys Asp Tyr Phe Pro Glu Pro Val Thr Val Ser
            165                 170                 175

Trp Asn Ser Gly Ala Leu Thr Ser Gly Val His Thr Phe Pro Ala Val
            180                 185                 190

Leu Gln Ser Ser Gly Leu Tyr Ser Leu Ser Ser Val Val Thr Val Pro
            195                 200                 205

Ser Ser Ser Leu Gly Thr Gln Thr Tyr Ile Cys Asn Val Asn His Lys
    210                 215                 220

Pro Ser Asn Thr Lys Val Asp Lys Arg Val Glu Pro Lys Ser Cys Asp
225                 230                 235                 240

Lys Thr His Thr Cys Pro Pro Cys Pro Ala Pro Glu Leu Leu Gly Gly
            245                 250                 255

Pro Ser Val Phe Leu Phe Pro Pro Lys Pro Lys Asp Thr Leu Met Ile
            260                 265                 270

Ser Arg Thr Pro Glu Val Thr Cys Val Val Val Asp Val Ser His Glu
    275                 280                 285

Asp Pro Glu Val Lys Phe Asn Trp Tyr Val Asp Gly Val Glu Val His
290                 295                 300

Asn Ala Lys Thr Lys Pro Arg Glu Glu Gln Tyr Asn Ser Thr Tyr Arg
305                 310                 315                 320

Val Val Ser Val Leu Thr Val Leu His Gln Asp Trp Leu Asn Gly Lys
            325                 330                 335

Glu Tyr Lys Cys Lys Val Ser Asn Lys Ala Leu Pro Ala Pro Ile Glu
            340                 345                 350

Lys Thr Ile Ser Lys Ala Lys Gly Gln Pro Arg Glu Pro Gln Val Tyr
            355                 360                 365

Thr Leu Pro Pro Ser Arg Glu Glu Met Thr Lys Asn Gln Val Ser Leu
    370                 375                 380

Thr Cys Leu Val Lys Gly Phe Tyr Pro Ser Asp Ile Ala Val Glu Trp
385                 390                 395                 400

Glu Ser Asn Gly Gln Pro Glu Asn Asn Tyr Lys Thr Thr Pro Pro Val

```
                       405                 410                 415
Leu Asp Ser Asp Gly Ser Phe Phe Leu Tyr Ser Lys Leu Thr Val Asp
            420                 425                 430

Lys Ser Arg Trp Gln Gln Gly Asn Val Phe Ser Cys Ser Val Met His
        435                 440                 445

Glu Ala Leu His Asn His Tyr Thr Gln Lys Ser Leu Ser Leu Ser Pro
    450                 455                 460

Gly Lys
465

<210> SEQ ID NO 30
<211> LENGTH: 705
<212> TYPE: DNA
<213> ORGANISM: artificial
<220> FEATURE:
<223> OTHER INFORMATION: Nucleotide Sequence coding hR198_L1

<400> SEQUENCE: 30
atggtgctgc agacccaggt gttcatctcc ctgctgctgt ggatctccgg cgcgtacggc    60
gatatccagc tgacccagag ccctagcagc ctgtctgcca gcgtgggcga cagagtgacc   120
atcacctgta gagccagcca gagcatcggc aacagcctga ctggttccag cagaaaccc    180 ggcaaggccc ccaagcggct gatctacagc accagcaccc tggaaagcgg cgtgcccagc   240
agattttctg gcagcggctc cggcaccgac tacaccctga caatcagcag cctgcagccc   300
gaggacttcg ccatgtacta ctgcctgcag ttcgccacct accccgacac ctttggccag   360
ggcaccaagg tggaaatcaa gcgtacggtg gccgccccct ccgtgttcat cttccccccc   420
tccgacgagc agctgaagtc cggcaccgcc tccgtggtgt gcctgctgaa taacttctac   480
cccagagagg ccaaggtgca gtggaaggtg gacaacgccc tgcagtccgg aactcccag    540 gagagcgtga ccgagcagga cagcaaggac agcacctaca gcctgagcag caccctgacc   600
ctgagcaaag ccgactacga gaagcacaag gtgtacgcct gcgaggtgac ccaccagggc   660
ctgagctccc ccgtcaccaa gagcttcaac agggggagt gttag                    705

<210> SEQ ID NO 31
<211> LENGTH: 234
<212> TYPE: PRT
<213> ORGANISM: artificial
<220> FEATURE:
<223> OTHER INFORMATION: Amino Acid Sequence of hR198_L1

<400> SEQUENCE: 31

Met Val Leu Gln Thr Gln Val Phe Ile Ser Leu Leu Leu Trp Ile Ser
1               5                   10                  15

Gly Ala Tyr Gly Asp Ile Gln Leu Thr Gln Ser Pro Ser Ser Leu Ser
            20                  25                  30

Ala Ser Val Gly Asp Arg Val Thr Ile Thr Cys Arg Ala Ser Gln Ser
        35                  40                  45

Ile Gly Asn Ser Leu Ser Trp Phe Gln Gln Lys Pro Gly Lys Ala Pro
    50                  55                  60

Lys Arg Leu Ile Tyr Ser Thr Ser Thr Leu Glu Ser Gly Val Pro Ser
65                  70                  75                  80

Arg Phe Ser Gly Ser Gly Ser Gly Thr Asp Tyr Thr Leu Thr Ile Ser
                85                  90                  95

Ser Leu Gln Pro Glu Asp Phe Ala Met Tyr Tyr Cys Leu Gln Phe Ala
            100                 105                 110
```

```
Thr Tyr Pro Asp Thr Phe Gly Gln Gly Thr Lys Val Glu Ile Lys Arg
            115                 120                 125
Thr Val Ala Ala Pro Ser Val Phe Ile Phe Pro Pro Ser Asp Glu Gln
        130                 135                 140
Leu Lys Ser Gly Thr Ala Ser Val Val Cys Leu Leu Asn Asn Phe Tyr
145                 150                 155                 160
Pro Arg Glu Ala Lys Val Gln Trp Lys Val Asp Asn Ala Leu Gln Ser
                165                 170                 175
Gly Asn Ser Gln Glu Ser Val Thr Glu Gln Asp Ser Lys Asp Ser Thr
            180                 185                 190
Tyr Ser Leu Ser Ser Thr Leu Thr Leu Ser Lys Ala Asp Tyr Glu Lys
        195                 200                 205
His Lys Val Tyr Ala Cys Glu Val Thr His Gln Gly Leu Ser Ser Pro
    210                 215                 220
Val Thr Lys Ser Phe Asn Arg Gly Glu Cys
225                 230
```

<210> SEQ ID NO 32
<211> LENGTH: 705
<212> TYPE: DNA
<213> ORGANISM: artificial
<220> FEATURE:
<223> OTHER INFORMATION: Nucleotide Sequence coding hR198_L2

<400> SEQUENCE: 32

```
atggtgctgc agacccaggt gttcatctcc ctgctgctgt ggatctccgg cgcgtacggc      60
gatatccagc tgacccagag ccctagcagc ctgtctgcca gcgtgggcga cagagtgacc     120
atcacctgta gagccagcca gagcatcggc aacagcctga ctggttcca gcagaaaccc     180
ggcaaggccg tgaagcggct gatctacagc accagcaccc tggaaagcgg cgtgcccagc     240
agattttctg gcagcggctc cggcaccgac tacaccctga caatcagcag cctgcagccc     300
gaggacttcg ccatgtacta ctgcctgcag ttcgccacct accccgacac ctttggccag     360
ggcaccaagg tggaaatcaa gcgtacggtg gccgcccct ccgtgttcat cttcccccc      420
tccgacgagc agctgaagtc cggcaccgcc tccgtggtgt gcctgctgaa taacttctac     480
cccagagagg ccaaggtgca gtggaaggtg gacaacgccc tgcagtccgg aactcccag      540
gagagcgtga ccgagcagga cagcaaggac agcaccctaca gcctgagcag caccctgacc    600
ctgagcaaag ccgactacga aagcacaag gtgtacgcct gcgaggtgac ccaccagggc      660
ctgagctccc ccgtcaccaa gagcttcaac agggggagt gttag                      705
```

<210> SEQ ID NO 33
<211> LENGTH: 234
<212> TYPE: PRT
<213> ORGANISM: artificial
<220> FEATURE:
<223> OTHER INFORMATION: Amino Acid Sequence of hR198_L2

<400> SEQUENCE: 33

```
Met Val Leu Gln Thr Gln Val Phe Ile Ser Leu Leu Leu Trp Ile Ser
1               5                   10                  15
Gly Ala Tyr Gly Asp Ile Gln Leu Thr Gln Ser Pro Ser Ser Leu Ser
            20                  25                  30
Ala Ser Val Gly Asp Arg Val Thr Ile Thr Cys Arg Ala Ser Gln Ser
        35                  40                  45
Ile Gly Asn Ser Leu Ser Trp Phe Gln Gln Lys Pro Gly Lys Ala Val
    50                  55                  60
```

```
Lys Arg Leu Ile Tyr Ser Thr Ser Thr Leu Glu Ser Gly Val Pro Ser
 65                  70                  75                  80

Arg Phe Ser Gly Ser Gly Ser Gly Thr Asp Tyr Thr Leu Thr Ile Ser
                 85                  90                  95

Ser Leu Gln Pro Glu Asp Phe Ala Met Tyr Tyr Cys Leu Gln Phe Ala
            100                 105                 110

Thr Tyr Pro Asp Thr Phe Gly Gln Gly Thr Lys Val Glu Ile Lys Arg
        115                 120                 125

Thr Val Ala Ala Pro Ser Val Phe Ile Phe Pro Pro Ser Asp Glu Gln
130                 135                 140

Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
                165                 170                 175

Gly Asn Ser Gln Glu Ser Val Thr Glu Gln Asp Ser Lys Asp Ser Thr
            180                 185                 190

Tyr Ser Leu Ser Ser Thr Leu Thr Leu Ser Lys Ala Asp Tyr Glu Lys
        195                 200                 205

His Lys Val Tyr Ala Cys Glu Val Thr His Gln Gly Leu Ser Ser Pro
    210                 215                 220

Val Thr Lys Ser Phe Asn Arg Gly Glu Cys
225                 230

<210> SEQ ID NO 34
<211> LENGTH: 705
<212> TYPE: DNA
<213> ORGANISM: artificial
<220> FEATURE:
<223> OTHER INFORMATION: Nucleotide Sequence coding hR198_L3

<400> SEQUENCE: 34
atggtgctgc agacccaggt gttcatctcc ctgctgctgt ggatctccgg cgcgtacggc      60
gatatccagc tgacccagag ccctagcagc ctgtctgcca gcgtgggcga cagagtgacc     120
atcacctgta gagccagcca gagcatcggc aacagcctga ctggttccag cagaaaccc     180 ggcaaggccc ccaagcggct gatctacagc accagcaccc tggaaagcgg cgtgcccagc     240 agatttctg gcagcggctc cggcaccgac tacaccctga caatcagcag cctgcagccc     300
gaggacttcg ccatgtacta ctgcctgcag ttcgccacct tccccgacac ctttggccag     360
ggcaccaagg tggaaatcaa gcgtacggtg gccgccccct ccgtgttcat cttcccccc     420 tccgacgagc agctgaagtc cggcaccgcc tccgtggtgt gcctgctgaa taacttctac     480
cccagagagg ccaaggtgca gtggaaggtg gacaacgccc tgcagtccgg gaactcccag     540
gagagcgtga ccgagcagga cagcaaggac agcacctaca gcctgagcag caccctgacc     600
ctgagcaaag ccgactacga gaagcacaag gtgtacgcct gcgaggtgac ccaccagggc     660
ctgagctccc ccgtcaccaa gagcttcaac agggggagt gttag                     705

<210> SEQ ID NO 35
<211> LENGTH: 234
<212> TYPE: PRT
<213> ORGANISM: artificial
<220> FEATURE:
<223> OTHER INFORMATION: Amino Acid Sequence of hR198_L3

<400> SEQUENCE: 35

Met Val Leu Gln Thr Gln Val Phe Ile Ser Leu Leu Leu Trp Ile Ser
```

```
1               5                   10                  15
Gly Ala Tyr Gly Asp Ile Gln Leu Thr Gln Ser Pro Ser Ser Leu Ser
            20                  25                  30

Ala Ser Val Gly Asp Arg Val Thr Ile Thr Cys Arg Ala Ser Gln Ser
            35                  40                  45

Ile Gly Asn Ser Leu Ser Trp Phe Gln Gln Lys Pro Gly Lys Ala Pro
        50                  55                  60

Lys Arg Leu Ile Tyr Ser Thr Ser Thr Leu Glu Ser Gly Val Pro Ser
65                  70                  75                  80

Arg Phe Ser Gly Ser Gly Ser Gly Thr Asp Tyr Thr Leu Thr Ile Ser
                85                  90                  95

Ser Leu Gln Pro Glu Asp Phe Ala Met Tyr Tyr Cys Leu Gln Phe Ala
            100                 105                 110

Thr Phe Pro Asp Thr Phe Gly Gln Gly Thr Lys Val Glu Ile Lys Arg
            115                 120                 125

Thr Val Ala Ala Pro Ser Val Phe Ile Phe Pro Pro Ser Asp Glu Gln
130                 135                 140

Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
                165                 170                 175

Gly Asn Ser Gln Glu Ser Val Thr Glu Gln Asp Ser Lys Asp Ser Thr
            180                 185                 190

Tyr Ser Leu Ser Ser Thr Leu Thr Leu Ser Lys Ala Asp Tyr Glu Lys
            195                 200                 205

His Lys Val Tyr Ala Cys Glu Val Thr His Gln Gly Leu Ser Ser Pro
210                 215                 220

Val Thr Lys Ser Phe Asn Arg Gly Glu Cys
225                 230

<210> SEQ ID NO 36
<211> LENGTH: 705
<212> TYPE: DNA
<213> ORGANISM: artificial
<220> FEATURE:
<223> OTHER INFORMATION: Nucleotide Sequence coding hR198_L4

<400> SEQUENCE: 36
atggtgctgc agacccaggt gttcatctcc ctgctgctgt ggatctccgg cgcgtacggc      60
gatatccagc tgacccagag ccctagcagc ctgtctgcca gcgtgggcga cagagtgacc     120
atcacctgta gagccagcca gagcatcggc aacagcctga gctggttcca gcagaaaccc     180
ggcaaggccg tgaagcggct gatctacagc accagcaccc tggaaagcgg cgtgcccagc     240 agatttctg gcagcggctc cggcaccgac tacaccctga caatcagcag cctgcagccc      300
gaggacttcg ccatgtacta ctgcctgcag ttcgccacct tccccgacac ctttggccag     360
ggcaccaagg tggaaatcaa gcgtacggtg gccgccccct ccgtgttcat cttcccccc      420 tccgacgagc agctgaagtc cggcaccgcc tccgtggtgt gcctgctgaa taacttctac     480
cccagagagg ccaaggtgca gtggaaggtg gacaacgccc tgcagtccgg aactcccag      540 gagagcgtga ccgagcagga cagcaaggac agcacctaca gcctgagcag caccctgacc     600
ctgagcaaag ccgactacga gaagcacaag gtgtacgcct gcgaggtgac ccaccagggc     660
ctgagctccc ccgtcaccaa gagcttcaac agggggggagt gttag                    705
```

```
<210> SEQ ID NO 37
<211> LENGTH: 234
<212> TYPE: PRT
<213> ORGANISM: artificial
<220> FEATURE:
<223> OTHER INFORMATION: Amino Acid Sequence of hR198_L4

<400> SEQUENCE: 37

Met Val Leu Gln Thr Gln Val Phe Ile Ser Leu Leu Trp Ile Ser
1               5                   10                  15

Gly Ala Tyr Gly Asp Ile Gln Leu Thr Gln Ser Pro Ser Ser Leu Ser
            20                  25                  30

Ala Ser Val Gly Asp Arg Val Thr Ile Thr Cys Arg Ala Ser Gln Ser
        35                  40                  45

Ile Gly Asn Ser Leu Ser Trp Phe Gln Gln Lys Pro Gly Lys Ala Val
    50                  55                  60

Lys Arg Leu Ile Tyr Ser Thr Ser Thr Leu Glu Ser Gly Val Pro Ser
65                  70                  75                  80

Arg Phe Ser Gly Ser Gly Ser Gly Thr Asp Tyr Thr Leu Thr Ile Ser
                85                  90                  95

Ser Leu Gln Pro Glu Asp Phe Ala Met Tyr Tyr Cys Leu Gln Phe Ala
            100                 105                 110

Thr Phe Pro Asp Thr Phe Gly Gln Gly Thr Lys Val Glu Ile Lys Arg
        115                 120                 125

Thr Val Ala Ala Pro Ser Val Phe Ile Phe Pro Pro Ser Asp Glu Gln
    130                 135                 140

Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
                165                 170                 175

Gly Asn Ser Gln Glu Ser Val Thr Glu Gln Asp Ser Lys Asp Ser Thr
            180                 185                 190

Tyr Ser Leu Ser Ser Thr Leu Thr Leu Ser Lys Ala Asp Tyr Glu Lys
        195                 200                 205

His Lys Val Tyr Ala Cys Glu Val Thr His Gln Gly Leu Ser Ser Pro
    210                 215                 220

Val Thr Lys Ser Phe Asn Arg Gly Glu Cys
225                 230

<210> SEQ ID NO 38
<211> LENGTH: 1401
<212> TYPE: DNA
<213> ORGANISM: artificial
<220> FEATURE:
<223> OTHER INFORMATION: Nucleotide Sequence coding hR198_H1

<400> SEQUENCE: 38
atgaaacacc tgtggttctt cctcctgctg gtggcagctc ccagatgggt gctgagccag      60
gtgcagctgg tgcagtctgg cgccgaagtg aagaaaccag cgccagcgt gaaggtgtcc      120 tgcaaggcct ctggctaccc cgtgaccagc tactacatca gctgggtcag acaggcccca      180
ggccagggcc tggaatacat cggctatgtg acatgggca acggccggac caactacaac      240
gagaagttca agggcagagc caccctgacc gtggacaaga gcaccagcac cgcctacatg      300
gaactgagca gcctgcggag cgaggacacc gccgtgtact actgcgccag agacagcaac      360
tggggcgtgg actattgggg ccagggcaca ctcgtgaccg tcagctcagc ctccaccaag      420
ggcccaagcg tcttcccct ggcaccctcc tccaagagca cctctggcgg cacagccgcc       480
```

-continued

```
ctgggctgcc tggtcaagga ctacttcccc gaacccgtga ccgtgagctg gaactcaggc    540
gccctgacca gcggcgtgca caccttcccc gctgtcctgc agtcctcagg actctactcc    600
ctcagcagcg tggtgaccgt gccctccagc agcttgggca cccagaccta catctgcaac    660
gtgaatcaca agcccagcaa caccaaggtg gacaagagag ttgagcccaa atcttgtgac    720
aaaactcaca catgcccacc ctgcccagca cctgaactcc tggggggacc ctcagtcttc    780
ctcttccccc caaaacccaa ggacaccctc atgatctccc ggaccctga ggtcacatgc     840 gtggtggtgg acgtgagcca cgaagaccct gaggtcaagt tcaactggta cgtggacggc    900
gtggaggtgc ataatgccaa gacaaagccc cgggaggagc agtacaacag cacgtaccgg    960
gtggtcagcg tcctcaccgt cctgcaccag gactggctga atggcaagga gtacaagtgc   1020
aaggtctcca acaaagccct cccagccccc atcgagaaaa ccatctccaa agccaaaggc   1080
cagccccggg aaccacaggt gtacaccctg cccccatccc gggaggagat gaccaagaac   1140
caggtcagcc tgacctgcct ggtcaaaggc ttctatccca gcgacatcgc cgtggagtgg   1200
gagagcaatg ggcagccga gaacaactac aagaccaccc ctcccgtgct ggactccgac   1260
ggctccttct tcctctacag caagctcacc gtggacaaga gcaggtggca gcagggcaac   1320
gtcttctcat gctccgtgat gcatgaggct ctgcacaacc actacaccca gaagagcctc   1380
tccctgtctc ccggcaaatg a                                             1401
```

<210> SEQ ID NO 39
<211> LENGTH: 466
<212> TYPE: PRT
<213> ORGANISM: artificial
<220> FEATURE:
<223> OTHER INFORMATION: Amino Acid Sequence of hR198_H1

<400> SEQUENCE: 39

```
Met Lys His Leu Trp Phe Phe Leu Leu Leu Val Ala Ala Pro Arg Trp
1               5                   10                  15

Val Leu Ser Gln Val Gln Leu Val Gln Ser Gly Ala Glu Val Lys Lys
                20                  25                  30

Pro Gly Ala Ser Val Lys Val Ser Cys Lys Ala Ser Gly Tyr Pro Val
            35                  40                  45

Thr Ser Tyr Tyr Ile Ser Trp Val Arg Gln Ala Pro Gly Gln Gly Leu
        50                  55                  60

Glu Tyr Ile Gly Tyr Val Asp Met Gly Asn Gly Arg Thr Asn Tyr Asn
65                  70                  75                  80

Glu Lys Phe Lys Gly Arg Ala Thr Leu Thr Val Asp Lys Ser Thr Ser
                85                  90                  95

Thr Ala Tyr Met Glu Leu Ser Ser Leu Arg Ser Glu Asp Thr Ala Val
            100                 105                 110

Tyr Tyr Cys Ala Arg Asp Ser Asn Trp Gly Val Asp Tyr Trp Gly Gln
        115                 120                 125

Gly Thr Leu Val Thr Val Ser Ser Ala Ser Thr Lys Gly Pro Ser Val
    130                 135                 140

Phe Pro Leu Ala Pro Ser Ser Lys Ser Thr Ser Gly Gly Thr Ala Ala
145                 150                 155                 160

Leu Gly Cys Leu Val Lys Asp Tyr Phe Pro Glu Pro Val Thr Val Ser
                165                 170                 175

Trp Asn Ser Gly Ala Leu Thr Ser Gly Val His Thr Phe Pro Ala Val
            180                 185                 190
```

-continued

```
Leu Gln Ser Ser Gly Leu Tyr Ser Leu Ser Ser Val Val Thr Val Pro
            195                 200                 205
Ser Ser Ser Leu Gly Thr Gln Thr Tyr Ile Cys Asn Val Asn His Lys
    210                 215                 220
Pro Ser Asn Thr Lys Val Asp Lys Arg Val Glu Pro Lys Ser Cys Asp
225                 230                 235                 240
Lys Thr His Thr Cys Pro Pro Cys Pro Ala Pro Glu Leu Leu Gly Gly
                245                 250                 255
Pro Ser Val Phe Leu Phe Pro Pro Lys Pro Lys Asp Thr Leu Met Ile
            260                 265                 270
Ser Arg Thr Pro Glu Val Thr Cys Val Val Val Asp Val Ser His Glu
        275                 280                 285
Asp Pro Glu Val Lys Phe Asn Trp Tyr Val Asp Gly Val Glu Val His
    290                 295                 300
Asn Ala Lys Thr Lys Pro Arg Glu Glu Gln Tyr Asn Ser Thr Tyr Arg
305                 310                 315                 320
Val Val Ser Val Leu Thr Val Leu His Gln Asp Trp Leu Asn Gly Lys
                325                 330                 335
Glu Tyr Lys Cys Lys Val Ser Asn Lys Ala Leu Pro Ala Pro Ile Glu
            340                 345                 350
Lys Thr Ile Ser Lys Ala Lys Gly Gln Pro Arg Glu Pro Gln Val Tyr
        355                 360                 365
Thr Leu Pro Pro Ser Arg Glu Glu Met Thr Lys Asn Gln Val Ser Leu
    370                 375                 380
Thr Cys Leu Val Lys Gly Phe Tyr Pro Ser Asp Ile Ala Val Glu Trp
385                 390                 395                 400
Glu Ser Asn Gly Gln Pro Glu Asn Asn Tyr Lys Thr Thr Pro Pro Val
                405                 410                 415
Leu Asp Ser Asp Gly Ser Phe Phe Leu Tyr Ser Lys Leu Thr Val Asp
            420                 425                 430
Lys Ser Arg Trp Gln Gln Gly Asn Val Phe Ser Cys Ser Val Met His
        435                 440                 445
Glu Ala Leu His Asn His Tyr Thr Gln Lys Ser Leu Ser Leu Ser Pro
    450                 455                 460
Gly Lys
465
```

<210> SEQ ID NO 40
<211> LENGTH: 1401
<212> TYPE: DNA
<213> ORGANISM: artificial
<220> FEATURE:
<223> OTHER INFORMATION: Nucleotide Sequence coding hR198_H2

<400> SEQUENCE: 40

| | | | | | |
|---|---|---|---|---|---|
| atgaaacacc | tgtggttctt | cctcctgctg | gtggcagctc | ccagatgggt | gctgagccag | 60 |
| gtgcagctgg | tgcagtctgg | cgccgaagtg | aagaaaccag | gcgccagcgt | gaaggtgtcc | 120 |
| tgcaaggcct | ctggctaccc | cgtgaccagc | tactacatca | gctggatcag | acaggcccca | 180 |
| ggccagggcc | tggaatacat | cggctatgtg | gacatgggca | acggccggac | caactacaac | 240 |
| gagaagttca | agggcagagc | caccctgacc | gtggacaaga | gcaccagcac | cgcctacatg | 300 |
| gaactgagca | gcctgcggag | cgaggacacc | gccgtgtact | actgcgccag | agacagcaac | 360 |
| tggggcgtgg | actattgggg | ccagggcaca | ctcgtgaccg | tcagctcagc | ctccaccaag | 420 |
| ggcccaagcg | tcttccccct | ggcaccctcc | tccaagagca | cctctggcgg | cacagccgcc | 480 |

```
ctgggctgcc tggtcaagga ctacttcccc gaacccgtga ccgtgagctg gaactcaggc    540
gccctgacca gcggcgtgca caccttcccc gctgtcctgc agtcctcagg actctactcc    600
ctcagcagcg tggtgaccgt gccctccagc agcttgggca cccagaccta catctgcaac    660
gtgaatcaca agcccagcaa caccaaggtg gacaagagag ttgagcccaa atcttgtgac    720
aaaactcaca catgcccacc ctgcccagca cctgaactcc tggggggacc ctcagtcttc    780
ctcttccccc caaaacccaa ggacaccctc atgatctccc ggacccctga ggtcacatgc    840
gtggtggtgg acgtgagcca cgaagaccct gaggtcaagt tcaactggta cgtggacggc    900
gtggaggtgc ataatgccaa gacaaagccc cgggaggagc agtacaacag cacgtaccgg    960
gtggtcagcg tcctcaccgt cctgcaccag gactggctga atggcaagga gtacaagtgc   1020
aaggtctcca acaaagccct cccagccccc atcgagaaaa ccatctccaa agccaaaggc   1080
cagccccggg aaccacaggt gtacaccctg cccccatccc gggaggagat gaccaagaac   1140
caggtcagcc tgacctgcct ggtcaaaggc ttctatccca gcgacatcgc cgtggagtgg   1200
gagagcaatg ggcagccgga gaacaactac aagaccaccc ctcccgtgct ggactccgac   1260
ggctccttct tcctctacag caagctcacc gtggacaaga gcaggtggca gcagggcaac   1320
gtcttctcat gctccgtgat gcatgaggct ctgcacaacc actacaccca gaagagcctc   1380
tccctgtctc ccggcaaatg a                                             1401

<210> SEQ ID NO 41
<211> LENGTH: 466
<212> TYPE: PRT
<213> ORGANISM: artificial
<220> FEATURE:
<223> OTHER INFORMATION: Amino Acid Sequence of hR198_H2

<400> SEQUENCE: 41

Met Lys His Leu Trp Phe Phe Leu Leu Leu Val Ala Ala Pro Arg Trp
1               5                   10                  15

Val Leu Ser Gln Val Gln Leu Val Gln Ser Gly Ala Glu Val Lys Lys
                20                  25                  30

Pro Gly Ala Ser Val Lys Val Ser Cys Lys Ala Ser Gly Tyr Pro Val
            35                  40                  45

Thr Ser Tyr Tyr Ile Ser Trp Ile Arg Gln Ala Pro Gly Gln Gly Leu
        50                  55                  60

Glu Tyr Ile Gly Tyr Val Asp Met Gly Asn Gly Arg Thr Asn Tyr Asn
65                  70                  75                  80

Glu Lys Phe Lys Gly Arg Ala Thr Leu Thr Val Asp Lys Ser Thr Ser
                85                  90                  95

Thr Ala Tyr Met Glu Leu Ser Ser Leu Arg Ser Glu Asp Thr Ala Val
            100                 105                 110

Tyr Tyr Cys Ala Arg Asp Ser Asn Trp Gly Val Asp Tyr Trp Gly Gln
        115                 120                 125

Gly Thr Leu Val Thr Val Ser Ser Ala Ser Thr Lys Gly Pro Ser Val
    130                 135                 140

Phe Pro Leu Ala Pro Ser Ser Lys Ser Thr Ser Gly Gly Thr Ala Ala
145                 150                 155                 160

Leu Gly Cys Leu Val Lys Asp Tyr Phe Pro Glu Pro Val Thr Val Ser
                165                 170                 175

Trp Asn Ser Gly Ala Leu Thr Ser Gly Val His Thr Phe Pro Ala Val
            180                 185                 190
```

```
Leu Gln Ser Ser Gly Leu Tyr Ser Leu Ser Ser Val Val Thr Val Pro
            195                 200                 205

Ser Ser Ser Leu Gly Thr Gln Thr Tyr Ile Cys Asn Val Asn His Lys
    210                 215                 220

Pro Ser Asn Thr Lys Val Asp Lys Arg Val Glu Pro Lys Ser Cys Asp
225                 230                 235                 240

Lys Thr His Thr Cys Pro Pro Cys Pro Ala Pro Glu Leu Leu Gly Gly
                245                 250                 255

Pro Ser Val Phe Leu Phe Pro Pro Lys Pro Lys Asp Thr Leu Met Ile
            260                 265                 270

Ser Arg Thr Pro Glu Val Thr Cys Val Val Val Asp Val Ser His Glu
    275                 280                 285

Asp Pro Glu Val Lys Phe Asn Trp Tyr Val Asp Gly Val Glu Val His
290                 295                 300

Asn Ala Lys Thr Lys Pro Arg Glu Glu Gln Tyr Asn Ser Thr Tyr Arg
305                 310                 315                 320

Val Val Ser Val Leu Thr Val Leu His Gln Asp Trp Leu Asn Gly Lys
                325                 330                 335

Glu Tyr Lys Cys Lys Val Ser Asn Lys Ala Leu Pro Ala Pro Ile Glu
            340                 345                 350

Lys Thr Ile Ser Lys Ala Lys Gly Gln Pro Arg Glu Pro Gln Val Tyr
    355                 360                 365

Thr Leu Pro Pro Ser Arg Glu Glu Met Thr Lys Asn Gln Val Ser Leu
370                 375                 380

Thr Cys Leu Val Lys Gly Phe Tyr Pro Ser Asp Ile Ala Val Glu Trp
385                 390                 395                 400

Glu Ser Asn Gly Gln Pro Glu Asn Asn Tyr Lys Thr Thr Pro Pro Val
                405                 410                 415

Leu Asp Ser Asp Gly Ser Phe Phe Leu Tyr Ser Lys Leu Thr Val Asp
            420                 425                 430

Lys Ser Arg Trp Gln Gln Gly Asn Val Phe Ser Cys Ser Val Met His
    435                 440                 445

Glu Ala Leu His Asn His Tyr Thr Gln Lys Ser Leu Ser Leu Ser Pro
450                 455                 460

Gly Lys
465

<210> SEQ ID NO 42
<211> LENGTH: 1401
<212> TYPE: DNA
<213> ORGANISM: artificial
<220> FEATURE:
<223> OTHER INFORMATION: Nucleotide Sequence coding hR198_H3

<400> SEQUENCE: 42
atgaaacacc tgtggttctt cctcctgctg gtggcagctc ccagatgggt gctgagccag      60
gtgcagctgg tgcagtctgg cgccgaagtg aagaaaccag cgccagcgt gaaggtgtcc     120 tgcaaggcct ctggctaccc cgtgaccgcc tactacatca gctgggtcag acaggcccca     180
ggccagggcc tggaatacgt gggctacatc gacatgggca acggccggac caactacaac     240
gcccggttta agggcagagc caccctgacc gtggacaaga gcaccagcac cgcctacatg     300
gaactgagca gcctgcggag cgaggacacc gccgtgtact actgcgccag agacagcaac     360
tggggcgtgg actattgggg ccagggcaca ctcgtgaccg tcagctcagc ctccaccaag     420
ggcccaagcg tcttcccccct ggcaccctcc tccaagagca cctctggcgg cacagccgcc     480
```

```
ctgggctgcc tggtcaagga ctacttcccc gaacccgtga ccgtgagctg gaactcaggc    540
gccctgacca gcggcgtgca caccttcccc gctgtcctgc agtcctcagg actctactcc    600
ctcagcagcg tggtgaccgt gccctccagc agcttgggca cccagaccta catctgcaac    660
gtgaatcaca gcccagcaa caccaaggtg gacaagagag ttgagcccaa atcttgtgac    720
aaaactcaca catgcccacc ctgcccagca cctgaactcc tggggggacc ctcagtcttc    780
ctcttccccc caaaacccaa ggacaccctc atgatctccc ggacccctga ggtcacatgc    840
gtggtggtgg acgtgagcca cgaagaccct gaggtcaagt tcaactggta cgtggacggc    900
gtggaggtgc ataatgccaa gacaaagccc cgggaggagc agtacaacag cacgtaccgg    960
gtggtcagcg tcctcaccgt cctgcaccag gactggctga atggcaagga gtacaagtgc   1020
aaggtctcca acaaagccct cccagccccc atcgagaaaa ccatctccaa agccaaaggc   1080
cagccccggg aaccacaggt gtacaccctg cccccatccc gggaggagat gaccaagaac   1140
caggtcagcc tgacctgcct ggtcaaaggc ttctatccca gcgacatcgc cgtggagtgg   1200
gagagcaatg gccagcccga gaacaactac aagaccaccc ctcccgtgct ggactccgac   1260
ggctccttct cctctacag caagctcacc gtggacaaga gcaggtggca gcagggcaac   1320
gtcttctcat gctccgtgat gcatgaggct ctgcacaacc actacaccca gaagagcctc   1380
tccctgtctc ccggcaaatg a                                              1401

<210> SEQ ID NO 43
<211> LENGTH: 466
<212> TYPE: PRT
<213> ORGANISM: artificial
<220> FEATURE:
<223> OTHER INFORMATION: Amino Acid Sequence of hR198_H3

<400> SEQUENCE: 43

Met Lys His Leu Trp Phe Phe Leu Leu Leu Val Ala Ala Pro Arg Trp
1               5                   10                  15

Val Leu Ser Gln Val Gln Leu Val Gln Ser Gly Ala Glu Val Lys Lys
                20                  25                  30

Pro Gly Ala Ser Val Lys Val Ser Cys Lys Ala Ser Gly Tyr Pro Val
            35                  40                  45

Thr Ala Tyr Tyr Ile Ser Trp Val Arg Gln Ala Pro Gly Gln Gly Leu
        50                  55                  60

Glu Tyr Val Gly Tyr Ile Asp Met Gly Asn Gly Arg Thr Asn Tyr Asn
65                  70                  75                  80

Ala Arg Phe Lys Gly Arg Ala Thr Leu Thr Val Asp Lys Ser Thr Ser
                85                  90                  95

Thr Ala Tyr Met Glu Leu Ser Ser Leu Arg Ser Glu Asp Thr Ala Val
            100                 105                 110

Tyr Tyr Cys Ala Arg Asp Ser Asn Trp Gly Val Asp Tyr Trp Gly Gln
        115                 120                 125

Gly Thr Leu Val Thr Val Ser Ser Ala Ser Thr Lys Gly Pro Ser Val
    130                 135                 140

Phe Pro Leu Ala Pro Ser Ser Lys Ser Thr Ser Gly Gly Thr Ala Ala
145                 150                 155                 160

Leu Gly Cys Leu Val Lys Asp Tyr Phe Pro Glu Pro Val Thr Val Ser
                165                 170                 175

Trp Asn Ser Gly Ala Leu Thr Ser Gly Val His Thr Phe Pro Ala Val
            180                 185                 190
```

Leu Gln Ser Ser Gly Leu Tyr Ser Leu Ser Ser Val Val Thr Val Pro
            195                 200                 205

Ser Ser Ser Leu Gly Thr Gln Thr Tyr Ile Cys Asn Val Asn His Lys
    210                 215                 220

Pro Ser Asn Thr Lys Val Asp Lys Arg Val Glu Pro Lys Ser Cys Asp
225                 230                 235                 240

Lys Thr His Thr Cys Pro Pro Cys Pro Ala Pro Glu Leu Leu Gly Gly
                245                 250                 255

Pro Ser Val Phe Leu Phe Pro Pro Lys Pro Lys Asp Thr Leu Met Ile
            260                 265                 270

Ser Arg Thr Pro Glu Val Thr Cys Val Val Val Asp Val Ser His Glu
    275                 280                 285

Asp Pro Glu Val Lys Phe Asn Trp Tyr Val Asp Gly Val Glu Val His
290                 295                 300

Asn Ala Lys Thr Lys Pro Arg Glu Glu Gln Tyr Asn Ser Thr Tyr Arg
305                 310                 315                 320

Val Val Ser Val Leu Thr Val Leu His Gln Asp Trp Leu Asn Gly Lys
                325                 330                 335

Glu Tyr Lys Cys Lys Val Ser Asn Lys Ala Leu Pro Ala Pro Ile Glu
            340                 345                 350

Lys Thr Ile Ser Lys Ala Lys Gly Gln Pro Arg Glu Pro Gln Val Tyr
    355                 360                 365

Thr Leu Pro Pro Ser Arg Glu Glu Met Thr Lys Asn Gln Val Ser Leu
370                 375                 380

Thr Cys Leu Val Lys Gly Phe Tyr Pro Ser Asp Ile Ala Val Glu Trp
385                 390                 395                 400

Glu Ser Asn Gly Gln Pro Glu Asn Asn Tyr Lys Thr Thr Pro Pro Val
                405                 410                 415

Leu Asp Ser Asp Gly Ser Phe Phe Leu Tyr Ser Lys Leu Thr Val Asp
            420                 425                 430

Lys Ser Arg Trp Gln Gln Gly Asn Val Phe Ser Cys Ser Val Met His
    435                 440                 445

Glu Ala Leu His Asn His Tyr Thr Gln Lys Ser Leu Ser Leu Ser Pro
450                 455                 460

Gly Lys
465

<210> SEQ ID NO 44
<211> LENGTH: 1401
<212> TYPE: DNA
<213> ORGANISM: artificial
<220> FEATURE:
<223> OTHER INFORMATION: Nucleotide Sequence coding hR198_H4

<400> SEQUENCE: 44
atgaaacacc tgtggttctt cctcctgctg gtggcagctc ccagatgggt gctgagccag      60
gtgcagctgg tgcagtctgg cgccgaagtg aagaaaccag cgccagcgt gaaggtgtcc     120 tgcaaggcct ctggctaccc cgtgaccgcc tactacatca gctggatcag acaggcccca     180
ggccagggcc tggaatacgt gggctacatc gacatgggca acggccggac caactacaac     240
gcccggttta agggcagagc caccctgacc gtggacaaga gcaccagcac cgcctacatg     300
gaactgagca gcctgcggag cgaggacacc gccgtgtact actgcgccag agacagcaac     360
tggggcgtgg actattgggg ccagggcaca ctcgtgaccg tcagctcagc ctccaccaag     420
ggcccaagcg tcttcccccct ggcaccctcc tccaagagca cctctggcgg cacagccgcc     480

```
ctgggctgcc tggtcaagga ctacttcccc gaacccgtga ccgtgagctg gaactcaggc    540
gccctgacca gcggcgtgca caccttcccc gctgtcctgc agtcctcagg actctactcc    600
ctcagcagcg tggtgaccgt gccctccagc agcttgggca cccagaccta catctgcaac    660
gtgaatcaca agcccagcaa caccaaggtg gacaagagag ttgagcccaa atcttgtgac    720
aaaactcaca catgcccacc ctgcccagca cctgaactcc tggggggacc ctcagtcttc    780
ctcttccccc caaaacccaa ggacaccctc atgatctccc ggacccctga ggtcacatgc    840
gtggtggtgg acgtgagcca cgaagaccct gaggtcaagt tcaactggta cgtggacggc    900
gtggaggtgc ataatgccaa gacaaagccc cgggaggagc agtacaacag cacgtaccgg    960
gtggtcagcg tcctcaccgt cctgcaccag gactggctga atggcaagga gtacaagtgc   1020
aaggtctcca acaaagccct cccagccccc atcgagaaaa ccatctccaa agccaaaggc   1080
cagccccggg aaccacaggt gtacaccctg cccccatccc gggaggagat gaccaagaac   1140
caggtcagcc tgacctgcct ggtcaaaggc ttctatccca gcgacatcgc cgtggagtgg   1200
gagagcaatg ggcagcccga gaacaactac aagaccaccc ctcccgtgct ggactccgac   1260
ggctccttct tcctctacag caagctcacc gtggacaaga gcaggtggca gcagggcaac   1320
gtcttctcat gctccgtgat gcatgaggct ctgcacaacc actacaccca gaagagcctc   1380
tccctgtctc cggcaaatga                                               1401

<210> SEQ ID NO 45
<211> LENGTH: 466
<212> TYPE: PRT
<213> ORGANISM: artificial
<220> FEATURE:
<223> OTHER INFORMATION: Amino Acid Sequence of hR198_H4

<400> SEQUENCE: 45

Met Lys His Leu Trp Phe Phe Leu Leu Leu Val Ala Ala Pro Arg Trp
1               5                   10                  15

Val Leu Ser Gln Val Gln Leu Val Gln Ser Gly Ala Glu Val Lys Lys
                20                  25                  30

Pro Gly Ala Ser Val Lys Val Ser Cys Lys Ala Ser Gly Tyr Pro Val
            35                  40                  45

Thr Ala Tyr Tyr Ile Ser Trp Ile Arg Gln Ala Pro Gly Gln Gly Leu
        50                  55                  60

Glu Tyr Val Gly Tyr Ile Asp Met Gly Asn Gly Arg Thr Asn Tyr Asn
65                  70                  75                  80

Ala Arg Phe Lys Gly Arg Ala Thr Leu Thr Val Asp Lys Ser Thr Ser
                85                  90                  95

Thr Ala Tyr Met Glu Leu Ser Ser Leu Arg Ser Glu Asp Thr Ala Val
            100                 105                 110

Tyr Tyr Cys Ala Arg Asp Ser Asn Trp Gly Val Asp Tyr Trp Gly Gln
        115                 120                 125

Gly Thr Leu Val Thr Val Ser Ser Ala Ser Thr Lys Gly Pro Ser Val
    130                 135                 140

Phe Pro Leu Ala Pro Ser Ser Lys Ser Thr Ser Gly Gly Thr Ala Ala
145                 150                 155                 160

Leu Gly Cys Leu Val Lys Asp Tyr Phe Pro Glu Pro Val Thr Val Ser
                165                 170                 175

Trp Asn Ser Gly Ala Leu Thr Ser Gly Val His Thr Phe Pro Ala Val
            180                 185                 190
```

```
Leu Gln Ser Ser Gly Leu Tyr Ser Leu Ser Val Val Thr Val Pro
            195                 200                 205
Ser Ser Ser Leu Gly Thr Gln Thr Tyr Ile Cys Asn Val Asn His Lys
210                 215                 220
Pro Ser Asn Thr Lys Val Asp Lys Arg Val Glu Pro Lys Ser Cys Asp
225                 230                 235                 240
Lys Thr His Thr Cys Pro Pro Cys Pro Ala Pro Glu Leu Leu Gly Gly
            245                 250                 255
Pro Ser Val Phe Leu Phe Pro Pro Lys Pro Lys Asp Thr Leu Met Ile
            260                 265                 270
Ser Arg Thr Pro Glu Val Thr Cys Val Val Val Asp Val Ser His Glu
            275                 280                 285
Asp Pro Glu Val Lys Phe Asn Trp Tyr Val Asp Gly Val Glu Val His
            290                 295                 300
Asn Ala Lys Thr Lys Pro Arg Glu Glu Gln Tyr Asn Ser Thr Tyr Arg
305                 310                 315                 320
Val Val Ser Val Leu Thr Val Leu His Gln Asp Trp Leu Asn Gly Lys
            325                 330                 335
Glu Tyr Lys Cys Lys Val Ser Asn Lys Ala Leu Pro Ala Pro Ile Glu
            340                 345                 350
Lys Thr Ile Ser Lys Ala Lys Gly Gln Pro Arg Glu Pro Gln Val Tyr
            355                 360                 365
Thr Leu Pro Pro Ser Arg Glu Glu Met Thr Lys Asn Gln Val Ser Leu
            370                 375                 380
Thr Cys Leu Val Lys Gly Phe Tyr Pro Ser Asp Ile Ala Val Glu Trp
385                 390                 395                 400
Glu Ser Asn Gly Gln Pro Glu Asn Asn Tyr Lys Thr Thr Pro Pro Val
            405                 410                 415
Leu Asp Ser Asp Gly Ser Phe Phe Leu Tyr Ser Lys Leu Thr Val Asp
            420                 425                 430
Lys Ser Arg Trp Gln Gln Gly Asn Val Phe Ser Cys Ser Val Met His
            435                 440                 445
Glu Ala Leu His Asn His Tyr Thr Gln Lys Ser Leu Ser Leu Ser Pro
            450                 455                 460
Gly Lys
465

<210> SEQ ID NO 46
<211> LENGTH: 23
<212> TYPE: DNA
<213> ORGANISM: artificial
<220> FEATURE:
<223> OTHER INFORMATION: PCR Primer Orai1 HF

<400> SEQUENCE: 46
atgcaagtcc aactggttca atc                                          23

<210> SEQ ID NO 47
<211> LENGTH: 21
<212> TYPE: DNA
<213> ORGANISM: artificial
<220> FEATURE:
<223> OTHER INFORMATION: PCR Primer Orai1 CH FR

<400> SEQUENCE: 47
tgacggagcc agcgggaaga c                                            21
```

<210> SEQ ID NO 48
<211> LENGTH: 21
<212> TYPE: DNA
<213> ORGANISM: artificial
<220> FEATURE:
<223> OTHER INFORMATION: PCR Primer M13 rev long

<400> SEQUENCE: 48
caggaaacag ctatgaccat g          21

<210> SEQ ID NO 49
<211> LENGTH: 31
<212> TYPE: DNA
<213> ORGANISM: artificial
<220> FEATURE:
<223> OTHER INFORMATION: PCR Primer SecM Stop R

<400> SEQUENCE: 49
ctcgagttat tcattaggtg aggcgttgag g          31

<210> SEQ ID NO 50
<211> LENGTH: 24
<212> TYPE: DNA
<213> ORGANISM: artificial
<220> FEATURE:
<223> OTHER INFORMATION: PCR Primer Orai1 Lc F

<400> SEQUENCE: 50
atggacattc aactgaccca aagc          24

<210> SEQ ID NO 51
<211> LENGTH: 24
<212> TYPE: DNA
<213> ORGANISM: artificial
<220> FEATURE:
<223> OTHER INFORMATION: PCR Primer Orai1 CL-FR

<400> SEQUENCE: 51
gataaaaaca ctcggggccg ccac          24

<210> SEQ ID NO 52
<211> LENGTH: 63
<212> TYPE: DNA
<213> ORGANISM: artificial
<220> FEATURE:
<223> OTHER INFORMATION: PCR Primer Orai1 HR-FLAG R

<400> SEQUENCE: 52
tcattatttg tcatcgtcat ctttatagtc gaattcttcg ccacgattaa aggatttggt          60
gac          63

<210> SEQ ID NO 53
<211> LENGTH: 63
<212> TYPE: DNA
<213> ORGANISM: artificial
<220> FEATURE:
<223> OTHER INFORMATION: PCR Primer Orai1 CL -FLAG R

<400> SEQUENCE: 53
tcattatttg tcatcgtcat ctttatagtc gaattcttcg ccacgattaa aggatttggt          60
gac          63

<210> SEQ ID NO 54
<211> LENGTH: 30
<212> TYPE: DNA

```
<213> ORGANISM: artificial
<220> FEATURE:
<223> OTHER INFORMATION: PCR Primer Myc-R

<400> SEQUENCE: 54
cagatcctcc tcagagatca gcttctgctc                                    30

<210> SEQ ID NO 55
<211> LENGTH: 705
<212> TYPE: DNA
<213> ORGANISM: artificial
<220> FEATURE:
<223> OTHER INFORMATION: Nucleotide Sequence coding hR198_LG1

<400> SEQUENCE: 55
atggtgctgc agacccaggt gttcatctcc ctgctgctgt ggatctccgg cgcgtacggc     60
gatatccagc tgacccagag ccctagcagc ctgtctgcca gcgtgggcga cagagtgacc    120
atcacctgta gagccagcca gagcatcggc ggcagcctga ctggttcca gcagaaaccc    180 ggcaaggccc ccaagcggct gatctacagc accagcaccc tggaaagcgg cgtgcccagc    240
agattttctg gcagcggctc cggcaccgac tacaccctga caatcagcag cctgcagccc    300
gaggacttcg ccatgtacta ctgcctgcag ttcgccatct cccccgacag ctttggccag    360
ggcaccaagg tggaaatcaa gcgtacggtg gccgccccct ccgtgttcat cttcccccc     420 tccgacgagc agctgaagtc cggcaccgcc tccgtggtgt gcctgctgaa taacttctac    480
cccagagagg ccaaggtgca gtggaaggtg gacaacgccc tgcagtccgg gaactcccag    540
gagagcgtga ccgagcagga cagcaaggac agcacctaca gcctgagcag caccctgacc    600
ctgagcaaag ccgactacga gaagcacaag gtgtacgcct gcgaggtgac ccaccagggc    660
ctgagctccc ccgtcaccaa gagcttcaac agggggagt gttag                    705

<210> SEQ ID NO 56
<211> LENGTH: 234
<212> TYPE: PRT
<213> ORGANISM: artificial
<220> FEATURE:
<223> OTHER INFORMATION: Amino Acid Sequence of hR198_LG1

<400> SEQUENCE: 56

Met Val Leu Gln Thr Gln Val Phe Ile Ser Leu Leu Leu Trp Ile Ser
1               5                   10                  15

Gly Ala Tyr Gly Asp Ile Gln Leu Thr Gln Ser Pro Ser Ser Leu Ser
            20                  25                  30

Ala Ser Val Gly Asp Arg Val Thr Ile Thr Cys Arg Ala Ser Gln Ser
        35                  40                  45

Ile Gly Gly Ser Leu Ser Trp Phe Gln Gln Lys Pro Gly Lys Ala Pro
    50                  55                  60

Lys Arg Leu Ile Tyr Ser Thr Ser Thr Leu Glu Ser Gly Val Pro Ser
65                  70                  75                  80

Arg Phe Ser Gly Ser Gly Ser Gly Thr Asp Tyr Thr Leu Thr Ile Ser
                85                  90                  95

Ser Leu Gln Pro Glu Asp Phe Ala Met Tyr Tyr Cys Leu Gln Phe Ala
            100                 105                 110

Ile Phe Pro Asp Ser Phe Gly Gln Gly Thr Lys Val Glu Ile Lys Arg
        115                 120                 125

Thr Val Ala Ala Pro Ser Val Phe Ile Phe Pro Pro Ser Asp Glu Gln
    130                 135                 140
```

```
Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
                165                 170                 175

Gly Asn Ser Gln Glu Ser Val Thr Glu Gln Asp Ser Lys Asp Ser Thr
            180                 185                 190

Tyr Ser Leu Ser Ser Thr Leu Thr Leu Ser Lys Ala Asp Tyr Glu Lys
        195                 200                 205

His Lys Val Tyr Ala Cys Glu Val Thr His Gln Gly Leu Ser Ser Pro
    210                 215                 220

Val Thr Lys Ser Phe Asn Arg Gly Glu Cys
225                 230
```

<210> SEQ ID NO 57
<211> LENGTH: 705
<212> TYPE: DNA
<213> ORGANISM: artificial
<220> FEATURE:
<223> OTHER INFORMATION: Nucleotide Sequence coding hR198_LG2

<400> SEQUENCE: 57

```
atggtgctgc agacccaggt gttcatctcc ctgctgctgt ggatctccgg cgcgtacggc    60
gatatccagc tgacccagag ccctagcagc ctgtctgcca gcgtgggcga cagagtgacc   120
atcacctgtc acgccagcca gaacatcggc ggcagcctga ctggttcca gcagaaaccc   180
ggcaaggccc ccaagcggct gatctacctg accagcaccc tggactgggg cgtgcccagc   240
agattttctg gcagcggctc cggcaccgac tacacccctg caatcagcag cctgcagccc   300
gaggacttcg ccatgtacta ctgcctgcag ttcgccatct ccccgacag ctttggccag   360
ggcaccaagg tggaaatcaa gcgtacggtg ccgccccct ccgtgttcat cttccccccc   420
tccgacgagc agctgaagtc cggcaccgcc tccgtggtgt gcctgctgaa taacttctac   480
cccagagagg ccaaggtgca gtggaaggtg acaacgccc tgcagtccgg aactcccag   540
gagagcgtga ccgagcagga cagcaaggac agcacctaca gcctgagcag caccctgacc   600
ctgagcaaag ccgactacga gaagcacaag gtgtacgcct gcgaggtgac ccaccagggc   660
ctgagctccc ccgtcaccaa gagcttcaac agggggagt gttag                   705
```

<210> SEQ ID NO 58
<211> LENGTH: 234
<212> TYPE: PRT
<213> ORGANISM: artificial
<220> FEATURE:
<223> OTHER INFORMATION: Amino Acid Sequence of hR198_LG2

<400> SEQUENCE: 58

```
Met Val Leu Gln Thr Gln Val Phe Ile Ser Leu Leu Leu Trp Ile Ser
1               5                   10                  15

Gly Ala Tyr Gly Asp Ile Gln Leu Thr Gln Ser Pro Ser Ser Leu Ser
            20                  25                  30

Ala Ser Val Gly Asp Arg Val Thr Ile Thr Cys His Ala Ser Gln Asn
        35                  40                  45

Ile Gly Gly Ser Leu Ser Trp Phe Gln Gln Lys Pro Gly Lys Ala Pro
    50                  55                  60

Lys Arg Leu Ile Tyr Leu Thr Ser Thr Leu Asp Trp Gly Val Pro Ser
65                  70                  75                  80

Arg Phe Ser Gly Ser Gly Ser Gly Thr Asp Tyr Thr Leu Thr Ile Ser
                85                  90                  95
```

```
Ser Leu Gln Pro Glu Asp Phe Ala Met Tyr Tyr Cys Leu Gln Phe Ala
            100                 105                 110

Ile Phe Pro Asp Ser Phe Gly Gln Gly Thr Lys Val Glu Ile Lys Arg
        115                 120                 125

Thr Val Ala Ala Pro Ser Val Phe Ile Phe Pro Pro Ser Asp Glu Gln
    130                 135                 140

Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
                165                 170                 175

Gly Asn Ser Gln Glu Ser Val Thr Glu Gln Asp Ser Lys Asp Ser Thr
            180                 185                 190

Tyr Ser Leu Ser Ser Thr Leu Thr Leu Ser Lys Ala Asp Tyr Glu Lys
        195                 200                 205

His Lys Val Tyr Ala Cys Glu Val Thr His Gln Gly Leu Ser Ser Pro
    210                 215                 220

Val Thr Lys Ser Phe Asn Arg Gly Glu Cys
225                 230
```

<210> SEQ ID NO 59
<211> LENGTH: 705
<212> TYPE: DNA
<213> ORGANISM: artificial
<220> FEATURE:
<223> OTHER INFORMATION: Nucleotide Sequence coding hR198_LG3

<400> SEQUENCE: 59

```
atggtgctgc agacccaggt gttcatctcc ctgctgctgt ggatctccgg cgcgtacggc    60
gatatccagc tgacccagag ccctagcagc ctgtctgcca gcgtgggcga cagagtgacc   120
atcacctgtc acgccagccg gaacatcggc ggcagcctga gctggttcca gcagaaaccc   180
ggcaaggccc ccaagcggct gatctacctg accagcagcc tggactgggg cgtgcccagc   240
agatttctg gcagcggctc cggcaccgac tacaccctga caatcagcag cctgcagccc   300
gaggacttcg ccatgtacta ctgcctgcag ttcgccatct tccccgacag ctttggccag   360
ggcaccaagg tggaaatcaa gcgtacggtg gccgccccct ccgtgttcat cttcccccc    420
tccgacgagc agctgaagtc cggcaccgcc tccgtggtgt gcctgctgaa taacttctac   480
cccagagagg ccaaggtgca gtggaaggtg gacaacgccc tgcagtccgg aactcccag    540
gagagcgtga ccgagcagga cagcaaggac agcacctaca gcctgagcag cacctgacc    600
ctgagcaaag ccgactacga aagcacaag gtgtacgcct gcgaggtgac ccaccagggc   660
ctgagctccc ccgtcaccaa gagcttcaac agggggagt gttag                    705
```

<210> SEQ ID NO 60
<211> LENGTH: 234
<212> TYPE: PRT
<213> ORGANISM: artificial
<220> FEATURE:
<223> OTHER INFORMATION: Amino Acid Sequence of hR198_LG3

<400> SEQUENCE: 60

```
Met Val Leu Gln Thr Gln Val Phe Ile Ser Leu Leu Leu Trp Ile Ser
1               5                   10                  15

Gly Ala Tyr Gly Asp Ile Gln Leu Thr Gln Ser Pro Ser Ser Leu Ser
            20                  25                  30

Ala Ser Val Gly Asp Arg Val Thr Ile Thr Cys His Ala Ser Arg Asn
```

```
                  35                  40                  45
Ile Gly Gly Ser Leu Ser Trp Phe Gln Gln Lys Pro Gly Lys Ala Pro
 50                  55                  60

Lys Arg Leu Ile Tyr Leu Thr Ser Ser Leu Asp Trp Gly Val Pro Ser
 65                  70                  75                  80

Arg Phe Ser Gly Ser Gly Ser Gly Thr Asp Tyr Thr Leu Thr Ile Ser
                 85                  90                  95

Ser Leu Gln Pro Glu Asp Phe Ala Met Tyr Tyr Cys Leu Gln Phe Ala
                100                 105                 110

Ile Phe Pro Asp Ser Phe Gly Gln Gly Thr Lys Val Glu Ile Lys Arg
                115                 120                 125

Thr Val Ala Ala Pro Ser Val Phe Ile Phe Pro Pro Ser Asp Glu Gln
130                 135                 140

Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
                165                 170                 175

Gly Asn Ser Gln Glu Ser Val Thr Glu Gln Asp Ser Lys Asp Ser Thr
                180                 185                 190

Tyr Ser Leu Ser Ser Thr Leu Thr Leu Ser Lys Ala Asp Tyr Glu Lys
                195                 200                 205

His Lys Val Tyr Ala Cys Glu Val Thr His Gln Gly Leu Ser Ser Pro
210                 215                 220

Val Thr Lys Ser Phe Asn Arg Gly Glu Cys
225                 230

<210> SEQ ID NO 61
<211> LENGTH: 1401
<212> TYPE: DNA
<213> ORGANISM: artificial
<220> FEATURE:
<223> OTHER INFORMATION: Nucleotide Sequence coding hR198_HG1

<400> SEQUENCE: 61
atgaaacacc tgtggttctt cctcctgctg gtggcagctc ccagatgggt gctgagccag      60
gtgcagctgg tgcagtctgg cgccgaagtg aagaaaccag gcgccagcgt gaaggtgtcc     120
tgcaaggcct ctggctaccc cgtgaccgcc tactacatca gctgggtcag acaggccccca    180 ggccagggcc tggaatacgt gggctacatc gacatgggca acggccggac cgactacaac     240
gcccggttta agggcagagc cacactgacc gtggacaaga gcaccagcac cgcctacatg     300
gaactgagca gcctgcggag cgaggacacc gccgtgtact actgcgccag agacagcaac     360
tggggcgccg actattgggg ccagggcaca ctcgtgaccg tcagctcagc tccaccaag     420 ggcccaagcg tcttccccct ggcaccctcc tccaagagca cctctggcgg cacagccgcc     480
ctgggctgcc tggtcaagga ctacttcccc gaacccgtga ccgtgagctg gaactcaggc     540
gccctgacca gcggcgtgca caccttcccc gctgtcctgc agtcctcagg actctactcc     600
ctcagcagcg tggtgaccgt gccctccagc agcttgggca cccagaccta catctgcaac     660
gtgaatcaca agcccagcaa caccaaggtg gacaagagag ttgagcccaa atcttgtgac     720
aaaactcaca catgcccacc ctgcccagca cctgaactcc tggggggacc ctcagtcttc     780
ctcttccccc caaaacccaa ggacaccctc atgatctccc ggacccctga ggtcacatgc     840
gtggtggtgg acgtgagcca cgaagaccct gaggtcaagt tcaactggta cgtggacggc     900
gtggaggtgc ataatgccaa gacaaagccc cgggaggagc agtacaacag cacgtaccgg     960
```

```
gtggtcagcg tcctcaccgt cctgcaccag gactggctga atggcaagga gtacaagtgc    1020
aaggtctcca acaaagccct cccagccccc atcgagaaaa ccatctccaa agccaaaggc    1080
cagccccggg aaccacaggt gtacaccctg cccccatccc gggaggagat gaccaagaac    1140
caggtcagcc tgacctgcct ggtcaaaggc ttctatccca gcgacatcgc cgtggagtgg    1200
gagagcaatg ccagcccga gaacaactac aagaccaccc ctcccgtgct ggactccgac    1260
ggctccttct tcctctacag caagctcacc gtggacaaga gcaggtggca gcagggcaac    1320
gtcttctcat gctccgtgat gcatgaggct ctgcacaacc actacaccca gaagagcctc    1380
tccctgtctc ccggcaaatg a                                              1401
```

<210> SEQ ID NO 62
<211> LENGTH: 466
<212> TYPE: PRT
<213> ORGANISM: artificial
<220> FEATURE:
<223> OTHER INFORMATION: Amino Acid Sequence of hR198_HG1

<400> SEQUENCE: 62

```
Met Lys His Leu Trp Phe Phe Leu Leu Leu Val Ala Ala Pro Arg Trp
1               5                   10                  15

Val Leu Ser Gln Val Gln Leu Val Gln Ser Gly Ala Glu Val Lys Lys
            20                  25                  30

Pro Gly Ala Ser Val Lys Val Ser Cys Lys Ala Ser Gly Tyr Pro Val
        35                  40                  45

Thr Ala Tyr Tyr Ile Ser Trp Val Arg Gln Ala Pro Gly Gln Gly Leu
    50                  55                  60

Glu Tyr Val Gly Tyr Ile Asp Met Gly Asn Gly Arg Thr Asp Tyr Asn
65                  70                  75                  80

Ala Arg Phe Lys Gly Arg Ala Thr Leu Thr Val Asp Lys Ser Thr Ser
                85                  90                  95

Thr Ala Tyr Met Glu Leu Ser Ser Leu Arg Ser Glu Asp Thr Ala Val
            100                 105                 110

Tyr Tyr Cys Ala Arg Asp Ser Asn Trp Gly Ala Asp Tyr Trp Gly Gln
        115                 120                 125

Gly Thr Leu Val Thr Val Ser Ser Ala Ser Thr Lys Gly Pro Ser Val
    130                 135                 140

Phe Pro Leu Ala Pro Ser Ser Lys Ser Thr Ser Gly Gly Thr Ala Ala
145                 150                 155                 160

Leu Gly Cys Leu Val Lys Asp Tyr Phe Pro Glu Pro Val Thr Val Ser
                165                 170                 175

Trp Asn Ser Gly Ala Leu Thr Ser Gly Val His Thr Phe Pro Ala Val
            180                 185                 190

Leu Gln Ser Ser Gly Leu Tyr Ser Leu Ser Ser Val Val Thr Val Pro
        195                 200                 205

Ser Ser Ser Leu Gly Thr Gln Thr Tyr Ile Cys Asn Val Asn His Lys
    210                 215                 220

Pro Ser Asn Thr Lys Val Asp Lys Arg Val Glu Pro Lys Ser Cys Asp
225                 230                 235                 240

Lys Thr His Thr Cys Pro Pro Cys Pro Ala Pro Glu Leu Leu Gly Gly
                245                 250                 255

Pro Ser Val Phe Leu Phe Pro Pro Lys Pro Lys Asp Thr Leu Met Ile
            260                 265                 270

Ser Arg Thr Pro Glu Val Thr Cys Val Val Val Asp Val Ser His Glu
```

```
                275                 280                 285
Asp Pro Glu Val Lys Phe Asn Trp Tyr Val Asp Gly Val Glu Val His
    290                 295                 300
Asn Ala Lys Thr Lys Pro Arg Glu Glu Gln Tyr Asn Ser Thr Tyr Arg
305                 310                 315                 320
Val Val Ser Val Leu Thr Val Leu His Gln Asp Trp Leu Asn Gly Lys
                325                 330                 335
Glu Tyr Lys Cys Lys Val Ser Asn Lys Ala Leu Pro Ala Pro Ile Glu
            340                 345                 350
Lys Thr Ile Ser Lys Ala Lys Gly Gln Pro Arg Glu Pro Gln Val Tyr
        355                 360                 365
Thr Leu Pro Pro Ser Arg Glu Glu Met Thr Lys Asn Gln Val Ser Leu
    370                 375                 380
Thr Cys Leu Val Lys Gly Phe Tyr Pro Ser Asp Ile Ala Val Glu Trp
385                 390                 395                 400
Glu Ser Asn Gly Gln Pro Glu Asn Asn Tyr Lys Thr Thr Pro Pro Val
                405                 410                 415
Leu Asp Ser Asp Gly Ser Phe Phe Leu Tyr Ser Lys Leu Thr Val Asp
            420                 425                 430
Lys Ser Arg Trp Gln Gln Gly Asn Val Phe Ser Cys Ser Val Met His
        435                 440                 445
Glu Ala Leu His Asn His Tyr Thr Gln Lys Ser Leu Ser Leu Ser Pro
    450                 455                 460
Gly Lys
465
```

<210> SEQ ID NO 63
<211> LENGTH: 1401
<212> TYPE: DNA
<213> ORGANISM: artificial
<220> FEATURE:
<223> OTHER INFORMATION: Nucleotide Sequence coding hR198_HG2

<400> SEQUENCE: 63

| | | | | | |
|---|---|---|---|---|---|
| atgaaacacc | tgtggttctt | cctcctgctg | gtggcagctc | ccagatgggt | gctgagccag | 60 |
| gtgcagctgg | tgcagtctgg | cgccgaagtg | aagaaaccag | gcgccagcgt | gaaggtgtcc | 120 |
| tgcaaggcct | ctggctaccc | catcaccgcc | tactacatca | gctgggtcag | acaggcccca | 180 |
| ggccagggcc | tggaatacgt | gggctacatc | gacatgggca | acggccggac | cgactacaac | 240 |
| gccggttta | agggcagagc | caccctgacc | gtggacaaga | gcaccagcac | cgcctacatg | 300 |
| gaactgagca | gcctgcggag | cgaggacacc | gccgtgtact | actgcgccag | agacagcaac | 360 |
| tggggcgccg | actattgggg | ccagggcaca | ctcgtgaccg | tcagctcagc | ctccaccaag | 420 |
| ggcccaagcg | tcttcccct | ggcaccctcc | tccaagagca | cctctggcgg | cacagccgcc | 480 |
| ctgggctgcc | tggtcaagga | ctacttcccc | gaacccgtga | ccgtgagctg | gaactcaggc | 540 |
| gccctgacca | gcggcgtgca | caccttcccc | gctgtcctgc | agtcctcagg | actctactcc | 600 |
| ctcagcagcg | tggtgaccgt | gccctccagc | agcttgggca | cccagaccta | catctgcaac | 660 |
| gtgaatcaca | agcccagcaa | caccaaggtg | gacaagagag | ttgagcccaa | atcttgtgac | 720 |
| aaaactcaca | catgcccacc | ctgcccagca | cctgaactcc | tggggggacc | ctcagtcttc | 780 |
| ctcttccccc | caaaacccaa | ggacaccctc | atgatctccc | ggacccctga | ggtcacatgc | 840 |
| gtggtggtgg | acgtgagcca | cgaagaccct | gaggtcaagt | tcaactggta | cgtggacggc | 900 |
| gtggaggtgc | ataatgccaa | gacaaagccc | cgggaggagc | agtacaacag | cacgtaccgg | 960 |

```
gtggtcagcg tcctcaccgt cctgcaccag gactggctga atggcaagga gtacaagtgc    1020
aaggtctcca acaaagccct cccagccccc atcgagaaaa ccatctccaa agccaaaggc    1080
cagccccggg aaccacaggt gtacaccctg cccccatccc gggaggagat gaccaagaac    1140
caggtcagcc tgacctgcct ggtcaaaggc ttctatccca gcgacatcgc cgtggagtgg    1200
gagagcaatg ccagcccga gaacaactac aagaccaccc ctcccgtgct ggactccgac    1260
ggctccttct cctctacag caagctcacc gtggacaaga gcaggtggca gcagggcaac    1320
gtcttctcat gctccgtgat gcatgaggct ctgcacaacc actacaccca gaagagcctc    1380
tccctgtctc ccggcaaatg a                                              1401

<210> SEQ ID NO 64
<211> LENGTH: 466
<212> TYPE: PRT
<213> ORGANISM: artificial
<220> FEATURE:
<223> OTHER INFORMATION: Amino Acid Sequence of hR198_HG2

<400> SEQUENCE: 64

Met Lys His Leu Trp Phe Phe Leu Leu Leu Val Ala Ala Pro Arg Trp
1               5                   10                  15

Val Leu Ser Gln Val Gln Leu Val Gln Ser Gly Ala Glu Val Lys Lys
            20                  25                  30

Pro Gly Ala Ser Val Lys Val Ser Cys Lys Ala Ser Gly Tyr Pro Ile
        35                  40                  45

Thr Ala Tyr Tyr Ile Ser Trp Val Arg Gln Ala Pro Gly Gln Gly Leu
    50                  55                  60

Glu Tyr Val Gly Tyr Ile Asp Met Gly Asn Gly Arg Thr Asp Tyr Asn
65                  70                  75                  80

Gly Arg Phe Lys Gly Arg Ala Thr Leu Thr Val Asp Lys Ser Thr Ser
                85                  90                  95

Thr Ala Tyr Met Glu Leu Ser Ser Leu Arg Ser Glu Asp Thr Ala Val
            100                 105                 110

Tyr Tyr Cys Ala Arg Asp Ser Asn Trp Gly Ala Asp Tyr Trp Gly Gln
        115                 120                 125

Gly Thr Leu Val Thr Val Ser Ser Ala Ser Thr Lys Gly Pro Ser Val
    130                 135                 140

Phe Pro Leu Ala Pro Ser Ser Lys Ser Thr Ser Gly Gly Thr Ala Ala
145                 150                 155                 160

Leu Gly Cys Leu Val Lys Asp Tyr Phe Pro Glu Pro Val Thr Val Ser
                165                 170                 175

Trp Asn Ser Gly Ala Leu Thr Ser Gly Val His Thr Phe Pro Ala Val
            180                 185                 190

Leu Gln Ser Ser Gly Leu Tyr Ser Leu Ser Ser Val Val Thr Val Pro
        195                 200                 205

Ser Ser Ser Leu Gly Thr Gln Thr Tyr Ile Cys Asn Val Asn His Lys
    210                 215                 220

Pro Ser Asn Thr Lys Val Asp Lys Arg Val Glu Pro Lys Ser Cys Asp
225                 230                 235                 240

Lys Thr His Thr Cys Pro Pro Cys Pro Ala Pro Glu Leu Leu Gly Gly
                245                 250                 255

Pro Ser Val Phe Leu Phe Pro Pro Lys Pro Lys Asp Thr Leu Met Ile
            260                 265                 270

Ser Arg Thr Pro Glu Val Thr Cys Val Val Val Asp Val Ser His Glu
```

```
            275                 280                 285
Asp Pro Glu Val Lys Phe Asn Trp Tyr Val Asp Gly Val Glu Val His
        290                 295                 300
Asn Ala Lys Thr Lys Pro Arg Glu Glu Gln Tyr Asn Ser Thr Tyr Arg
305                 310                 315                 320
Val Val Ser Val Leu Thr Val Leu His Gln Asp Trp Leu Asn Gly Lys
                325                 330                 335
Glu Tyr Lys Cys Lys Val Ser Asn Lys Ala Leu Pro Ala Pro Ile Glu
            340                 345                 350
Lys Thr Ile Ser Lys Ala Lys Gly Gln Pro Arg Glu Pro Gln Val Tyr
        355                 360                 365
Thr Leu Pro Pro Ser Arg Glu Glu Met Thr Lys Asn Gln Val Ser Leu
    370                 375                 380
Thr Cys Leu Val Lys Gly Phe Tyr Pro Ser Asp Ile Ala Val Glu Trp
385                 390                 395                 400
Glu Ser Asn Gly Gln Pro Glu Asn Asn Tyr Lys Thr Thr Pro Pro Val
                405                 410                 415
Leu Asp Ser Asp Gly Ser Phe Phe Leu Tyr Ser Lys Leu Thr Val Asp
            420                 425                 430
Lys Ser Arg Trp Gln Gln Gly Asn Val Phe Ser Cys Ser Val Met His
        435                 440                 445
Glu Ala Leu His Asn His Tyr Thr Gln Lys Ser Leu Ser Leu Ser Pro
    450                 455                 460
Gly Lys
465

<210> SEQ ID NO 65
<211> LENGTH: 1401
<212> TYPE: DNA
<213> ORGANISM: artificial
<220> FEATURE:
<223> OTHER INFORMATION: Nucleotide Sequence coding hR198_HG3

<400> SEQUENCE: 65
atgaaacacc tgtggttctt cctcctgctg gtggcagctc ccagatgggt gctgagccag      60
gtgcagctgg tgcagtctgg cgccgaagtg aagaaaccag gcgccagcgt gaaggtgtcc     120
tgcaaggcct ctggctaccc catcaccgcc tactacatca gctgggtcag acaggcccca     180
ggccagggcc tggaatacgt gggctacatc gacatgggca acggccggac cgactacaac     240
atgcggttta agggcagagc caccctgacc gtggacaaga gcaccagcac cgcctacatg     300
gaactgagca gcctgcggag cgaggacacc gccgtgtact actgcgccag agacagcaac     360
tggggcgccg actattgggg ccagggcaca ctcgtgaccg tcagctcagc tccaccaag      420 ggcccaagcg tcttccccct ggcaccctcc tccaagagca cctctggcgg cacagccgcc     480
ctgggctgcc tggtcaagga ctacttcccc gaacccgtga ccgtgagctg gaactcaggc     540
gccctgacca gcggcgtgca caccttcccc gctgtcctgc agtcctcagg actctactcc     600
ctcagcagcg tggtgaccgt gccctccagc agcttgggca cccagaccta catctgcaac     660
gtgaatcaca agcccagcaa caccaaggtg gacaagagag ttgagcccaa atcttgtgac     720
aaaactcaca catgcccacc ctgcccagca cctgaactcc tggggggacc ctcagtcttc     780
ctcttccccc caaaacccaa ggacaccctc atgatctccc ggacccctga ggtcacatgc     840
gtggtggtgg acgtgagcca cgaagaccct gaggtcaagt tcaactggta cgtggacggc     900
gtggaggtgc ataatgccaa gacaaagccc cgggaggagc agtacaacag cacgtaccgg     960
```

-continued

```
gtggtcagcg tcctcaccgt cctgcaccag gactggctga atggcaagga gtacaagtgc    1020
aaggtctcca acaaagccct cccagccccc atcgagaaaa ccatctccaa agccaaaggc    1080
cagccccggg aaccacaggt gtacaccctg cccccatccc gggaggagat gaccaagaac    1140
caggtcagcc tgacctgcct ggtcaaaggc ttctatccca gcgacatcgc cgtggagtgg    1200
gagagcaatg ccagcccga gaacaactac aagaccaccc ctcccgtgct ggactccgac    1260
ggctccttct cctctacag caagctcacc gtggacaaga gcaggtggca gcagggcaac    1320
gtcttctcat gctccgtgat gcatgaggct ctgcacaacc actacaccca gaagagcctc    1380
tccctgtctc ccggcaaatg a                                              1401
```

<210> SEQ ID NO 66
<211> LENGTH: 466
<212> TYPE: PRT
<213> ORGANISM: artificial
<220> FEATURE:
<223> OTHER INFORMATION: Amino Acid Sequence of hR198_HG3

<400> SEQUENCE: 66

```
Met Lys His Leu Trp Phe Phe Leu Leu Leu Val Ala Ala Pro Arg Trp
1               5                   10                  15

Val Leu Ser Gln Val Gln Leu Val Gln Ser Gly Ala Glu Val Lys Lys
            20                  25                  30

Pro Gly Ala Ser Val Lys Val Ser Cys Lys Ala Ser Gly Tyr Pro Ile
        35                  40                  45

Thr Ala Tyr Tyr Ile Ser Trp Val Arg Gln Ala Pro Gly Gln Gly Leu
    50                  55                  60

Glu Tyr Val Gly Tyr Ile Asp Met Gly Asn Gly Arg Thr Asp Tyr Asn
65                  70                  75                  80

Met Arg Phe Lys Gly Arg Ala Thr Leu Thr Val Asp Lys Ser Thr Ser
                85                  90                  95

Thr Ala Tyr Met Glu Leu Ser Ser Leu Arg Ser Glu Asp Thr Ala Val
            100                 105                 110

Tyr Tyr Cys Ala Arg Asp Ser Asn Trp Gly Ala Asp Tyr Trp Gly Gln
        115                 120                 125

Gly Thr Leu Val Thr Val Ser Ser Ala Ser Thr Lys Gly Pro Ser Val
    130                 135                 140

Phe Pro Leu Ala Pro Ser Ser Lys Ser Thr Ser Gly Gly Thr Ala Ala
145                 150                 155                 160

Leu Gly Cys Leu Val Lys Asp Tyr Phe Pro Glu Pro Val Thr Val Ser
                165                 170                 175

Trp Asn Ser Gly Ala Leu Thr Ser Gly Val His Thr Phe Pro Ala Val
            180                 185                 190

Leu Gln Ser Ser Gly Leu Tyr Ser Leu Ser Ser Val Val Thr Val Pro
        195                 200                 205

Ser Ser Ser Leu Gly Thr Gln Thr Tyr Ile Cys Asn Val Asn His Lys
    210                 215                 220

Pro Ser Asn Thr Lys Val Asp Lys Arg Val Glu Pro Lys Ser Cys Asp
225                 230                 235                 240

Lys Thr His Thr Cys Pro Pro Cys Pro Ala Pro Glu Leu Leu Gly Gly
                245                 250                 255

Pro Ser Val Phe Leu Phe Pro Pro Lys Pro Lys Asp Thr Leu Met Ile
            260                 265                 270

Ser Arg Thr Pro Glu Val Thr Cys Val Val Val Asp Val Ser His Glu
```

```
                275                 280                 285
Asp Pro Glu Val Lys Phe Asn Trp Tyr Val Asp Gly Val Glu Val His
    290                 295                 300
Asn Ala Lys Thr Lys Pro Arg Glu Glu Gln Tyr Asn Ser Thr Tyr Arg
305                 310                 315                 320
Val Val Ser Val Leu Thr Val Leu His Gln Asp Trp Leu Asn Gly Lys
                325                 330                 335
Glu Tyr Lys Cys Lys Val Ser Asn Lys Ala Leu Pro Ala Pro Ile Glu
            340                 345                 350
Lys Thr Ile Ser Lys Ala Lys Gly Gln Pro Arg Glu Pro Gln Val Tyr
        355                 360                 365
Thr Leu Pro Pro Ser Arg Glu Glu Met Thr Lys Asn Gln Val Ser Leu
    370                 375                 380
Thr Cys Leu Val Lys Gly Phe Tyr Pro Ser Asp Ile Ala Val Glu Trp
385                 390                 395                 400
Glu Ser Asn Gly Gln Pro Glu Asn Asn Tyr Lys Thr Thr Pro Pro Val
                405                 410                 415
Leu Asp Ser Asp Gly Ser Phe Phe Leu Tyr Ser Lys Leu Thr Val Asp
            420                 425                 430
Lys Ser Arg Trp Gln Gln Gly Asn Val Phe Ser Cys Ser Val Met His
        435                 440                 445
Glu Ala Leu His Asn His Tyr Thr Gln Lys Ser Leu Ser Leu Ser Pro
    450                 455                 460
Gly Lys
465
```

<210> SEQ ID NO 67
<211> LENGTH: 1401
<212> TYPE: DNA
<213> ORGANISM: artificial
<220> FEATURE:
<223> OTHER INFORMATION: Nucleotide Sequence coding hR198_H4-LALA

<400> SEQUENCE: 67

```
atgaaacacc tgtggttctt cctcctgctg gtggcagctc ccagatgggt gctgagccag      60
gtgcagctgg tgcagtctgg cgccgaagtg aagaaaccag gcgccagcgt gaaggtgtcc     120
tgcaaggcct ctggctaccc cgtgaccgcc tactacatca gctggatcag acaggcccca     180
ggccagggcc tggaatacgt gggctacatc gacatgggca acggccggac caactacaac     240
gcccggttta agggcagagc cacccctgac gtggacaaga gcaccagcac cgcctacatg     300
gaactgagca gcctgcggag cgaggacacc gccgtgtact actgcgccag agacagcaac     360
tggggcgtgg actattgggg ccagggcaca ctcgtgaccg tcagctcagc tccaccaag     420
ggcccaagcg tcttccccct ggcaccctcc tccaagagca cctctggcgg cacagccgcc     480
ctgggctgcc tggtcaagga ctacttcccc gaacccgtga ccgtgagctg gaactcaggc     540
gccctgacca gcggcgtgca caccttcccc gctgtcctgc agtcctcagg actctactcc     600
ctcagcagcg tggtgaccgt gccctccagc agcttgggca cccagaccta catctgcaac     660
gtgaatcaca gcccagcaa caccaaggtg gacaagagag ttgagcccaa atcttgtgac     720
aaaactcaca catgcccacc ctgcccagca cctgaagccg cggggggacc ctcagtcttc     780
ctcttcccccc aaaacccaa ggacaccctc atgatctccc ggaccccctga ggtcacatgc     840
gtggtggtgg acgtgagcca cgaagaccct gaggtcaagt tcaactggta cgtggacggc     900
gtggaggtgc ataatgccaa gacaaagccc cgggaggagc agtacaacag cacgtaccgg     960
```

```
gtggtcagcg tcctcaccgt cctgcaccag gactggctga atggcaagga gtacaagtgc   1020
aaggtctcca acaaagccct cccagccccc atcgagaaaa ccatctccaa agccaaaggc   1080
cagccccggg aaccacaggt gtacaccctg cccccatccc gggaggagat gaccaagaac   1140
caggtcagcc tgacctgcct ggtcaaaggc ttctatccca gcgacatcgc cgtggagtgg   1200
gagagcaatg ccagcccga gaacaactac aagaccaccc ctcccgtgct ggactccgac   1260
ggctccttct cctctacag caagctcacc gtggacaaga gcaggtggca gcagggcaac   1320
gtcttctcat gctccgtgat gcatgaggct ctgcacaacc actacaccca gaagagcctc   1380
tccctgtctc ccggcaaatg a                                             1401
```

<210> SEQ ID NO 68
<211> LENGTH: 466
<212> TYPE: PRT
<213> ORGANISM: artificial
<220> FEATURE:
<223> OTHER INFORMATION: Amino Acid Sequence of hR198_H4-LALA

<400> SEQUENCE: 68

```
Met Lys His Leu Trp Phe Phe Leu Leu Leu Val Ala Ala Pro Arg Trp
1               5                   10                  15

Val Leu Ser Gln Val Gln Leu Val Gln Ser Gly Ala Glu Val Lys Lys
            20                  25                  30

Pro Gly Ala Ser Val Lys Val Ser Cys Lys Ala Ser Gly Tyr Pro Val
        35                  40                  45

Thr Ala Tyr Tyr Ile Ser Trp Ile Arg Gln Ala Pro Gly Gln Gly Leu
    50                  55                  60

Glu Tyr Val Gly Tyr Ile Asp Met Gly Asn Gly Arg Thr Asn Tyr Asn
65                  70                  75                  80

Ala Arg Phe Lys Gly Arg Ala Thr Leu Thr Val Asp Lys Ser Thr Ser
                85                  90                  95

Thr Ala Tyr Met Glu Leu Ser Ser Leu Arg Ser Glu Asp Thr Ala Val
            100                 105                 110

Tyr Tyr Cys Ala Arg Asp Ser Asn Trp Gly Val Asp Tyr Trp Gly Gln
        115                 120                 125

Gly Thr Leu Val Thr Val Ser Ser Ala Ser Thr Lys Gly Pro Ser Val
    130                 135                 140

Phe Pro Leu Ala Pro Ser Ser Lys Ser Thr Ser Gly Gly Thr Ala Ala
145                 150                 155                 160

Leu Gly Cys Leu Val Lys Asp Tyr Phe Pro Glu Pro Val Thr Val Ser
                165                 170                 175

Trp Asn Ser Gly Ala Leu Thr Ser Gly Val His Thr Phe Pro Ala Val
            180                 185                 190

Leu Gln Ser Ser Gly Leu Tyr Ser Leu Ser Ser Val Val Thr Val Pro
        195                 200                 205

Ser Ser Ser Leu Gly Thr Gln Thr Tyr Ile Cys Asn Val Asn His Lys
    210                 215                 220

Pro Ser Asn Thr Lys Val Asp Lys Arg Val Glu Pro Lys Ser Cys Asp
225                 230                 235                 240

Lys Thr His Thr Cys Pro Pro Cys Pro Ala Pro Glu Ala Ala Gly Gly
                245                 250                 255

Pro Ser Val Phe Leu Phe Pro Pro Lys Pro Lys Asp Thr Leu Met Ile
            260                 265                 270

Ser Arg Thr Pro Glu Val Thr Cys Val Val Val Asp Val Ser His Glu
```

```
                  275                 280                 285
Asp Pro Glu Val Lys Phe Asn Trp Tyr Val Asp Gly Val Glu Val His
        290                 295                 300
Asn Ala Lys Thr Lys Pro Arg Glu Glu Gln Tyr Asn Ser Thr Tyr Arg
305                 310                 315                 320
Val Val Ser Val Leu Thr Val Leu His Gln Asp Trp Leu Asn Gly Lys
                325                 330                 335
Glu Tyr Lys Cys Lys Val Ser Asn Lys Ala Leu Pro Ala Pro Ile Glu
            340                 345                 350
Lys Thr Ile Ser Lys Ala Lys Gly Gln Pro Arg Glu Pro Gln Val Tyr
        355                 360                 365
Thr Leu Pro Pro Ser Arg Glu Glu Met Thr Lys Asn Gln Val Ser Leu
    370                 375                 380
Thr Cys Leu Val Lys Gly Phe Tyr Pro Ser Asp Ile Ala Val Glu Trp
385                 390                 395                 400
Glu Ser Asn Gly Gln Pro Glu Asn Asn Tyr Lys Thr Thr Pro Pro Val
                405                 410                 415
Leu Asp Ser Asp Gly Ser Phe Phe Leu Tyr Ser Lys Leu Thr Val Asp
            420                 425                 430
Lys Ser Arg Trp Gln Gln Gly Asn Val Phe Ser Cys Ser Val Met His
        435                 440                 445
Glu Ala Leu His Asn His Tyr Thr Gln Lys Ser Leu Ser Leu Ser Pro
    450                 455                 460
Gly Lys
465

<210> SEQ ID NO 69
<211> LENGTH: 1401
<212> TYPE: DNA
<213> ORGANISM: artificial
<220> FEATURE:
<223> OTHER INFORMATION: Nucleotide Sequence coding hR198_HG1-LALA

<400> SEQUENCE: 69
atgaaacacc tgtggttctt cctcctgctg gtggcagctc ccagatgggt gctgagccag      60
gtgcagctgg tgcagtctgg cgccgaagtg aagaaaccag gcgccagcgt gaaggtgtcc     120
tgcaaggcct ctggctaccc cgtgaccgcc tactacatca gctgggtcag acaggcccca     180
ggccagggcc tggaatacgt gggctacatc gacatgggca acggccggac cgactacaac     240
gcccggttta agggcagagc cacccctgac gtggacaaga gcaccagcac cgcctacatg     300
gaactgagca gcctgcggag cgaggacacc gccgtgtact actgcgccag agacagcaac     360
tggggcgccg actattgggg ccagggcaca ctcgtgaccg tcagctcagc tccaccaag      420 ggcccaagcg tcttcccccct ggcaccctcc tccaagagca cctctggcgg cacagccgcc     480
ctgggctgcc tggtcaagga ctacttcccc gaacccgtga ccgtgagctg gaactcaggc     540
gccctgacca gcggcgtgca caccttcccc gctgtcctgc agtcctcagg actctactcc     600
ctcagcagcg tggtgaccgt gccctccagc agcttgggca cccagaccta catctgcaac     660
gtgaatcaca agcccagcaa caccaaggtg gacaagagag ttgagcccaa atcttgtgac     720
aaaactcaca catgcccacc ctgcccagca cctgaagccg cggggggacc ctcagtcttc     780
ctcttccccc caaaacccaa ggacaccctc atgatctccc ggacccctga ggtcacatgc     840
gtggtggtgg acgtgagcca cgaagaccct gaggtcaagt tcaactggta cgtggacggc     900
gtggaggtgc ataatgccaa gacaaagccc cgggaggagc agtacaacag cacgtaccgg     960
```

-continued

```
gtggtcagcg tcctcaccgt cctgcaccag gactggctga atggcaagga gtacaagtgc    1020
aaggtctcca acaaagccct cccagccccc atcgagaaaa ccatctccaa agccaaaggc    1080
cagccccggg aaccacaggt gtacaccctg cccccatccc gggaggagat gaccaagaac    1140
caggtcagcc tgacctgcct ggtcaaaggc ttctatccca gcgacatcgc cgtggagtgg    1200
gagagcaatg ccagcccga gaacaactac aagaccaccc ctcccgtgct ggactccgac    1260
ggctccttct tcctctacag caagctcacc gtggacaaga gcaggtggca gcagggcaac    1320
gtcttctcat gctccgtgat gcatgaggct ctgcacaacc actacaccca gaagagcctc    1380
tccctgtctc ccggcaaatg a                                              1401
```

<210> SEQ ID NO 70
<211> LENGTH: 466
<212> TYPE: PRT
<213> ORGANISM: artificial
<220> FEATURE:
<223> OTHER INFORMATION: Amino Acid Sequence of hR198_HG1-LALA

<400> SEQUENCE: 70

```
Met Lys His Leu Trp Phe Phe Leu Leu Leu Val Ala Ala Pro Arg Trp
1               5                   10                  15

Val Leu Ser Gln Val Gln Leu Val Gln Ser Gly Ala Glu Val Lys Lys
            20                  25                  30

Pro Gly Ala Ser Val Lys Val Ser Cys Lys Ala Ser Gly Tyr Pro Val
        35                  40                  45

Thr Ala Tyr Tyr Ile Ser Trp Val Arg Gln Ala Pro Gly Gln Gly Leu
    50                  55                  60

Glu Tyr Val Gly Tyr Ile Asp Met Gly Asn Gly Arg Thr Asp Tyr Asn
65                  70                  75                  80

Ala Arg Phe Lys Gly Arg Ala Thr Leu Thr Val Asp Lys Ser Thr Ser
                85                  90                  95

Thr Ala Tyr Met Glu Leu Ser Ser Leu Arg Ser Glu Asp Thr Ala Val
            100                 105                 110

Tyr Tyr Cys Ala Arg Asp Ser Asn Trp Gly Ala Asp Tyr Trp Gly Gln
        115                 120                 125

Gly Thr Leu Val Thr Val Ser Ser Ala Ser Thr Lys Gly Pro Ser Val
    130                 135                 140

Phe Pro Leu Ala Pro Ser Ser Lys Ser Thr Ser Gly Gly Thr Ala Ala
145                 150                 155                 160

Leu Gly Cys Leu Val Lys Asp Tyr Phe Pro Glu Pro Val Thr Val Ser
                165                 170                 175

Trp Asn Ser Gly Ala Leu Thr Ser Gly Val His Thr Phe Pro Ala Val
            180                 185                 190

Leu Gln Ser Ser Gly Leu Tyr Ser Leu Ser Ser Val Val Thr Val Pro
        195                 200                 205

Ser Ser Ser Leu Gly Thr Gln Thr Tyr Ile Cys Asn Val Asn His Lys
    210                 215                 220

Pro Ser Asn Thr Lys Val Asp Lys Arg Val Glu Pro Lys Ser Cys Asp
225                 230                 235                 240

Lys Thr His Thr Cys Pro Pro Cys Pro Ala Pro Glu Ala Ala Gly Gly
                245                 250                 255

Pro Ser Val Phe Leu Phe Pro Pro Lys Pro Lys Asp Thr Leu Met Ile
            260                 265                 270

Ser Arg Thr Pro Glu Val Thr Cys Val Val Val Asp Val Ser His Glu
```

```
                275                 280                 285
Asp Pro Glu Val Lys Phe Asn Trp Tyr Val Asp Gly Val Glu Val His
    290                 295                 300
Asn Ala Lys Thr Lys Pro Arg Glu Glu Gln Tyr Asn Ser Thr Tyr Arg
305                 310                 315                 320
Val Val Ser Val Leu Thr Val Leu His Gln Asp Trp Leu Asn Gly Lys
                325                 330                 335
Glu Tyr Lys Cys Lys Val Ser Asn Lys Ala Leu Pro Ala Pro Ile Glu
            340                 345                 350
Lys Thr Ile Ser Lys Ala Lys Gly Gln Pro Arg Glu Pro Gln Val Tyr
        355                 360                 365
Thr Leu Pro Pro Ser Arg Glu Glu Met Thr Lys Asn Gln Val Ser Leu
    370                 375                 380
Thr Cys Leu Val Lys Gly Phe Tyr Pro Ser Asp Ile Ala Val Glu Trp
385                 390                 395                 400
Glu Ser Asn Gly Gln Pro Glu Asn Asn Tyr Lys Thr Thr Pro Pro Val
                405                 410                 415
Leu Asp Ser Asp Gly Ser Phe Phe Leu Tyr Ser Lys Leu Thr Val Asp
            420                 425                 430
Lys Ser Arg Trp Gln Gln Gly Asn Val Phe Ser Cys Ser Val Met His
        435                 440                 445
Glu Ala Leu His Asn His Tyr Thr Gln Lys Ser Leu Ser Leu Ser Pro
    450                 455                 460
Gly Lys
465

<210> SEQ ID NO 71
<211> LENGTH: 1118
<212> TYPE: DNA
<213> ORGANISM: artificial
<220> FEATURE:
<223> OTHER INFORMATION: Nucleotide Sequence coding Human Heavy Chain
      Secretory Signal and Human IgG2 Constant Region

<400> SEQUENCE: 71
gcctccggac tctagagcca ccatgaaaca cctgtggttc ttcctcctgc tggtggcagc      60
tcccagatgg gtgctgagcc aggtgcaatt gtgcaggcgg ttagctcagc cagcaccaag     120
ggcccttccg tgttccctct ggccccttgt agccgttcca ccagcgagtc caccgccgcc     180
cttggctgtc tggtgaagga ctacttccct gagcctgtga ccgtgagctg aactccgga     240 gcccttacca gcggcgtgca cacctttccct gccgtgctgc agtccagcgg cctttactcc     300
ctgagctccg tggtgaccgt gcctagctcc aacttcggca cccaaaccta cacctgtaac     360
gtggaccaca gcctagcaa caccaaggtg gacaagaccg tggagcgtaa gtgttgtgtg     420
gagtgtcctc cttgtcctgc ccctcctgtg gccggacctt ccgtgttcct tttccctcct     480
aagcctaagg acaccctgat gatcagccgt acccctgagg tgacctgtgt ggtggtggac     540
gtgtcccacg aggaccctga ggtgcagttc aactggtacg tggacggcgt ggaggtgcac     600
aacgccaaga ccaagcctcg tgaggagcaa ttcaacagca ccttccgtgt ggtgtccgtg     660
cttaccgtgg tgcaccaaga ctggctgaac ggcaaggagt acaagtgtaa ggtgagcaac     720
aagggacttc ctgccccctat cgagaagacc atctccaaga ccaagggcca acctcgtgag     780
cctcaagtgt acacccttcc tcctagccgt gaggagatga ccaagaacca agtgtccctt     840
acctgtctgg tgaagggctt ctaccctagc gacatcgccg tggagtggga gtccaacgga     900
```

```
caacctgaga acaactacaa gaccacccct cctatgcttg acagcgacgg ctccttcttc      960
ctgtacagca agctgaccgt ggacaagtcc cgttggcaac aaggcaacgt gttcagctgt     1020
tccgtgatgc acgaggccct gcacaaccac tacacccaaa agagcctttc cctgagccct     1080
ggaaagtgat atcgggcccg tttaaacggg ggaggcta                             1118
```

<210> SEQ ID NO 72
<211> LENGTH: 1395
<212> TYPE: DNA
<213> ORGANISM: artificial
<220> FEATURE:
<223> OTHER INFORMATION: Nucleotide Sequence coding Heavy Chain of 2C1.1

<400> SEQUENCE: 72

```
atgaaacacc tgtggttctt cctcctgctg gtggcagctc ccagatgggt gctgagccag       60
gtgcagctgc agcagtgggg agccggcctg ctgaagccca gcgagacact gagcctgacc      120
tgcgctgtgt acggaggcag cttcagcggc tactactggt cctggatccg gcagccccct      180
ggcaagggcc tggaatggat cggcgagatc gaccacagcg gcagcaccaa ctacaacccc      240
gccctgaagt cccggctgac catcagcgtg gacaccagca gaaccagtt cagcctgaag       300 ctgagcagcg tgacagccgc cgacaccgcc gtgtactact gtgccagagc cggcagcggc      360
ggctacgagg attggttcga tccttggggc cagggcaccc tggtgaccgt cagctcagcc      420
agcaccaagg gcccttccgt gttccctctg gccccttgta gccgttccac cagcgagtcc      480
accgccgccc ttggctgtct ggtgaaggac tacttccctg agcctgtgac cgtgagctgg      540
aactccggag cccttaccag cggcgtgcac accttccctg ccgtgctgca gtccagcggc      600
ctttactccc tgagctccgt ggtgaccgtg cctagctcca acttcggcac ccaaacctac      660
acctgtaacg tggaccacaa gcctagcaac accaaggtgg acaagaccgt ggagcgtaag      720
tgttgtgtgg agtgtcctcc ttgtcctgcc cctcctgtgg ccggaccttc cgtgttcctt      780
ttccctccta agcctaagga caccctgatg atcagccgta cccctgaggt gacctgtgtg      840
gtggtggacg tgtcccacga ggaccctgag gtgcagttca actggtacgt ggacggcgtg      900
gaggtgcaca cgccaagac caagcctcgt gaggagcaat tcaacagcac cttccgtgtg      960
gtgtccgtgc ttaccgtggt gcaccaagac tggctgaacg gcaaggagta caagtgtaag     1020
gtgagcaaca agggacttcc tgcccctatc gagaagacca tctccaagac caagggccaa     1080
cctcgtgagc ctcaagtgta caccttcct cctagccgtg aggagatgac caagaaccaa     1140
gtgtccctta cctgtctggt gaagggcttc taccctagcg acatcgccgt ggagtgggag     1200
tccaacggac aacctgagaa caactacaag accacccctc ctatgcttga cagcgacggc     1260
tccttcttcc tgtacagcaa gctgaccgtg gacaagtccc gttggcaaca aggcaacgtg     1320
ttcagctgtt ccgtgatgca cgaggccctg cacaaccact acacccaaaa gagcctttcc     1380
ctgagccctg aaag                                                       1395
```

<210> SEQ ID NO 73
<211> LENGTH: 465
<212> TYPE: PRT
<213> ORGANISM: artificial
<220> FEATURE:
<223> OTHER INFORMATION: Amino Acid Sequence of Heavy Chain of 2C1.1

<400> SEQUENCE: 73

Met Lys His Leu Trp Phe Phe Leu Leu Leu Val Ala Ala Pro Arg Trp
1               5                   10                  15

```
Val Leu Ser Gln Val Gln Leu Gln Gln Trp Gly Ala Gly Leu Leu Lys
             20                  25                  30

Pro Ser Glu Thr Leu Ser Leu Thr Cys Ala Val Tyr Gly Gly Ser Phe
         35                  40                  45

Ser Gly Tyr Tyr Trp Ser Trp Ile Arg Gln Pro Pro Gly Lys Gly Leu
 50                  55                  60

Glu Trp Ile Gly Glu Ile Asp His Ser Gly Ser Thr Asn Tyr Asn Pro
 65                  70                  75                  80

Ala Leu Lys Ser Arg Leu Thr Ile Ser Val Asp Thr Ser Lys Asn Gln
                 85                  90                  95

Phe Ser Leu Lys Leu Ser Ser Val Thr Ala Ala Asp Thr Ala Val Tyr
             100                 105                 110

Tyr Cys Ala Arg Ala Gly Ser Gly Gly Tyr Glu Asp Trp Phe Asp Pro
         115                 120                 125

Trp Gly Gln Gly Thr Leu Val Thr Val Ser Ser Ala Ser Thr Lys Gly
130                 135                 140

Pro Ser Val Phe Pro Leu Ala Pro Cys Ser Arg Ser Thr Ser Glu Ser
145                 150                 155                 160

Thr Ala Ala Leu Gly Cys Leu Val Lys Asp Tyr Phe Pro Glu Pro Val
                165                 170                 175

Thr Val Ser Trp Asn Ser Gly Ala Leu Thr Ser Gly Val His Thr Phe
            180                 185                 190

Pro Ala Val Leu Gln Ser Ser Gly Leu Tyr Ser Leu Ser Ser Val Val
        195                 200                 205

Thr Val Pro Ser Ser Asn Phe Gly Thr Gln Thr Tyr Thr Cys Asn Val
210                 215                 220

Asp His Lys Pro Ser Asn Thr Lys Val Asp Lys Thr Val Glu Arg Lys
225                 230                 235                 240

Cys Cys Val Glu Cys Pro Pro Cys Pro Ala Pro Pro Val Ala Gly Pro
                245                 250                 255

Ser Val Phe Leu Phe Pro Pro Lys Pro Lys Asp Thr Leu Met Ile Ser
            260                 265                 270

Arg Thr Pro Glu Val Thr Cys Val Val Val Asp Val Ser His Glu Asp
        275                 280                 285

Pro Glu Val Gln Phe Asn Trp Tyr Val Asp Gly Val Glu Val His Asn
290                 295                 300

Ala Lys Thr Lys Pro Arg Glu Glu Gln Phe Asn Ser Thr Phe Arg Val
305                 310                 315                 320

Val Ser Val Leu Thr Val Val His Gln Asp Trp Leu Asn Gly Lys Glu
                325                 330                 335

Tyr Lys Cys Lys Val Ser Asn Lys Gly Leu Pro Ala Pro Ile Glu Lys
            340                 345                 350

Thr Ile Ser Lys Thr Lys Gly Gln Pro Arg Glu Pro Gln Val Tyr Thr
        355                 360                 365

Leu Pro Pro Ser Arg Glu Glu Met Thr Lys Asn Gln Val Ser Leu Thr
370                 375                 380

Cys Leu Val Lys Gly Phe Tyr Pro Ser Asp Ile Ala Val Glu Trp Glu
385                 390                 395                 400

Ser Asn Gly Gln Pro Glu Asn Asn Tyr Lys Thr Thr Pro Pro Met Leu
                405                 410                 415

Asp Ser Asp Gly Ser Phe Phe Leu Tyr Ser Lys Leu Thr Val Asp Lys
            420                 425                 430

Ser Arg Trp Gln Gln Gly Asn Val Phe Ser Cys Ser Val Met His Glu
```

435                 440                 445
Ala Leu His Asn His Tyr Thr Gln Lys Ser Leu Ser Leu Ser Pro Gly
         450                 455                 460

Lys
465

<210> SEQ ID NO 74
<211> LENGTH: 739
<212> TYPE: DNA
<213> ORGANISM: artificial
<220> FEATURE:
<223> OTHER INFORMATION: Nucleotide Sequence coding Light Chain of 2C1.1

<400> SEQUENCE: 74

```
atggtgctgc agacccaggt gttcatctcc ctgctgctgt ggatctccgg cgcgtacggc      60
cagtccgtgc tgacccagcc tccttccgtg tctggcgccc tggccagag agtgaccatc     120
agctgtaccg gcagcagcag caacatcgga gccggctaca acgtgcactg gtatcagcag    180
ttcccccgga ccgaccccaa gctgctgatc tacgtgtaca acatccggcc cagcggcgtg    240
cccgaccggt tttctggcag cagaagcggc acaagcgcca gcctggccat caccggcctg    300
cagaccgagg acgaggccga ctactactgc cagagctacg acagcagcct gagcggcgtg    360
gtgttcggcg aggcaccaa gctgacagtg ctgggccagc ccaaggccaa ccccaccgtg    420
accctgttcc ccccaagcag cgaggaactg caggccaaca aggccaccct ggtgtgcctg    480
atcagcgact tctaccctgg cgccgtgaca gtggcctgga aggccgatgg atctcccgtg    540
aaggccggcg tggaaaccac caagcccagc aagcagagca caacaaata cgccgccagc    600
agctacctga gcctgacccc cgagcagtgg aagtcccacc ggtcctacag ctgccaggtg    660
acacacgagg gcagcaccgt ggaaaagacc gtggccccca ccgagtgcag ctaggggccc    720
gtttaaacgg gggaggcta                                                 739
```

<210> SEQ ID NO 75
<211> LENGTH: 237
<212> TYPE: PRT
<213> ORGANISM: artificial
<220> FEATURE:
<223> OTHER INFORMATION: Amino Acid Sequence of Light Chain of 2C1.1

<400> SEQUENCE: 75

Met Val Leu Gln Thr Gln Val Phe Ile Ser Leu Leu Trp Ile Ser
1               5                   10                  15

Gly Ala Tyr Gly Gln Ser Val Leu Thr Gln Pro Pro Ser Val Ser Gly
            20                  25                  30

Ala Pro Gly Gln Arg Val Thr Ile Ser Cys Thr Gly Ser Ser Ser Asn
        35                  40                  45

Ile Gly Ala Gly Tyr Asn Val His Trp Tyr Gln Gln Phe Pro Arg Thr
    50                  55                  60

Asp Pro Lys Leu Leu Ile Tyr Val Tyr Asn Ile Arg Pro Ser Gly Val
65                  70                  75                  80

Pro Asp Arg Phe Ser Gly Ser Arg Ser Gly Thr Ser Ala Ser Leu Ala
                85                  90                  95

Ile Thr Gly Leu Gln Thr Glu Asp Glu Ala Asp Tyr Tyr Cys Gln Ser
            100                 105                 110

Tyr Asp Ser Ser Leu Ser Gly Val Val Phe Gly Gly Gly Thr Lys Leu
        115                 120                 125

Thr Val Leu Gly Gln Pro Lys Ala Asn Pro Thr Val Thr Leu Phe Pro

```
            130              135              140
Pro Ser Ser Glu Glu Leu Gln Ala Asn Lys Ala Thr Leu Val Cys Leu
145                 150                 155                 160

Ile Ser Asp Phe Tyr Pro Gly Ala Val Thr Val Ala Trp Lys Ala Asp
                165                 170                 175

Gly Ser Pro Val Lys Ala Gly Val Glu Thr Thr Lys Pro Ser Lys Gln
                180                 185                 190

Ser Asn Asn Lys Tyr Ala Ala Ser Ser Tyr Leu Ser Leu Thr Pro Glu
            195                 200                 205

Gln Trp Lys Ser His Arg Ser Tyr Ser Cys Gln Val Thr His Glu Gly
        210                 215                 220

Ser Thr Val Glu Lys Thr Val Ala Pro Thr Glu Cys Ser
225                 230                 235

<210> SEQ ID NO 76
<211> LENGTH: 1395
<212> TYPE: DNA
<213> ORGANISM: artificial
<220> FEATURE:
<223> OTHER INFORMATION: Nucleotide Sequence coding Heavy Chain of 5H3.1

<400> SEQUENCE: 76
atgaaacacc tgtggttctt cctcctgctg gtggcagctc ccagatgggt gctgagccag      60
gtgcagctgg tgcagtctgg cgccgaagtg aagaaacctg gcgctagcgt gaaggtgtcc     120
tgcaaggcca gcggctacac cttcaccgac tactacatga actgggtgcg ccaggctcca     180
ggacagggcc tggaatggat gggctggatc aaccccaaca gcggcggcac caaatacgcc     240
cagaaattcc agggcagagt gaccatgacc cgggacacca gcatccggac cgcctacatg     300
gaactgagcc ggctgagaag cgacgacacc gccgtgtact actgcgccag agagtacggc     360
ggcaacagcg attggttcga ccctggggc cagggcaccc tggtgaccgt cagctcagcc     420
agcaccaagg gcccttccgt gttccctctg cccccttgta gccgttccac cagcgagtcc     480
accgccgccc ttggctgtct ggtgaaggac tacttccctg agcctgtgac cgtgagctgg     540
aactccggag cccttaccag cggcgtgcac accttccctg ccgtgctgca gtccagcggc     600
ctttactccc tgagctccgt ggtgaccgtg cctagctcca acttcggcac ccaaacctac     660
acctgtaacg tggaccacaa gcctagcaac accaaggtgg acaagaccgt ggagcgtaag     720
tgttgtgtgg agtgtcctcc ttgtcctgcc cctcctgtgg ccggaccttc cgtgttcctt     780
ttccctccta gcctaagga caccctgatg atcagccgta cccctgaggt gacctgtgtg     840
gtggtggacg tgtcccacga ggaccctgag gtgcagttca ctggtacgt ggacggcgtg     900 gaggtgcaca cgccaagac caagcctcgt gaggagcaat tcaacagcac cttccgtgtg     960
gtgtccgtgc ttaccgtggt gcaccaagac tggctgaacg gcaaggagta caagtgtaag    1020
gtgagcaaca aggacttcc tgcccctatc gagaagacca tctccaagac caagggccaa    1080
cctcgtgagc tcaagtgtta caccttcct cctagccgtg aggagatgac caagaaccaa    1140
gtgtccctta cctgtctggt gaagggcttc taccctagcg acatcgccgt ggagtgggag    1200
tccaacggac aacctgagaa caactacaag accaccctc ctatgcttga cagcgacggc    1260
tccttcttcc tgtacagcaa gctgaccgtg gacaagtccc gttggcaaca aggcaacgtg    1320
ttcagctgtt ccgtgatgca cgaggccctg cacaaccact acacccaaaa gagcctttcc    1380
ctgagccctg gaaag                                                     1395
```

-continued

```
<210> SEQ ID NO 77
<211> LENGTH: 465
<212> TYPE: PRT
<213> ORGANISM: artificial
<220> FEATURE:
<223> OTHER INFORMATION: Amino Acid Sequence of Heavy Chain of 5H3.1

<400> SEQUENCE: 77

Met Lys His Leu Trp Phe Phe Leu Leu Leu Val Ala Ala Pro Arg Trp
1               5                   10                  15

Val Leu Ser Gln Val Gln Leu Val Gln Ser Gly Ala Glu Val Lys Lys
            20                  25                  30

Pro Gly Ala Ser Val Lys Val Ser Cys Lys Ala Ser Gly Tyr Thr Phe
        35                  40                  45

Thr Asp Tyr Tyr Met Asn Trp Val Arg Gln Ala Pro Gly Gln Gly Leu
    50                  55                  60

Glu Trp Met Gly Trp Ile Asn Pro Asn Ser Gly Gly Thr Lys Tyr Ala
65                  70                  75                  80

Gln Lys Phe Gln Gly Arg Val Thr Met Thr Arg Asp Thr Ser Ile Arg
                85                  90                  95

Thr Ala Tyr Met Glu Leu Ser Arg Leu Arg Ser Asp Asp Thr Ala Val
            100                 105                 110

Tyr Tyr Cys Ala Arg Glu Tyr Gly Gly Asn Ser Asp Trp Phe Asp Pro
        115                 120                 125

Trp Gly Gln Gly Thr Leu Val Thr Val Ser Ser Ala Ser Thr Lys Gly
    130                 135                 140

Pro Ser Val Phe Pro Leu Ala Pro Cys Ser Arg Ser Thr Ser Glu Ser
145                 150                 155                 160

Thr Ala Ala Leu Gly Cys Leu Val Lys Asp Tyr Phe Pro Glu Pro Val
                165                 170                 175

Thr Val Ser Trp Asn Ser Gly Ala Leu Thr Ser Gly Val His Thr Phe
            180                 185                 190

Pro Ala Val Leu Gln Ser Ser Gly Leu Tyr Ser Leu Ser Ser Val Val
        195                 200                 205

Thr Val Pro Ser Ser Asn Phe Gly Thr Gln Thr Tyr Thr Cys Asn Val
    210                 215                 220

Asp His Lys Pro Ser Asn Thr Lys Val Asp Lys Thr Val Glu Arg Lys
225                 230                 235                 240

Cys Cys Val Glu Cys Pro Pro Cys Pro Ala Pro Pro Val Ala Gly Pro
                245                 250                 255

Ser Val Phe Leu Phe Pro Pro Lys Pro Lys Asp Thr Leu Met Ile Ser
            260                 265                 270

Arg Thr Pro Glu Val Thr Cys Val Val Val Asp Val Ser His Glu Asp
        275                 280                 285

Pro Glu Val Gln Phe Asn Trp Tyr Val Asp Gly Val Glu Val His Asn
    290                 295                 300

Ala Lys Thr Lys Pro Arg Glu Glu Gln Phe Asn Ser Thr Phe Arg Val
305                 310                 315                 320

Val Ser Val Leu Thr Val Val His Gln Asp Trp Leu Asn Gly Lys Glu
                325                 330                 335

Tyr Lys Cys Lys Val Ser Asn Lys Gly Leu Pro Ala Pro Ile Glu Lys
            340                 345                 350

Thr Ile Ser Lys Thr Lys Gly Gln Pro Arg Glu Pro Gln Val Tyr Thr
        355                 360                 365

Leu Pro Pro Ser Arg Glu Glu Met Thr Lys Asn Gln Val Ser Leu Thr
```

```
                370             375             380
Cys Leu Val Lys Gly Phe Tyr Pro Ser Asp Ile Ala Val Glu Trp Glu
385             390             395             400

Ser Asn Gly Gln Pro Glu Asn Asn Tyr Lys Thr Thr Pro Pro Met Leu
            405             410             415

Asp Ser Asp Gly Ser Phe Phe Leu Tyr Ser Lys Leu Thr Val Asp Lys
            420             425             430

Ser Arg Trp Gln Gln Gly Asn Val Phe Ser Cys Ser Val Met His Glu
            435             440             445

Ala Leu His Asn His Tyr Thr Gln Lys Ser Leu Ser Leu Ser Pro Gly
        450             455             460

Lys
465

<210> SEQ ID NO 78
<211> LENGTH: 742
<212> TYPE: DNA
<213> ORGANISM: artificial
<220> FEATURE:
<223> OTHER INFORMATION: Nucleotide Sequence coding Light Chain of 5H3.1

<400> SEQUENCE: 78
atggtgctgc agacccaggt gttcatctcc ctgctgctgt ggatctccgg cgcgtacggc      60
cagtccgtgc tgacccagcc tccttccgtg tctggcgccc tggccagag agtgaccatc     120 agctgtaccg gcagcagcag caacatcgga gctggatacg acgtgcactg gtatcagcag     180
ctgcccggca cgcccccaa gctgctgatc tacggcaaca gcaaccggcc cagcggcgtg     240
cccgatagat tcagcggcag caagagcggc accagcgcca gcctggccat taccggactg     300
caggccgagg acgaggccga ctactactgc cagagctacg acaaccggct gagcgacagc     360
gtggtgatcg gcggaggcac caagctggcc gtgcagggac agcccaaggc caaccccacc     420
gtgaccctgt tccccccaag cagcgaggaa ctgcaggcca caaggccac cctggtgtgc     480 ctgatcagcg acttctaccc tggcgccgtg acagtggcct ggaaggccga tggatctccc     540
gtgaaggccg gcgtggaaac caccaagccc agcaagcaga gcaacaacaa atacgccgcc     600
agcagctacc tgagcctgac ccccgagcag tggaagtccc accggtccta cagctgccag     660
gtgacacacg agggcagcac cgtggaaaag accgtggccc ccaccgagtg cagctagggg     720
cccgtttaaa cgggggaggc ta                                              742

<210> SEQ ID NO 79
<211> LENGTH: 238
<212> TYPE: PRT
<213> ORGANISM: artificial
<220> FEATURE:
<223> OTHER INFORMATION: Amino Acid Sequence of Light Chain of 5H3.1

<400> SEQUENCE: 79

Met Val Leu Gln Thr Gln Val Phe Ile Ser Leu Leu Leu Trp Ile Ser
1               5                   10                  15

Gly Ala Tyr Gly Gln Ser Val Leu Thr Gln Pro Pro Ser Val Ser Gly
            20                  25                  30

Ala Pro Gly Gln Arg Val Thr Ile Ser Cys Thr Gly Ser Ser Ser Asn
        35                  40                  45

Ile Gly Ala Gly Tyr Asp Val His Trp Tyr Gln Gln Leu Pro Gly Thr
    50                  55                  60

Ala Pro Lys Leu Leu Ile Tyr Gly Asn Ser Asn Arg Pro Ser Gly Val
```

|    |    |    | 65 |    |    |    | 70 |    |    |    | 75 |    |    |    | 80 |
|----|----|----|----|----|----|----|----|----|----|----|----|----|----|----|----|

Pro Asp Arg Phe Ser Gly Ser Lys Ser Gly Thr Ser Ala Ser Leu Ala
                    85                  90                  95

Ile Thr Gly Leu Gln Ala Glu Asp Glu Ala Asp Tyr Tyr Cys Gln Ser
            100                 105                 110

Tyr Asp Asn Arg Leu Ser Asp Ser Val Val Ile Gly Gly Thr Lys
        115                 120                 125

Leu Ala Val Gln Gly Gln Pro Lys Ala Asn Pro Thr Val Thr Leu Phe
    130                 135                 140

Pro Pro Ser Ser Glu Glu Leu Gln Ala Asn Lys Ala Thr Leu Val Cys
145                 150                 155                 160

Leu Ile Ser Asp Phe Tyr Pro Gly Ala Val Thr Val Ala Trp Lys Ala
                165                 170                 175

Asp Gly Ser Pro Val Lys Ala Gly Val Glu Thr Thr Lys Pro Ser Lys
            180                 185                 190

Gln Ser Asn Asn Lys Tyr Ala Ala Ser Ser Tyr Leu Ser Leu Thr Pro
        195                 200                 205

Glu Gln Trp Lys Ser His Arg Ser Tyr Ser Cys Gln Val Thr His Glu
    210                 215                 220

Gly Ser Thr Val Glu Lys Thr Val Ala Pro Thr Glu Cys Ser
225                 230                 235

<210> SEQ ID NO 80
<211> LENGTH: 1433
<212> TYPE: DNA
<213> ORGANISM: artificial
<220> FEATURE:
<223> OTHER INFORMATION: Nucleotide Sequence coding Heavy Chain of 10F8

<400> SEQUENCE: 80
ccagcctccg gactctagag ccaccatgaa gcacctgtgg ttctttctgc tgctggtggc     60
cgctcccaga tgggtgctgt ctcaggtgca gctgcagcag tctggcgccg aactcgtgcg    120
gcctggaagc agcgtgaaga tcagctgcaa ggccagcggc tacgccttcc ggtcctactg    180
gatgaactgg gtcaagcaga ggccaggcca gggcctggaa tggatcggcc acatctatcc    240
cggcgacggc gacaccaact acaacggcaa gttcaagggc aaggccaccc tgaccgccga    300
caagagcagc agcacagcct acatgcagct gtccagcctg accagcgagg acagcgccgt    360
gtacctgtgt ggcagaggcg gcacaaccgt ggtggtggat tattgggggcc agggcaccac    420 actgaccgtg tccagcgcca agaccacccc cccatctgtg tatcctctgg cccctggatc    480
tgccgcccag accaacagca tggtcaccct gggctgcctc gtgaagggct acttccctga    540
gcctgtgacc gtgacctgga acagcggctc tctgtctagc ggcgtgcaca ccttcccagc    600
cgtgctgcag agcgacctgt acaccctgag cagctccgtg accgtgccta gcagcacctg    660
gcctagcgag acagtgacct gcaacgtggc ccaccctgcc agctctacca aggtggacaa    720
gaaaatcgtg ccccgggact gcggctgcaa gccctgtatc tgtaccgtgc ccgaggtgtc    780
ctccgtgttc atcttcccac ccaagcccaa ggacgtgctg accatcaccc tgacacccaa    840
agtgacatgt gtggtggtgg acatcagcaa ggacgacccc gaggtgcagt tcagttggtt    900
cgtggacgac gtggaagtgc acacagccca gacccagccc agagaggaac agttcaacag    960
caccttcaga agcgtgtccg agctgcccat catgcaccag gactggctga acggcaaaga   1020
attcaagtgc agagtgaaca cgccgccctt ccctgcccc atcgagaaaa ccatctccaa   1080
gaccaagggc agacccaagg ccccccaggt gtacacaatc cccccaccca agaacagat   1140

-continued

```
ggccaaggac aaggtgtccc tgacctgcat gatcaccgat ttcttcccag aggacatcac    1200
cgtggaatgg cagtggaacg gccagcccgc cgagaactac aagaacaccc agcctatcat    1260
ggacaccgac ggcagctact tcgtgtacag caagctgaac gtgcagaagt ccaactggga    1320
ggccggcaac accttcacct gtagcgtgct gacgagggc ctgcacaatc accaccga     1380 gaagtccctg tcccacagcc ccggcaaatg agtttaaacg ggggaggcta act         1433
```

<210> SEQ ID NO 81
<211> LENGTH: 461
<212> TYPE: PRT
<213> ORGANISM: artificial
<220> FEATURE:
<223> OTHER INFORMATION: Amino Acid Sequence of Heavy Chain of 10F8

<400> SEQUENCE: 81

```
Met Lys His Leu Trp Phe Phe Leu Leu Leu Val Ala Ala Pro Arg Trp
1               5                   10                  15

Val Leu Ser Gln Val Gln Leu Gln Gln Ser Gly Ala Glu Leu Val Arg
            20                  25                  30

Pro Gly Ser Ser Val Lys Ile Ser Cys Lys Ala Ser Gly Tyr Ala Phe
        35                  40                  45

Arg Ser Tyr Trp Met Asn Trp Val Lys Gln Arg Pro Gly Gln Gly Leu
    50                  55                  60

Glu Trp Ile Gly His Ile Tyr Pro Gly Asp Gly Asp Thr Asn Tyr Asn
65                  70                  75                  80

Gly Lys Phe Lys Gly Lys Ala Thr Leu Thr Ala Asp Lys Ser Ser Ser
                85                  90                  95

Thr Ala Tyr Met Gln Leu Ser Ser Leu Thr Ser Glu Asp Ser Ala Val
            100                 105                 110

Tyr Leu Cys Gly Arg Gly Gly Thr Val Val Asp Tyr Trp Gly
        115                 120                 125

Gln Gly Thr Thr Leu Thr Val Ser Ser Ala Lys Thr Thr Pro Pro Ser
    130                 135                 140

Val Tyr Pro Leu Ala Pro Gly Ser Ala Ala Gln Thr Asn Ser Met Val
145                 150                 155                 160

Thr Leu Gly Cys Leu Val Lys Gly Tyr Phe Pro Glu Pro Val Thr Val
                165                 170                 175

Thr Trp Asn Ser Gly Ser Leu Ser Ser Gly Val His Thr Phe Pro Ala
            180                 185                 190

Val Leu Gln Ser Asp Leu Tyr Thr Leu Ser Ser Ser Val Thr Val Pro
        195                 200                 205

Ser Ser Thr Trp Pro Ser Glu Thr Val Thr Cys Asn Val Ala His Pro
    210                 215                 220

Ala Ser Ser Thr Lys Val Asp Lys Lys Ile Val Pro Arg Asp Cys Gly
225                 230                 235                 240

Cys Lys Pro Cys Ile Cys Thr Val Pro Glu Val Ser Ser Val Phe Ile
                245                 250                 255

Phe Pro Pro Lys Pro Lys Asp Val Leu Thr Ile Thr Leu Thr Pro Lys
            260                 265                 270

Val Thr Cys Val Val Asp Ile Ser Lys Asp Asp Pro Glu Val Gln
        275                 280                 285

Phe Ser Trp Phe Val Asp Asp Val Glu Val His Thr Ala Gln Thr Gln
    290                 295                 300

Pro Arg Glu Glu Gln Phe Asn Ser Thr Phe Arg Ser Val Ser Glu Leu
```

```
                305                 310                 315                 320
Pro Ile Met His Gln Asp Trp Leu Asn Gly Lys Glu Phe Lys Cys Arg
                    325                 330                 335

Val Asn Ser Ala Ala Phe Pro Ala Pro Ile Glu Lys Thr Ile Ser Lys
                340                 345                 350

Thr Lys Gly Arg Pro Lys Ala Pro Gln Val Tyr Thr Ile Pro Pro Pro
                355                 360                 365

Lys Glu Gln Met Ala Lys Asp Lys Val Ser Leu Thr Cys Met Ile Thr
    370                 375                 380

Asp Phe Phe Pro Glu Asp Ile Thr Val Glu Trp Gln Trp Asn Gly Gln
385                 390                 395                 400

Pro Ala Glu Asn Tyr Lys Asn Thr Gln Pro Ile Met Asp Thr Asp Gly
                405                 410                 415

Ser Tyr Phe Val Tyr Ser Lys Leu Asn Val Gln Lys Ser Asn Trp Glu
                420                 425                 430

Ala Gly Asn Thr Phe Thr Cys Ser Val Leu His Glu Gly Leu His Asn
                435                 440                 445

His His Thr Glu Lys Ser Leu Ser His Ser Pro Gly Lys
    450                 455                 460

<210> SEQ ID NO 82
<211> LENGTH: 770
<212> TYPE: DNA
<213> ORGANISM: artificial
<220> FEATURE:
<223> OTHER INFORMATION: Nucleotide Sequence coding Light Chain of 10F8

<400> SEQUENCE: 82
ccagcctccg gactctagag ccaccatggt gctgcagacc caggtgttca tcagcctgct      60
gctgtggatc agcggcgcct acggcgacat cgtgatgagc cagagcccta gcagcctggc     120
cgtgtctgcc ggcgagaaag tgaccatgag ctgcaagagc agccagtccc tgctgaacag     180
ccggacccgg aagaactacc tggcctggta tcagcagaag cccggccagt cccccaagct     240
gctgatctac tgggccagca ccagagaaag cggcgtgccc gatagattca ccggcagcgg     300
ctctggcacc gacttcaccc tgacaatcag cagcgtgcag gccgaggacc tggctgtgta     360
ctactgcaag cagagctaca acctgccctg gaccttcggc ggaggcacca agctggaaat     420
caagagagcc gacgccgctc ccaccgtgtc catctttcca cctagcagcg agcagctgac     480
cagcggcgga gctagcgtcg tgtgcttcct gaacaacttc taccccaagg acatcaacgt     540
gaagtggaag atcgacggca cgagcggca gaacggcgtg ctgaatagct ggaccgacca     600
ggacagcaag gactccacct acagcatgtc cagcaccctg accctgacca aggacgagta     660
cgagcggcac aacagctaca catgcgaggc cacccacaag accagcacct cccccatcgt     720
gaagtccttc aaccggaacg agtgctgagt ttaaacgggg aggctaact                 770

<210> SEQ ID NO 83
<211> LENGTH: 240
<212> TYPE: PRT
<213> ORGANISM: artificial
<220> FEATURE:
<223> OTHER INFORMATION: Amino Acid Sequence of Light Chain of 10F8

<400> SEQUENCE: 83

Met Val Leu Gln Thr Gln Val Phe Ile Ser Leu Leu Leu Trp Ile Ser
1               5                   10                  15

Gly Ala Tyr Gly Asp Ile Val Met Ser Gln Ser Pro Ser Ser Leu Ala
```

```
                    20                  25                  30
Val Ser Ala Gly Glu Lys Val Thr Met Ser Cys Lys Ser Gln Ser
        35                  40                  45

Leu Leu Asn Ser Arg Thr Arg Lys Asn Tyr Leu Ala Trp Tyr Gln Gln
    50                  55                  60

Lys Pro Gly Gln Ser Pro Lys Leu Leu Ile Tyr Trp Ala Ser Thr Arg
65                  70                  75                  80

Glu Ser Gly Val Pro Asp Arg Phe Thr Gly Ser Gly Ser Gly Thr Asp
                85                  90                  95

Phe Thr Leu Thr Ile Ser Ser Val Gln Ala Glu Asp Leu Ala Val Tyr
            100                 105                 110

Tyr Cys Lys Gln Ser Tyr Asn Leu Pro Trp Thr Phe Gly Gly Gly Thr
        115                 120                 125

Lys Leu Glu Ile Lys Arg Ala Asp Ala Ala Pro Thr Val Ser Ile Phe
130                 135                 140

Pro Pro Ser Ser Glu Gln Leu Thr Ser Gly Gly Ala Ser Val Val Cys
145                 150                 155                 160

Phe Leu Asn Asn Phe Tyr Pro Lys Asp Ile Asn Val Lys Trp Lys Ile
                165                 170                 175

Asp Gly Ser Glu Arg Gln Asn Gly Val Leu Asn Ser Trp Thr Asp Gln
            180                 185                 190

Asp Ser Lys Asp Ser Thr Tyr Ser Met Ser Ser Thr Leu Thr Leu Thr
        195                 200                 205

Lys Asp Glu Tyr Glu Arg His Asn Ser Tyr Thr Cys Glu Ala Thr His
    210                 215                 220

Lys Thr Ser Thr Ser Pro Ile Val Lys Ser Phe Asn Arg Asn Glu Cys
225                 230                 235                 240

<210> SEQ ID NO 84
<211> LENGTH: 1436
<212> TYPE: DNA
<213> ORGANISM: artificial
<220> FEATURE:
<223> OTHER INFORMATION: Nucleotide Sequence coding Heavy Chain of 14F74

<400> SEQUENCE: 84
ccagcctccg gactctagag ccaccatgaa gcacctgtgg ttctttctgc tgctggtggc      60
cgctcccaga tgggtgctgt ctcaggtgca gctgcagcag tctggcgccg aactcgtgcg     120
gcctggaagc agcgtgaaga tcagctgcaa ggccagcggc tacgccttca gcagctactg     180
gatgaactgg gtcaagcagc ggccaggcca gggcctggaa tggatcggcc atatctatcc     240
cggcgacggc gacaccaact acaacggcaa gttcaagggc aaggccaccc tgaccgccga     300
caagagcagc agcacagcct acatgcagct gagcggcctg accagcgagg acagcgccgt     360
gtacttctgc gccagaagcg gcagactgag attcgccatg gactactggg gccagggcac     420
cagcgtgaca gtgtctagcg ccaagaccac ccccccagc gtgtaccctc tggctcctgg     480
atctgccgcc cagaccaaca gcatggtcac cctgggctgc ctcgtgaagg ctacttccc     540 tgagcctgtg accgtgacct ggaacagcgg ctctctgtct agcggcgtgc acacctttcc     600
agccgtgctg cagagcgacc tgtacaccct gagcagctcc gtgaccgtgc ctagcagcac     660
ctggcctagc gagacagtga cctgcaacgt ggcccaccct gccagctcta ccaaggtgga     720
caagaaaatc gtgccccggg actgcggctg caagccctgt atctgtaccg tgcccgaggt     780
gtccagcgtg ttcatcttcc cacccaagcc caaggacgtg ctgaccatca ccctgacacc     840
```

```
caaagtgacc tgtgtggtgg tggacatcag caaggacgac cccgaggtgc agttcagttg    900
gttcgtggac gacgtggaag tgcacacagc ccagacccag cccagagagg aacagttcaa    960
cagcaccttc agaagcgtgt ccgagctgcc catcatgcac caggactggc tgaacggcaa   1020
agaattcaag tgcagagtga acagcgccgc cttccctgcc cccatcgaga aaaccatctc   1080
caagaccaag ggcagaccca aggcccctca ggtgtacaca atccccccac ccaaagaaca   1140
gatggccaag gacaaggtgt ccctgacctg catgatcacc gatttcttcc cagaggacat   1200
caccgtggaa tggcagtgga acggccagcc cgccgagaac tacaagaaca cccagcctat   1260
catggacacc gacggcagct acttcgtgta cagcaagctg aacgtgcaga gtccaactg    1320 ggaggccggc aacaccttca cctgtagcgt gctgcacgag ggcctgcaca atcaccacac   1380
cgagaagtcc ctgtcccaca gccccggcaa atgagtttaa acggggagg ctaact        1436
```

<210> SEQ ID NO 85
<211> LENGTH: 462
<212> TYPE: PRT
<213> ORGANISM: artificial
<220> FEATURE:
<223> OTHER INFORMATION: Amino Acid Sequence of Heavy Chain of 14F74

<400> SEQUENCE: 85

```
Met Lys His Leu Trp Phe Phe Leu Leu Leu Val Ala Ala Pro Arg Trp
1               5                   10                  15

Val Leu Ser Gln Val Gln Leu Gln Gln Ser Gly Ala Glu Leu Val Arg
            20                  25                  30

Pro Gly Ser Ser Val Lys Ile Ser Cys Lys Ala Ser Gly Tyr Ala Phe
        35                  40                  45

Ser Ser Tyr Trp Met Asn Trp Val Lys Gln Arg Pro Gly Gln Gly Leu
    50                  55                  60

Glu Trp Ile Gly His Ile Tyr Pro Gly Asp Gly Asp Thr Asn Tyr Asn
65                  70                  75                  80

Gly Lys Phe Lys Gly Lys Ala Thr Leu Thr Ala Asp Lys Ser Ser Ser
                85                  90                  95

Thr Ala Tyr Met Gln Leu Ser Gly Leu Thr Ser Glu Asp Ser Ala Val
            100                 105                 110

Tyr Phe Cys Ala Arg Ser Gly Arg Leu Arg Phe Ala Met Asp Tyr Trp
        115                 120                 125

Gly Gln Gly Thr Ser Val Thr Val Ser Ser Ala Lys Thr Thr Pro Pro
    130                 135                 140

Ser Val Tyr Pro Leu Ala Pro Gly Ser Ala Ala Gln Thr Asn Ser Met
145                 150                 155                 160

Val Thr Leu Gly Cys Leu Val Lys Gly Tyr Phe Pro Glu Pro Val Thr
                165                 170                 175

Val Thr Trp Asn Ser Gly Ser Leu Ser Ser Gly Val His Thr Phe Pro
            180                 185                 190

Ala Val Leu Gln Ser Asp Leu Tyr Thr Leu Ser Ser Ser Val Thr Val
        195                 200                 205

Pro Ser Ser Thr Trp Pro Ser Glu Thr Val Thr Cys Asn Val Ala His
    210                 215                 220

Pro Ala Ser Ser Thr Lys Val Asp Lys Lys Ile Val Pro Arg Asp Cys
225                 230                 235                 240

Gly Cys Lys Pro Cys Ile Cys Thr Val Pro Glu Val Ser Ser Val Phe
                245                 250                 255

Ile Phe Pro Pro Lys Pro Lys Asp Val Leu Thr Ile Thr Leu Thr Pro
```

|       |       |       | 260   |       |       |       | 265   |       |       |       | 270   |       |
|-------|-------|-------|-------|-------|-------|-------|-------|-------|-------|-------|-------|-------|

Lys Val Thr Cys Val Val Asp Ile Ser Lys Asp Pro Glu Val
            275                 280                 285

Gln Phe Ser Trp Phe Val Asp Asp Val Glu Val His Thr Ala Gln Thr
        290                 295                 300

Gln Pro Arg Glu Glu Gln Phe Asn Ser Thr Phe Arg Ser Val Ser Glu
305                 310                 315                 320

Leu Pro Ile Met His Gln Asp Trp Leu Asn Gly Lys Glu Phe Lys Cys
                325                 330                 335

Arg Val Asn Ser Ala Ala Phe Pro Ala Pro Ile Glu Lys Thr Ile Ser
                340                 345                 350

Lys Thr Lys Gly Arg Pro Lys Ala Pro Gln Val Tyr Thr Ile Pro Pro
            355                 360                 365

Pro Lys Glu Gln Met Ala Lys Asp Lys Val Ser Leu Thr Cys Met Ile
        370                 375                 380

Thr Asp Phe Phe Pro Glu Asp Ile Thr Val Glu Trp Gln Trp Asn Gly
385                 390                 395                 400

Gln Pro Ala Glu Asn Tyr Lys Asn Thr Gln Pro Ile Met Asp Thr Asp
                405                 410                 415

Gly Ser Tyr Phe Val Tyr Ser Lys Leu Asn Val Gln Lys Ser Asn Trp
                420                 425                 430

Glu Ala Gly Asn Thr Phe Thr Cys Ser Val Leu His Glu Gly Leu His
            435                 440                 445

Asn His His Thr Glu Lys Ser Leu Ser His Ser Pro Gly Lys
450                 455                 460

<210> SEQ ID NO 86
<211> LENGTH: 767
<212> TYPE: DNA
<213> ORGANISM: artificial
<220> FEATURE:
<223> OTHER INFORMATION: Nucleotide Sequence coding Light Chain of 14F74

<400> SEQUENCE: 86
ccagcctccg gactctagag ccaccatggt gctgcagacc caggtgttca tcagcctgct      60
gctgtggatc agcggcgcct acggcgacat cgtgatgagc cagagcccta gcagcctggc     120
cgtgtctgcc ggcgagaaag tgaccatgag ctgcaagagc agccagtccc tgctgaacag     180
ccggacccgg aagaactacc tggcctggta tcagcagaag cccggccagt cccccaagct     240
gctgatctac tgggccagca ccagagaaag cggcgtgccc gatagattca ccggcagcgg     300
ctctggcacc gacttcaccc tgacaatcag cagcgtgcag gccgaggacc tggctgtgta     360
ctactgcaag cagagctaca acctgcggac cttcggcgga ggcaccaagc tggaaatcca     420
gagagccgac gccgctccca ccgtgtccat ctttccacct agcagcgagc agctgaccag     480
cggcggagct agcgtcgtgt gcttcctgaa caacttctac cccaaggaca tcaacgtgaa     540
gtggaagatc gacggcagcg agcggcagaa cggcgtgctg aatagctgga ccgaccagga     600
cagcaaggac tccacctaca gcatgtccag caccctgacc ctgaccaagg acgagtacga     660
gcggcacaac agctacacat gcgaggccac ccacaagacc agcaccctcc ccatcgtgaa     720
gtccttcaac cggaacgagt gctgagttta aacgggggag gctaact                    767

<210> SEQ ID NO 87
<211> LENGTH: 239
<212> TYPE: PRT
<213> ORGANISM: artificial

<220> FEATURE:
<223> OTHER INFORMATION: Amino Acid Sequence of Light Chain of 14F74

<400> SEQUENCE: 87

```
Met Val Leu Gln Thr Gln Val Phe Ile Ser Leu Leu Trp Ile Ser
1               5                   10                  15

Gly Ala Tyr Gly Asp Ile Val Met Ser Gln Ser Pro Ser Ser Leu Ala
            20                  25                  30

Val Ser Ala Gly Glu Lys Val Thr Met Ser Cys Lys Ser Ser Gln Ser
        35                  40                  45

Leu Leu Asn Ser Arg Thr Arg Lys Asn Tyr Leu Ala Trp Tyr Gln Gln
    50                  55                  60

Lys Pro Gly Gln Ser Pro Lys Leu Leu Ile Tyr Trp Ala Ser Thr Arg
65                  70                  75                  80

Glu Ser Gly Val Pro Asp Arg Phe Thr Gly Ser Gly Ser Gly Thr Asp
                85                  90                  95

Phe Thr Leu Thr Ile Ser Ser Val Gln Ala Glu Asp Leu Ala Val Tyr
            100                 105                 110

Tyr Cys Lys Gln Ser Tyr Asn Leu Arg Thr Phe Gly Gly Gly Thr Lys
        115                 120                 125

Leu Glu Ile Gln Arg Ala Asp Ala Ala Pro Thr Val Ser Ile Phe Pro
    130                 135                 140

Pro Ser Ser Glu Gln Leu Thr Ser Gly Gly Ala Ser Val Val Cys Phe
145                 150                 155                 160

Leu Asn Asn Phe Tyr Pro Lys Asp Ile Asn Val Lys Trp Lys Ile Asp
                165                 170                 175

Gly Ser Glu Arg Gln Asn Gly Val Leu Asn Ser Trp Thr Asp Gln Asp
            180                 185                 190

Ser Lys Asp Ser Thr Tyr Ser Met Ser Ser Thr Leu Thr Leu Thr Lys
        195                 200                 205

Asp Glu Tyr Glu Arg His Asn Ser Tyr Thr Cys Glu Ala Thr His Lys
    210                 215                 220

Thr Ser Thr Ser Pro Ile Val Lys Ser Phe Asn Arg Asn Glu Cys
225                 230                 235
```

<210> SEQ ID NO 88
<211> LENGTH: 1436
<212> TYPE: DNA
<213> ORGANISM: artificial
<220> FEATURE:
<223> OTHER INFORMATION: Nucleotide Sequence coding Heavy Chain of 17F6

<400> SEQUENCE: 88

```
ccagcctccg gactctagag ccaccatgaa gcacctgtgg ttctttctgc tgctggtggc      60
cgctcccaga tgggtgctgt ctcaggtgca gctgcagcag tctggcgccg aactcgtgcg     120
gcctggaagc agcgtgaaga tcagctgcaa ggccagcggc tacgccttca gcagctactg     180
gatgaactgg gtcaagcagc ggccaggcca gggcctggaa tggatcggcc atatctatcc     240
cggcgacgcc gacaccaact acaacggcaa gttcaagggc aaggccaccc tgaccgccga     300
caagagcagc agcacagcct acatgcacct gtccagcctg accagcgagg acagcgccgt     360
gtacttctgc agccggcagc tgggcttcag atacgccatg gactattggg gccagggcac     420
cagcgtgacc gtgtctagcg ccaagaccac cccccctagc gtgtaccctc tggcccctgg     480
atctgccgcc cagaccaaca gcatggtcac cctgggctgc ctcgtgaagg gctacttccc     540
tgagcctgtg accgtgacct ggaacagcgg ctctctgtct agcggcgtgc acacctttcc     600
```

```
agccgtgctg cagagcgacc tgtacaccct gagcagctcc gtgacagtgc ccagctctac    660
ctggcccagc gagacagtga cctgcaacgt ggcccaccct gccagcagca ccaaggtgga    720
caagaaaatc gtgccccggg actgcggctg caagccctgt atctgtaccg tgcccgaggt    780
gtccagcgtg ttcatcttcc cacccaagcc caaggacgtg ctgaccatca ccctgacacc    840
caaagtgacc tgtgtggtgg tggacatcag caaggacgac cccgaggtgc agttcagttg    900
gttcgtggac gacgtggaag tgcacacagc ccagacccag cccagagagg aacagttcaa    960
cagcaccttc agaagcgtgt ccgagctgcc catcatgcac caggactggc tgaacggcaa   1020
agaattcaag tgcagagtga acagcgccgc cttccctgcc cccatcgaga aaaccatctc   1080
caagaccaag ggcagaccca aggccccccca ggtgtacaca atcccccccac ccaaagaaca   1140 gatggccaag acaaggtgt ccctgacctg catgatcacc gatttcttcc cagaggacat   1200
caccgtggaa tggcagtgga acggccagcc cgccgagaac tacaagaaca cccagcctat   1260
catggacacc gacggcagct acttcgtgta cagcaagctg aacgtgcaga agtccaactg   1320
ggaggccggc aacaccttca cctgtagcgt gctgcacgag ggcctgcaca atcaccacac   1380
cgagaagtcc ctgtcccaca gccccggcaa atgagtttaa acgggggagg ctaact       1436

<210> SEQ ID NO 89
<211> LENGTH: 462
<212> TYPE: PRT
<213> ORGANISM: artificial
<220> FEATURE:
<223> OTHER INFORMATION: Amino Acid Sequence of Heavy Chain of 17F6

<400> SEQUENCE: 89

Met Lys His Leu Trp Phe Phe Leu Leu Leu Val Ala Ala Pro Arg Trp
1               5                   10                  15

Val Leu Ser Gln Val Gln Leu Gln Gln Ser Gly Ala Glu Leu Val Arg
            20                  25                  30

Pro Gly Ser Ser Val Lys Ile Ser Cys Lys Ala Ser Gly Tyr Ala Phe
        35                  40                  45

Ser Ser Tyr Trp Met Asn Trp Val Lys Gln Arg Pro Gly Gln Gly Leu
    50                  55                  60

Glu Trp Ile Gly His Ile Tyr Pro Gly Asp Ala Asp Thr Asn Tyr Asn
65                  70                  75                  80

Gly Lys Phe Lys Gly Lys Ala Thr Leu Thr Ala Asp Lys Ser Ser Ser
                85                  90                  95

Thr Ala Tyr Met His Leu Ser Ser Leu Thr Ser Glu Asp Ser Ala Val
            100                 105                 110

Tyr Phe Cys Ser Arg Gln Leu Gly Phe Arg Tyr Ala Met Asp Tyr Trp
        115                 120                 125

Gly Gln Gly Thr Ser Val Thr Val Ser Ser Ala Lys Thr Thr Pro Pro
    130                 135                 140

Ser Val Tyr Pro Leu Ala Pro Gly Ser Ala Ala Gln Thr Asn Ser Met
145                 150                 155                 160

Val Thr Leu Gly Cys Leu Val Lys Gly Tyr Phe Pro Glu Pro Val Thr
                165                 170                 175

Val Thr Trp Asn Ser Gly Ser Leu Ser Ser Gly Val His Thr Phe Pro
            180                 185                 190

Ala Val Leu Gln Ser Asp Leu Tyr Thr Leu Ser Ser Ser Val Thr Val
        195                 200                 205

Pro Ser Ser Thr Trp Pro Ser Glu Thr Val Thr Cys Asn Val Ala His
```

```
                  210                 215                 220
Pro Ala Ser Ser Thr Lys Val Asp Lys Ile Val Pro Arg Asp Cys
225                 230                 235                 240

Gly Cys Lys Pro Cys Ile Cys Thr Val Pro Glu Val Ser Ser Val Phe
                245                 250                 255

Ile Phe Pro Pro Lys Pro Lys Asp Val Leu Thr Ile Thr Leu Thr Pro
            260                 265                 270

Lys Val Thr Cys Val Val Val Asp Ile Ser Lys Asp Asp Pro Glu Val
                275                 280                 285

Gln Phe Ser Trp Phe Val Asp Asp Val Glu Val His Thr Ala Gln Thr
    290                 295                 300

Gln Pro Arg Glu Glu Gln Phe Asn Ser Thr Phe Arg Ser Val Ser Glu
305                 310                 315                 320

Leu Pro Ile Met His Gln Asp Trp Leu Asn Gly Lys Glu Phe Lys Cys
                325                 330                 335

Arg Val Asn Ser Ala Ala Phe Pro Ala Pro Ile Glu Lys Thr Ile Ser
            340                 345                 350

Lys Thr Lys Gly Arg Pro Lys Ala Pro Gln Val Tyr Thr Ile Pro Pro
        355                 360                 365

Pro Lys Glu Gln Met Ala Lys Asp Lys Val Ser Leu Thr Cys Met Ile
    370                 375                 380

Thr Asp Phe Phe Pro Glu Asp Ile Thr Val Glu Trp Gln Trp Asn Gly
385                 390                 395                 400

Gln Pro Ala Glu Asn Tyr Lys Asn Thr Gln Pro Ile Met Asp Thr Asp
                405                 410                 415

Gly Ser Tyr Phe Val Tyr Ser Lys Leu Asn Val Gln Lys Ser Asn Trp
            420                 425                 430

Glu Ala Gly Asn Thr Phe Thr Cys Ser Val Leu His Glu Gly Leu His
        435                 440                 445

Asn His His Thr Glu Lys Ser Leu Ser His Ser Pro Gly Lys
    450                 455                 460

<210> SEQ ID NO 90
<211> LENGTH: 767
<212> TYPE: DNA
<213> ORGANISM: artificial
<220> FEATURE:
<223> OTHER INFORMATION: Nucleotide Sequence coding Light Chain of 17F6

<400> SEQUENCE: 90
ccagcctccg gactctagag ccaccatggt gctgcagacc caggtgttca tcagcctgct      60
gctgtggatc agcggcgcct acggcgacat cgtgatgagc cagagcccta gcagcctggc     120
cgtgtctgcc ggcgagaaag tgaccatgag ctgcaagagc agccagtccc tgctgaacag     180
ccggacccgg aagaactacc tggcctggta tcagcagaag cccggccagt cccccaagct     240
gctgatctac tgggccagca ccagagaaag cggcgtgccc gatagattca ccggcagcgg     300
ctctggcacc gacttcaccc tgacaatcag cagcgtgcag gccgaggacc tggctgtgta     360
ctactgcaag cagagctaca acctgcggac cttcggcgga ggcaccaagc tggaaatcaa     420
agagagccga ccgctcccca ccgtgtccat ctttccacct agcagcgagc agctgaccag     480
cggcggagct agcgtcgtgt gcttcctgaa caacttctac cccaaggaca tcaacgtgaa     540
gtggaagatc gacggcagcg agcggcagaa cggcgtgctg aatagctgga ccgaccagga     600
cagcaaggac tccacctaca gcatgtccag caccctgacc ctgaccaagg acgagtacga     660
```

```
gcggcacaac agctacacat gcgaggccac ccacaagacc agcacctccc ccatcgtgaa      720
gtccttcaac cggaacgagt gctgagttta aacgggggag gctaact                    767
```

<210> SEQ ID NO 91
<211> LENGTH: 239
<212> TYPE: PRT
<213> ORGANISM: artificial
<220> FEATURE:
<223> OTHER INFORMATION: Amino Acid Sequence of Light Chain of 17F6

<400> SEQUENCE: 91

```
Met Val Leu Gln Thr Gln Val Phe Ile Ser Leu Leu Leu Trp Ile Ser
1               5                   10                  15

Gly Ala Tyr Gly Asp Ile Val Met Ser Gln Ser Pro Ser Ser Leu Ala
            20                  25                  30

Val Ser Ala Gly Glu Lys Val Thr Met Ser Cys Lys Ser Ser Gln Ser
        35                  40                  45

Leu Leu Asn Ser Arg Thr Arg Lys Asn Tyr Leu Ala Trp Tyr Gln Gln
    50                  55                  60

Lys Pro Gly Gln Ser Pro Lys Leu Leu Ile Tyr Trp Ala Ser Thr Arg
65                  70                  75                  80

Glu Ser Gly Val Pro Asp Arg Phe Thr Gly Ser Gly Ser Gly Thr Asp
                85                  90                  95

Phe Thr Leu Thr Ile Ser Ser Val Gln Ala Glu Asp Leu Ala Val Tyr
            100                 105                 110

Tyr Cys Lys Gln Ser Tyr Asn Leu Arg Thr Phe Gly Gly Gly Thr Lys
        115                 120                 125

Leu Glu Ile Lys Arg Ala Asp Ala Ala Pro Thr Val Ser Ile Phe Pro
    130                 135                 140

Pro Ser Ser Glu Gln Leu Thr Ser Gly Gly Ala Ser Val Val Cys Phe
145                 150                 155                 160

Leu Asn Asn Phe Tyr Pro Lys Asp Ile Asn Val Lys Trp Lys Ile Asp
                165                 170                 175

Gly Ser Glu Arg Gln Asn Gly Val Leu Asn Ser Trp Thr Asp Gln Asp
            180                 185                 190

Ser Lys Asp Ser Thr Tyr Ser Met Ser Ser Thr Leu Thr Leu Thr Lys
        195                 200                 205

Asp Glu Tyr Glu Arg His Asn Ser Tyr Thr Cys Glu Ala Thr His Lys
    210                 215                 220

Thr Ser Thr Ser Pro Ile Val Lys Ser Phe Asn Arg Asn Glu Cys
225                 230                 235
```

<210> SEQ ID NO 92
<211> LENGTH: 11
<212> TYPE: PRT
<213> ORGANISM: Rattus rattus

<400> SEQUENCE: 92

```
Arg Ala Ser Gln Ser Ile Gly Asn Ser Leu Ser
1               5                   10
```

<210> SEQ ID NO 93
<211> LENGTH: 11
<212> TYPE: PRT
<213> ORGANISM: artificial
<220> FEATURE:
<223> OTHER INFORMATION: CDRL1 of hR198_LG1

<400> SEQUENCE: 93

```
Arg Ala Ser Gln Ser Ile Gly Gly Ser Leu Ser
1               5                   10

<210> SEQ ID NO 94
<211> LENGTH: 11
<212> TYPE: PRT
<213> ORGANISM: artificial
<220> FEATURE:
<223> OTHER INFORMATION: CDRL1 of hR198_LG2

<400> SEQUENCE: 94

His Ala Ser Gln Asn Ile Gly Gly Ser Leu Ser
1               5                   10

<210> SEQ ID NO 95
<211> LENGTH: 11
<212> TYPE: PRT
<213> ORGANISM: artificial
<220> FEATURE:
<223> OTHER INFORMATION: CDRL1 of hR198_LG3

<400> SEQUENCE: 95

His Ala Ser Arg Asn Ile Gly Gly Ser Leu Ser
1               5                   10

<210> SEQ ID NO 96
<211> LENGTH: 7
<212> TYPE: PRT
<213> ORGANISM: Rattus rattus

<400> SEQUENCE: 96

Ser Thr Ser Thr Leu Glu Ser
1               5

<210> SEQ ID NO 97
<211> LENGTH: 7
<212> TYPE: PRT
<213> ORGANISM: artificial
<220> FEATURE:
<223> OTHER INFORMATION: CDRL2 of hR198_LG2

<400> SEQUENCE: 97

Leu Thr Ser Thr Leu Asp Trp
1               5

<210> SEQ ID NO 98
<211> LENGTH: 7
<212> TYPE: PRT
<213> ORGANISM: artificial
<220> FEATURE:
<223> OTHER INFORMATION: CDRL2 of hR198_LG3

<400> SEQUENCE: 98

Leu Thr Ser Ser Leu Asp Trp
1               5

<210> SEQ ID NO 99
<211> LENGTH: 9
<212> TYPE: PRT
<213> ORGANISM: Rattus rattus

<400> SEQUENCE: 99

Leu Gln Phe Ala Thr Phe Pro Asp Thr
1               5
```

```
<210> SEQ ID NO 100
<211> LENGTH: 9
<212> TYPE: PRT
<213> ORGANISM: Rattus rattus

<400> SEQUENCE: 100

Leu Gln Phe Ala Thr Tyr Pro Asp Thr
1               5

<210> SEQ ID NO 101
<211> LENGTH: 9
<212> TYPE: PRT
<213> ORGANISM: artificial
<220> FEATURE:
<223> OTHER INFORMATION: CDRL3 of hR198_LG1 to LG3

<400> SEQUENCE: 101

Leu Gln Phe Ala Ile Phe Pro Asp Ser
1               5

<210> SEQ ID NO 102
<211> LENGTH: 5
<212> TYPE: PRT
<213> ORGANISM: Rattus rattus

<400> SEQUENCE: 102

Ala Tyr Tyr Ile Ser
1               5

<210> SEQ ID NO 103
<211> LENGTH: 5
<212> TYPE: PRT
<213> ORGANISM: Rattus rattus

<400> SEQUENCE: 103

Ser Tyr Tyr Ile Ser
1               5

<210> SEQ ID NO 104
<211> LENGTH: 17
<212> TYPE: PRT
<213> ORGANISM: Rattus rattus

<400> SEQUENCE: 104

Tyr Ile Asp Met Gly Asn Gly Arg Thr Asn Tyr Asn Ala Arg Phe Lys
1               5                   10                  15

Gly

<210> SEQ ID NO 105
<211> LENGTH: 17
<212> TYPE: PRT
<213> ORGANISM: Rattus rattus

<400> SEQUENCE: 105

Tyr Val Asp Met Gly Asn Gly Arg Thr Asn Tyr Asn Glu Lys Phe Lys
1               5                   10                  15

Gly

<210> SEQ ID NO 106
<211> LENGTH: 17
<212> TYPE: PRT
<213> ORGANISM: artificial
<220> FEATURE:
<223> OTHER INFORMATION: CDRH2 of hR198_HG1
```

```
<400> SEQUENCE: 106

Tyr Ile Asp Met Gly Asn Gly Arg Thr Asp Tyr Asn Ala Arg Phe Lys
1               5                   10                  15

Gly

<210> SEQ ID NO 107
<211> LENGTH: 17
<212> TYPE: PRT
<213> ORGANISM: artificial
<220> FEATURE:
<223> OTHER INFORMATION: CDRH2 of hR198_HG2

<400> SEQUENCE: 107

Tyr Ile Asp Met Gly Asn Gly Arg Thr Asp Tyr Asn Gly Arg Phe Lys
1               5                   10                  15

Gly

<210> SEQ ID NO 108
<211> LENGTH: 17
<212> TYPE: PRT
<213> ORGANISM: artificial
<220> FEATURE:
<223> OTHER INFORMATION: CDRH2 of hR198_HG3

<400> SEQUENCE: 108

Tyr Ile Asp Met Gly Asn Gly Arg Thr Asp Tyr Asn Met Arg Phe Lys
1               5                   10                  15

Gly

<210> SEQ ID NO 109
<211> LENGTH: 8
<212> TYPE: PRT
<213> ORGANISM: Rattus rattus

<400> SEQUENCE: 109

Asp Ser Asn Trp Gly Val Asp Tyr
1               5

<210> SEQ ID NO 110
<211> LENGTH: 8
<212> TYPE: PRT
<213> ORGANISM: artificial
<220> FEATURE:
<223> OTHER INFORMATION: CDRH3 of hR198_HG1 to HG3

<400> SEQUENCE: 110

Asp Ser Asn Trp Gly Ala Asp Tyr
1               5

<210> SEQ ID NO 111
<211> LENGTH: 1401
<212> TYPE: DNA
<213> ORGANISM: artificial
<220> FEATURE:
<223> OTHER INFORMATION: Nucleotide Sequence coding hR198_H0

<400> SEQUENCE: 111
atgaaacacc tgtggttctt cctcctgctg gtggcagctc ccagatgggt gctgagccag      60
gtgcagctgg tgcagtctgg cgccgaagtg aagaaaccag gcgccagcgt gaaggtgtcc     120
tgcaaggcct ctggctaccc cgtgaccagc tactacatca gctggatcag acaggccca      180 ggccagggcc tggaatggat cggctatgtg acatgggca acggccggac caactacaac      240
```

-continued

```
gagaagttca agggcagagc caccctgacc gtggacaaga gcaccagcac cgcctacatg    300
gaactgagca gcctgcggag cgaggacacc gccgtgtact actgcgccag agacagcaac    360
tggggcgtgg actattgggg ccagggcaca ctcgtgaccg tcagctcagc ctccaccaag    420
ggcccaagcg tcttcccect ggcaccctcc tccaagagca cctctggcgg cacagccgcc    480
ctgggctgcc tggtcaagga ctacttcccc gaacccgtga ccgtgagctg gaactcaggc    540
gccctgacca gcggcgtgca caccttcccc gctgtcctgc agtcctcagg actctactcc    600
ctcagcagcg tggtgaccgt gccctccagc agcttgggca cccagaccta catctgcaac    660
gtgaatcaca agcccagcaa caccaaggtg gacaagagag ttgagcccaa atcttgtgac    720
aaaactcaca catgcccacc ctgcccagca cctgaactcc tggggggacc ctcagtcttc    780 ctcttcccec caaaacccaa ggacaccctc atgatctccc ggaccectga ggtcacatgc    840 gtggtggtgg acgtgagcca cgaagaccct gaggtcaagt tcaactggta cgtggacggc    900
gtggaggtgc ataatgccaa gacaaagccc cgggaggagc agtacaacag cacgtaccgg    960
gtggtcagcg tcctcaccgt cctgcaccag gactggctga atggcaagga gtacaagtgc   1020
aaggtctcca acaaagccct cccagccccc atcgagaaaa ccatctccaa agccaaaggc   1080
cagccccggg aaccacaggt gtacaccctg cccccatccc gggaggagat gaccaagaac   1140
caggtcagcc tgacctgcct ggtcaaaggc ttctatccca gcgacatcgc cgtggagtgg   1200
gagagcaatg gccagcccga gaacaactac aagaccaccc tcccegtgct ggactccgac   1260 ggctccttct tcctctacag caagctcacc gtggacaaga gcaggtggca gcagggcaac   1320
gtcttctcat gctccgtgat gcatgaggct ctgcacaacc actacaccca gaagagcctc   1380
tccctgtctc cggcaaatg a                                              1401
```

<210> SEQ ID NO 112
<211> LENGTH: 466
<212> TYPE: PRT
<213> ORGANISM: artificial
<220> FEATURE:
<223> OTHER INFORMATION: Amino Acid Sequence of hR198_H0

<400> SEQUENCE: 112

```
Met Lys His Leu Trp Phe Phe Leu Leu Val Ala Ala Pro Arg Trp
1               5                   10                  15

Val Leu Ser Gln Val Gln Leu Val Gln Ser Gly Ala Glu Val Lys Lys
                20                  25                  30

Pro Gly Ala Ser Val Lys Val Ser Cys Lys Ala Ser Gly Tyr Pro Val
            35                  40                  45

Thr Ser Tyr Tyr Ile Ser Trp Ile Arg Gln Ala Pro Gly Gln Gly Leu
        50                  55                  60

Glu Trp Ile Gly Tyr Val Asp Met Gly Asn Gly Arg Thr Asn Tyr Asn
65                  70                  75                  80

Glu Lys Phe Lys Gly Arg Ala Thr Leu Thr Val Asp Lys Ser Thr Ser
                85                  90                  95

Thr Ala Tyr Met Glu Leu Ser Ser Leu Arg Ser Glu Asp Thr Ala Val
            100                 105                 110

Tyr Tyr Cys Ala Arg Asp Ser Asn Trp Gly Val Asp Tyr Trp Gly Gln
        115                 120                 125

Gly Thr Leu Val Thr Val Ser Ser Ala Ser Thr Lys Gly Pro Ser Val
    130                 135                 140

Phe Pro Leu Ala Pro Ser Ser Lys Ser Thr Ser Gly Gly Thr Ala Ala
145                 150                 155                 160
```

Leu Gly Cys Leu Val Lys Asp Tyr Phe Pro Glu Pro Val Thr Val Ser
            165                 170                 175

Trp Asn Ser Gly Ala Leu Thr Ser Gly Val His Thr Phe Pro Ala Val
            180                 185                 190

Leu Gln Ser Ser Gly Leu Tyr Ser Leu Ser Ser Val Val Thr Val Pro
            195                 200                 205

Ser Ser Ser Leu Gly Thr Gln Thr Tyr Ile Cys Asn Val Asn His Lys
210                 215                 220

Pro Ser Asn Thr Lys Val Asp Lys Arg Val Glu Pro Lys Ser Cys Asp
225                 230                 235                 240

Lys Thr His Thr Cys Pro Pro Cys Pro Ala Pro Glu Leu Leu Gly Gly
            245                 250                 255

Pro Ser Val Phe Leu Phe Pro Pro Lys Pro Lys Asp Thr Leu Met Ile
            260                 265                 270

Ser Arg Thr Pro Glu Val Thr Cys Val Val Val Asp Val Ser His Glu
            275                 280                 285

Asp Pro Glu Val Lys Phe Asn Trp Tyr Val Asp Gly Val Glu Val His
290                 295                 300

Asn Ala Lys Thr Lys Pro Arg Glu Glu Gln Tyr Asn Ser Thr Tyr Arg
305                 310                 315                 320

Val Val Ser Val Leu Thr Val Leu His Gln Asp Trp Leu Asn Gly Lys
            325                 330                 335

Glu Tyr Lys Cys Lys Val Ser Asn Lys Ala Leu Pro Ala Pro Ile Glu
            340                 345                 350

Lys Thr Ile Ser Lys Ala Lys Gly Gln Pro Arg Glu Pro Gln Val Tyr
            355                 360                 365

Thr Leu Pro Pro Ser Arg Glu Glu Met Thr Lys Asn Gln Val Ser Leu
            370                 375                 380

Thr Cys Leu Val Lys Gly Phe Tyr Pro Ser Asp Ile Ala Val Glu Trp
385                 390                 395                 400

Glu Ser Asn Gly Gln Pro Glu Asn Asn Tyr Lys Thr Thr Pro Pro Val
            405                 410                 415

Leu Asp Ser Asp Gly Ser Phe Phe Leu Tyr Ser Lys Leu Thr Val Asp
            420                 425                 430

Lys Ser Arg Trp Gln Gln Gly Asn Val Phe Ser Cys Ser Val Met His
            435                 440                 445

Glu Ala Leu His Asn His Tyr Thr Gln Lys Ser Leu Ser Leu Ser Pro
    450                 455                 460

Gly Lys
465

<210> SEQ ID NO 113
<211> LENGTH: 1401
<212> TYPE: DNA
<213> ORGANISM: artificial
<220> FEATURE:
<223> OTHER INFORMATION: Nucleotide Sequence coding hR198_H5

<400> SEQUENCE: 113
atgaaacacc tgtggttctt cctcctgctg gtggcagctc ccagatgggt gctgagccag     60
gtgcagctgg tgcagtctgg cgccgaagtg aagaaaccag gcgccagcgt gaaggtgtcc    120
tgcaaggcct ctggctaccc cgtgaccgcc tactacatca gctggatcag acaggcccca    180
ggccagggcc tggaatggat cggctacatc gacatgggca acggccggac caactacaac    240

```
gcccggttta agggcagagc caccctgacc gtggacaaga gcaccagcac cgcctacatg    300
gaactgagca gcctgcggag cgaggacacc gccgtgtact actgcgccag agacagcaac    360
tggggcgtgg actattgggg ccagggcaca ctcgtgaccg tcagctcagc ctccaccaag    420
ggcccaagcg tcttccccct ggcaccctcc tccaagagca cctctggcgg cacagccgcc    480
ctgggctgcc tggtcaagga ctacttcccc gaacccgtga ccgtgagctg gaactcaggc    540
gccctgacca gcggcgtgca caccttcccc gctgtcctgc agtcctcagg actctactcc    600
ctcagcagcg tggtgaccgt gccctccagc agcttgggca cccagaccta catctgcaac    660
gtgaatcaca gcccagcaa caccaaggtg gacaagagag ttgagcccaa atcttgtgac    720
aaaactcaca catgcccacc ctgcccagca cctgaactcc tggggggacc ctcagtcttc    780
ctcttccccc caaaacccaa ggacaccctc atgatctccc ggacccctga ggtcacatgc    840
gtggtggtgg acgtgagcca cgaagaccct gaggtcaagt tcaactggta cgtggacggc    900
gtggaggtgc ataatgccaa gacaaagccc cgggaggagc agtacaacag cacgtaccgg    960
gtggtcagcg tcctcaccgt cctgcaccag gactggctga atggcaagga gtacaagtgc   1020
aaggtctcca acaaagccct cccagccccc atcgagaaaa ccatctccaa agccaaaggc   1080
cagccccggg aaccacaggt gtacaccctg cccccatccc gggaggagat gaccaagaac   1140
caggtcagcc tgacctgcct ggtcaaaggc ttctatccca gcgacatcgc cgtggagtgg   1200
gagagcaatg gccagcccga gaacaactac aagaccaccc tcccgtgct ggactccgac   1260 ggctccttct cctctacag caagctcacc gtggacaaga gcaggtggca gcagggcaac   1320
gtcttctcat gctccgtgat gcatgaggct ctgcacaacc actacaccca gaagagcctc   1380
tccctgtctc ccggcaaatg a                                             1401
```

<210> SEQ ID NO 114
<211> LENGTH: 466
<212> TYPE: PRT
<213> ORGANISM: artificial
<220> FEATURE:
<223> OTHER INFORMATION: Amino Acid Sequence of hR198_H5

<400> SEQUENCE: 114

Met Lys His Leu Trp Phe Phe Leu Leu Val Ala Ala Pro Arg Trp
1               5                   10                  15

Val Leu Ser Gln Val Gln Leu Val Gln Ser Gly Ala Glu Val Lys Lys
            20                  25                  30

Pro Gly Ala Ser Val Lys Val Ser Cys Lys Ala Ser Gly Tyr Pro Val
        35                  40                  45

Thr Ala Tyr Tyr Ile Ser Trp Ile Arg Gln Ala Pro Gly Gln Gly Leu
    50                  55                  60

Glu Trp Ile Gly Tyr Ile Asp Met Gly Asn Gly Arg Thr Asn Tyr Asn
65                  70                  75                  80

Ala Arg Phe Lys Gly Arg Ala Thr Leu Thr Val Asp Lys Ser Thr Ser
                85                  90                  95

Thr Ala Tyr Met Glu Leu Ser Ser Leu Arg Ser Glu Asp Thr Ala Val
            100                 105                 110

Tyr Tyr Cys Ala Arg Asp Ser Asn Trp Gly Val Asp Tyr Trp Gly Gln
        115                 120                 125

Gly Thr Leu Val Thr Val Ser Ser Ala Ser Thr Lys Gly Pro Ser Val
    130                 135                 140

Phe Pro Leu Ala Pro Ser Ser Lys Ser Thr Ser Gly Gly Thr Ala Ala
145                 150                 155                 160

```
Leu Gly Cys Leu Val Lys Asp Tyr Phe Pro Glu Pro Val Thr Val Ser
                165                 170                 175

Trp Asn Ser Gly Ala Leu Thr Ser Gly Val His Thr Phe Pro Ala Val
            180                 185                 190

Leu Gln Ser Ser Gly Leu Tyr Ser Leu Ser Ser Val Val Thr Val Pro
        195                 200                 205

Ser Ser Ser Leu Gly Thr Gln Thr Tyr Ile Cys Asn Val Asn His Lys
    210                 215                 220

Pro Ser Asn Thr Lys Val Asp Lys Arg Val Glu Pro Lys Ser Cys Asp
225                 230                 235                 240

Lys Thr His Thr Cys Pro Pro Cys Pro Ala Pro Glu Leu Leu Gly Gly
                245                 250                 255

Pro Ser Val Phe Leu Phe Pro Pro Lys Pro Lys Asp Thr Leu Met Ile
            260                 265                 270

Ser Arg Thr Pro Glu Val Thr Cys Val Val Val Asp Val Ser His Glu
        275                 280                 285

Asp Pro Glu Val Lys Phe Asn Trp Tyr Val Asp Gly Val Glu Val His
    290                 295                 300

Asn Ala Lys Thr Lys Pro Arg Glu Glu Gln Tyr Asn Ser Thr Tyr Arg
305                 310                 315                 320

Val Val Ser Val Leu Thr Val Leu His Gln Asp Trp Leu Asn Gly Lys
                325                 330                 335

Glu Tyr Lys Cys Lys Val Ser Asn Lys Ala Leu Pro Ala Pro Ile Glu
            340                 345                 350

Lys Thr Ile Ser Lys Ala Lys Gly Gln Pro Arg Glu Pro Gln Val Tyr
        355                 360                 365

Thr Leu Pro Pro Ser Arg Glu Glu Met Thr Lys Asn Gln Val Ser Leu
    370                 375                 380

Thr Cys Leu Val Lys Gly Phe Tyr Pro Ser Asp Ile Ala Val Glu Trp
385                 390                 395                 400

Glu Ser Asn Gly Gln Pro Glu Asn Asn Tyr Lys Thr Thr Pro Pro Val
                405                 410                 415

Leu Asp Ser Asp Gly Ser Phe Phe Leu Tyr Ser Lys Leu Thr Val Asp
            420                 425                 430

Lys Ser Arg Trp Gln Gln Gly Asn Val Phe Ser Cys Ser Val Met His
        435                 440                 445

Glu Ala Leu His Asn His Tyr Thr Gln Lys Ser Leu Ser Leu Ser Pro
    450                 455                 460

Gly Lys
465

<210> SEQ ID NO 115
<211> LENGTH: 48
<212> TYPE: PRT
<213> ORGANISM: Homo sapiens

<400> SEQUENCE: 115

Ser Gly Ser Gly Phe Leu Pro Leu Lys Lys Gln Pro Gly Gln Pro Arg
1               5                   10                  15

Pro Thr Ser Lys Pro Pro Ala Ser Gly Ala Ala Ala Asn Val Ser Thr
            20                  25                  30

Ser Gly Ile Thr Pro Gly Gln Ala Ala Ala Ile Ala Ser Thr Thr Ile
        35                  40                  45
```

```
<210> SEQ ID NO 116
<211> LENGTH: 11
<212> TYPE: PRT
<213> ORGANISM: Rattus rattus

<400> SEQUENCE: 116

Arg Ala Ser Gln Ser Ile Ser Asn Ser Leu Ser
1               5                   10
```